United States Patent
Muller et al.

(10) Patent No.: US 10,401,365 B2
(45) Date of Patent: Sep. 3, 2019

(54) INHIBITION OF CHEMOKINE CCL7 OR RECEPTOR CCR3 OF SAME FOR THE TREATMENT AND DIAGNOSIS OF PROSTATE CANCER

(71) Applicants: Universite Paul Sabatier (Toulouse III), Toulouse (FR); Centre National de la Recherche Scientifique, Paris (FR); Centre Hospitalier Universitaire de Toulouse, Toulouse (FR); Institute National de la Sante et de la Recherche Medicale (INSERM), Paris (FR)

(72) Inventors: Catherine Muller, Toulouse (FR); Victor Laurent, Saint Sulpice (FR); Adrien Guerard, Toulouse (FR); Philippe Valet, Toulouse (FR); Bernard Malavaud, Toulouse (FR)

(73) Assignees: Universite Paul Sabatier (Toulouse III), Toulouse (FR); Centre National de la Recherche Scientifique, Paris (FR); Centre Hospitalier Universitaire de Toulouse, Toulouse (FR); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 15/318,777

(22) PCT Filed: Jun. 16, 2015

(86) PCT No.: PCT/IB2015/054550
§ 371 (c)(1),
(2) Date: Dec. 14, 2016

(87) PCT Pub. No.: WO2015/193813
PCT Pub. Date: Dec. 23, 2015

(65) Prior Publication Data
US 2017/0131282 A1 May 11, 2017

(30) Foreign Application Priority Data

Jun. 16, 2014 (FR) .................................. 14 55491

(51) Int. Cl.
| | | |
|---|---|---|
| *C07K 16/24* | (2006.01) | |
| *C07K 16/28* | (2006.01) | |
| *G01N 33/68* | (2006.01) | |
| *A61K 31/453* | (2006.01) | |
| *A61K 31/713* | (2006.01) | |
| *C07K 14/715* | (2006.01) | |
| *C12N 15/113* | (2010.01) | |
| *G01N 33/574* | (2006.01) | |

(52) U.S. Cl.
CPC ..... *G01N 33/57434* (2013.01); *A61K 31/453* (2013.01); *A61K 31/713* (2013.01); *C07K 14/7158* (2013.01); *C07K 16/24* (2013.01); *C07K 16/2866* (2013.01); *C12N 15/1138* (2013.01); *G01N 33/57492* (2013.01); *G01N 33/6863* (2013.01); *C07K 2317/73* (2013.01); *C07K 2317/76* (2013.01); *C12N 2310/14* (2013.01); *G01N 2333/7158* (2013.01); *G01N 2800/56* (2013.01)

(58) Field of Classification Search
CPC ...... C07K 16/24; C07K 16/28; C07K 14/715; G01N 33/68; G01N 33/574; A61K 31/453; A61K 31/713
See application file for complete search history.

(56) References Cited

FOREIGN PATENT DOCUMENTS

| | | |
|---|---|---|
| WO | 2005/106492 A2 | 11/2005 |
| WO | 2008/121132 A2 | 10/2008 |
| WO | 2010/123956 A2 | 10/2010 |
| WO | 2012/122499 A2 | 9/2012 |

OTHER PUBLICATIONS

Jung et al. 2010. In J. Cancer 127:332-344). (Year: 2010).*
Sacca et al.( cell Physiol Biochem 2012; 30: 113-112).*
Zhu et al., "Eotaxin-1 promotes prostate cancer cell invasion via activation of the CCR3-ERK pathway and upregulation of the MMP-3 expression," Oncology Reports, 31: 2049-2054 (2014).
Sabroe et al., "A small molecule antagonist of chemokine receptors CCR1 and CCR3. Potent inhibition of eosinophil function and CCR3-mediated HIV-1 entry," Journal of Biological Chemistry, 75: 25985-25992 (2000).
Wise et al., "Small Molecule Receptor Agonists and Antagonists of CCR3 Provide Insight into Mechanisms of Chemokine Receptor Activation," Journal of Biological Chemistry, 282: 27935-27943 (2007).
Jöhrer et al., "Up-Regulation of Functional Chemokine Receptor CCR3 in Human Renal Cell Carcinoma," Clinical Cancer Research, 11: 2459-2465 (2005).
Xu et al., "Screening and identification of significant genes related to tumor metastasis and PSMA in prostate cancer using microarray analysis," Oncology Reports, 30: 1920-1928 (2013).

(Continued)

Primary Examiner — Shirley V Gembeh
(74) Attorney, Agent, or Firm — Morgan, Lewis & Bockius LLP

(57) ABSTRACT

The invention concerns an inhibitor of the expression of chemokine CCL7 or an inhibitor of the expression of the receptor CCR3 or an inhibitor of CCL7/CCR3 interaction for the use of same to prevent or treat the extension of prostate cancer outside the prostatic capsule in a subject. The invention also concerns a method for determining the degree of aggressiveness of a prostate cancer tumor in a subject suffering from prostate cancer, comprising a step of determining the concentration or level of expression of the receptor CCR3 in a sample of prostate tumor cells obtained from said subject.

6 Claims, 14 Drawing Sheets

Figure 1A:
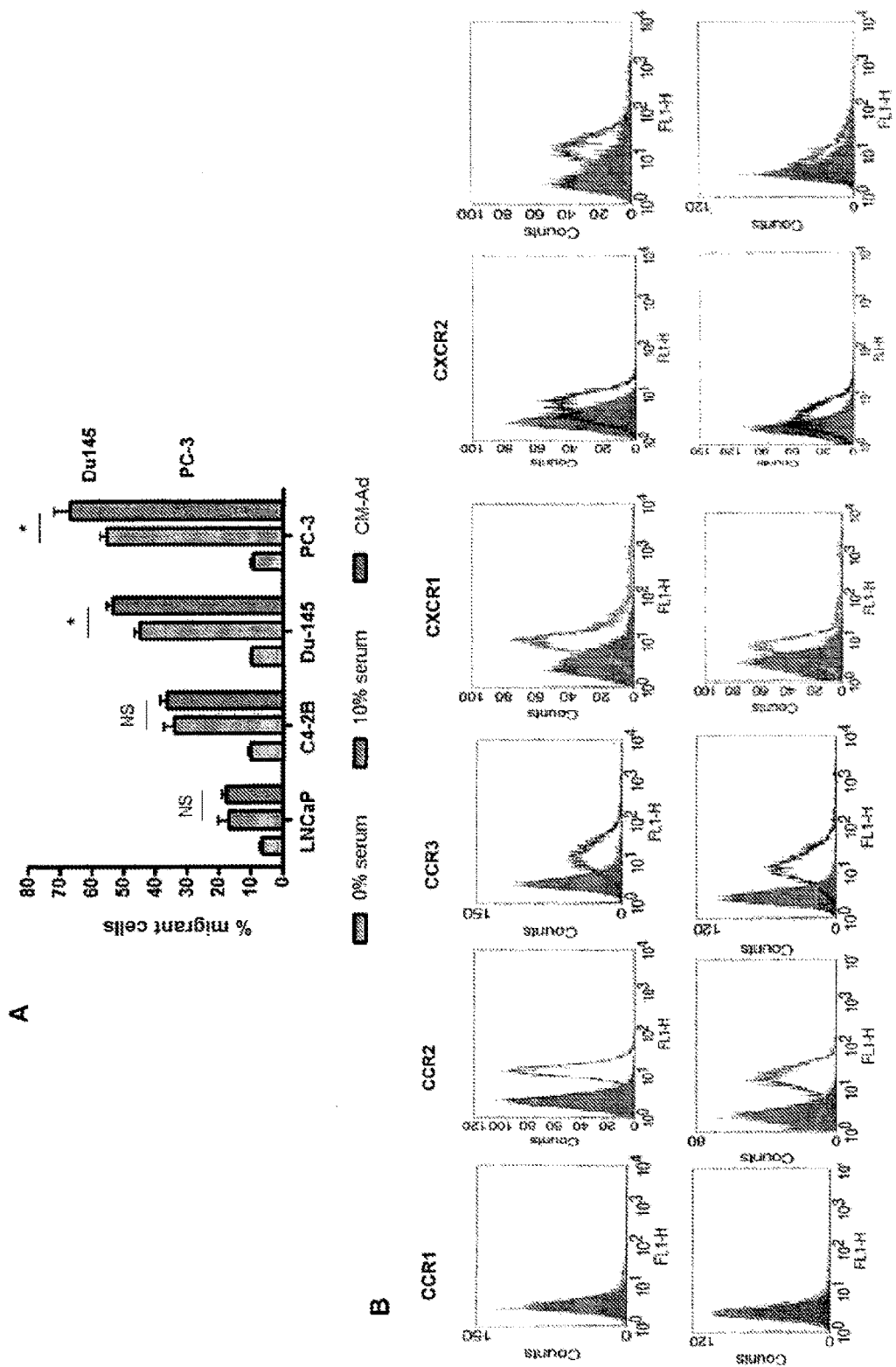

Specification includes a Sequence Listing.

(56) References Cited

OTHER PUBLICATIONS

O'Hayre et al., "Chemokines and cancer: migration, intracellular signalling and intercellular communication in the microenvironment," Biochemical Journal, 409: 635-649 (2008).
Laurent et al., "Periprostatic adipose tissue acts as a driving force for the local invasion of prostate cancer in obesity: role of the CCR3/CCL7 axis," Obesite, 9: 331-343 (2014).
International Search Report issued in corresponding International Patent Application No. PCT/IB2015/054550 dated Sep. 28, 2015.

\* cited by examiner

```
                            SEQUENCE LISTING

<160> NUMBER OF SEQ ID NOS: 25

<210> SEQ ID NO 1
<211> LENGTH: 67
<212> TYPE: DNA
<213> ORGANISM: Artificial Sequence
<220> FEATURE:
<223> OTHER INFORMATION: shRNA

<400> SEQUENCE: 1
cgcgtcccca gaccacaccc tatgaatatt caagagatat tcatagggtg tggtcttttt      60
tggaaat                                                               67

<210> SEQ ID NO 2
<211> LENGTH: 67
<212> TYPE: DNA
<213> ORGANISM: Artificial Sequence
<220> FEATURE:
<223> OTHER INFORMATION: shRNA

<400> SEQUENCE: 2
cgcgtccccg accacaccct atgaatattt caagagaata ttcatagggt gtggtctttt      60
tggaaat                                                               67

<210> SEQ ID NO 3
<211> LENGTH: 68
<212> TYPE: DNA
<213> ORGANISM: Artificial Sequence
<220> FEATURE:
<223> OTHER INFORMATION: shRNA

<400> SEQUENCE: 3
cgccgtcccc ggtgagaggt tccggaaact tcaagagagt ttccggaacc tctcaccttt      60
ttggaaat                                                              68

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
aaacctccaa ttctcatgtg gaa                                             23

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
cagaagtgct gcagaggctt t                                               21

<210> SEQ ID NO 6
<211> LENGTH: 23
<212> TYPE: DNA
```

```
<213> ORGANISM: Artificial Sequence
<220> FEATURE:
<223> OTHER INFORMATION: Primer

<400> SEQUENCE: 6
aaacctccaa ttctcatgtg gaa                                              23

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cttcccaggg acaccgacta                                                  20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tgcaccacca actgcttagc                                                  20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ggcatggact gtggtcatga g                                                21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tgacactggc aaaacaatgc a                                                21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcttgcgacc ttgaccatct                                                  20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tggccatctg cctagtaaag c                                                21
```

```
<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ggacgcagca actgacattt c                                              21

<210> SEQ ID NO 14
<211> LENGTH: 19
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (9)..(9)
<223> OTHER INFORMATION: Replace = 2,6-Diaminopurine
<220> FEATURE:
<221> NAME/KEY: modified_base
<222> LOCATION: (15)..(15)
<223> OTHER INFORMATION: Replace = 2,6-Diaminopurine

<400> SEQUENCE: 14
gggtctgcag cgggatggt                                                 19

<210> SEQ ID NO 15
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<223> OTHER INFORMATION: Replace = 2,6-Diaminopurine
<220> FEATURE:
<221> NAME/KEY: modified_base
<222> LOCATION: (7)..(7)
<223> OTHER INFORMATION: Replace = 2,6-Diaminopurine
<220> FEATURE:
<221> NAME/KEY: modified_base
<222> LOCATION: (13)..(13)
<223> OTHER INFORMATION: Replace = 2,6-Diaminopurine

<400> SEQUENCE: 15
gttactactt ccacctgcct g                                              21

<210> SEQ ID NO 16
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(19)
<223> OTHER INFORMATION: All linkages are phophorothioate

<400> SEQUENCE: 16
cacctctgtc accagcatg                                                 19

<210> SEQ ID NO 17
<211> LENGTH: 19
<212> TYPE: DNA
<213> ORGANISM: Artificial Sequence
<220> FEATURE:
```

```
<223> OTHER INFORMATION: Antisens oligonucleotide
<220> FEATURE:
<221> NAME/KEY: misc_feature
<222> LOCATION: (1)..(2)
<223> OTHER INFORMATION: Linkage to next nucleotide is phophorothioate
<220> FEATURE:
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: misc_feature
<222> LOCATION: (5)..(6)
<223> OTHER INFORMATION: Linkage to next nucleotide is phophorothioate
<220> FEATURE:
<221> NAME/KEY: misc_feature
<222> LOCATION: (9)..(10)
<223> OTHER INFORMATION: Linkage to next nucleotide is phophorothioate
<220> FEATURE:
<221> NAME/KEY: modified_base
<222> LOCATION: (11)..(11)
<223> OTHER INFORMATION: Replace = 2-amino-2'-deoxyadenosine
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(14)
<223> OTHER INFORMATION: Linkage to next nucleotide is phophorothioate
<220> FEATURE:
<221> NAME/KEY: modified_base
<222> LOCATION: (14)..(14)
<223> OTHER INFORMATION: Replace = 2-amino-2'-deoxyadenosine
<220> FEATURE:
<221> NAME/KEY: modified_base
<222> LOCATION: (17)..(17)
<223> OTHER INFORMATION: Replace = 2-amino-2'-deoxyadenosine
<220> FEATURE:
<221> NAME/KEY: misc_feature
<222> LOCATION: (17)..(18)
<223> OTHER INFORMATION: Linkage to next nucleotide is phophorothioate

<400> SEQUENCE: 17
cacctctgtc nccagcatg                                                19

<210> SEQ ID NO 18
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(3)
<223> OTHER INFORMATION: Linkage to next nucleotide is phophorothioate
<220> FEATURE:
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: misc_feature
<222> LOCATION: (6)..(7)
<223> OTHER INFORMATION: Linkage to next nucleotide is phophorothioate
<220> FEATURE:
<221> NAME/KEY: modified_base
<222> LOCATION: (11)..(11)
<223> OTHER INFORMATION: Replace = 2-amino-2'-deoxyadenosine
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (12)..(13)
<223> OTHER INFORMATION: Linkage to next nucleotide is phophorothioate
<220> FEATURE:
<221> NAME/KEY: modified_base
```

```
<222> LOCATION: (14)..(14)
<223> OTHER INFORMATION: Replace = 2-amino-2'-deoxyadenosine
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(18)
<223> OTHER INFORMATION: Linkage to next nucleotide is phophorothioate
<220> FEATURE:
<221> NAME/KEY: modified_base
<222> LOCATION: (17)..(17)
<223> OTHER INFORMATION: Replace = 2-amino-2'-deoxyadenosine

<400> SEQUENCE: 18
cacctctgtc nccngcatg                                             19

<210> SEQ ID NO 19
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(2)
<223> OTHER INFORMATION: Linkage to next nucleotide is phophorothioate
<220> FEATURE:
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: misc_feature
<222> LOCATION: (6)..(7)
<223> OTHER INFORMATION: Linkage to next nucleotide is phophorothioate
<220> FEATURE:
<221> NAME/KEY: modified_base
<222> LOCATION: (11)..(11)
<223> OTHER INFORMATION: Replace = 2-amino-2'-deoxyadenosine
<220> FEATURE:
<221> NAME/KEY: misc_feature
<222> LOCATION: (11)..(12)
<223> OTHER INFORMATION: Linkage to next nucleotide is phophorothioate
<220> FEATURE:
<221> NAME/KEY: modified_base
<222> LOCATION: (14)..(14)
<223> OTHER INFORMATION: Replace = 2-amino-2'-deoxyadenosine
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(18)
<223> OTHER INFORMATION: Linkage to next nucleotide is phophorothioate
<220> FEATURE:
<221> NAME/KEY: modified_base
<222> LOCATION: (17)..(17)
<223> OTHER INFORMATION: Replace = 2-amino-2'-deoxyadenosine

<400> SEQUENCE: 19
cacctctgtc accngcatg                                             19

<210> SEQ ID NO 20
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(2)
<223> OTHER INFORMATION: Linkage to next nucleotide is phophorothioate
<220> FEATURE:
```

```
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: misc_feature
<222> LOCATION: (6)..(7)
<223> OTHER INFORMATION: Linkage to next nucleotide is phophorothioate
<220> FEATURE:
<221> NAME/KEY: modified_base
<222> LOCATION: (11)..(11)
<223> OTHER INFORMATION: Replace = 2-amino-2'-deoxyadenosine
<220> FEATURE:
<221> NAME/KEY: misc_feature
<222> LOCATION: (11)..(12)
<223> OTHER INFORMATION: Linkage to next nucleotide is phophorothioate
<220> FEATURE:
<221> NAME/KEY: modified_base
<222> LOCATION: (14)..(14)
<223> OTHER INFORMATION: Replace = 2-amino-2'-deoxyadenosine
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: modified_base
<222> LOCATION: (17)..(17)
<223> OTHER INFORMATION: Replace = 2-amino-2'-deoxyadenosine
<220> FEATURE:
<221> NAME/KEY: misc_feature
<222> LOCATION: (17)..(18)
<223> OTHER INFORMATION: Linkage to next nucleotide is phophorothioate

<400> SEQUENCE: 20
cacctctgtc accngcatg                                              19

<210> SEQ ID NO 21
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(3)
<223> OTHER INFORMATION: Linkage to next nucleotide is phophorothioate
<220> FEATURE:
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: misc_feature
<222> LOCATION: (5)..(6)
<223> OTHER INFORMATION: Linkage to next nucleotide is phophorothioate
<220> FEATURE:
<221> NAME/KEY: misc_feature
<222> LOCATION: (8)..(10)
<223> OTHER INFORMATION: Linkage to next nucleotide is phophorothioate
<220> FEATURE:
<221> NAME/KEY: modified_base
<222> LOCATION: (11)..(11)
<223> OTHER INFORMATION: Replace = 2-amino-2'-deoxyadenosine
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (12)..(15)
<223> OTHER INFORMATION: Linkage to next nucleotide is phophorothioate
<220> FEATURE:
<221> NAME/KEY: modified_base
<222> LOCATION: (14)..(14)
<223> OTHER INFORMATION: Replace = 2-amino-2'-deoxyadenosine
<220> FEATURE:
<221> NAME/KEY: modified_base
<222> LOCATION: (17)..(17)
<223> OTHER INFORMATION: Replace = 2-amino-2'-deoxyadenosine
```

```
<220> FEATURE:
<221> NAME/KEY: misc_feature
<222> LOCATION: (17)..(18)
<223> OTHER INFORMATION: Linkage to next nucleotide is phophorothioate

<400> SEQUENCE: 21
cacctctgtc nccagcatg                                                    19

<210> SEQ ID NO 22
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(2)
<223> OTHER INFORMATION: Linkage to next nucleotide is phophorothioate
<220> FEATURE:
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: misc_feature
<222> LOCATION: (5)..(8)
<223> OTHER INFORMATION: Linkage to next nucleotide is phophorothioate
<220> FEATURE:
<221> NAME/KEY: modified_base
<222> LOCATION: (11)..(11)
<223> OTHER INFORMATION: Replace = 2-amino-2'-deoxyadenosine
<220> FEATURE:
<221> NAME/KEY: misc_feature
<222> LOCATION: (11)..(13)
<223> OTHER INFORMATION: Linkage to next nucleotide is phophorothioate
<220> FEATURE:
<221> NAME/KEY: modified_base
<222> LOCATION: (14)..(14)
<223> OTHER INFORMATION: Replace = 2-amino-2'-deoxyadenosine
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(18)
<223> OTHER INFORMATION: Linkage to next nucleotide is phophorothioate
<220> FEATURE:
<221> NAME/KEY: modified_base
<222> LOCATION: (17)..(17)
<223> OTHER INFORMATION: Replace = 2-amino-2'-deoxyadenosine

<400> SEQUENCE: 22
cacctctgtc accngcatg                                                    19

<210> SEQ ID NO 23
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(6)
<223> OTHER INFORMATION: Linkage to next nucleotide is phophorothioate
<220> FEATURE:
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: modified_base
<222> LOCATION: (11)..(11)
<223> OTHER INFORMATION: Replace = 2-amino-2'-deoxyadenosine
<220> FEATURE:
<221> NAME/KEY: misc_feature
<222> LOCATION: (11)..(11)
```

```
<223> OTHER INFORMATION: n is a, c, g, or t
<220> FEATURE:
<221> NAME/KEY: misc_feature
<222> LOCATION: (13)..(18)
<223> OTHER INFORMATION: Linkage to next nucleotide is phophorothioate
<220> FEATURE:
<221> NAME/KEY: modified_base
<222> LOCATION: (14)..(14)
<223> OTHER INFORMATION: Replace = 2-amino-2'-deoxyadenosine
<220> FEATURE:
<221> NAME/KEY: modified_base
<222> LOCATION: (17)..(17)
<223> OTHER INFORMATION: Replace = 2-amino-2'-deoxyadenosine

<400> SEQUENCE: 23
cacctctgtc nccagcatg                                             19

<210> SEQ ID NO 24
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(7)
<223> OTHER INFORMATION: Linkage to next nucleotide is phophorothioate
<220> FEATURE:
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: modified_base
<222> LOCATION: (11)..(11)
<223> OTHER INFORMATION: Replace = 2-amino-2'-deoxyadenosine
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (12)..(18)
<223> OTHER INFORMATION: Linkage to next nucleotide is phophorothioate
<220> FEATURE:
<221> NAME/KEY: modified_base
<222> LOCATION: (14)..(14)
<223> OTHER INFORMATION: Replace = 2-amino-2'-deoxyadenosine
<220> FEATURE:
<221> NAME/KEY: modified_base
<222> LOCATION: (17)..(17)
<223> OTHER INFORMATION: Replace = 2-amino-2'-deoxyadenosine

<400> SEQUENCE: 24
cacctctgtc nccagcatg                                             19

<210> SEQ ID NO 25
<211> LENGTH: 19
<212> TYPE: DNA
<213> ORGANISM: Artificial Sequence
<220> FEATURE:
<223> OTHER INFORMATION: Antisens oligonucleotide
<220> FEATURE:
<221> NAME/KEY: misc_feature
<222> LOCATION: (1)..(2)
<223> OTHER INFORMATION: Linkage to next nucleotide is phophorothioate
<220> FEATURE:
<221> NAME/KEY: modified_base
<222> LOCATION: (2)..(2)
<223> OTHER INFORMATION: Replace = 2-amino-2'-deoxyadenosine
<220> FEATURE:
<221> NAME/KEY: misc_feature
<222> LOCATION: (6)..(12)
<223> OTHER INFORMATION: Linkage to next nucleotide is phophorothioate
<220> FEATURE:
<221> NAME/KEY: modified_base
```

```
<222> LOCATION: (11)..(11)
<223> OTHER INFORMATION: Replace = 2-amino-2'-deoxyadenosine
<220> FEATURE:
<221> NAME/KEY: modified_base
<222> LOCATION: (14)..(14)
<223> OTHER INFORMATION: Replace = 2-amino-2'-deoxyadenosine
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(18)
<223> OTHER INFORMATION: Linkage to next nucleotide is phophorothioate
<220> FEATURE:
<221> NAME/KEY: modified_base
<222> LOCATION: (17)..(17)
<223> OTHER INFORMATION: Replace = 2-amino-2'-deoxyadenosine

<400> SEQUENCE: 25
cacctctgtc accngcatg                                                       19
```

INHIBITION OF CHEMOKINE CCL7 OR RECEPTOR CCR3 OF SAME FOR THE TREATMENT AND DIAGNOSIS OF PROSTATE CANCER

SEQUENCE LISTING SUBMISSION VIA EFS-WEB

A computer readable text file, entitled "SequenceListing.txt," created on or about 6 Dec. 2016 with a file size of about 14 kb contains the sequence listing for this application and is hereby incorporated by reference in its entirety.

The present invention relates to the field of the diagnosis and medicinal products intended for the treatment of prostate cancer.

Prostate cancer is the cancer most frequently observed in men over 50 years of age and represents the second cause of cancer-related death in developed countries. As for all solid cancers, the extension of the prostate cancer is based on the TNM classification (T for tumor, N for "nodes" or lymph node involvement, M for metastasis) (Ohori, Wheeler et al. 1994; Salomon, Azria et al. 2010).

Prostate cancers are thus classified in four stages:

1) localized prostate cancer: T1 [tumor not palpable or not visible with imaging] and T2 [tumor limited to the prostate (including apex and capsule)], N0, M0;

2) locally advanced prostate cancer: T3 [extension beyond prostatic capsule] and T4 [Extension to adjacent organs (neck of bladder, urethral sphincter, rectum, pelvic wall) or tumor attached to pelvic wall], N0, M0;

3) prostate cancer with lymph node involvement, all T, N1, M0; and 4) metastatic prostate cancer: all T, all N, M1.

The prostate is surrounded by adipose tissue (periprostatic adipose tissue or PPAT). The presence of the tumor in periprostatic adipose tissue thus represents the first stage of local extension of prostate cancer (stage pT3a) and is an established criterion of poor prognosis (Magi-Galluzzi, Evans et al. 2011; Houimel and Mazzucchelli 2013). The invasion of the surrounding tissues may be followed by remote dissemination of cancer cell (metastasis). These metastases are essentially localized in the bone and are the cause of the majority of disease-related deaths (mortality rate of approximately 90%). The bones, essentially consisting of bone tissue, also contain hematopoietic tissue, adipose tissue, vessels, nerves, cartilaginous tissue and connective tissue. As such, adipose tissue is present both at the local and remote dissemination stages of prostate cancer.

Among the cells making up adipose tissue, particularly periprostatic adipose tissue, mature adipocytes are mainly found along with, in a so-called "stromal vascular" fraction, other cells such as progenitor cells (Adipose Derived Stem Cells [ADSCs] and preadipocytes), fibroblasts, macrophages, lymphocytes, pericytes and endothelial cells (Ouchi, Parker et al. 2011). Adipocytes have a role in the energy fluctuations induced by food intake or fasting states by storing energy in the form of triglycerides or by releasing same in the form of fatty acids (FAs). Adipocytes are also active endocrine cells which secrete a great variety of molecules (called adipokines), which are particularly involved in appetite and energy balance regulation, the lipid metabolism, insulin sensitivity and blood pressure regulation (Ouchi, Parker et al. 2011). Adipocyte secretions include growth factors, chemokines, pro-angiogenic molecules or pro-inflammatory molecules (Ouchi, Parker et al. 2011). Tourniaire, Romier-Crouzet et al. (2013) reported that, under obesity conditions, the secretory profile of adipocytes is modified, and the secretion of certain chemokines may be increased. Furthermore, as summarized in Allott, Masko et al. (2013), a convincing set of epidemiological data demonstrates that obesity is a factor of poor prognosis in prostate cancer with an increase in local and remote dissemination. Finally, independently of obesity, recent data demonstrate that the extent of the PPAT is positively associated with the aggressiveness of prostate cancer (Kiss, Longden et al. 2009).

Chemokines represent a large group of small proteins (of approximately 8 to 11 kDa) which interact with receptors belonging to the superfamily of G-protein-coupled seven-transmembrane domains receptors (GPCRs). Most of these have four characteristic cysteine residues which form two disulfide bridges, one between the first and the third cysteine residue and one between the second and fourth cysteine residue. According to the number of amino acids present between the first two cysteines (situated in the N-terminal part), chemokines are classified into four groups: C, CC, CXC and CX3C. Chemokines have various functions, the most studied whereof is attraction (chemotaxis) and immune system cell activation state control. In cancer, these chemokines and the receptors thereof are known for regulating the tumoral process (proliferation, migration, invasion, angiogenesis, leukocyte infiltration). Some of these are produced by the tumor cells themselves, but also by stromal cells such as cancer-associated fibroblasts (CAFs), endothelial cells or immune cells (macrophages, lymphocytes) (Balkwill 2004).

Of the chemokine receptors potentially involved in cancer, the receptor CXCR4 is currently considered to be one of the most important receptors. The interaction of CXCR4 with the ligand CXCL12 thereof plays a role in the cellular migration of many cancers, including the prostate, in particularly in the context of bone metastasis (Taichman, Cooper et al. 2002). In vitro studies have demonstrated that CXCL12 stimulates the invasive nature of prostate tumor cells and that it can be blocked using a pharmacological inhibitor (for example the CXCR4 antagonist called AMD3100) or a blocking antibody. The interaction between the receptor CCR2 and the chemokine CCL2 has also been identified for the involvement thereof in prostate tumor cell migration (Loberg, Day et al. 2010). Furthermore, the expression of the receptor CCR2 is correlated with the aggressiveness of prostate tumors (Lu, Cai et al. 2007). Further chemokine receptors such as CXCR1 and CXCR2 have been described as playing a role in the invasion and growth of prostate tumor cells via the chemokines CXCL1, CXCL5 or CXCL8 (Inoue, Slaton et al. 2000; Begley, Kasina et al. 2008).

Further chemokine receptors liable to interact in the migration of tumor cells in other types of cancers have also been identified, such as for example the receptors CCR1 (GeneID: 1230) (Loetscher, Pellegrino et al. 2001) and CCR3 (GeneID: 1232) (Loetscher, Pellegrino et al. 2001; Jung, Che et al. 2010; Johrer, Zelle-Rieser et al. 2005; Lee, Kim et al. 2010). The latter are very strongly expressed by eosinophils or basophiles and less significantly by lymphocytes (Th1 and Th2) and some epithelial cells. CCR1 and CCR3 are also involved in eosinophil migration regulation and play a major role in numerous inflammatory diseases such as asthma (Joubert, Jajoie-Kadoch et al. 2008). To date, a number of ligands of CCR3 have been identified: CCL5, CCL7, CCL11, CCL13, CCL15, CCL24, CCL26 and CCL28. Jung, Che et al. (2010) demonstrated in carcinomas of the upper airways that CCR3 may play a role in cell migration via the chemokine CCL7 (GeneID:6354; Kuri-Harcuch and Green 1978). It has been demonstrated that the receptor CCR3 is overexpressed in kidney tumors (Jung, Che et al. 2010) and melanoma (Lee, Kim et al. 2010). Very recently, a preliminary study relating to a single prostate cancer line Du-145 demonstrates that the receptor CCR3 promotes, via CCL11 (a different chemokine from CCL7), in vitro migration and invasion of cancer cells. In this study, the authors did not focus on the chemokines secreted by adipose tissue (Zhu, Liao et al. 2013). Furthermore, the in vivo effect of the inhibition of the receptor CCR3 and the expression thereof in human prostate tumors were not addressed in this study.

In all these studies relating to the role of chemokines in prostate cancer progression, the role of PPAT secretions was not envisaged, nor was the link with obesity and/or the extent of the periprostatic adipose tissue mentioned.

The therapeutic strategy for localized tumors is currently based on the D'Amico classification if the characteristics of the cancer are considered exclusively (Guide ALD30, HAS/INCA, 2012). Indeed, further factors such as the characteristics of the patient and his/her preferences (in particular in the case where therapeutic alternatives having an equivalent benefit/risk ratio exist) are also considered. The D'Amico classification (Agrawal, Maxwell et al. 2009; Ohori, Wheeler et al. 1994) makes it possible to account for the following criteria: the size of the tumor, the Gleason score (Kiss, Longden et al. 2009) and the serum marker PSA (Prostate-Specific Antigen). The Gleason classification is based on the degree of differentiation of the tumor, scored from grade 1 (differentiated) to 5 (very poorly differentiated). This score is the sum of the two grades most frequently represented in the tumor analyzed. It varies from 2 to 10. The score of 2 corresponds to a tumor very similar to benign tissue. The higher the score, the more aggressive the tumor. The D'Amico classification defines three subgroups of localized prostate cancer according to the risk of recurrence (referring to the risk of biological recurrence 10 years after a local treatment), i.e. three cancer progression risk levels: a low risk, an intermediate risk and a high risk. The three subgroups defined according to the clinical and biological characteristics thereof are:

1) low-risk localized prostate cancer: TNM≤T2a (involvement of half of one lobe or less) and Gleason Score≤6 and PSA value (ng/ml)≤10;

2) intermediate-risk prostate cancer: TNM≥T2b (involvement of more than half of one lobe without involvement of the other lobe) and Gleason Score=7 and PSA value (ng/ml)=10-20; and 3) high-risk localized prostate cancer: TNM≥T2c (involvement of both lobes) and Gleason Score≥8 and PSA value (ng/ml)>20.

There is currently a need to develop treatments suitable for delaying or preventing the local and remote dissemination stages in order to make it possible not only to prevent the development of metastatic disease but also to maintain the prostate cancer in a potentially curable form for as long as possible.

There is also a need to identify using a diagnostic method localized prostate cancer tumors having a high aggressive potential in order to treat same suitably.

Within the scope of their research work, the inventors characterized a specific regulation pathway of the local dissemination process of prostate cancer via the involvement of the chemokine receptor CCR3 under the dependency of one of these ligands, CCL7, expressed by PPAT.

The inventors demonstrated in vitro that a conditioned medium from mature adipocytes (CM-Ad) obtained from the differentiation of the mouse pre-adipocyte line F442A stimulates the migration of human and mouse prostate cells. This migration is inhibited by the use of a known CCR1/CCR3 inhibitor (UCB35625) in all the prostate cancer cell lines studied whereas CCR1 not expressed in these lines. The importance of CCR3 in the MC-Ad-induced migration of cancerous prostate cells was confirmed by the absence of effect of UCB35625 on the migration of different tumor lines representative of different cancers (breast, colon, pancreas, melanoma), apart from a slight effect on the migration of the aggressive breast cancer line MDA-MB 231. Inhibition was also observed for blocking antibodies targeted against CCR3 in all the models studied and when CCR3 expression is invalidated. In MC-Ad, a single CCR3 ligand was detected: CCL7. The inhibition of this ligand by a blocking antibody inhibits the migration of human and mouse prostatic cells against CM-Ad. This ligand is also present in the conditioned medium from mouse perigonadal and human periprostatic adipose tissue and the conditioned medium from primary adipocytes isolated from mouse perigonadal adipose tissue. The capability of inducing the migration of prostate tumor cells along a CCR3/CCL7 pathway was also detected for conditioned medium from mouse perigonadal and human periprostatic adipose tissue and the conditioned medium from primary adipocytes isolated from mouse perigonadal adipose tissue.

The inventors also demonstrated in vivo that intraprostatic injection of tumor lines invalidated for CCR3 results in a reduction in tumoral mass along with a lack of disappearance of periprostatic adipose tissue under the effect of tumoral infiltration. Furthermore, the inventors demonstrated that the receptor CCR3 is expressed in human tumors and that this expression is linked with the aggressiveness of the tumors (correlation with the Gleason score, the percentage of non-differentiated cells, the peripheral site of the tumor) and with the extra-prostatic dissemination thereof (TNM stage). The expression is of the receptor CCR3 is also correlated with biological recurrence and surgical treatment failure. Finally, medullary adipocytes are capable of secreting CCL7 and the conditioned medium from these adipocytes induces the migration of prostate tumor cells, said migration being inhibited by UCB35625 or a blocking antibody targeted against CCR3 and/or CCL7. These results were obtained with mouse medullary adipocytes (obtained from the ex vivo differentiation of adipocyte progenitors) and human medullary adipocytes (isolated directly from human yellow marrow). All these data demonstrate that the CCR3/CCL7 pathway appears to be involved in remote dissemination (bone metastasis) of prostate cancer via the ability of medullary adipocytes to secrete CCL7. These data also demonstrate the interest of inhibiting CCR3 or CCL7 in prostate cancer with a view to inhibiting local or remote extension.

Furthermore, this strategy aimed at inhibiting CCR3 or CCL7 is of particular interest for obese subjects or subjects with abundant PPAT (the surface area whereof is greater than or equal to 10 $cm^2$). Indeed, the inventors demonstrated that the genic expression of CCL7 is increased in the adipose tissues of obese mice and subjects. The secretion thereof is increased in conditioned medium from perigonadal tissue from obese mice and conditioned medium from primary adipocytes isolated from perigonadal tissue from obese mice. The migration of human prostatic cancer cells against conditioned medium from perigonadal tissue from obese mice and conditioned medium from primary adipocytes isolated from perigonadal tissue from obese mice is increased with respect to the same media obtained with animals of normal weight. This increase completely inhibited by UCB35625 or blocking antibodies targeted against CCR3 or CCL7. In vivo, the increase in tumoral mass observed under obesity conditions is no longer present when the receptor of CCR3 is invalidated. In humans, expression of the receptor CCR3 is significantly increased in obese subjects. Furthermore, there is a correlation between the extent of the PPAT viewed using nuclear magnetic resonance imaging (MRI) or tomodensitometry and CCR3 expression. Finally, in humans, the medullary adipocytes obtained from obese subjects have an increased capability of inducing the migration of prostate tumor cells and this effect is inhibited by UCB35625.

The present invention consequently relates to an inhibitor of the expression of the chemokine CCL7 or an inhibitor of the expression of the receptor CCR3 or an inhibitor of the expression of the receptor CCR3 or an inhibitor of CCL7/CCR3 interaction for the use thereof to prevent or treat the extension of prostate cancer outside the prostatic capsule in a subject.

The term "extension of prostate cancer outside the prostatic capsule" denotes locally advanced prostate cancer (as per the TNM classification: T3 or T4, N0, M0), prostate cancer with pelvic lymph node involvement (as per the TNM classification: all T, N1, M0) or metastatic prostate cancer (as per the TNM classification: all T, all N, M1).

According to one preferred embodiment of the invention, said inhibitor is used in an adult male who is obese or has abundant periprostatic adipose tissue.

Obesity is a state characterized by an excess of adipose mass. The Body Mass Index (BMI) is an international standard for measuring overweight and obesity. It is defined as the weight divided by the height squared, expressed in $kg/m^2$. A subject is considered to be obese when this value is greater than or equal to 30 $kg/m^2$.

The term abundant periprostatic adipose tissue (PPAT) denotes a PPAT wherein the surface area is greater than or equal to 10 $cm^2$. Advantageously, the PPAT surface area is measured using a method for measuring and calculating the area of an ellipse using images, obtained for example by CT or MRI imaging on said subject, of cross-sections at the femur at the point where the fusion of the symphysis pubis starts. The periprostatic adipose tissue deposit for which an image is obtained is situated between the anterior part of the prostate and the symphysis pubis. Such a method is described in the Materials and Methods section hereinafter.

The limit of 10 $cm^2$ was defined statistically as being the surface area beyond which all patients have a significantly more aggressive cancer (Gleason score greater than or equal to 7).

The inhibitors of the expression of CCL7 or CCR3 include nucleic acids such as optionally modified antisense oligonucleotides, interfering RNA, small hairpin RNA (shRNA or miRNA) or ribozymes, targeting the gene encoding CCL7 or the gene encoding CCR3. Such inhibitors are described by Zhu, Liao et al. 2013; Agrawal, Maxwell et al. 2009; Zhu, Liu et al. 2014.

According to one preferred embodiment, the inhibitor of the expression of CCR3 is a shRNA targeting the gene CCR3. It is advantageously chosen from the shRNA: m4CCR3 (SEQ ID NO: 1), m5CCR3 (SEQ ID NO: 2), m6CCR3 (SEQ ID NO: 3).

According to one preferred embodiment, the inhibitor of the expression of CCR3 is an antisense oligonucleotide, optionally modified, targeting the gene CCR3. It is advantageously chosen from the group consisting of the antisense oligonucleotides TOP004 having the sequence SEQ ID NO: 14, TOP005 having the sequence SEQ ID NO: 15, TOP030 having the sequence SEQ ID NO: 16, TOP030-$P^2M$-7-DAP having the sequence SEQ ID NO: 17, TOP030-$P^2M$-8-DAP having the sequence SEQ ID NO: 18, TOP030-$P^2M$-9-DAP having the sequence SEQ ID NO: 19, TOP030-$P^2M$-10-DAP having the sequence SEQ ID NO: 20, TOP030-$P^2M$-11-DAP having the sequence SEQ ID NO: 21, TOP030-$P^2M$-12-DAP having the sequence SEQ ID NO: 22, TOP030-$P^2M$-13-DAP having the sequence SEQ ID NO: 23, TOP030-$P^2M$-14-DAP having the sequence SEQ ID NO: 24 and TOP030-$P^2M$-15-DAP having the sequence SEQ ID NO: 25.

The term "an inhibitor of CCL7/CCR3 interaction" denotes a compound capable of inhibiting the activation of CCR3 by CCL7, without activating CCR3 itself. An inhibitor of CCL7-CCR3 interaction includes compounds capable of interacting with CCL7 and inhibiting the bonding thereof with CCR3 or inhibiting the activation of CCR3 resulting from said bonding, along with compounds capable of interacting with CCR3, and inhibiting the bonding thereof with CCL7 or the activation thereof resulting from said bonding. In particular, an inhibitor of CCL7/CCR3 interaction includes competitive and non-competitive CCR3 antagonists (referred to as CCR3 antagonists), preferably competitive CCR3 antagonists.

The inhibitors of CCL7/CCR3 interaction include organic molecules. By way of example of organic molecules inhibiting CCL7/CCR3 interaction, mention may be made of the compounds I to DCCLXXXIV, as set forth in Table 7 below, preferably the compound U0B356625 (C301137C17IN702) having formula DLI 30 (hereinafter).

Table 7: Organic molecules that inhibit the CCL7/CCR3 interaction.

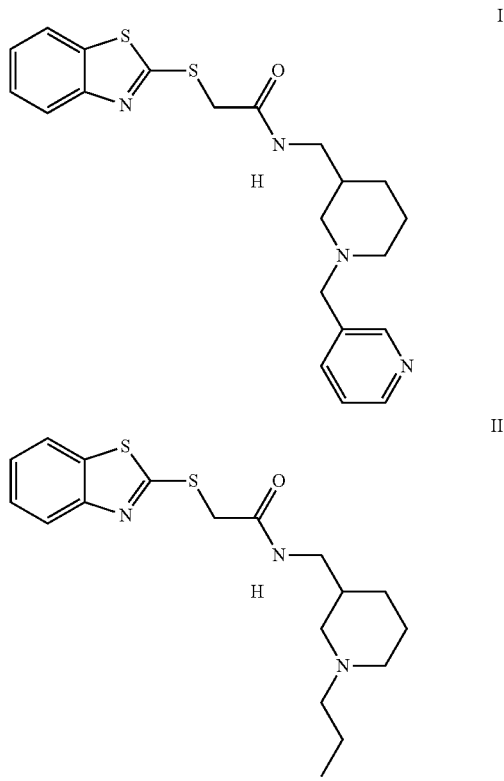

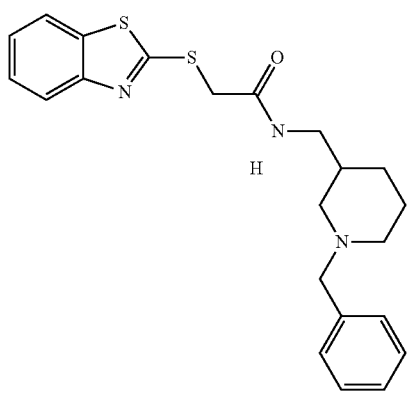
III
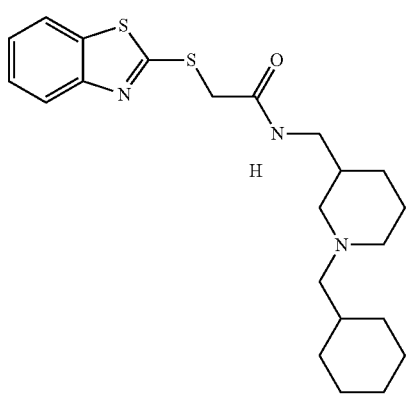
VII
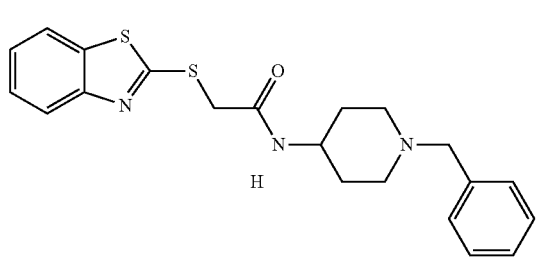
IV
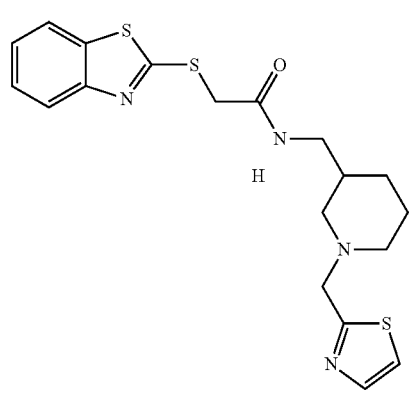
V
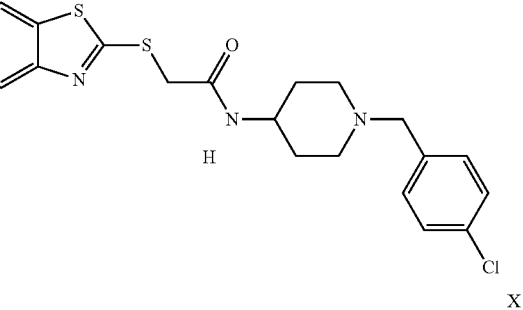
VIII
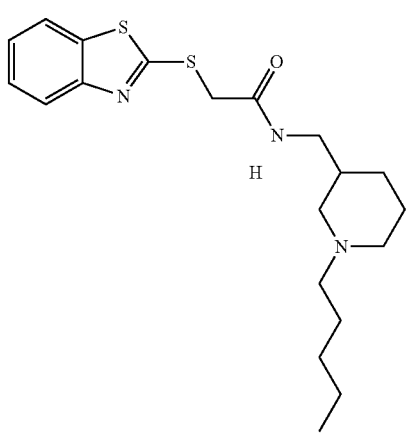
VI
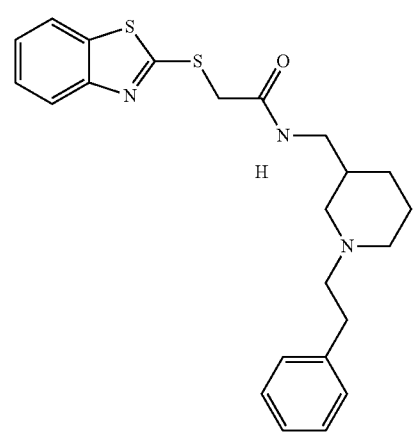
IX
X XI
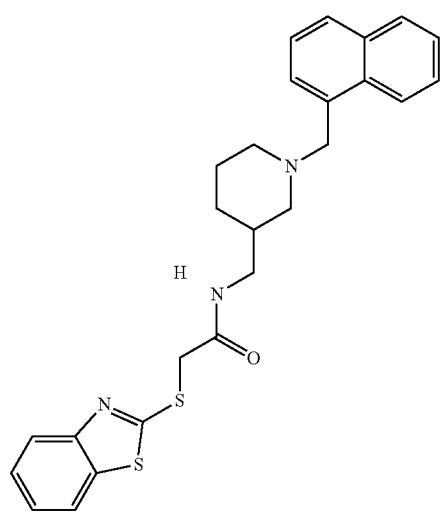
XIV
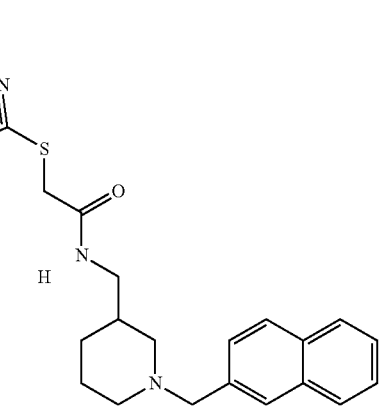
XII
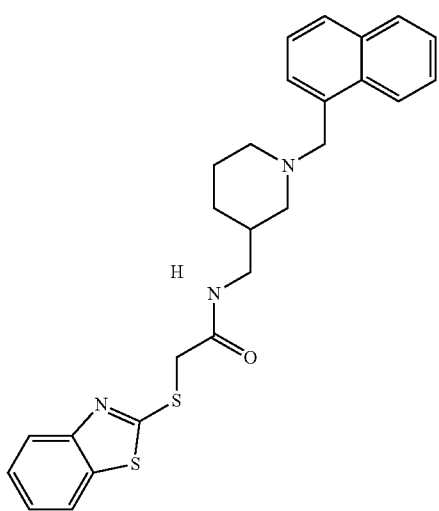
XV
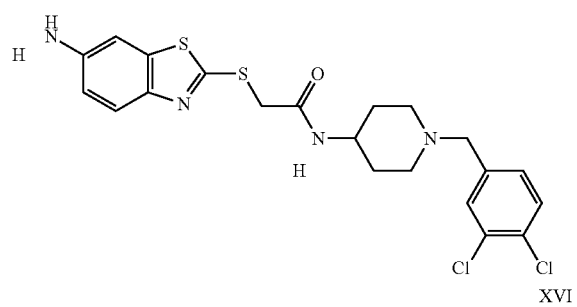
XVI
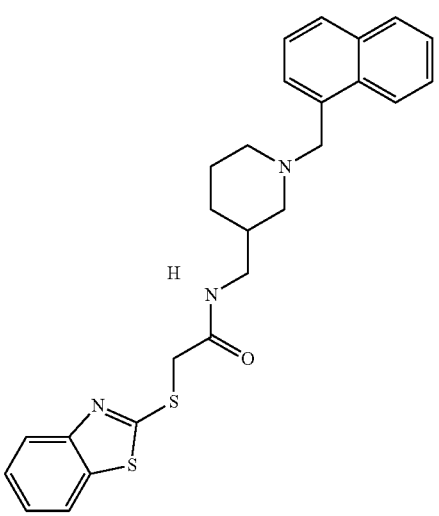
XIII
XVII
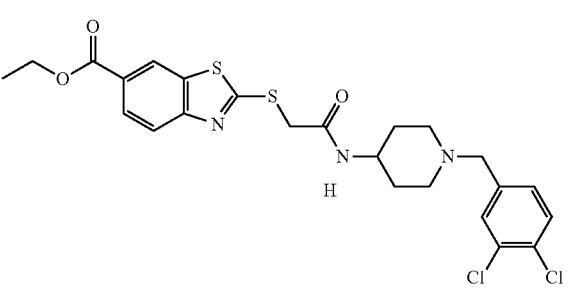
XVIII
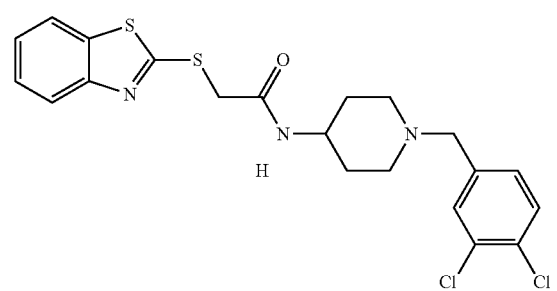

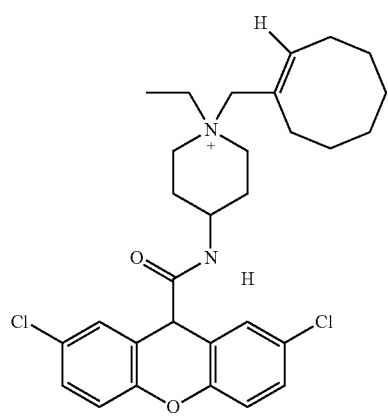
XIX
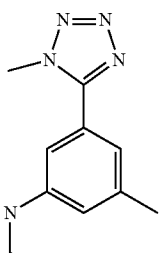
XXII
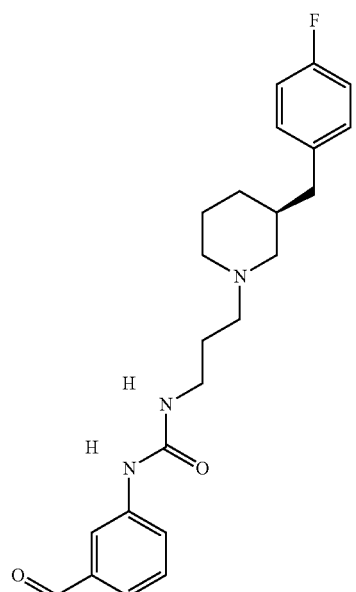
XXIII
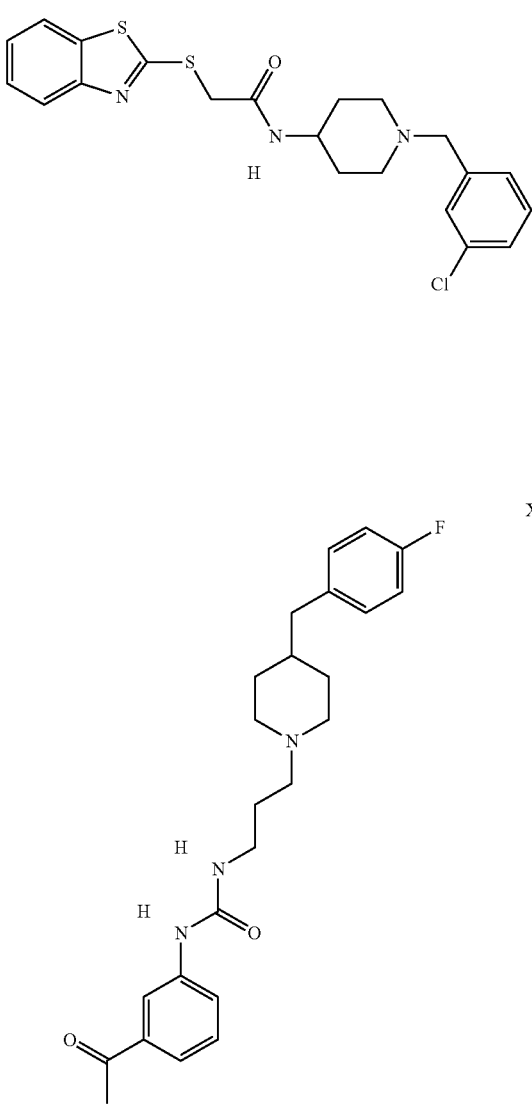
XX
XXI
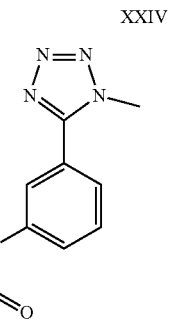
XXIV

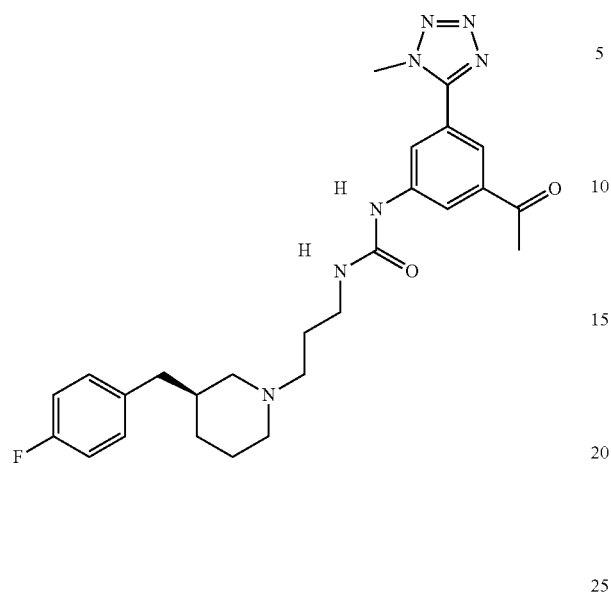
XXV
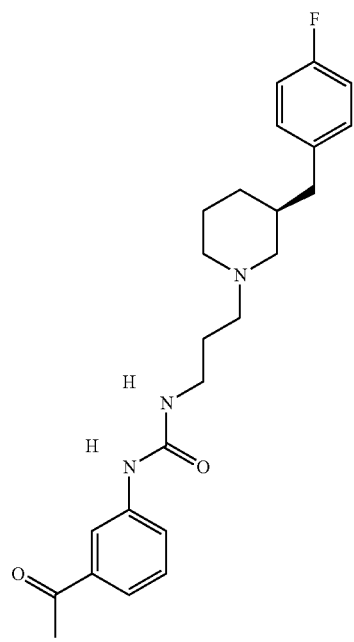
XXVII
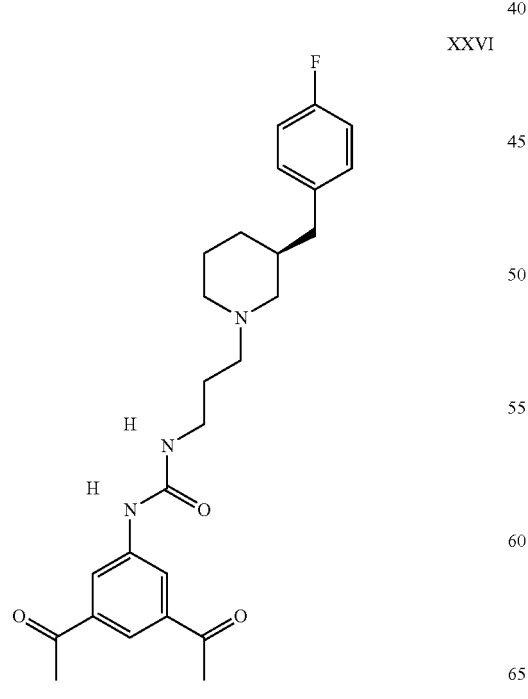
XXVI
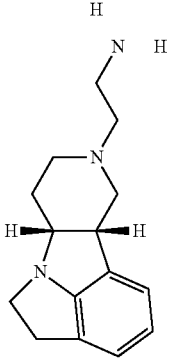
XXVIII
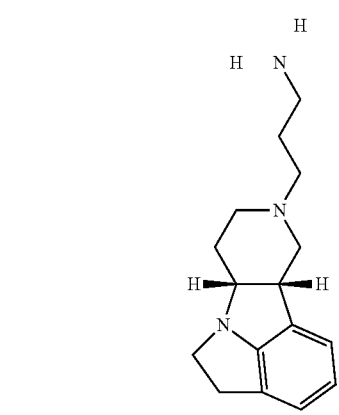
XXIX

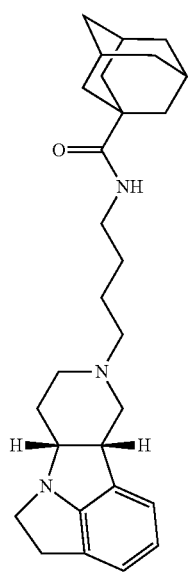
XXX
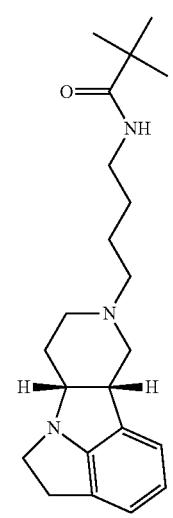
XXXI
XXXII
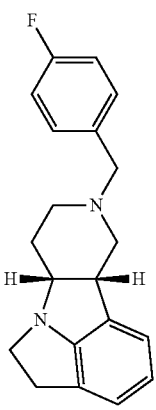
XXXIII
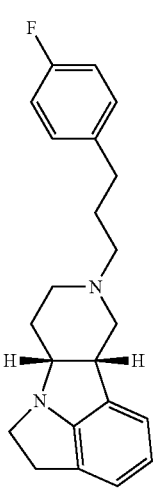
XXXIV
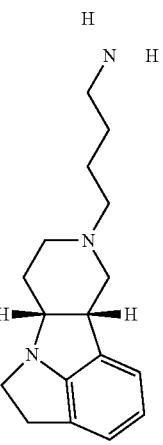
XXXV -continued
XXXVI
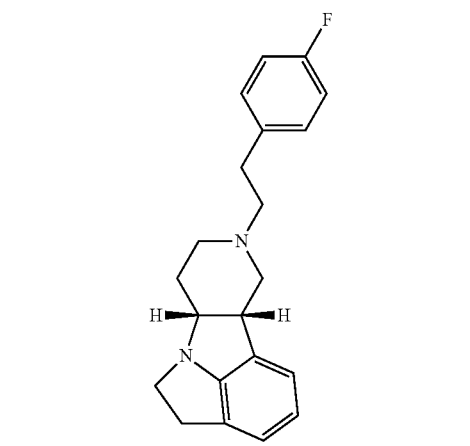
XXXVII
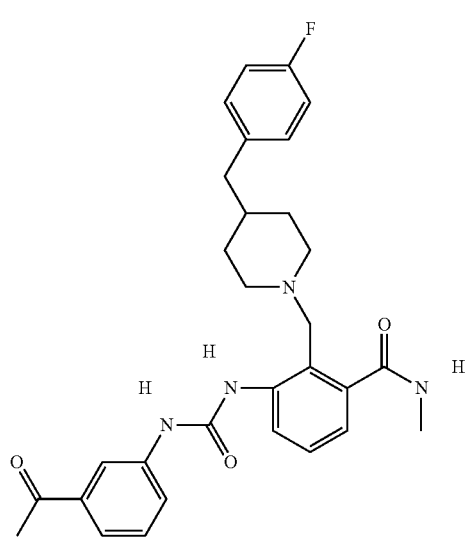
XXXVIII
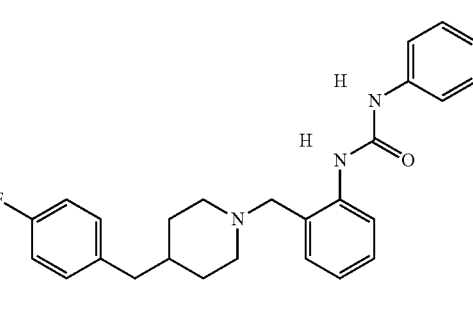
XXXIX
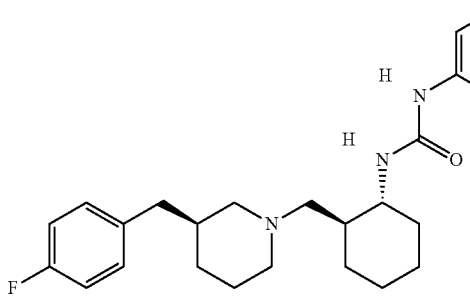
-continued
XL
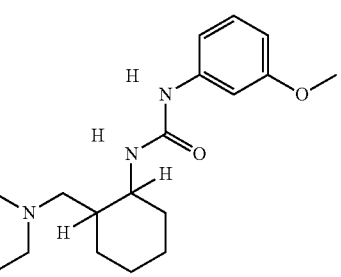
XLI
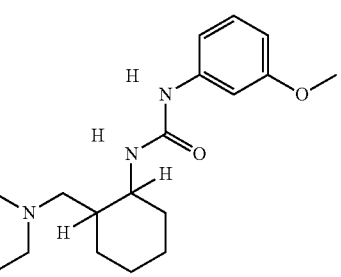
XLII
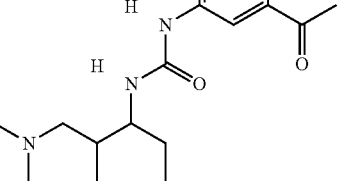
XLIII
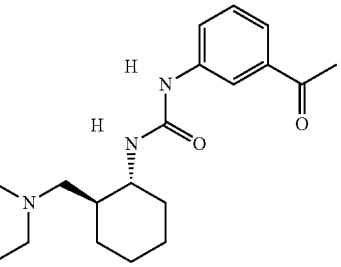
XLIV
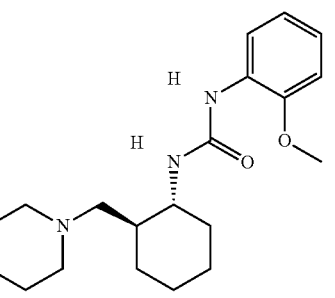

-continued
XLV
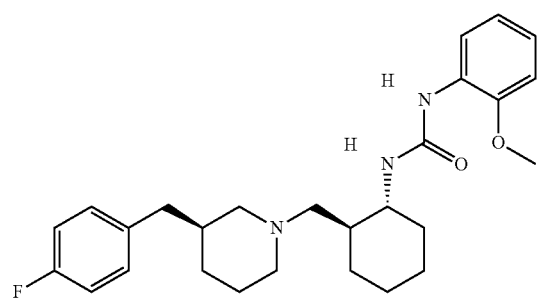
XLVI
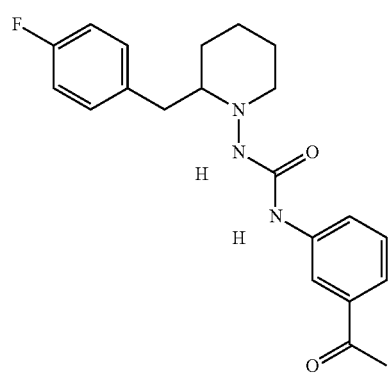
XLVII
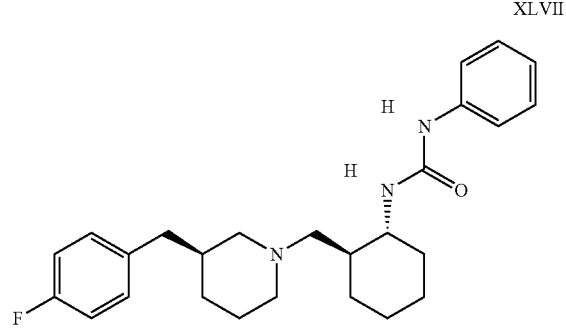
XLVIII
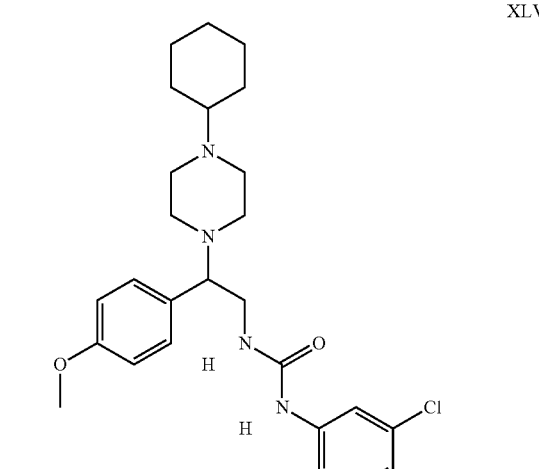
XLIX
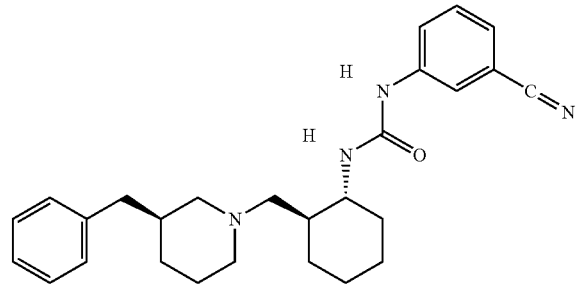
L
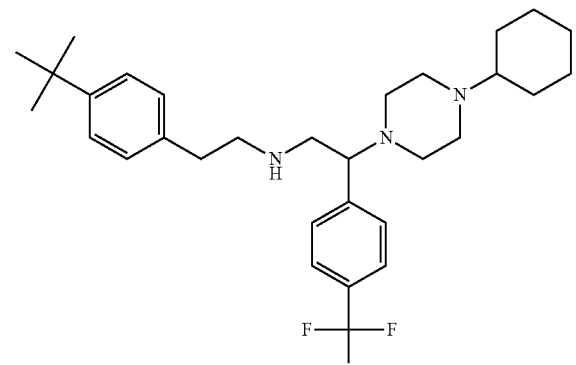
LI
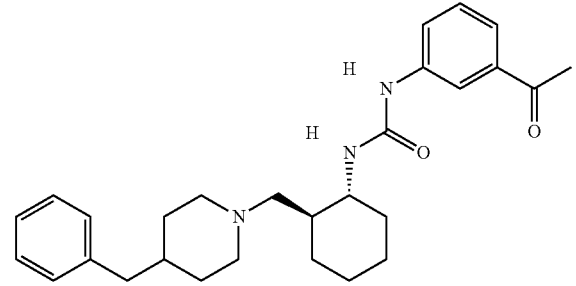
LII
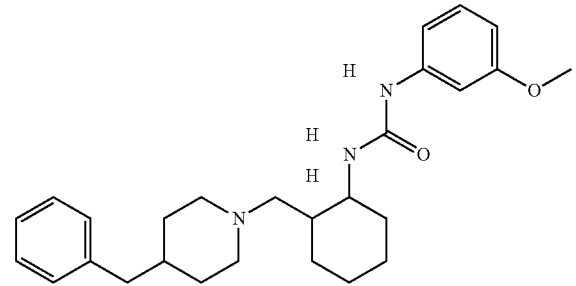
LIII LIV
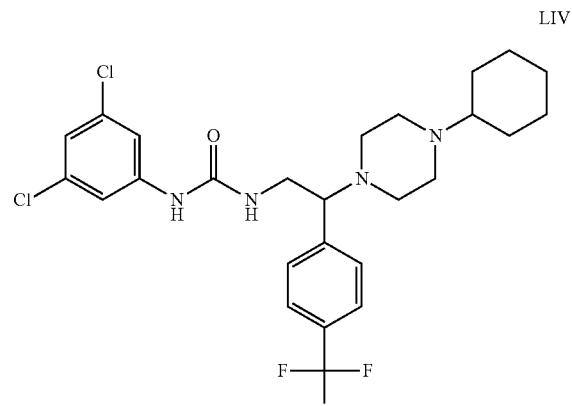
LV
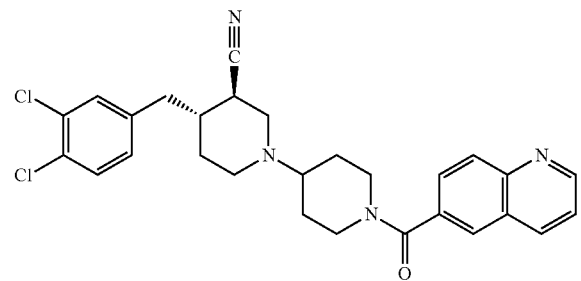
LVI
LVII
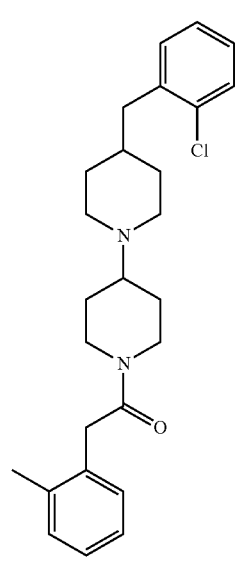
LVIII
LIX
LX
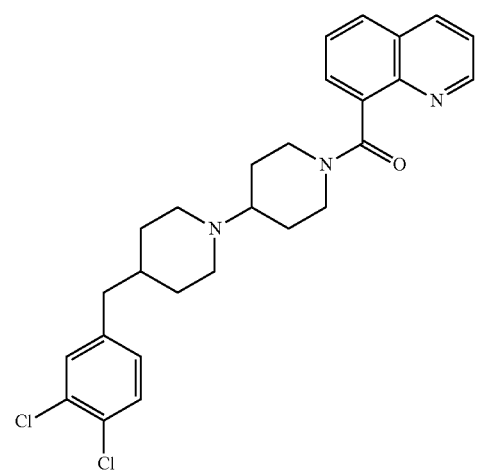

LXI
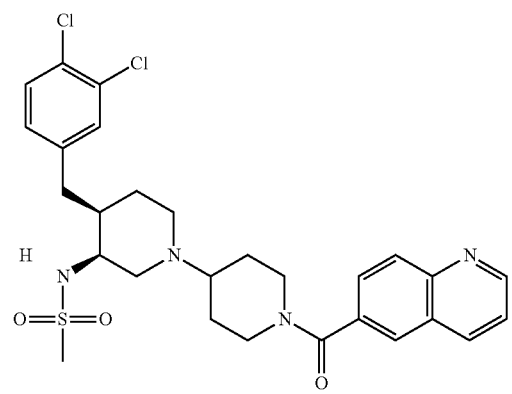
LXII
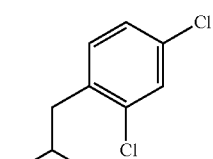
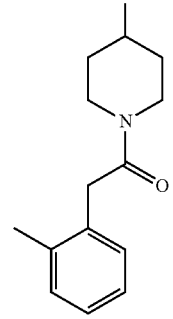
LXIII
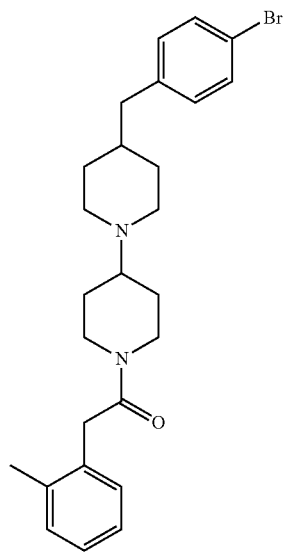
LXIV
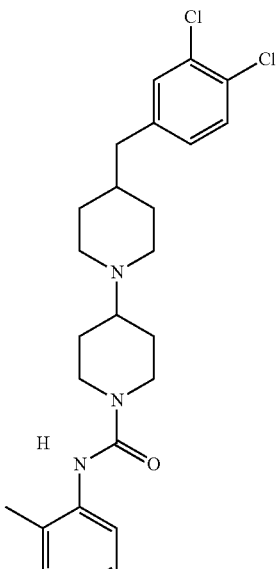
LXV
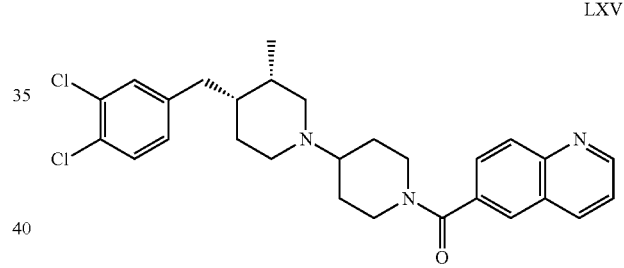
LXVI
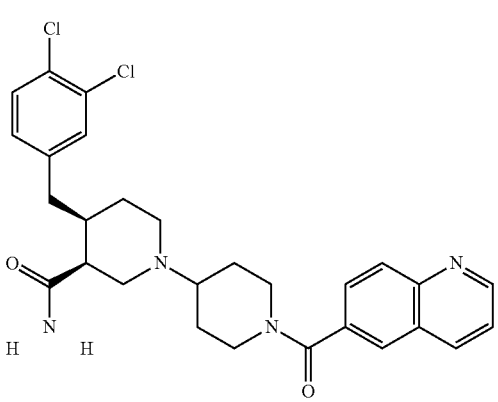

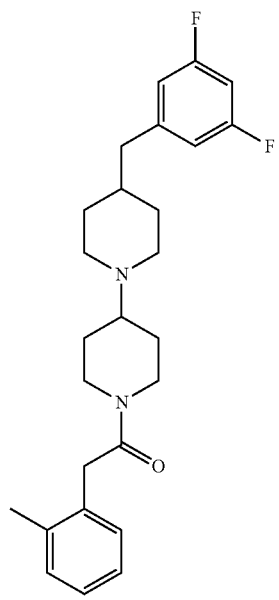
LXVII
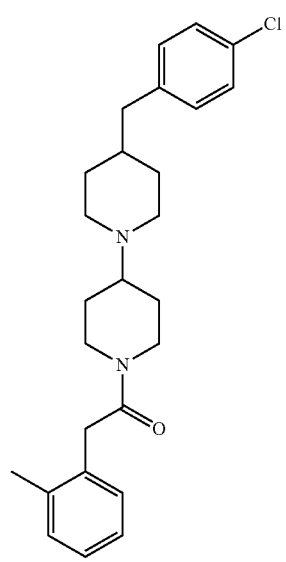
LXVIII
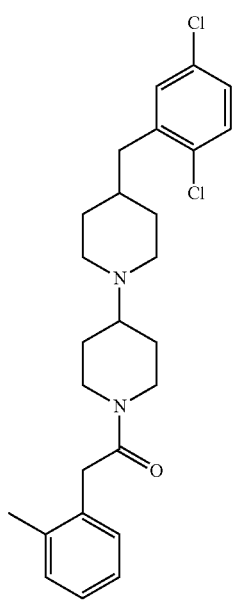
LXIX
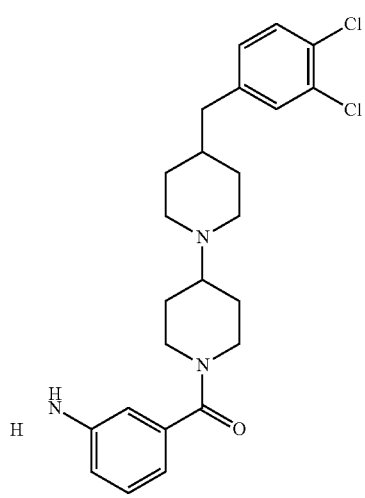
LXX
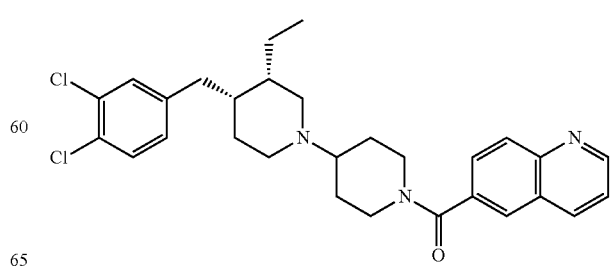
LXXI LXXII
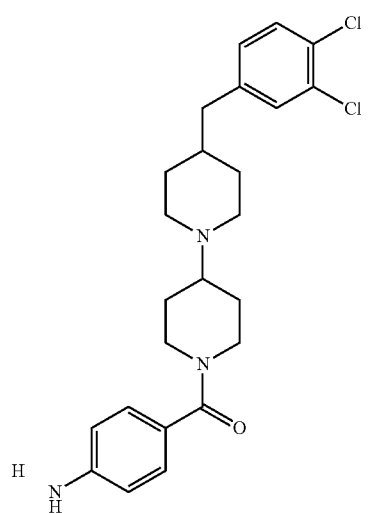
LXXIII
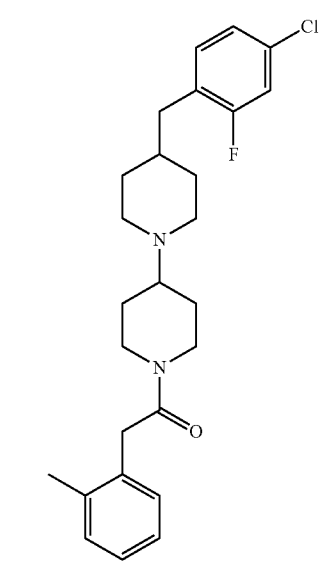
LXXIV
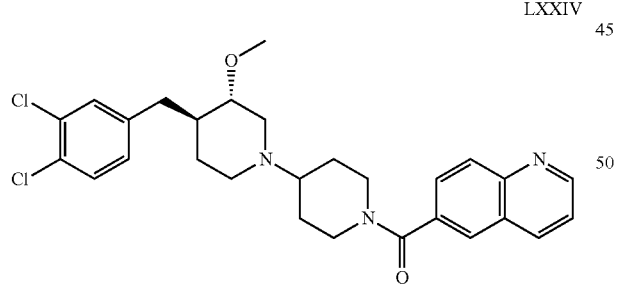
LXXV
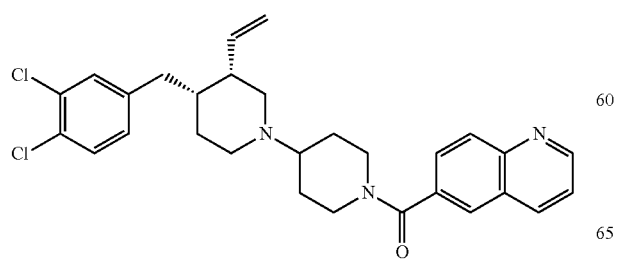
LXXVI
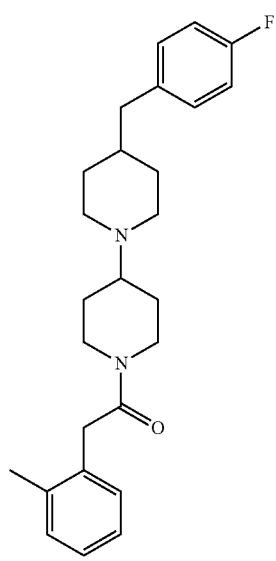
LXXVII
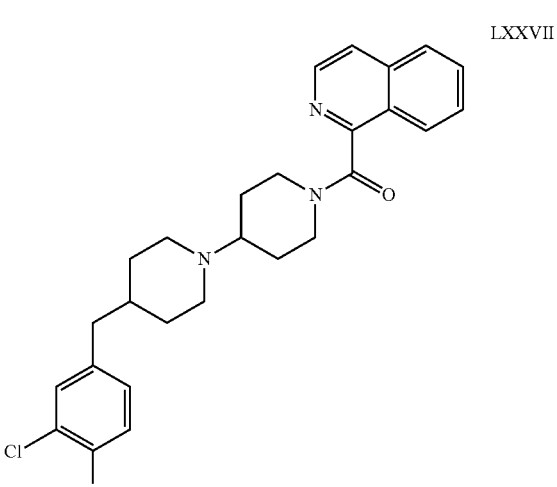
LXXVIII
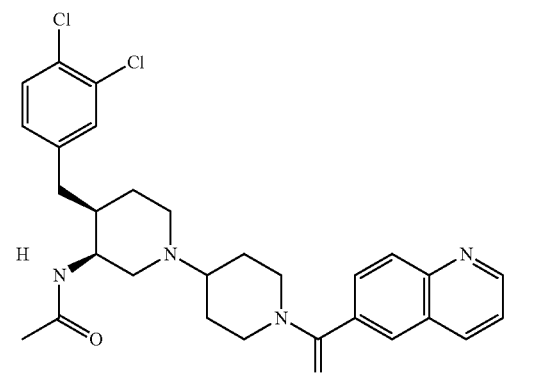

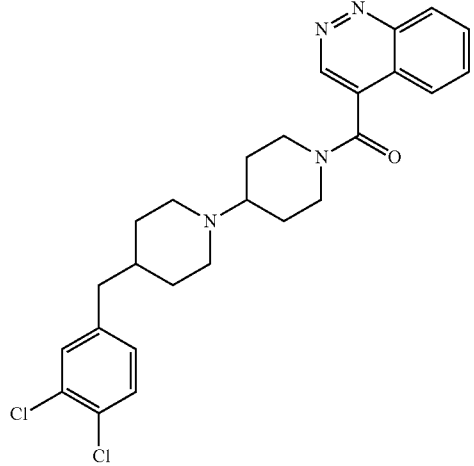
LXXIX
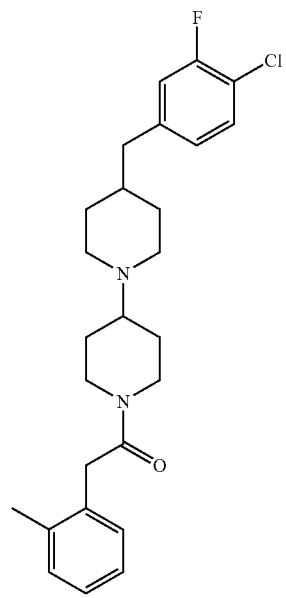
LXXXI
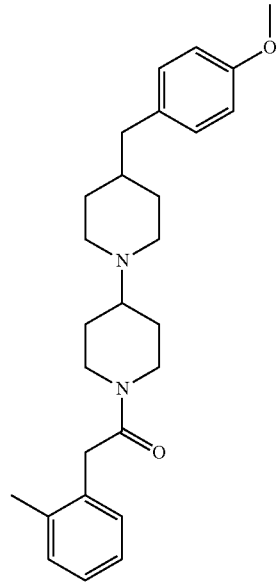
LXXXII
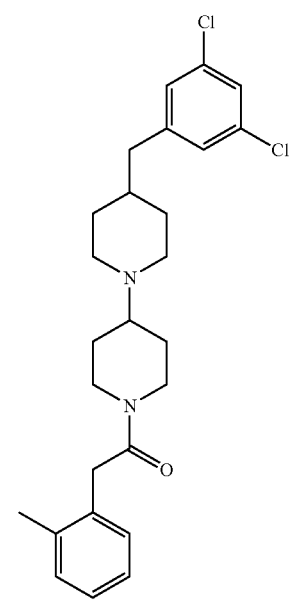
LXXX
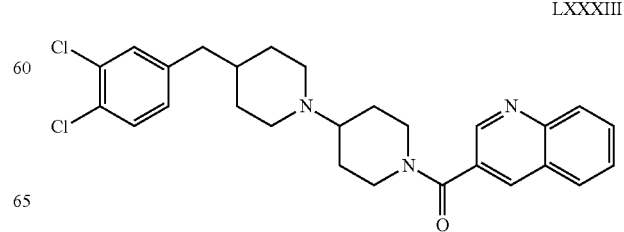
LXXXIII LXXXIV
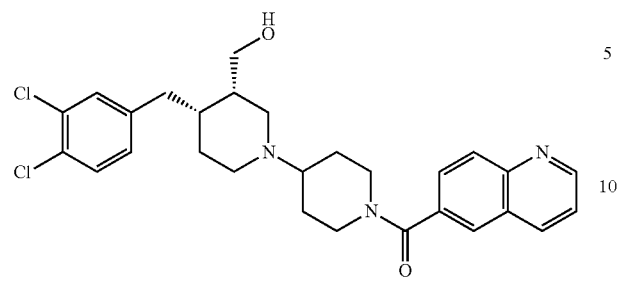
LXXXVIII
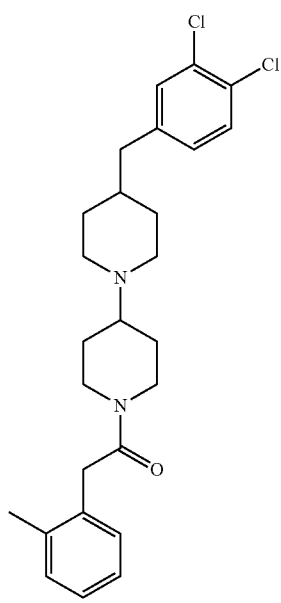
LXXXV
LXXXVI
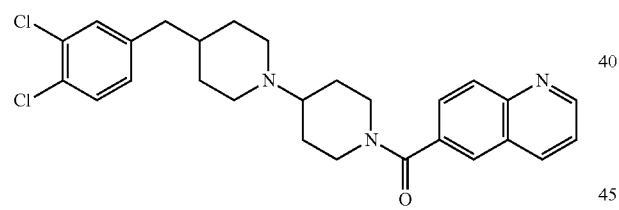
LXXXVII
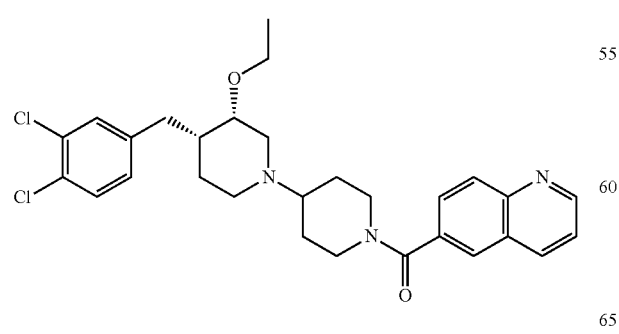
LXXXIX
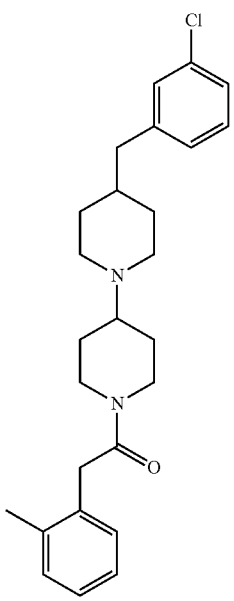

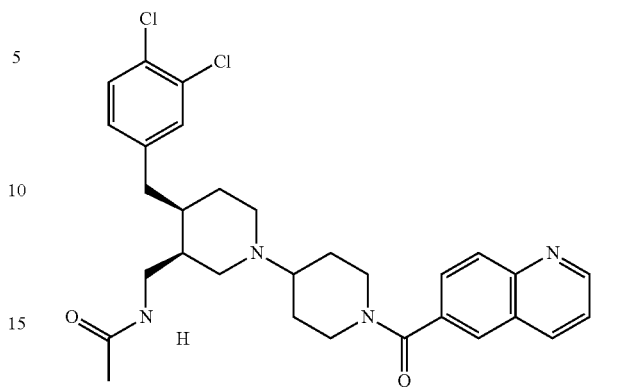
XC
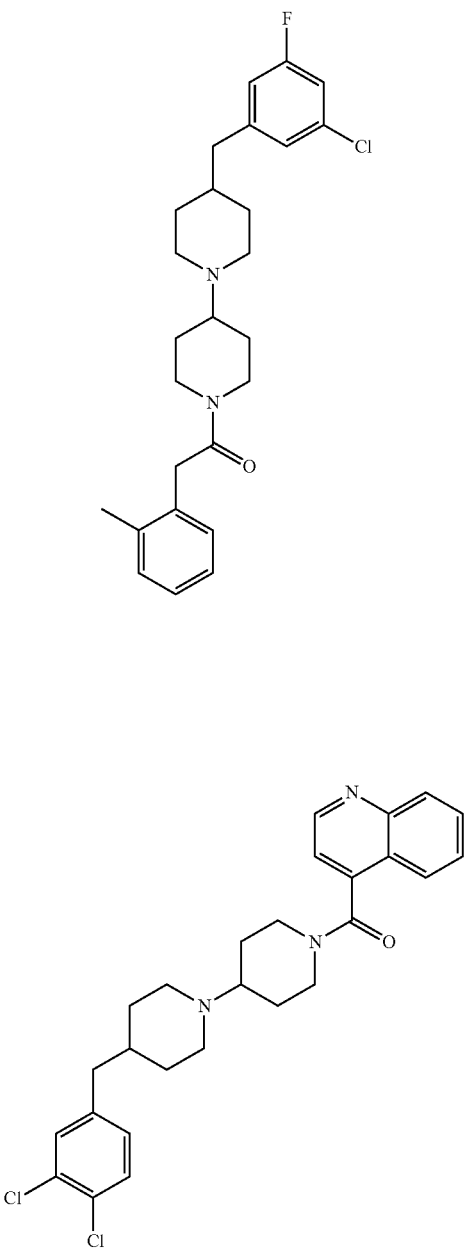
XCI
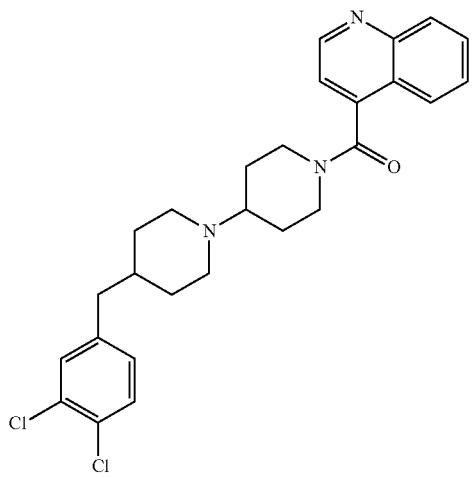
XCII
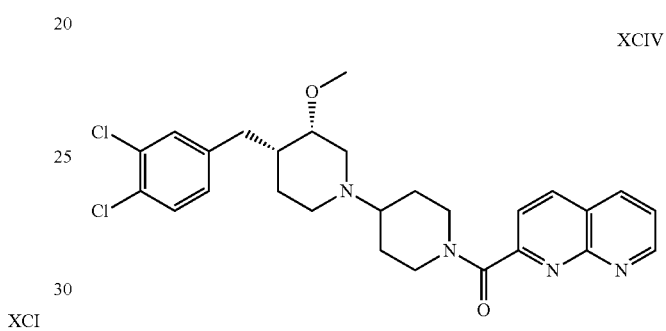
XCIII
XCIV
XCV
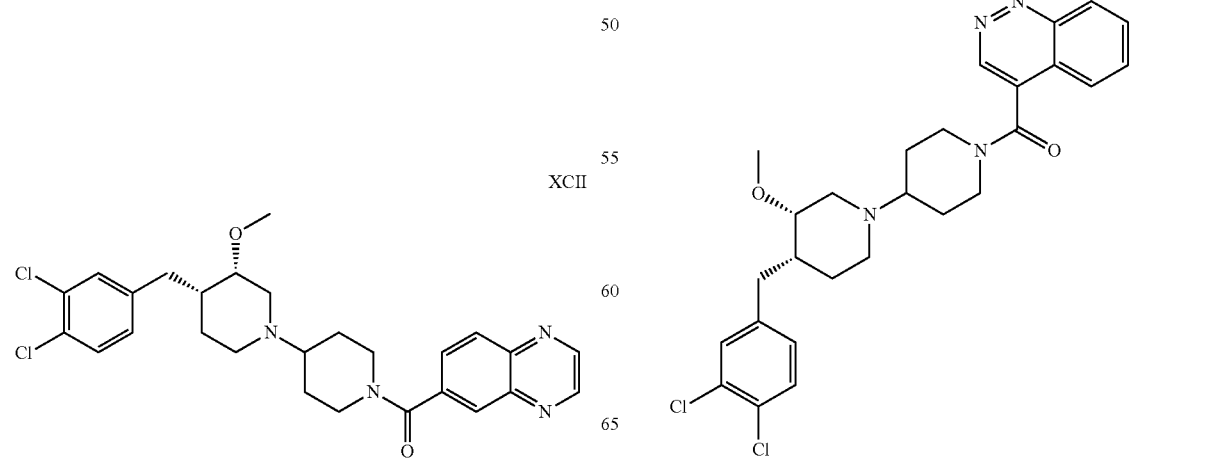
XCVI -continued
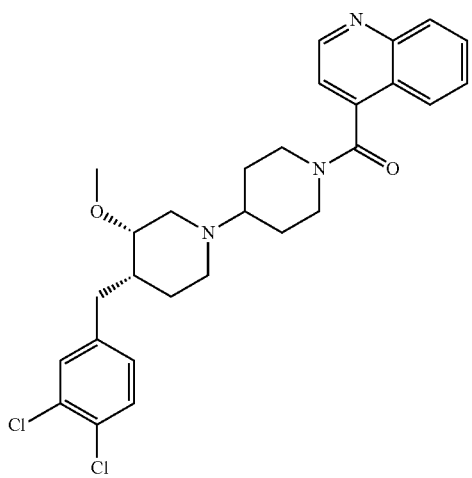
XCVII
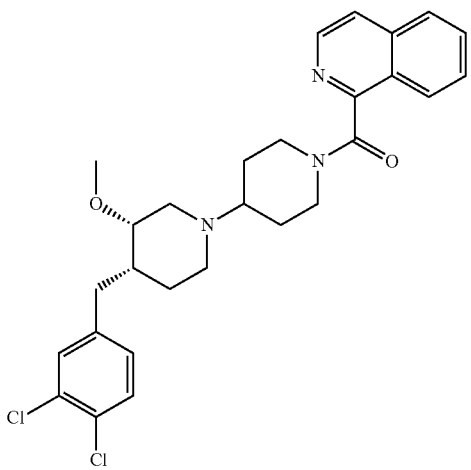
C
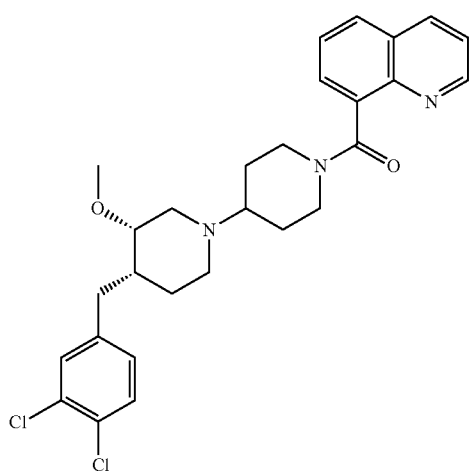
XCVIII
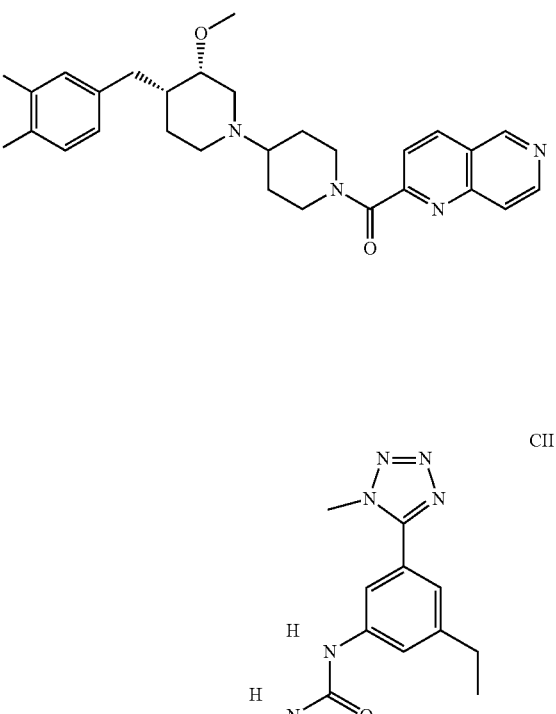
CI
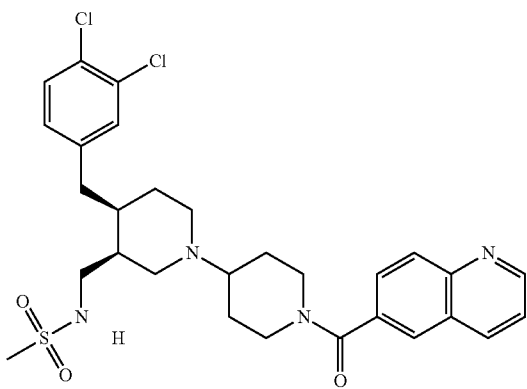
XCIX
CII 37
-continued
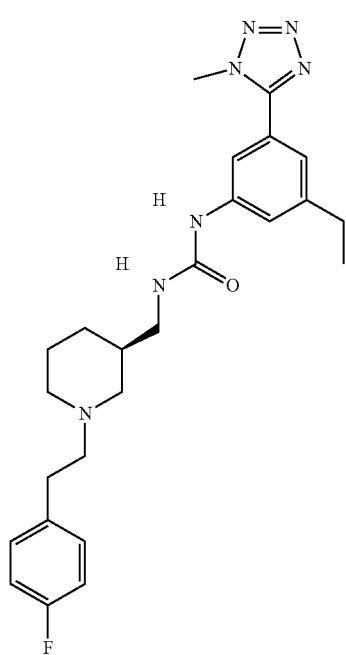
CIII
CIV
38
-continued
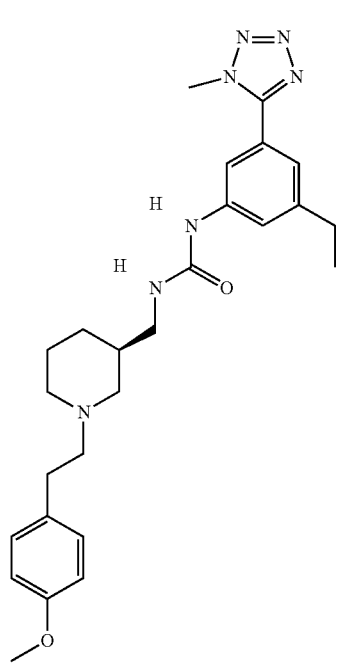
CV
CVI -continued
CVII
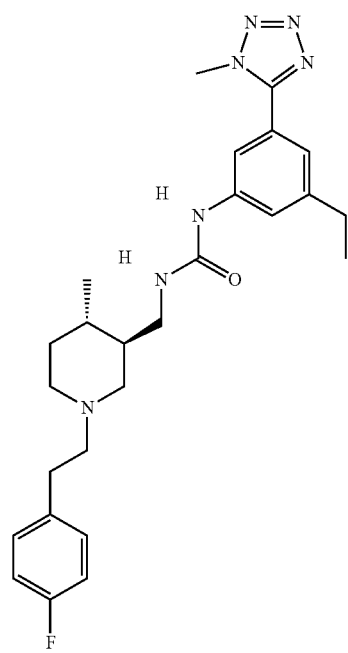
CVIII
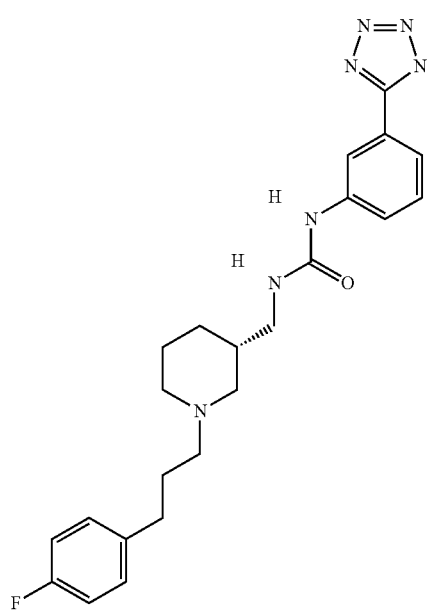
-continued
CIX
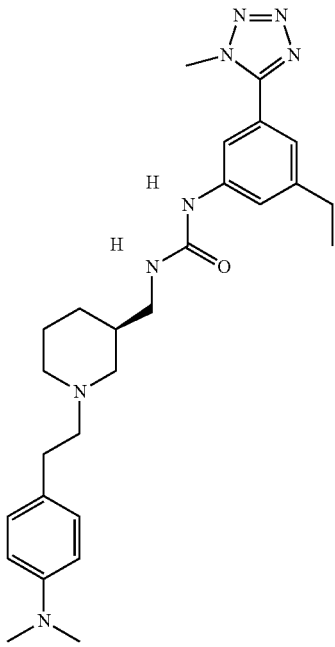
CX

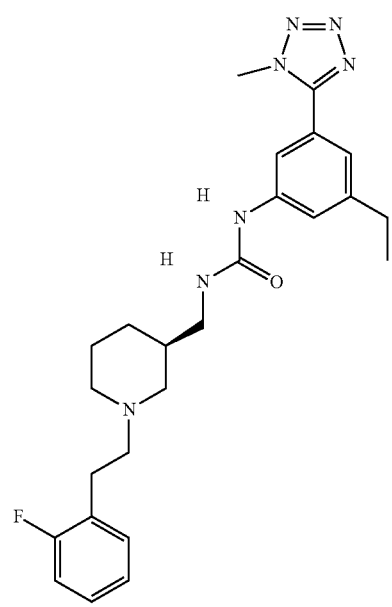
CXI
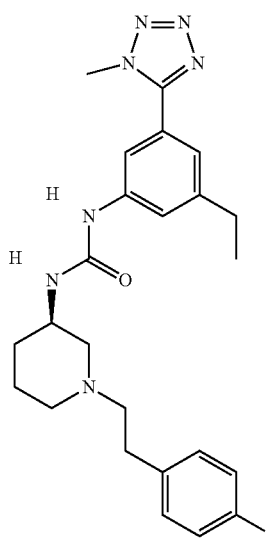
CXIII
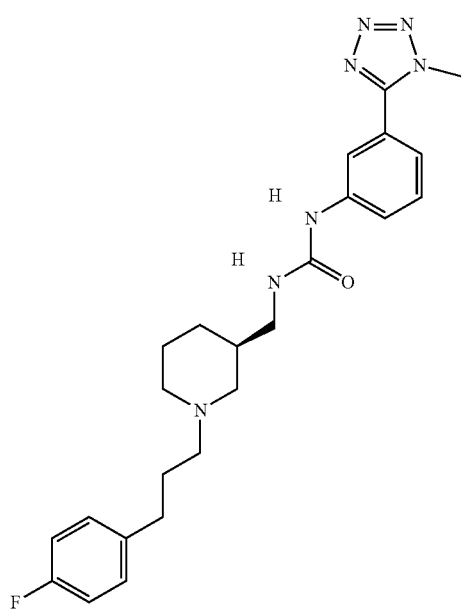
CXII
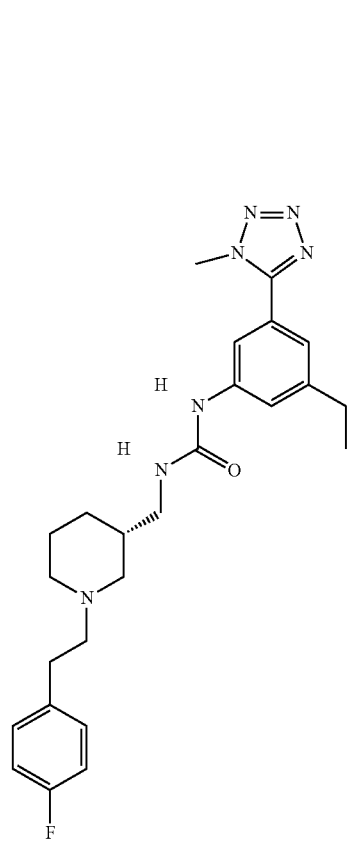
CXIV

CXV
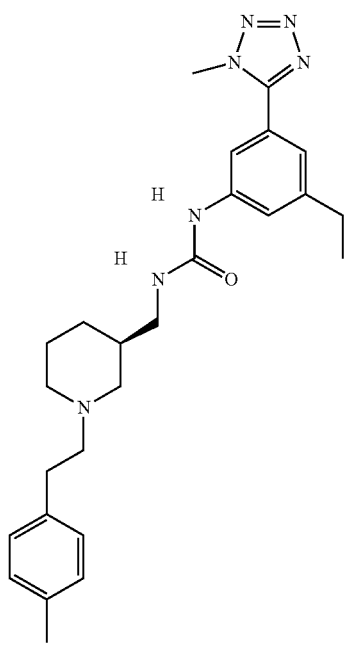
CXVII
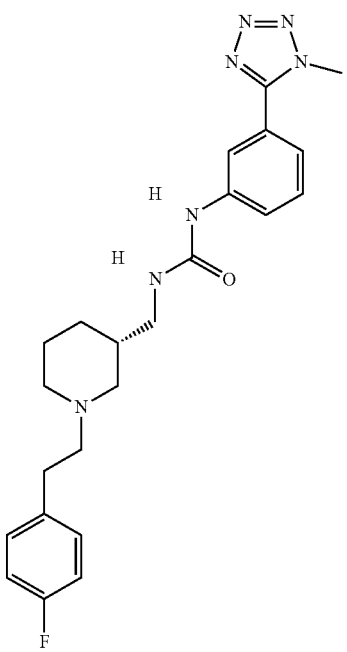
CXVI
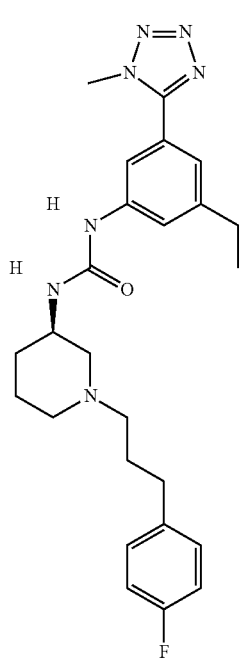
CXVIII
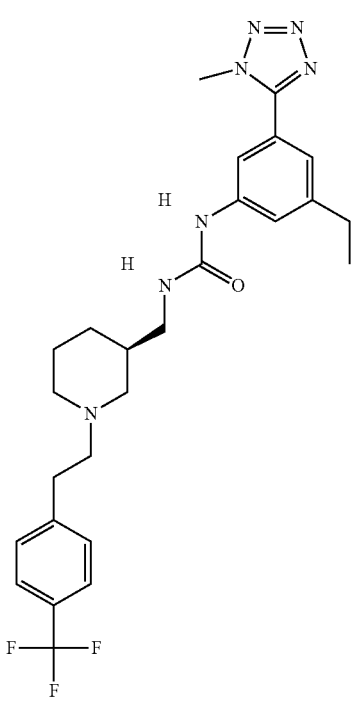

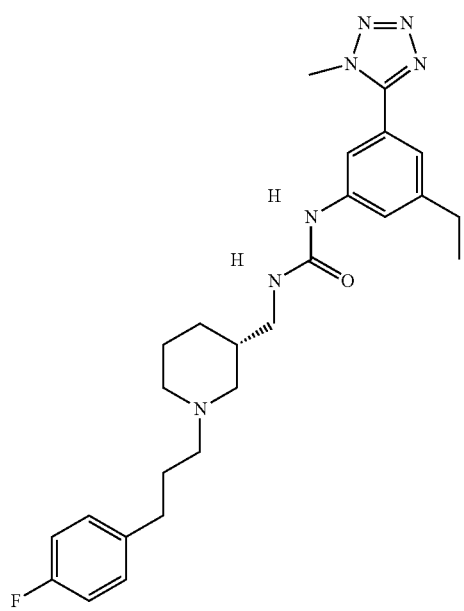
CXIX
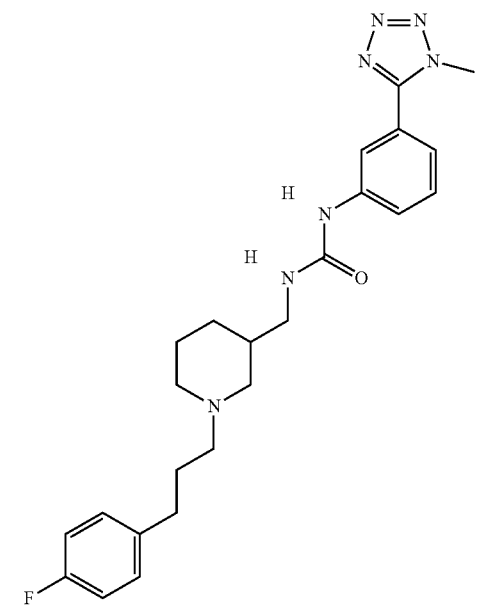
CXXI
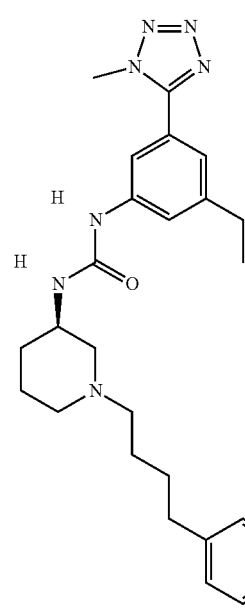
CXX
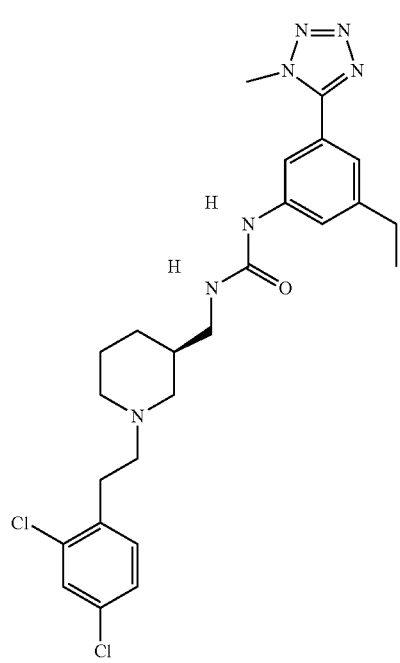
CXXII

-continued
CXXIII
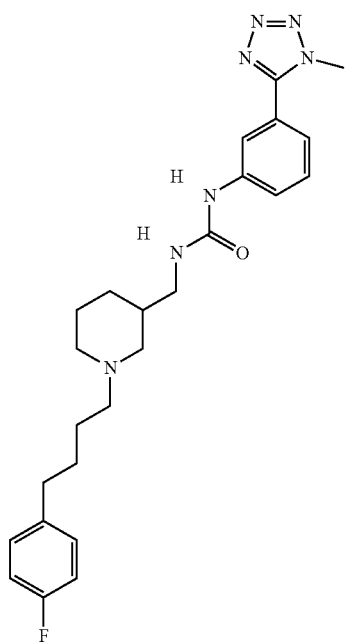
CXXIV
CXXV
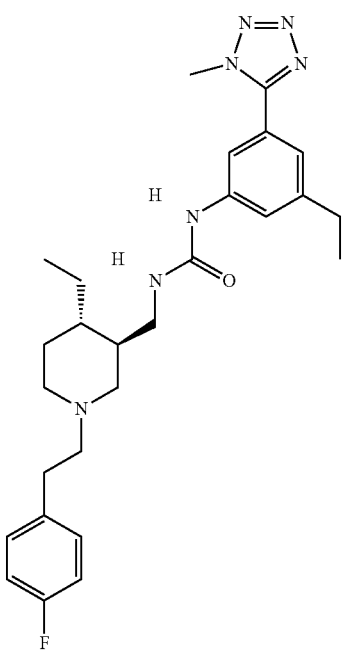
CXXVI

-continued
CXXVII
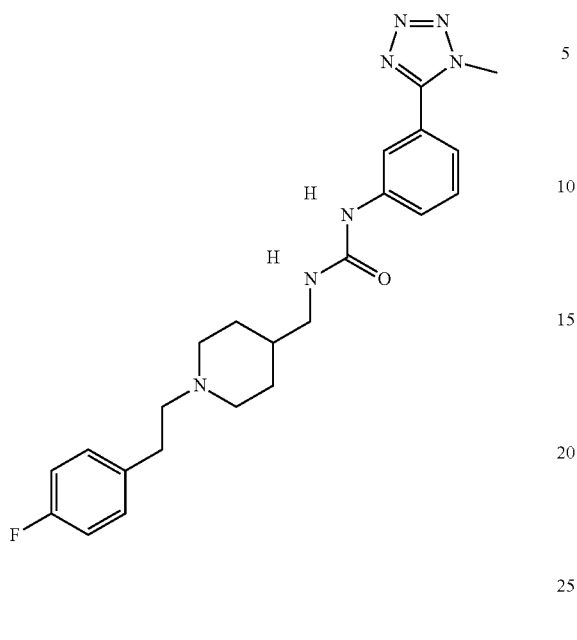
CXXVIII
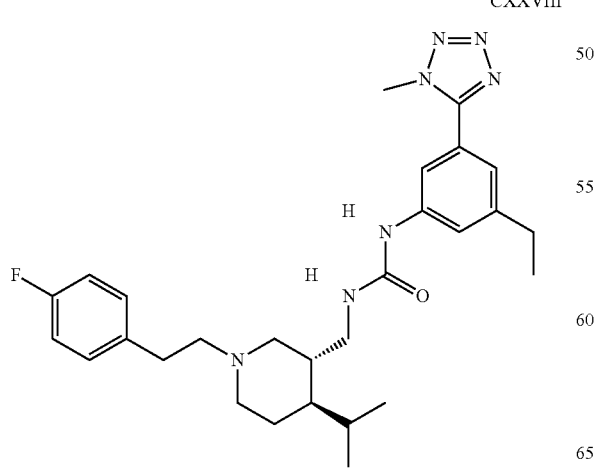
-continued
CXXIX
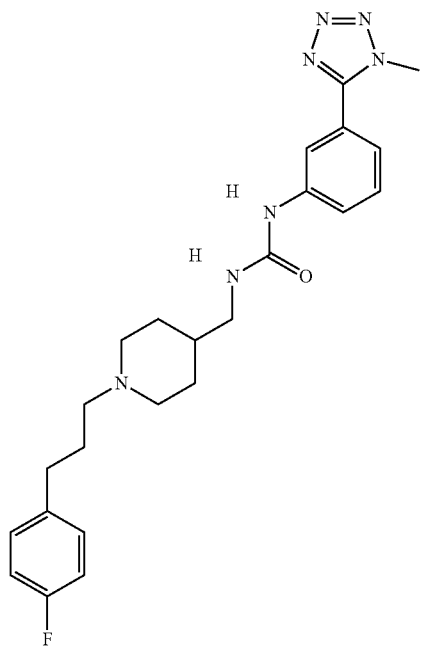
CXXX
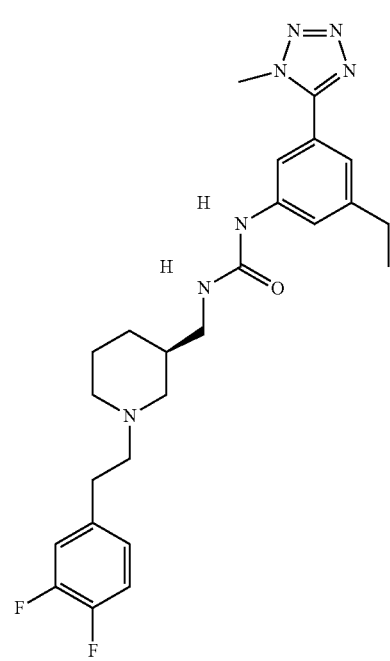

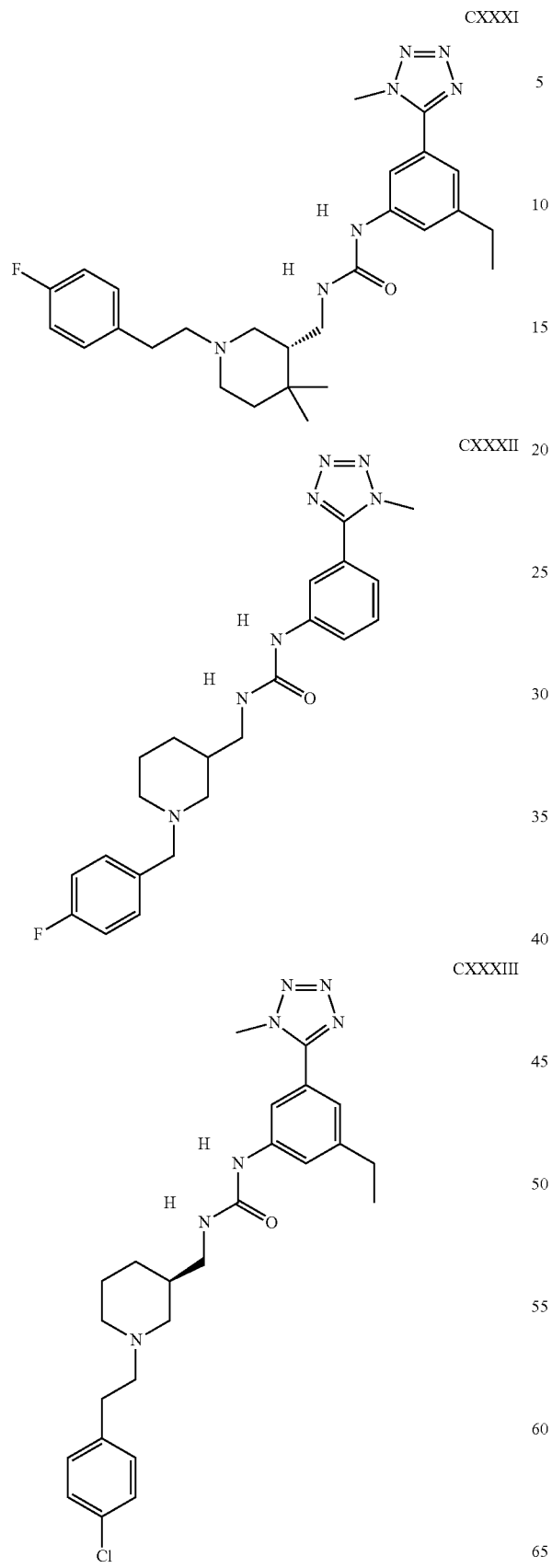
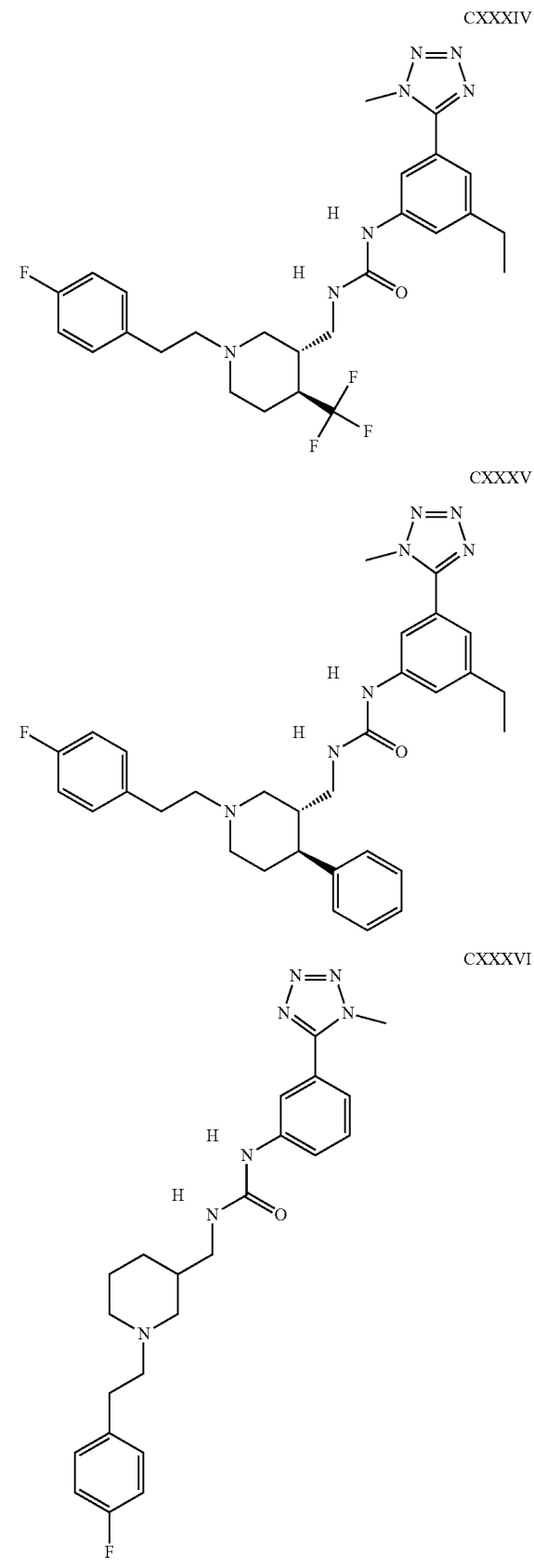

CXXXVII
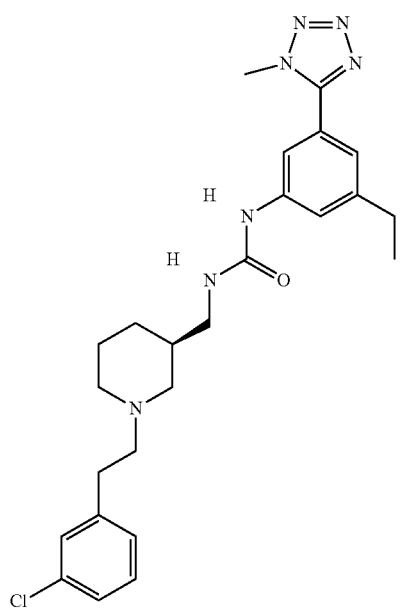
CXXXVIII
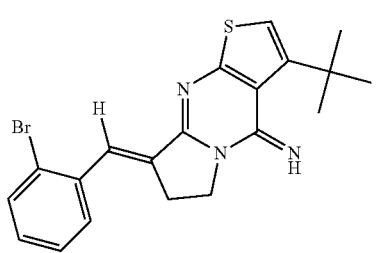
CXXXIX
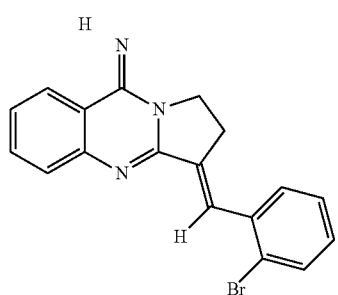
CXL
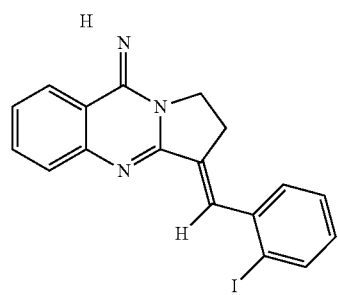
CXLI
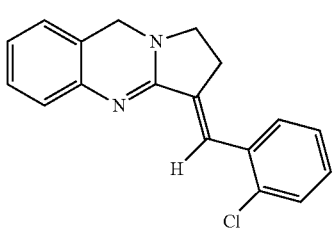
CXLII
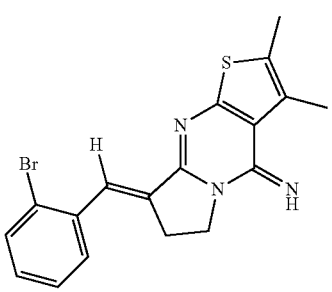
CXLIII
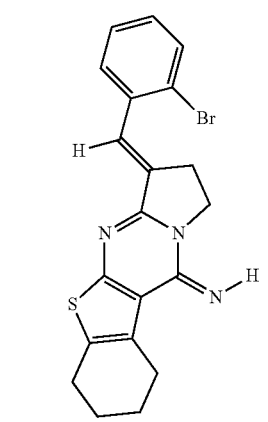
CXLIV
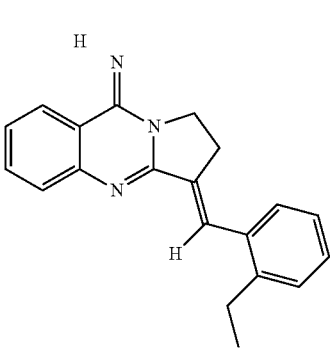
CXLV
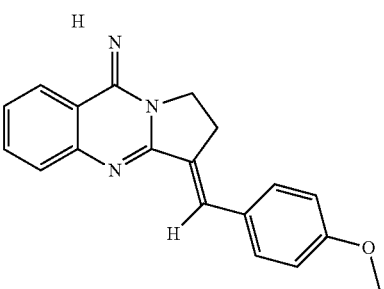

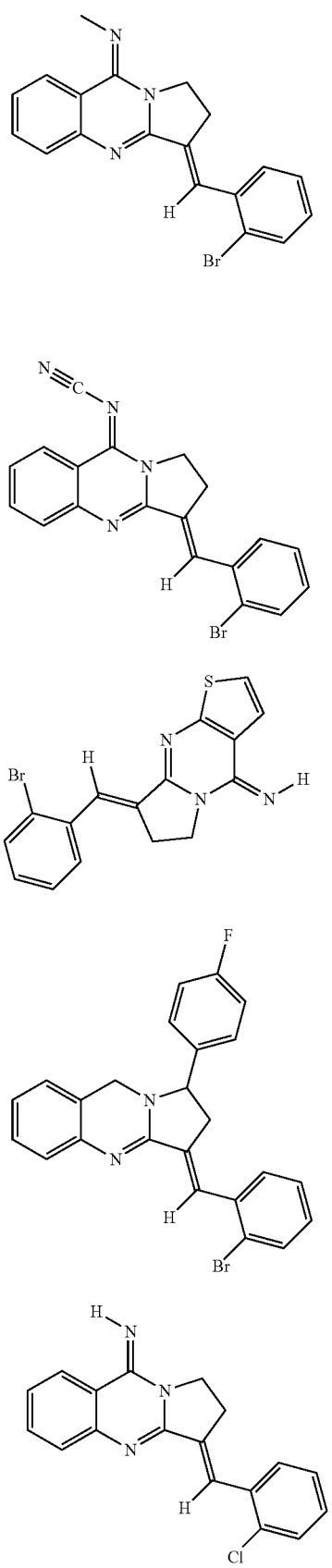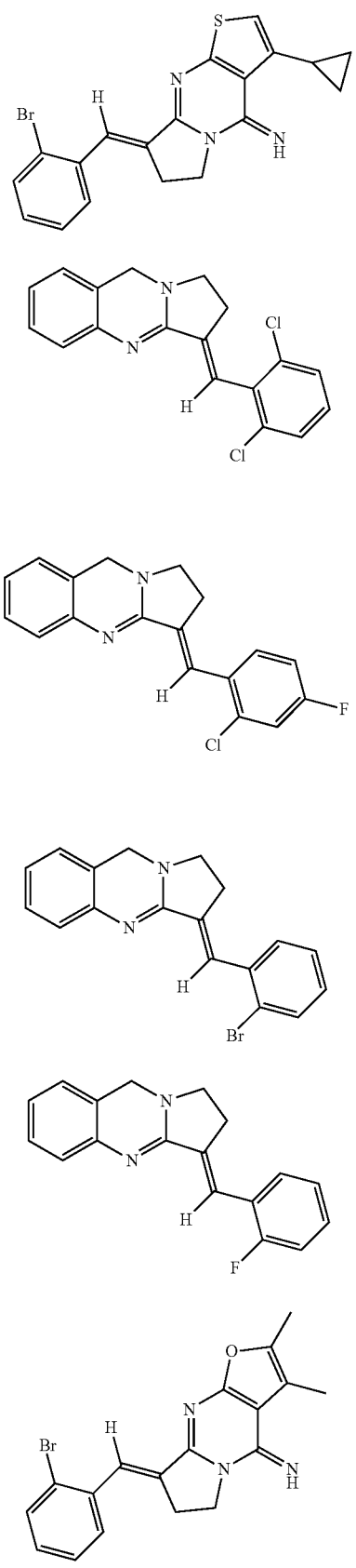

CLVII
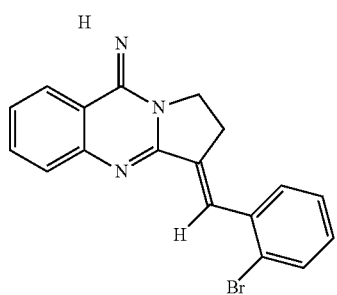
CLVIII
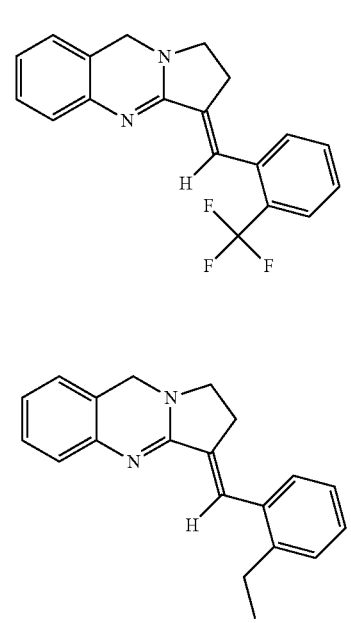
CLIX
CLX
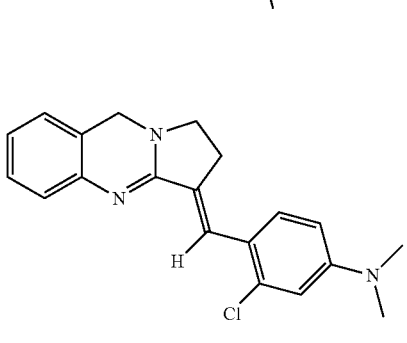
CLXI
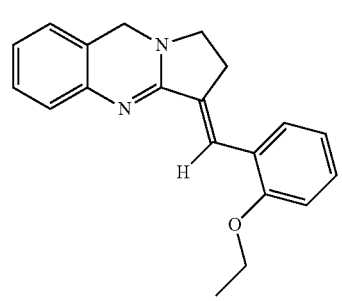
CLXII
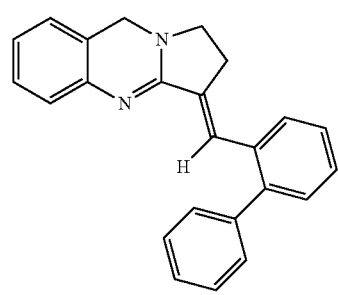
CLXIII
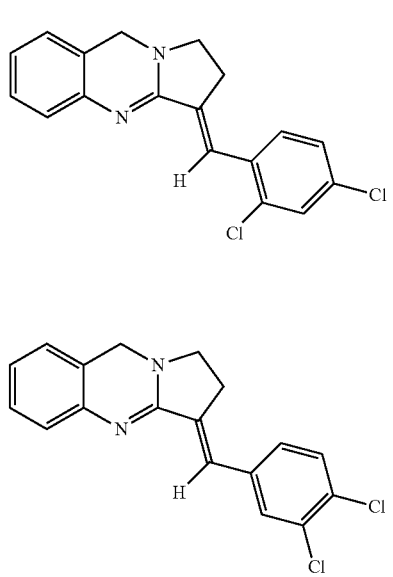
CLXIV
CLXV
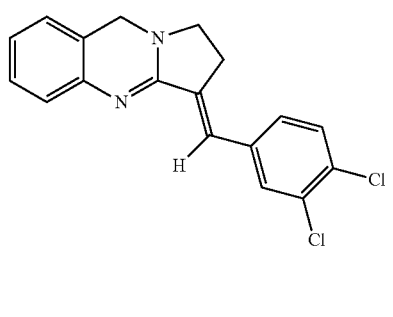
CLXVI
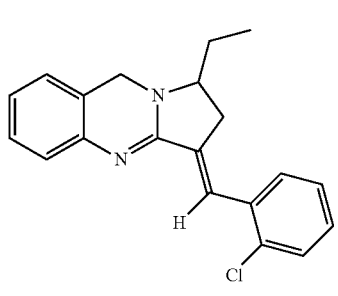

CLXVII
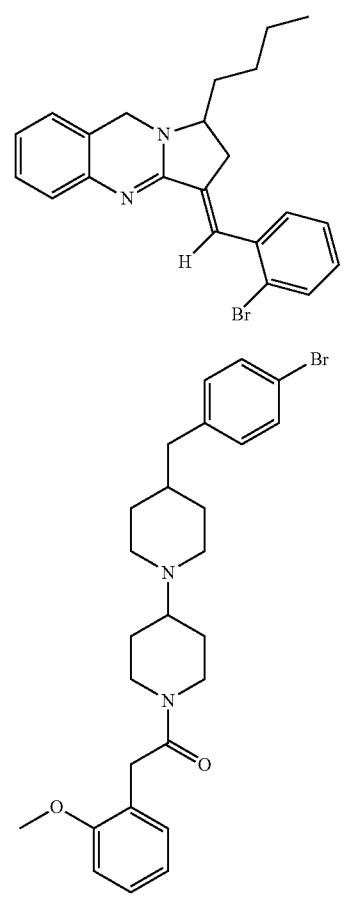
CLXVIII
CLXIX
CLXX
CLXXI
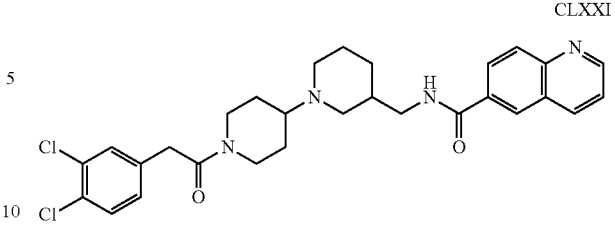
CLXXII
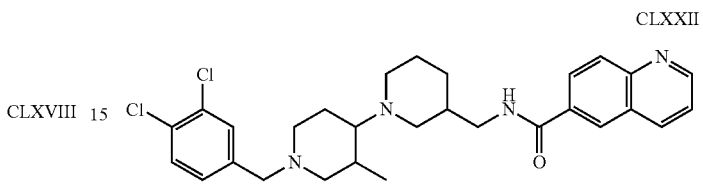
CLXXIII
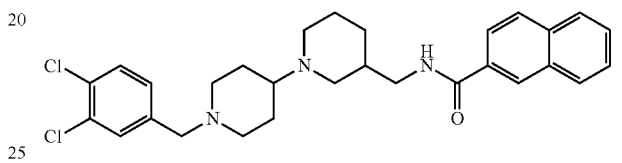
CLXXIV
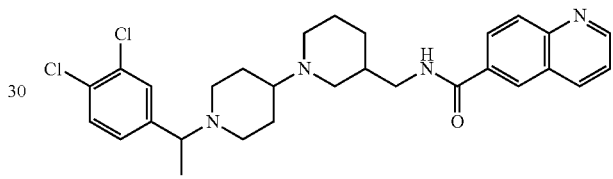
CLXXV
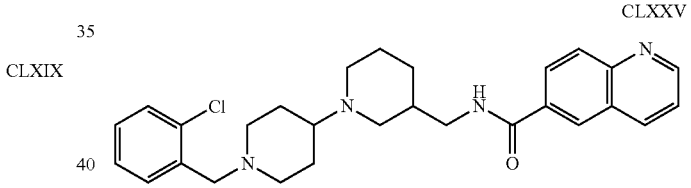
CLXXVI
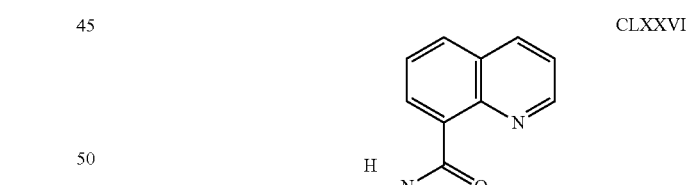
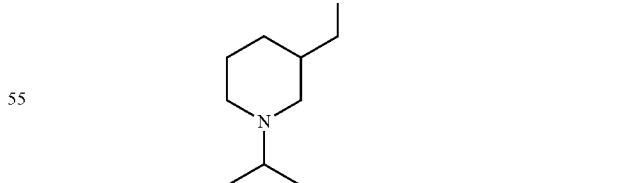
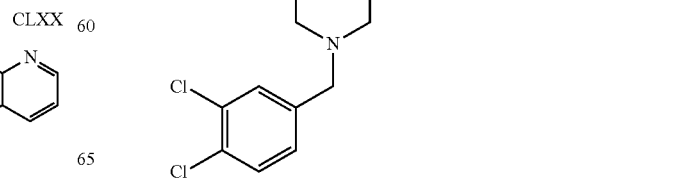
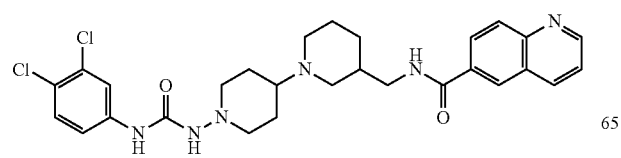

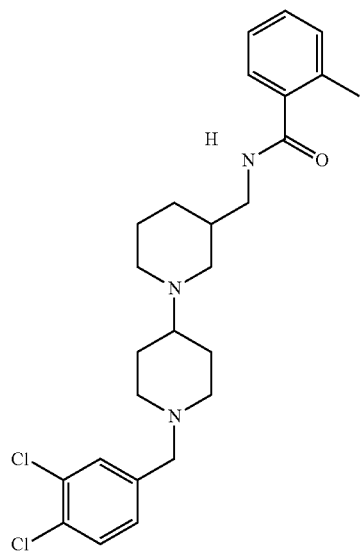
CLXXVII
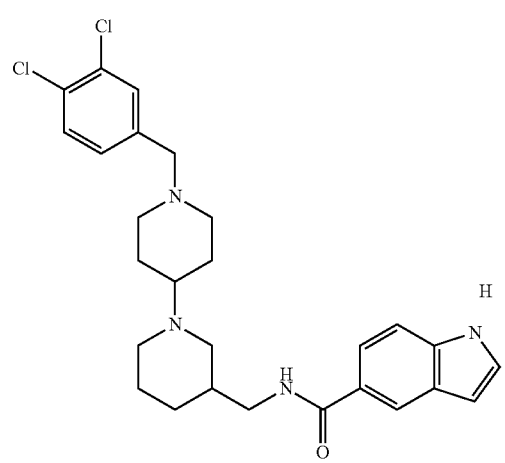
CLXXVIII
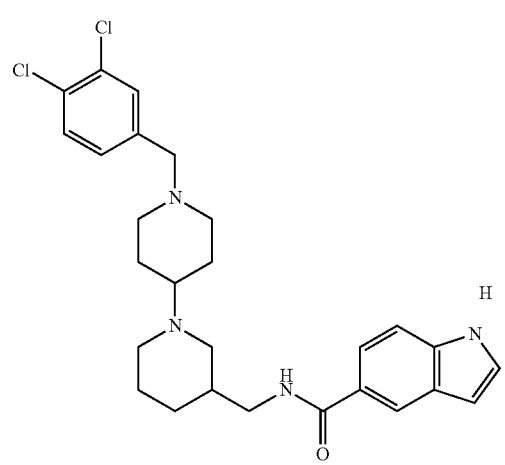
CLXXIX
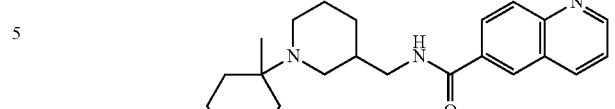
CLXXX
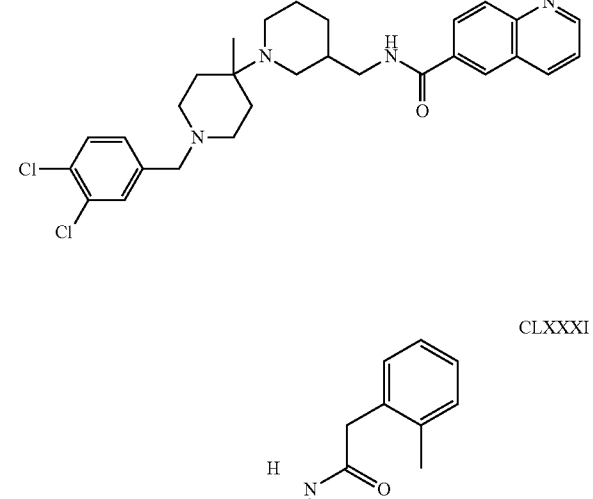
CLXXXI
CLXXXII
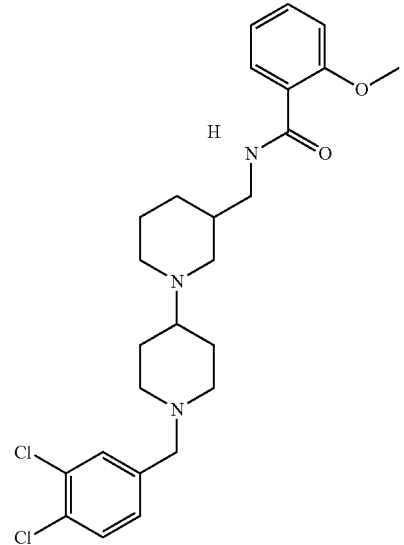
CLXXXIII -continued
CLXXXIV
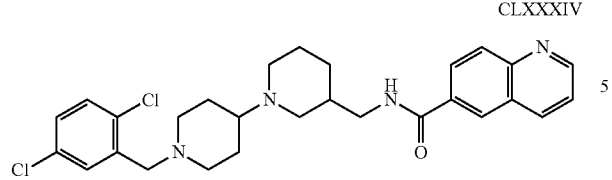
CLXXXV
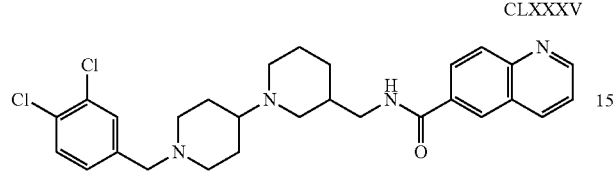
CLXXXVI
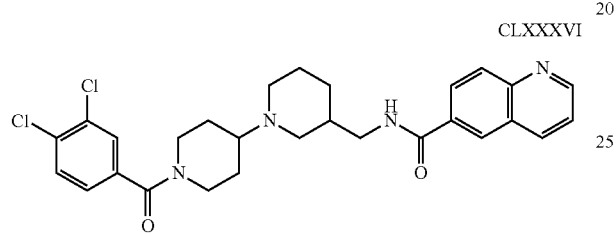
CLXXXVII
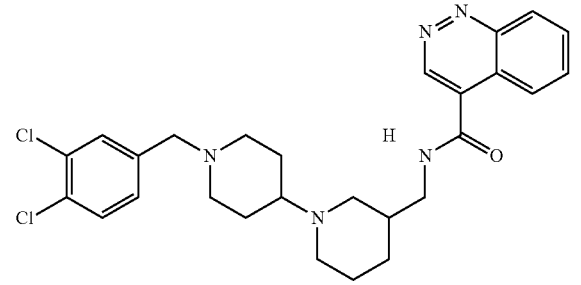
CLXXXVIII
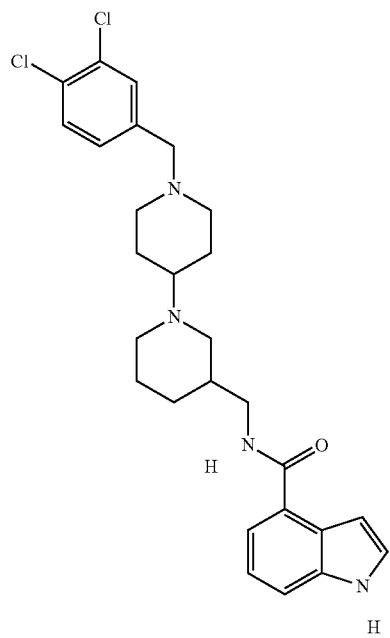
-continued
CLXXXIX
CXC
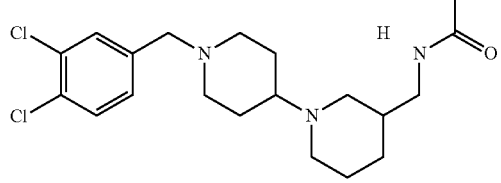
CXCI
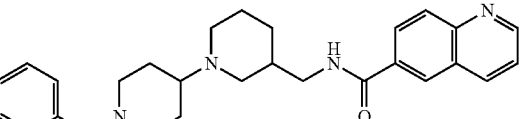
CXCII
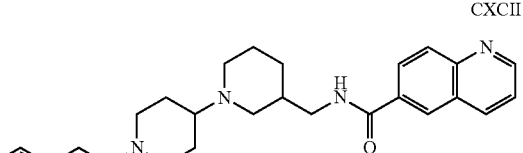

CXCIII
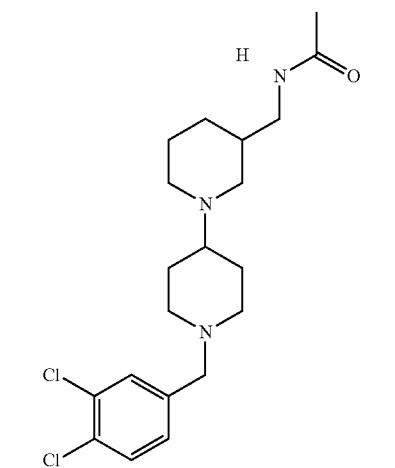
CXCIV
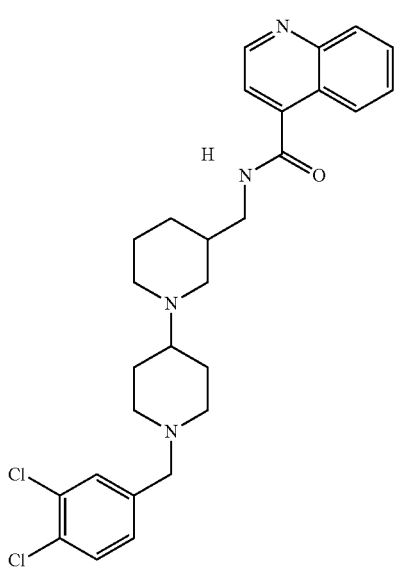
CXCV
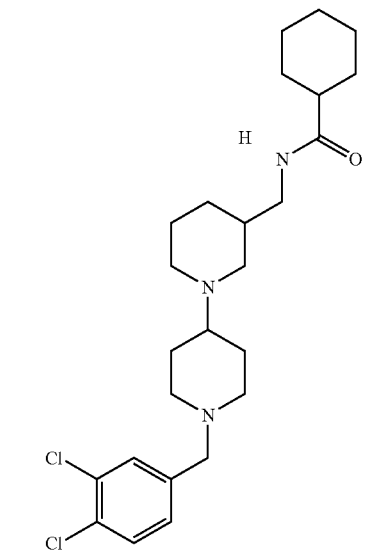
CXCVI
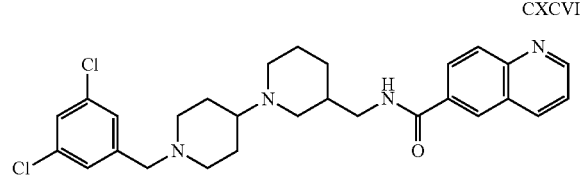
CXCVII
CXCVIII
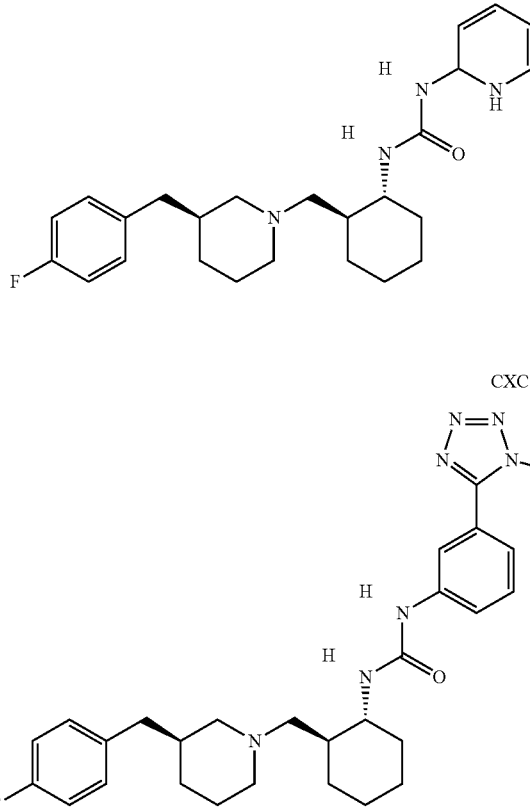
CXCIX
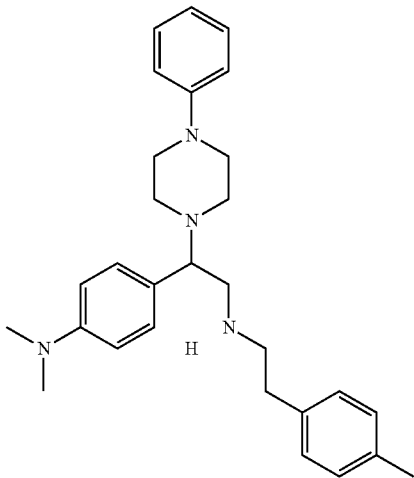

CC
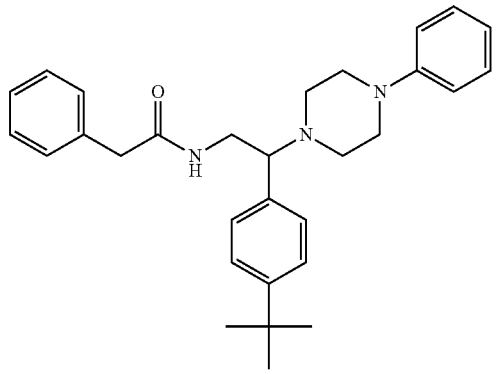
CCIII
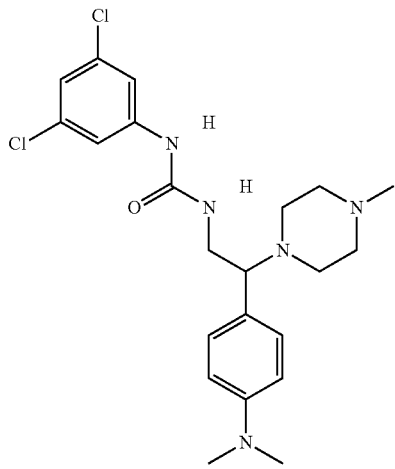
CCI
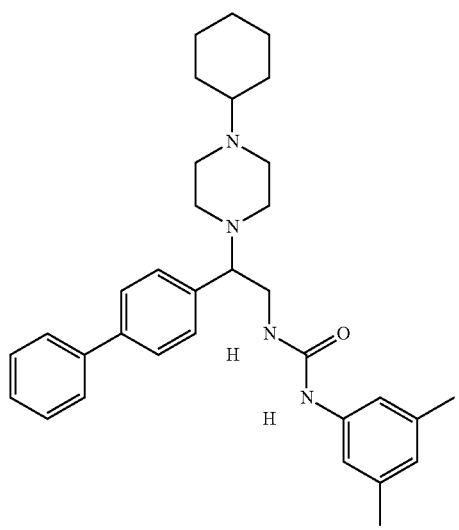
CCIV
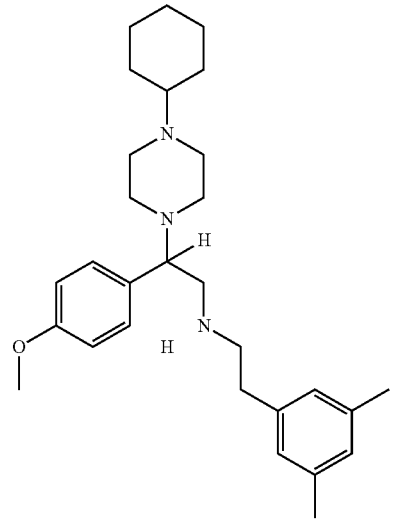
CCII
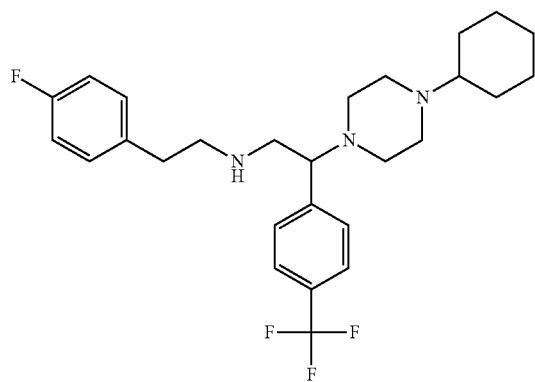
CCV
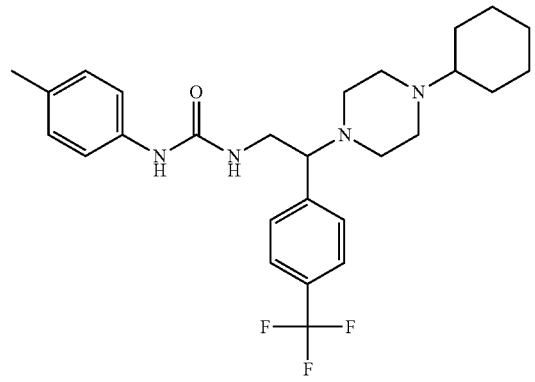

CCVI
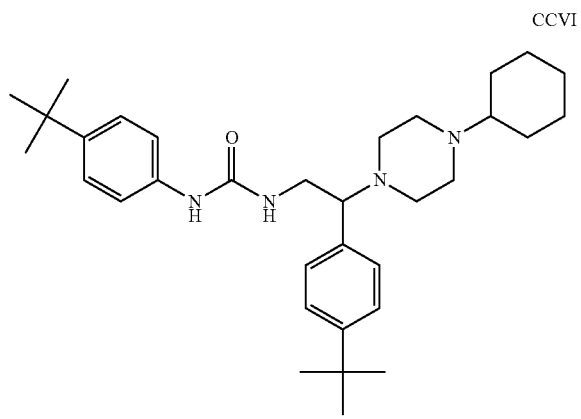
CCVII
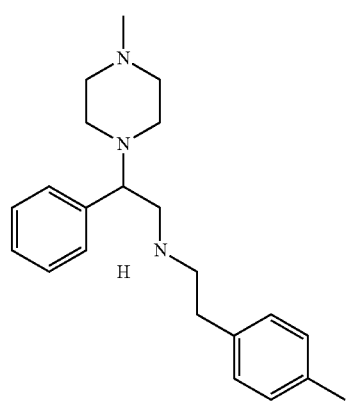
CCVIII
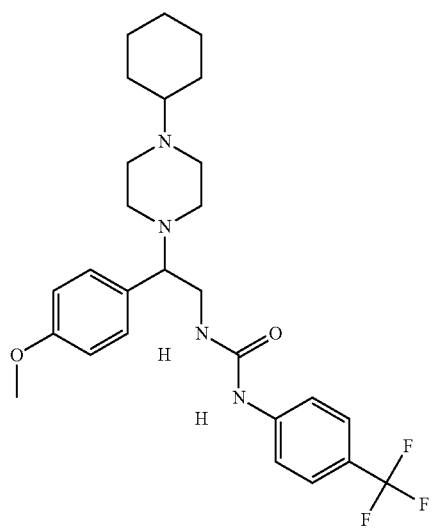
CCIX
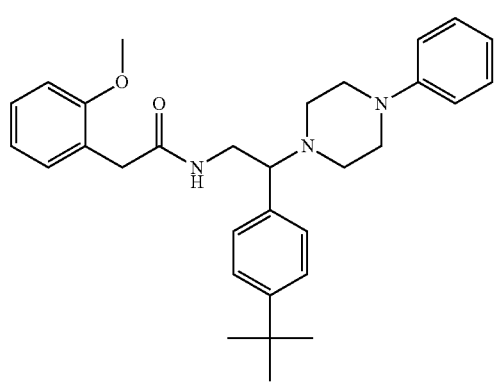
CCX
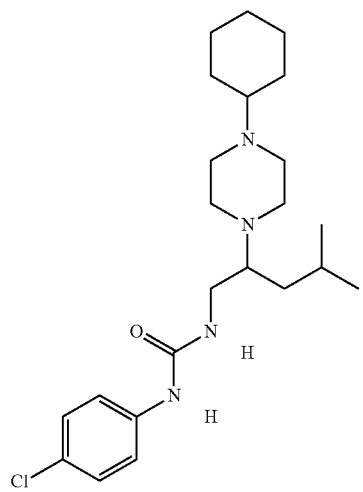
CCXI
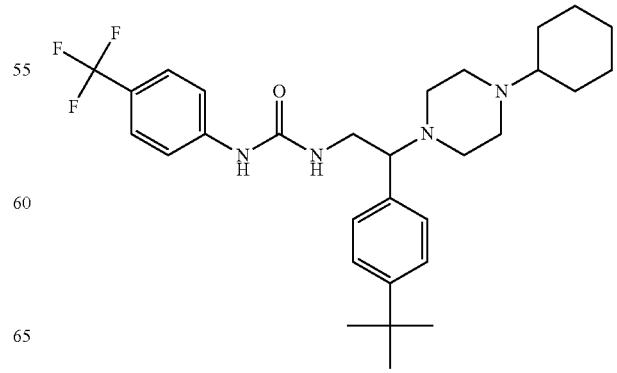

CCXII
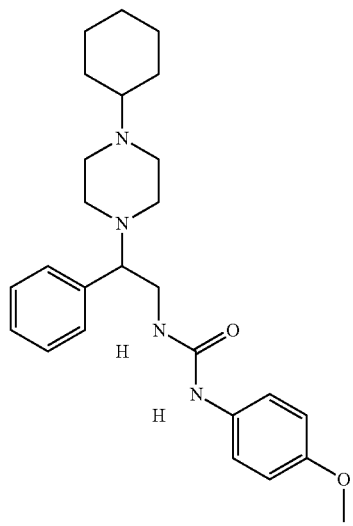
CCXV
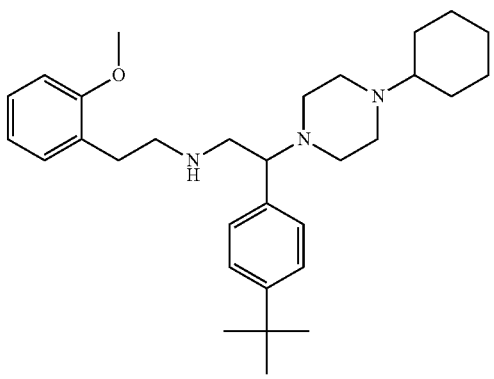
CCXIII
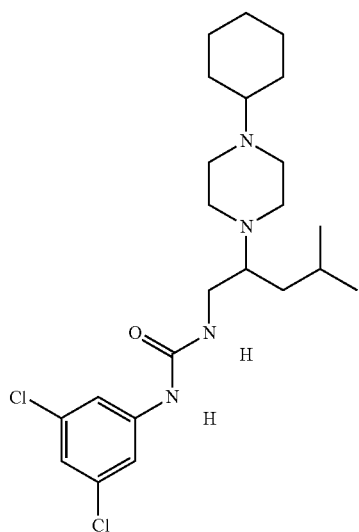
CCXVI
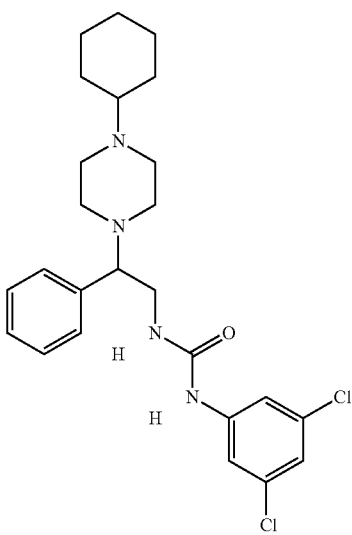
CCXIV
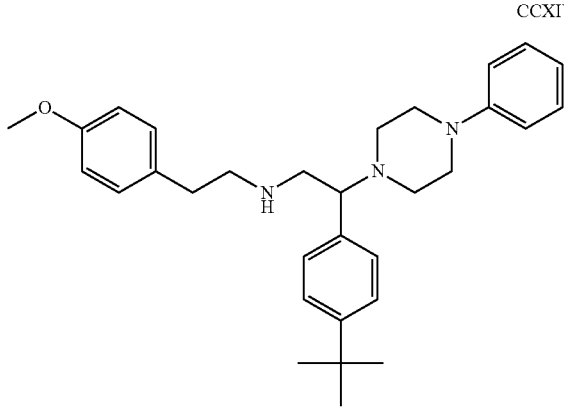
CCXVII
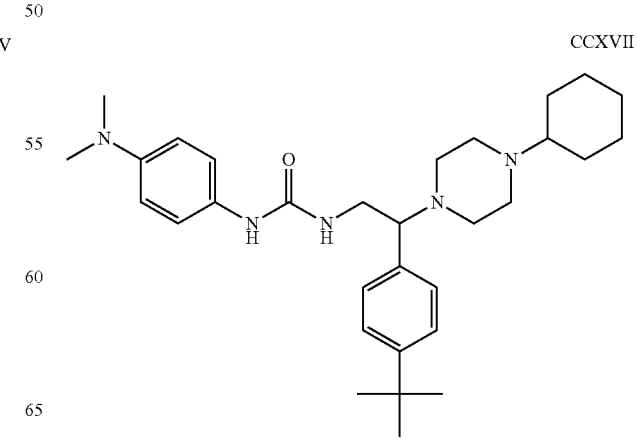

CCXVIII
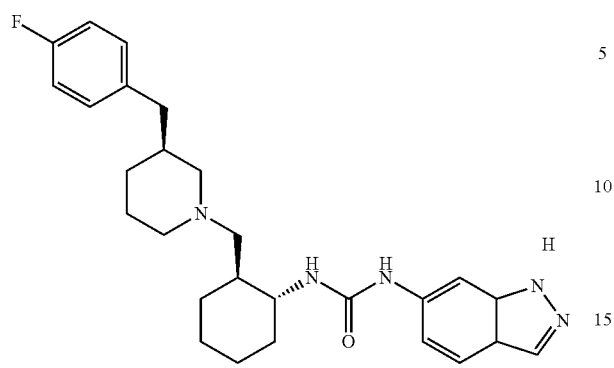
CCXXI
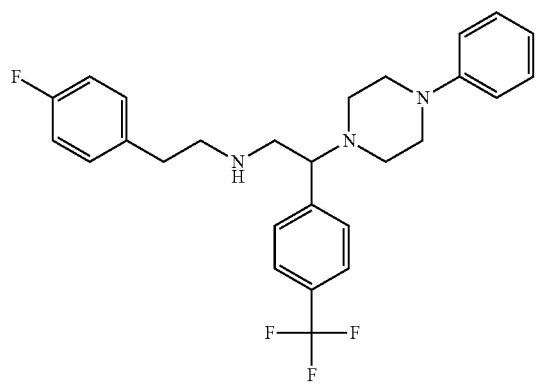
CCXIX
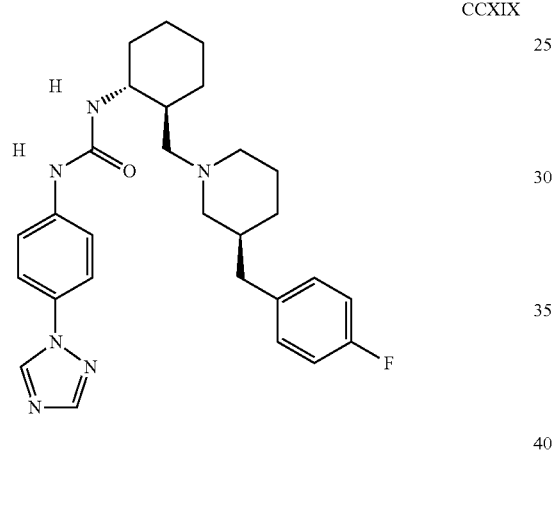
CCXXII
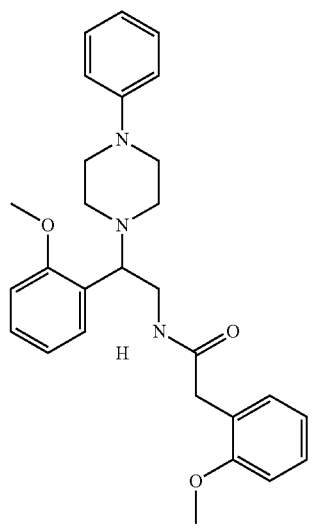
CCXX
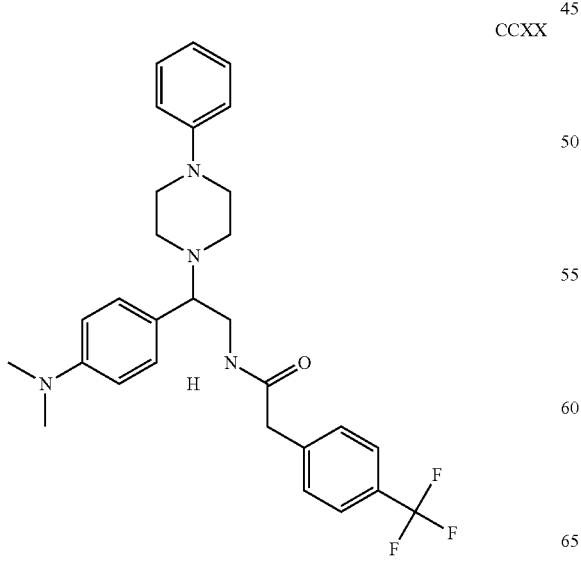
CCXXIII
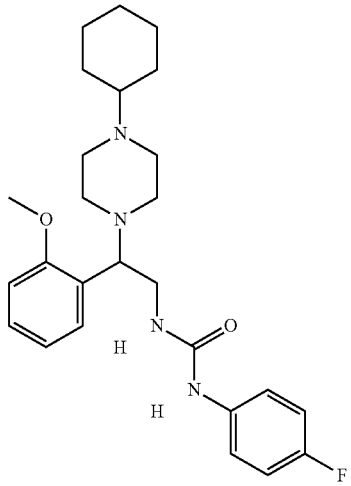

CCXXIV
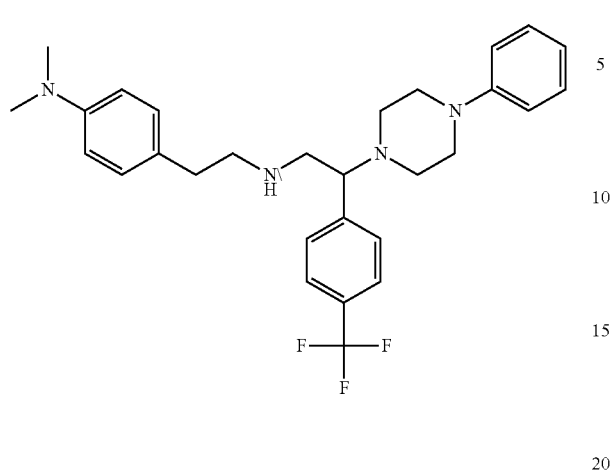
CCXXVII
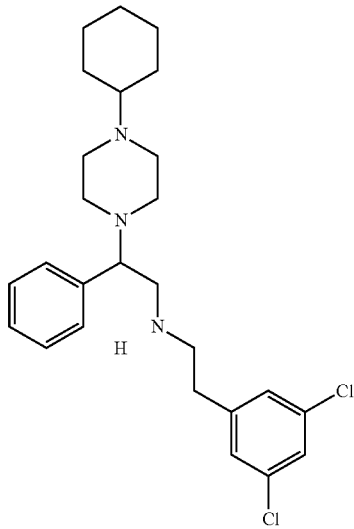
CCXXV
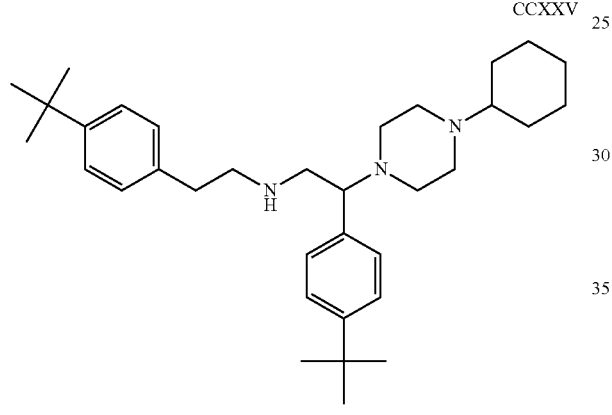
CCXXVIII
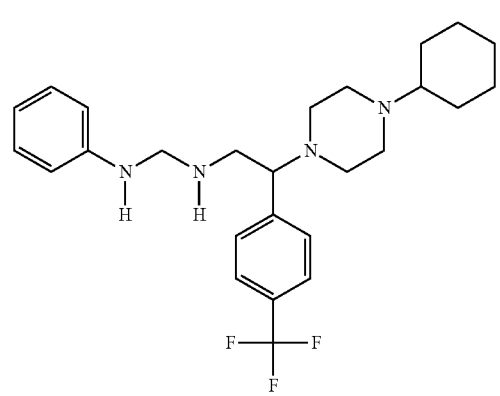
CCXXVI
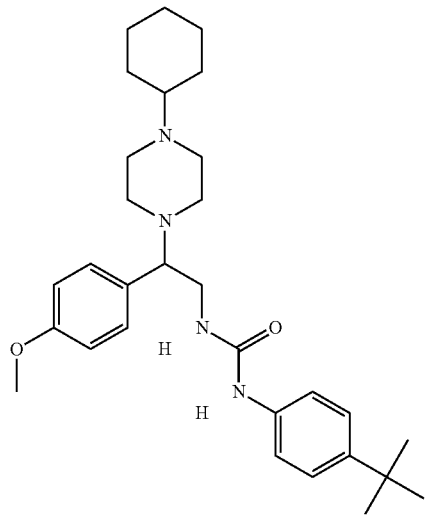
CCXXIX
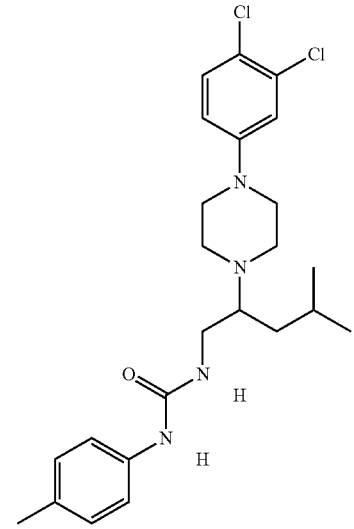

CCXXX
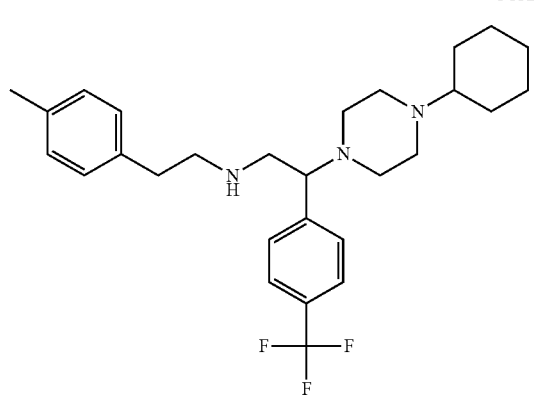
CCXXXIII
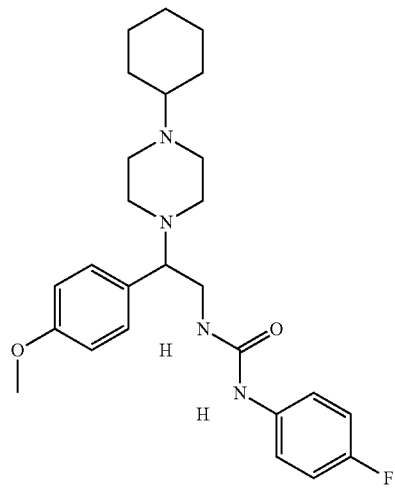
CCXXXI
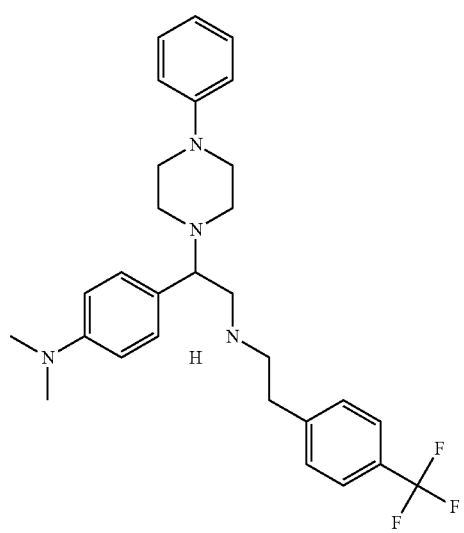
CCXXXIV
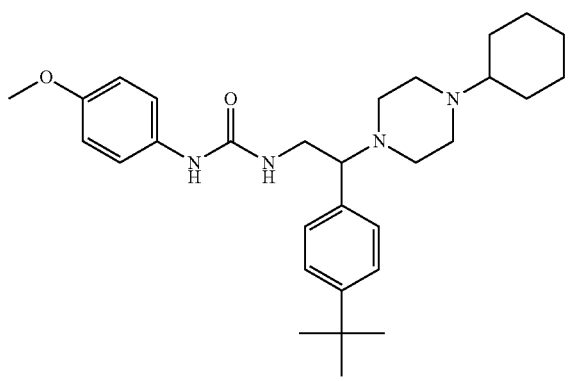
CCXXXII
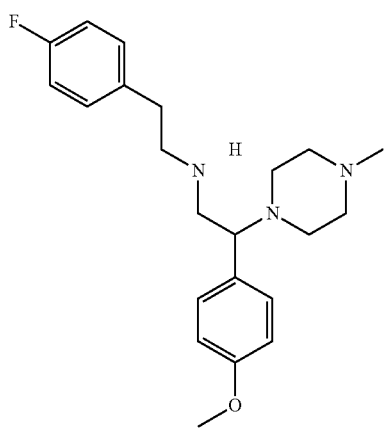
CCXXXV
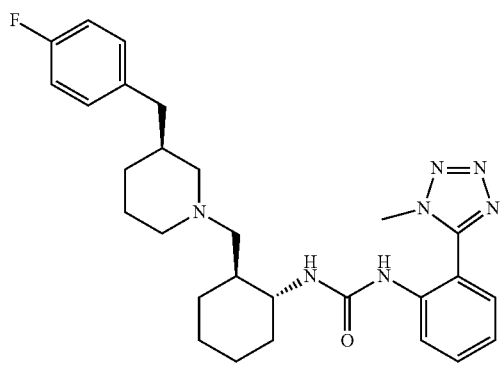

CCXXXVI
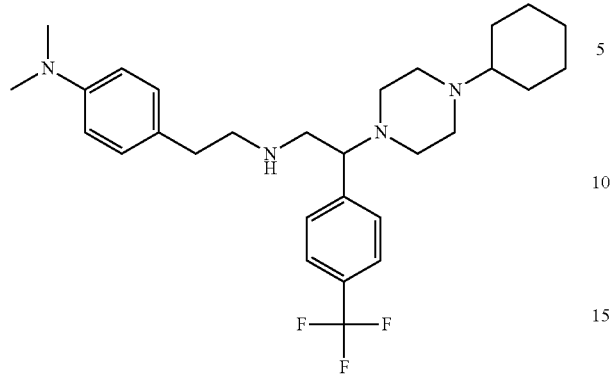
CCXXXIX
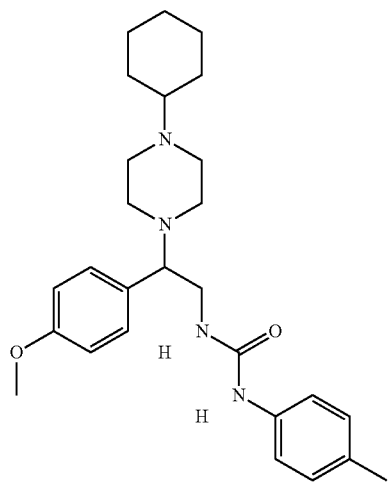
CCXXXVII
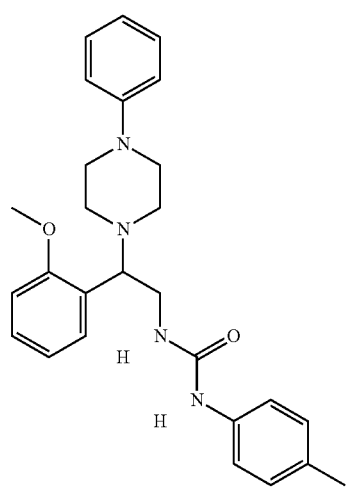
CCXL
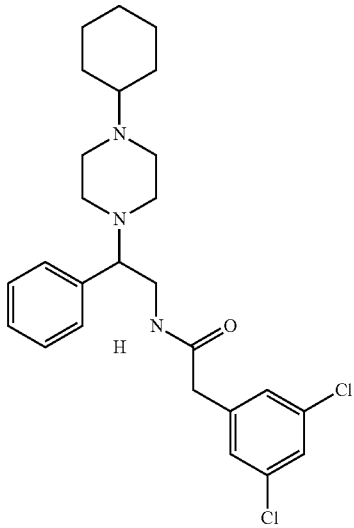
CCXXXVIII
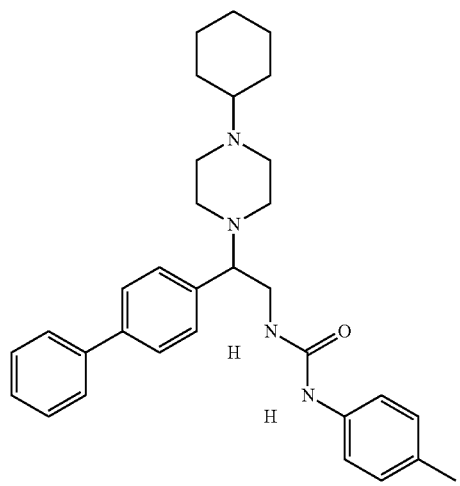
CCXLI
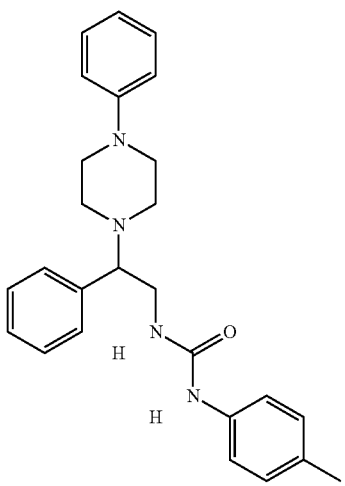

CCXLII
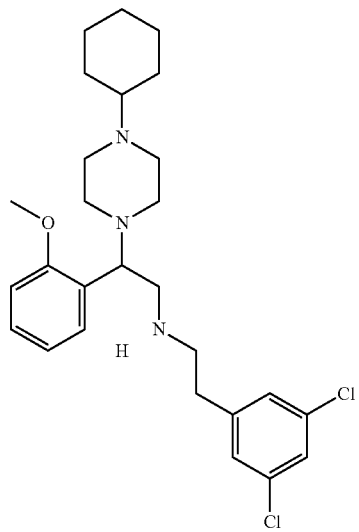
CCXLIII
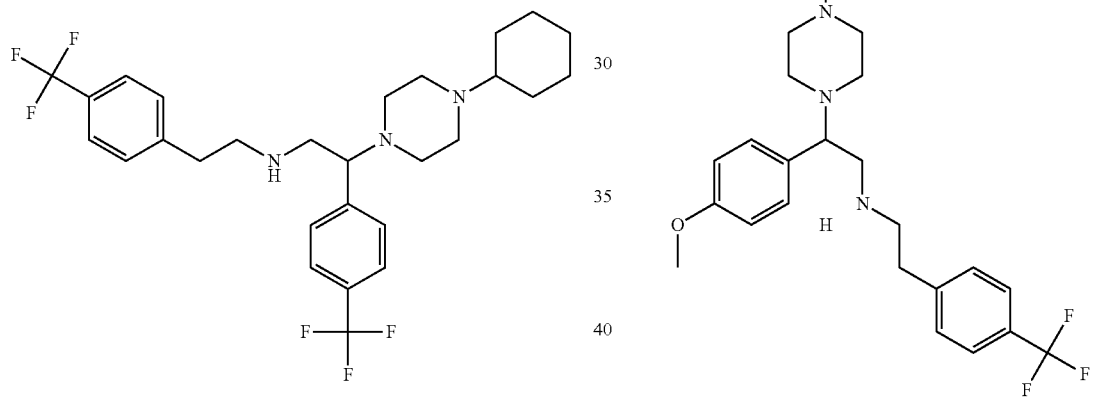
CCXLIV
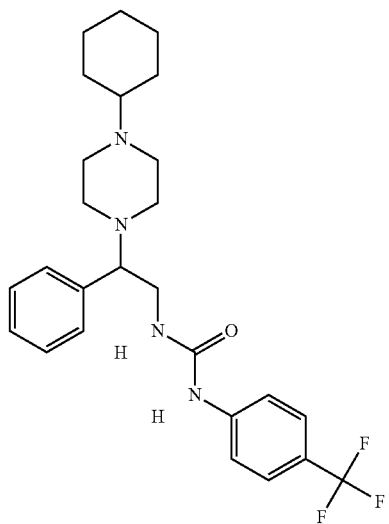
CCXLV
CCXLVI
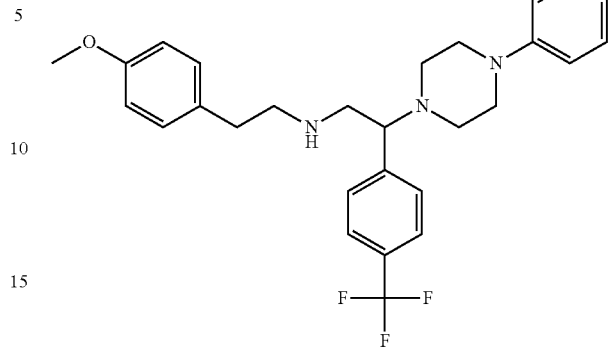
CCXLVII
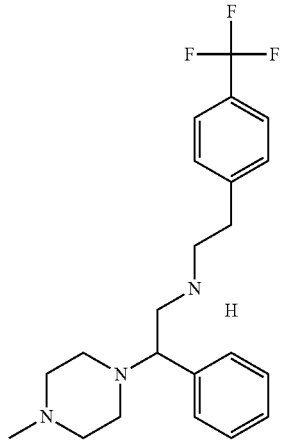

CCXLVIII
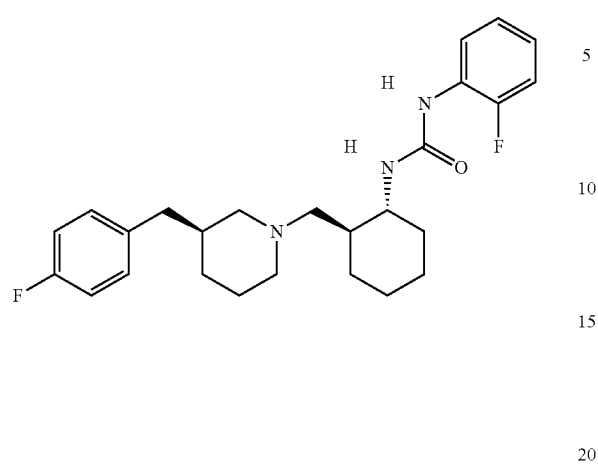
CCXLIX
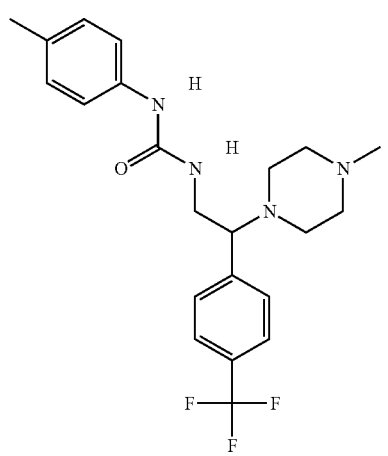
CCL
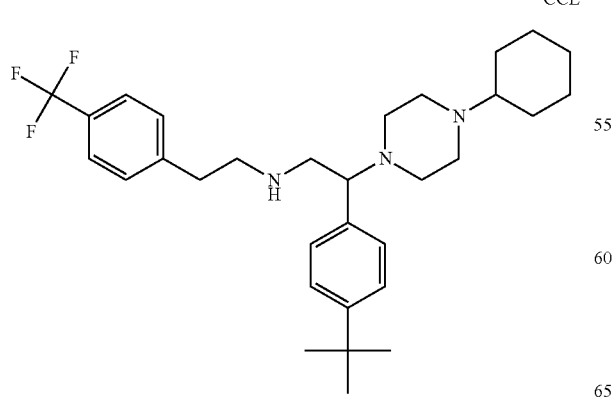
CCLI
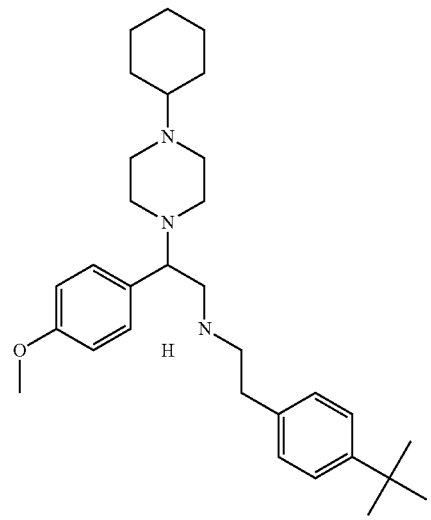
CCLII
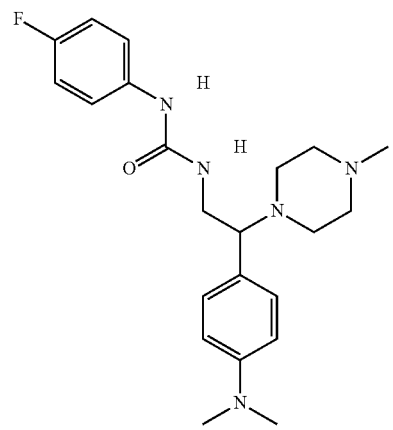
CCLIII
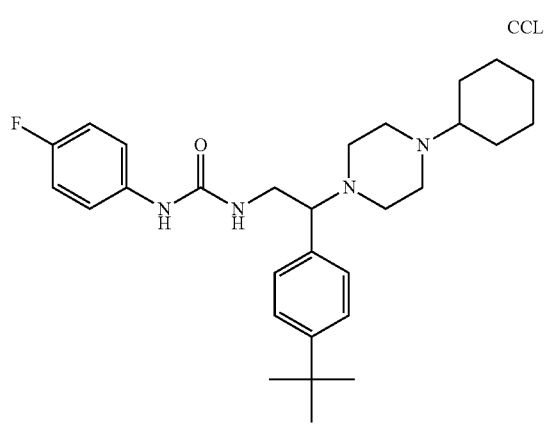

CCLIV
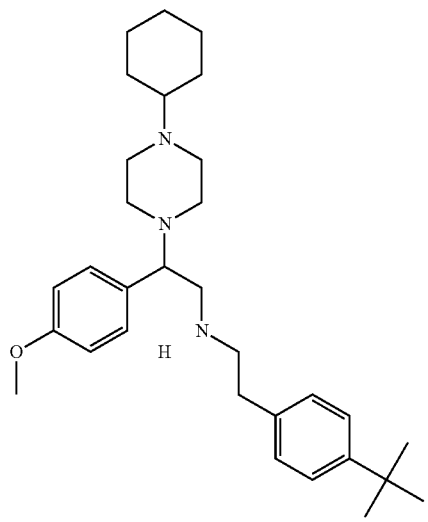
CCLVII
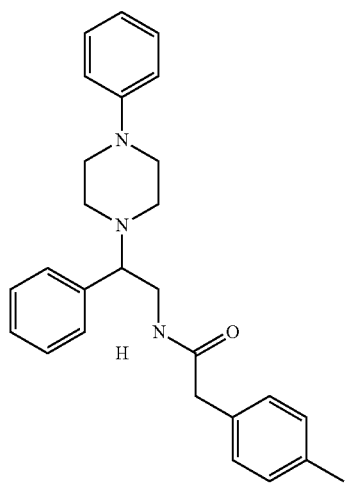
CCLV
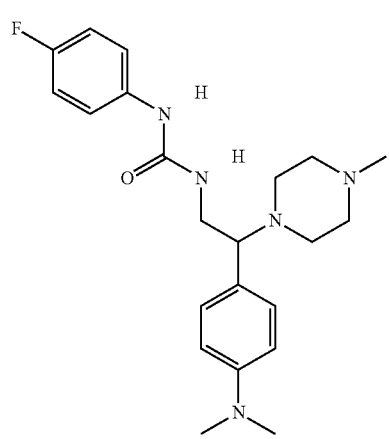
CCLVIII
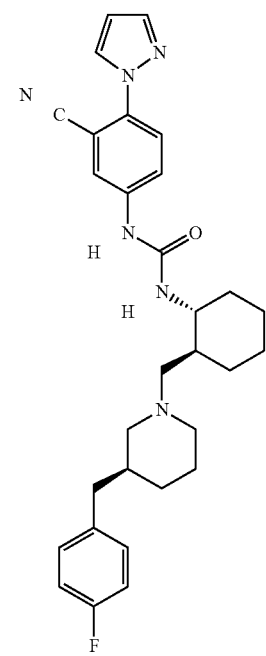
CCLVI
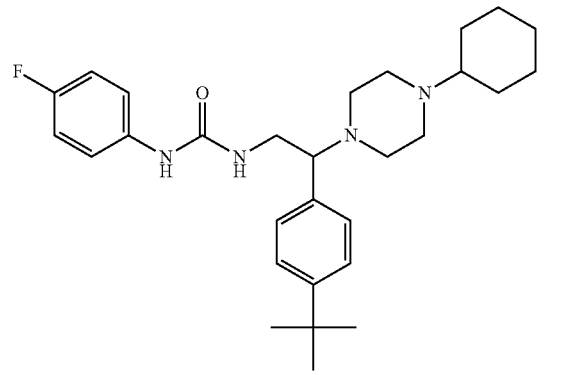
CCLIX
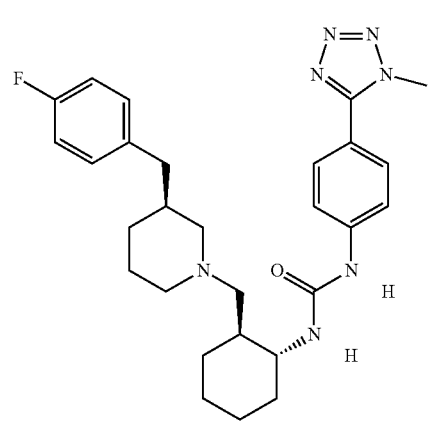

CCLX
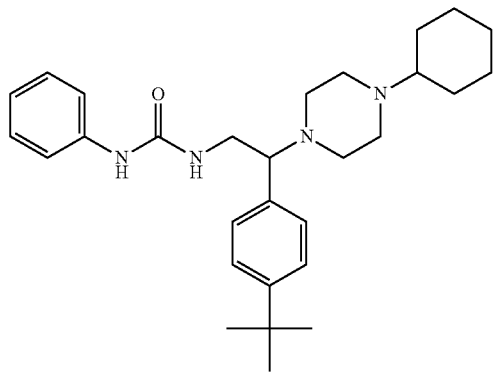
CCLXIII
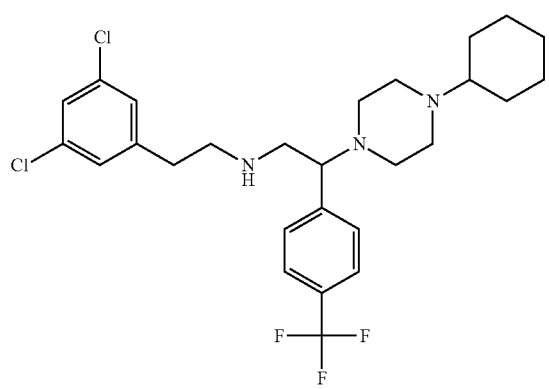
CCLXI
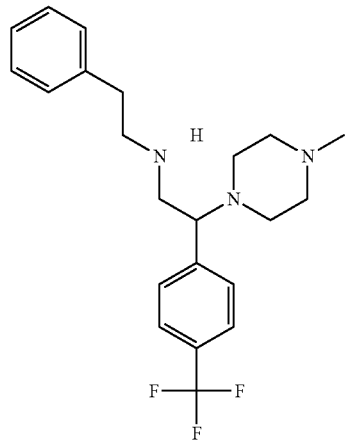
CCLXIV
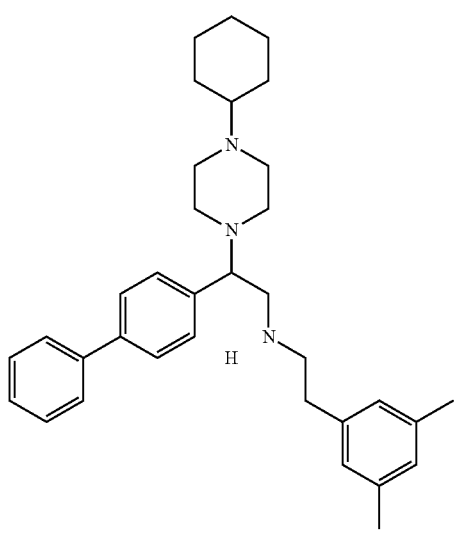
CCLXII
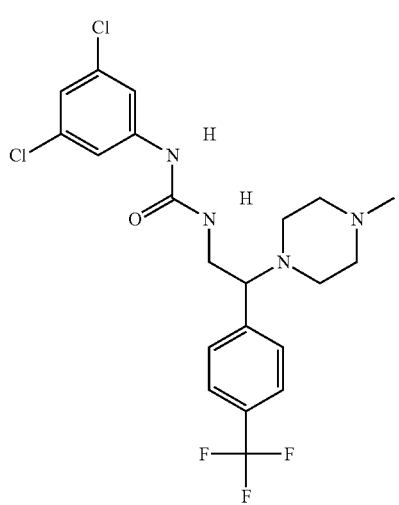
CCLXV
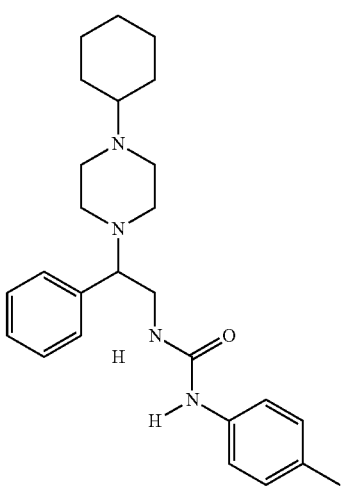

CCLXVI
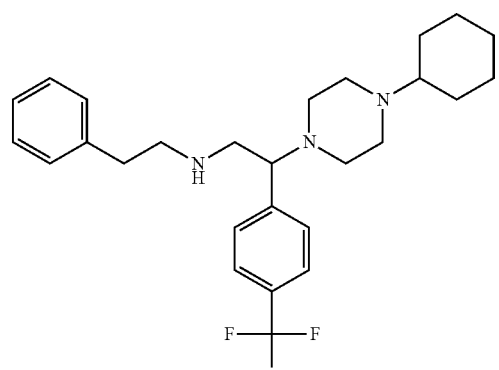
CCLXIX
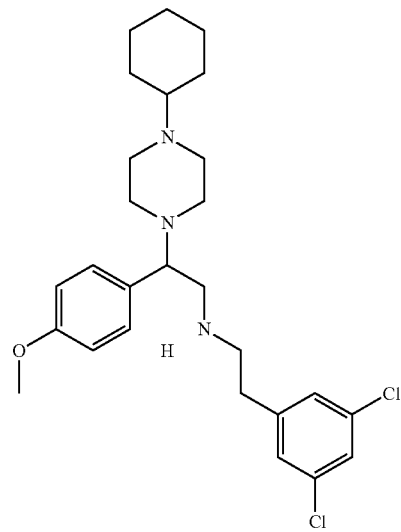
CCLXVII
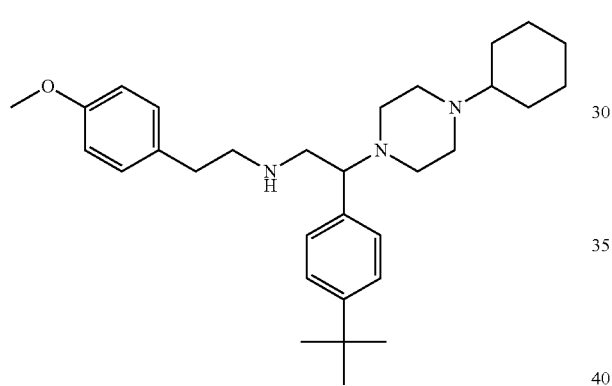
CCLXX
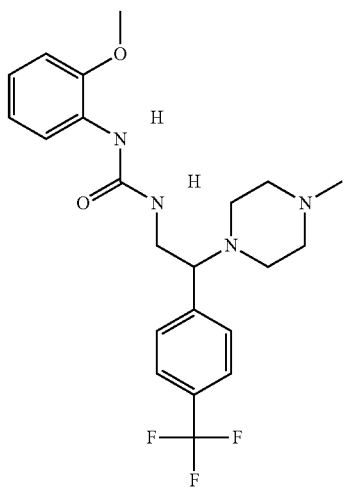
CCLXVIII
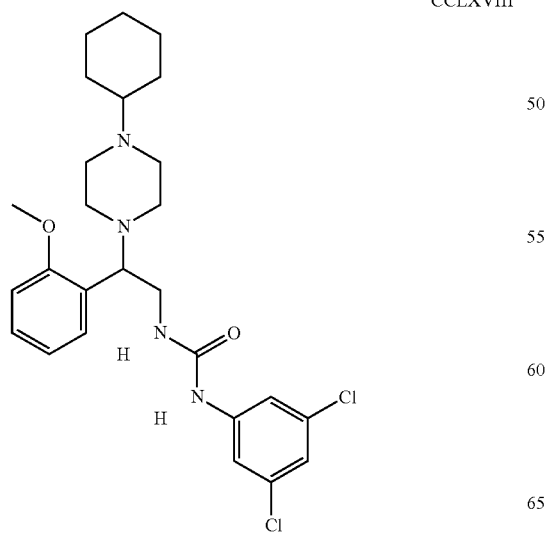
CCLXXI
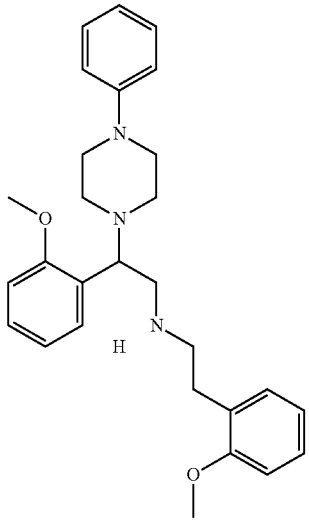

CCLXXII
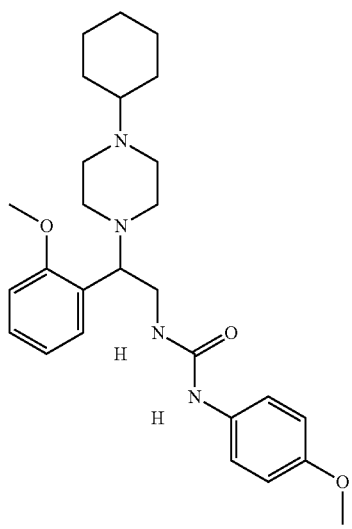
CCLXXIII
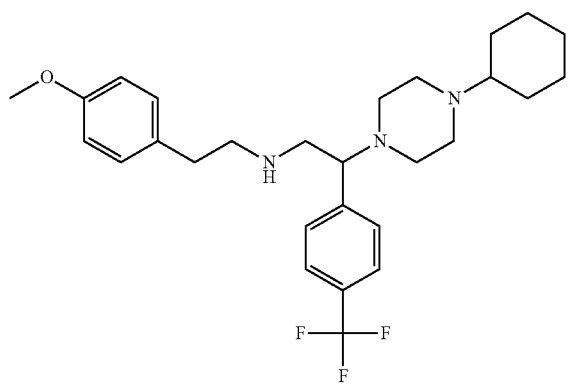
CCLXXIV
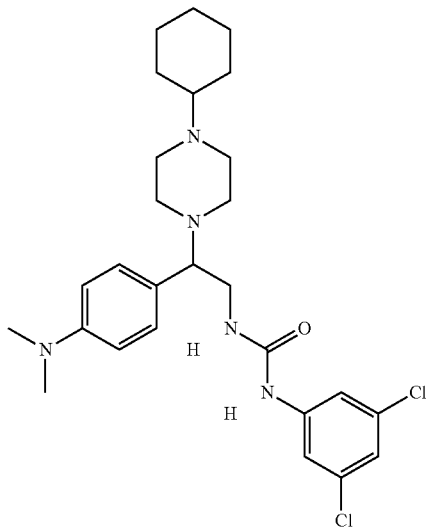
CCLXXV
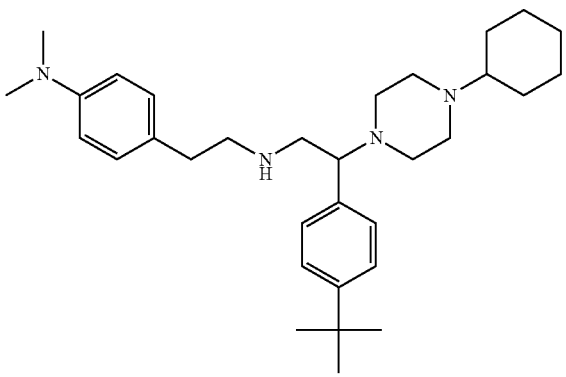
CCLXXVI
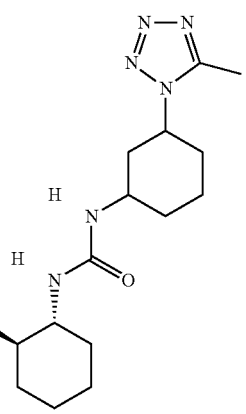
CCLXXVII
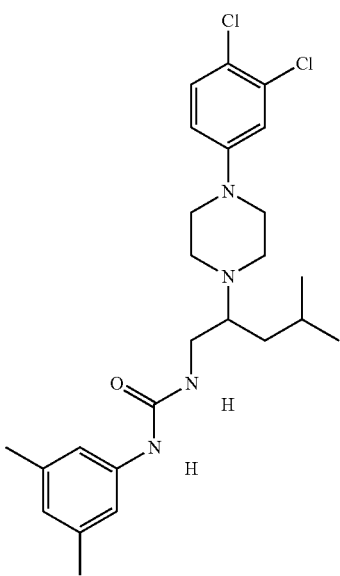

CCLXXVIII
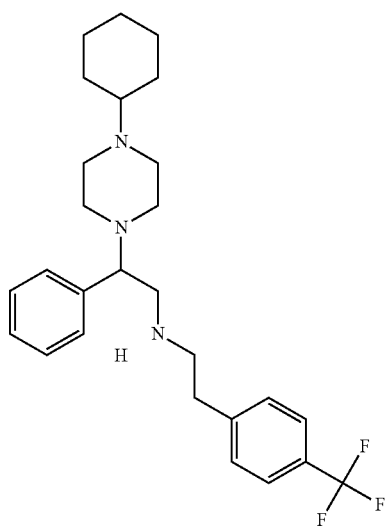
CCLXXXI
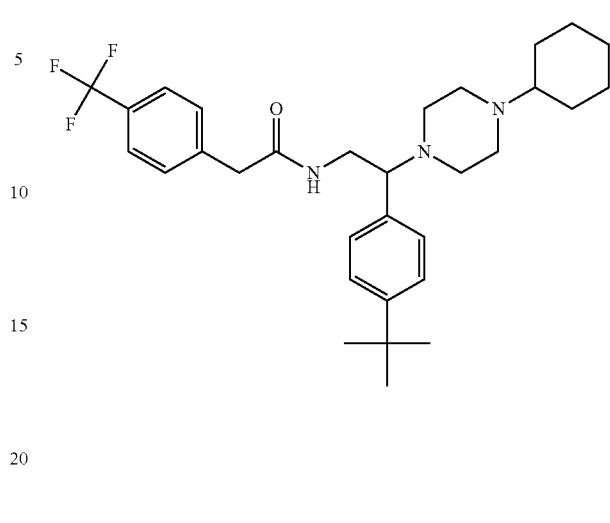
CCLXXIX
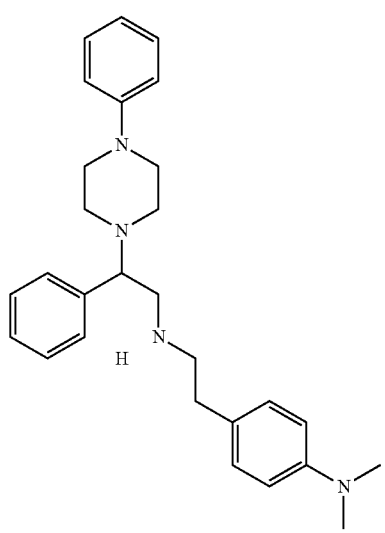
CCLXXXII
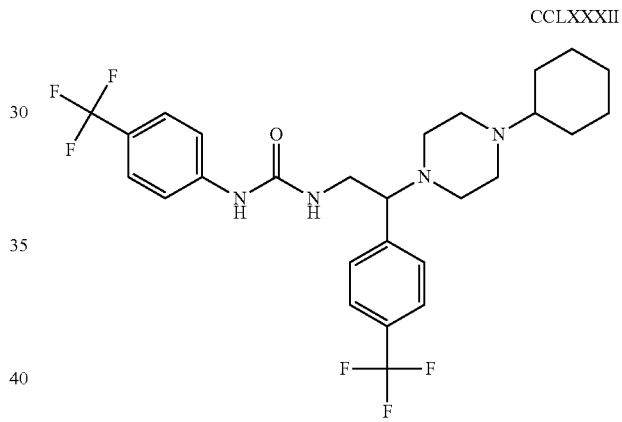
CCLXXX
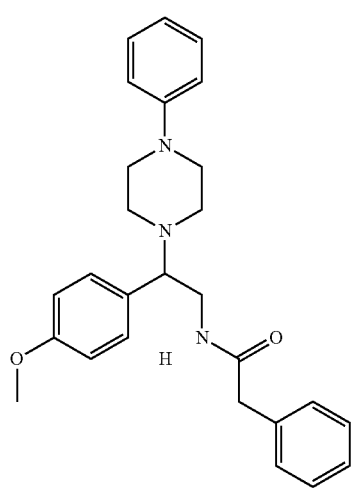
CCLXXXIII
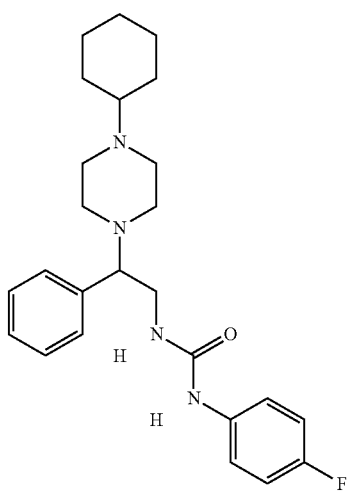

CCLXXXIV
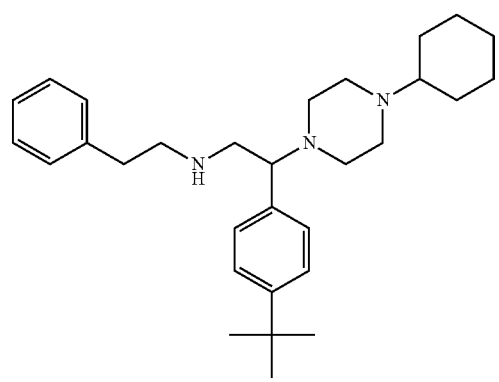
CCLXXXV
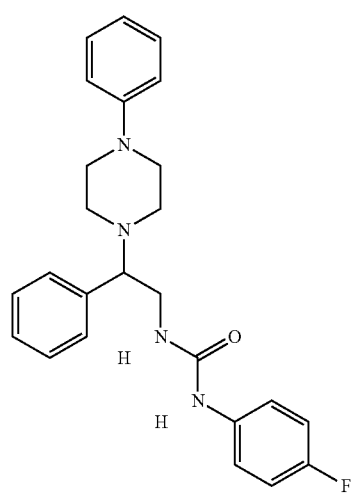
CCLXXXVI
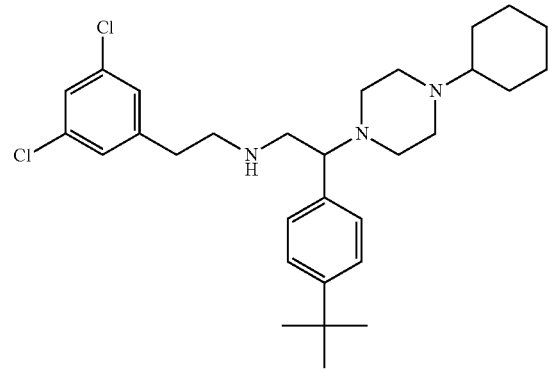
CCLXXXVII
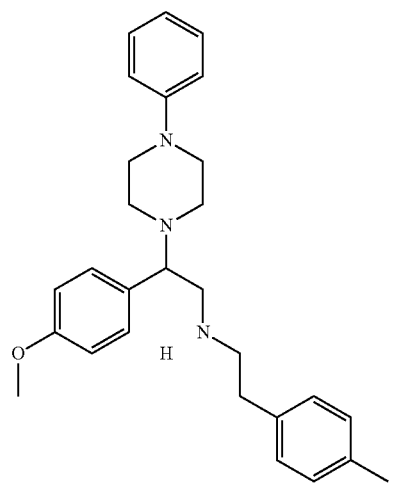
CCLXXXVIII
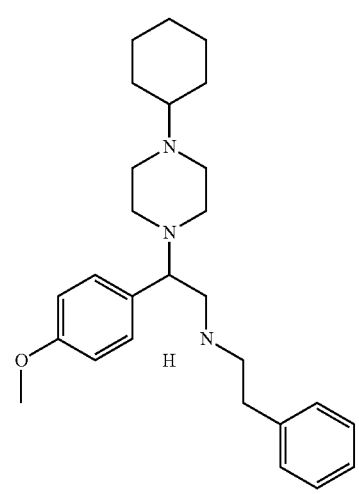
CCLXXXIX
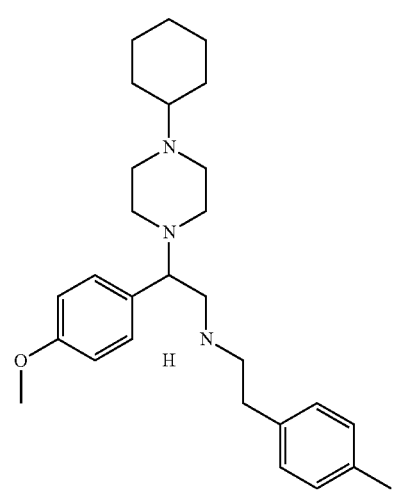

CCXC
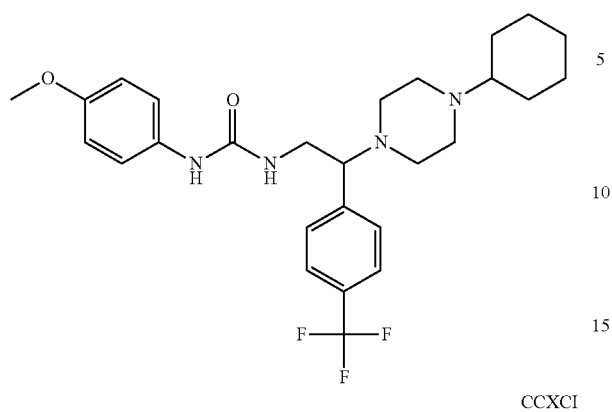
CCXCI
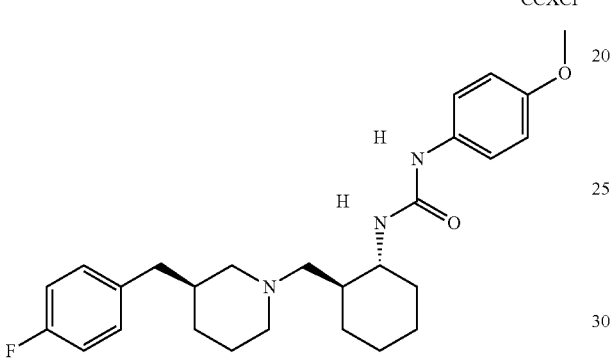
CCXCII
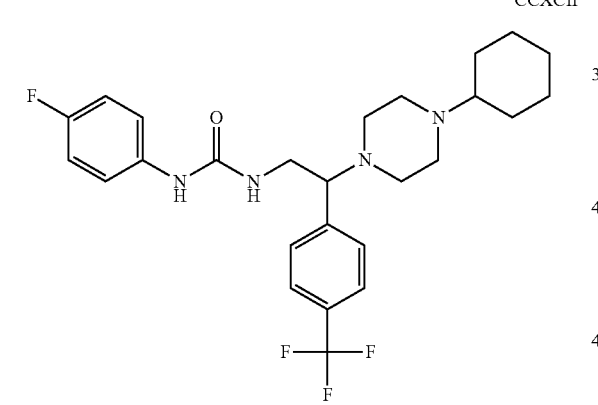
CCXCIII
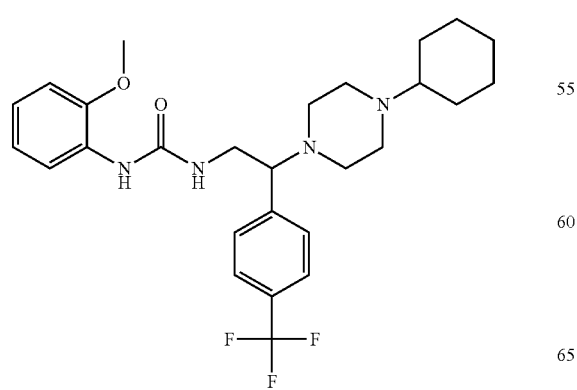
CCXCIV
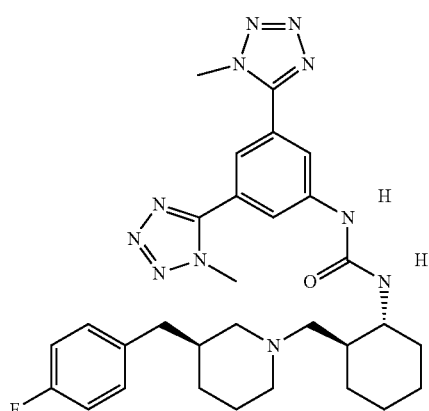
CCXCV
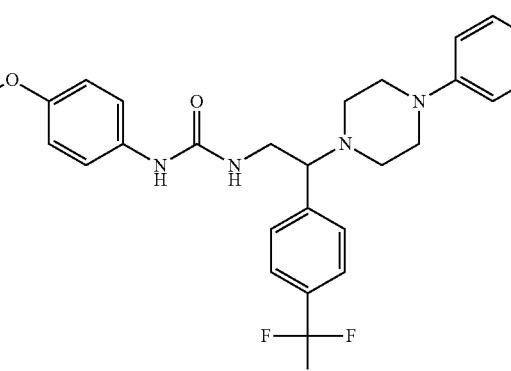
CCXCVI
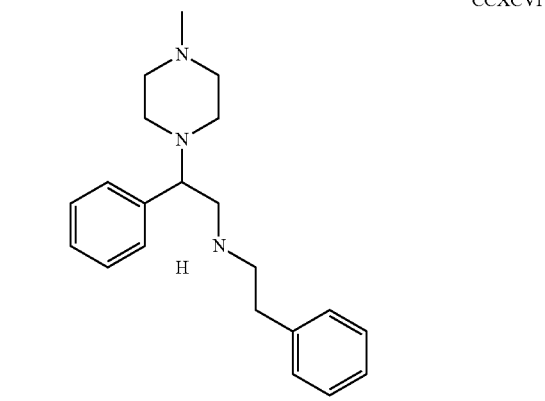
CCXCVII
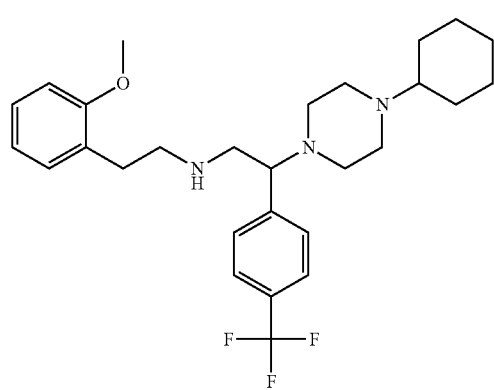

CCXCVIII
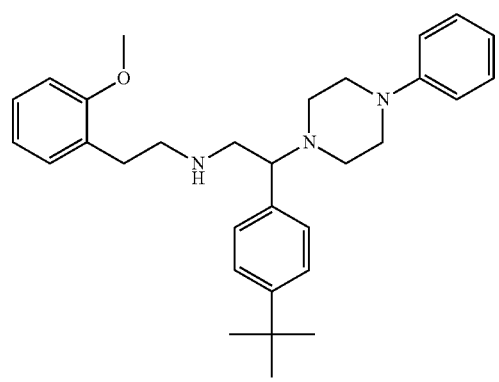
CCXCIX
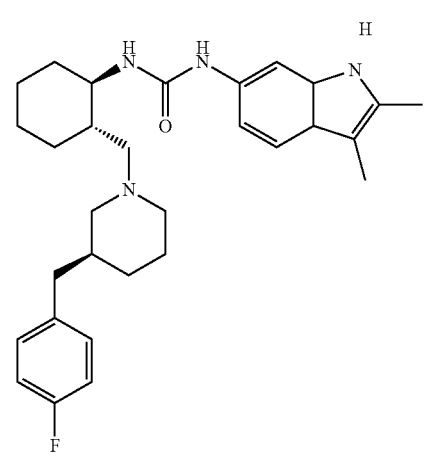
CCC
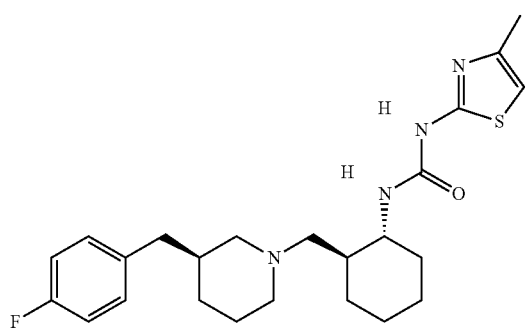
CCCI
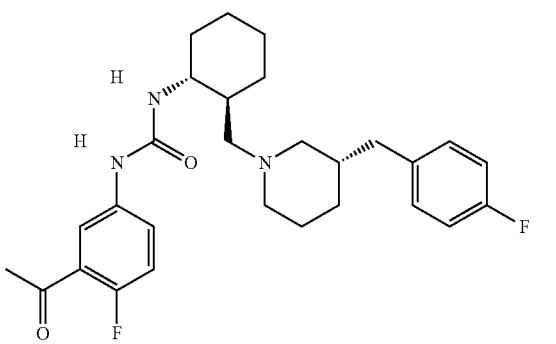
CCCII
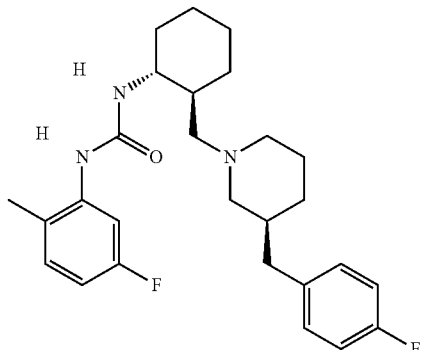
CCCIII
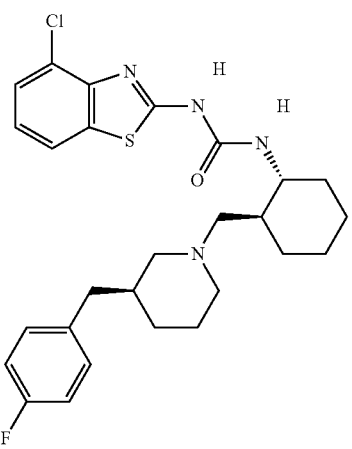
CCCIV
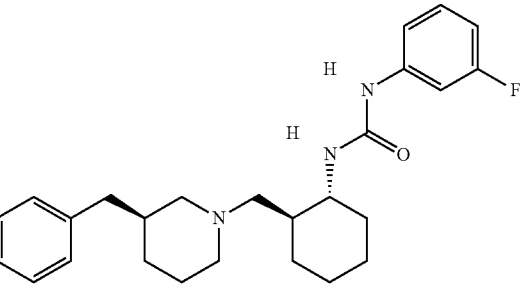
CCCV
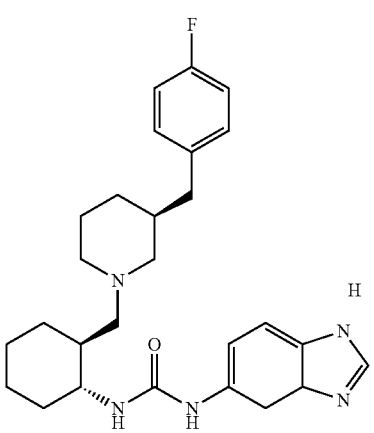

101
-continued
CCCVI
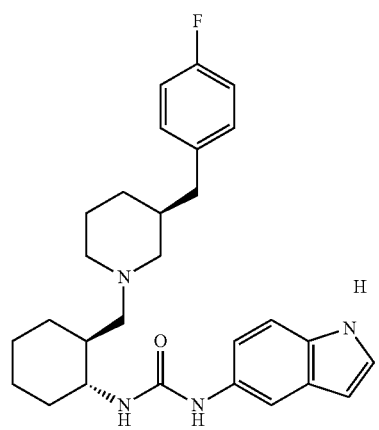
CCCVII
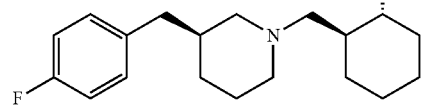
CCCVIII
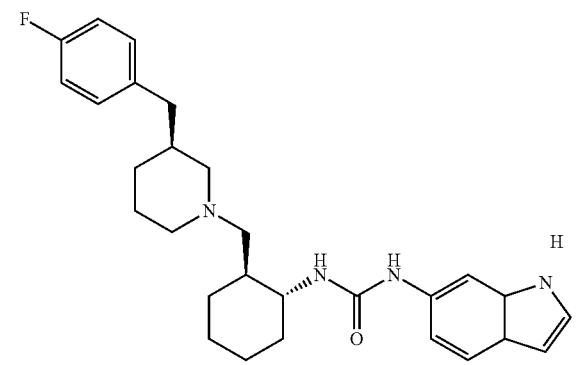
CCCIX
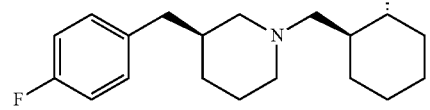
102
-continued
CCCX
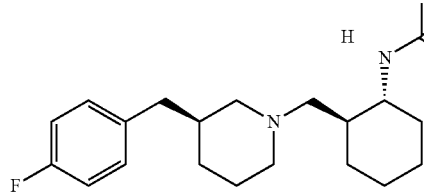
CCCXI
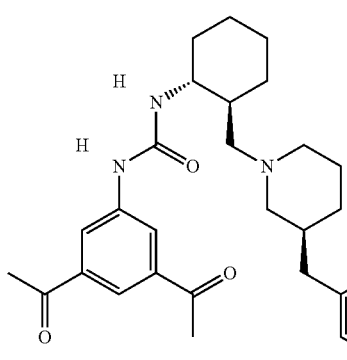
CCCXII
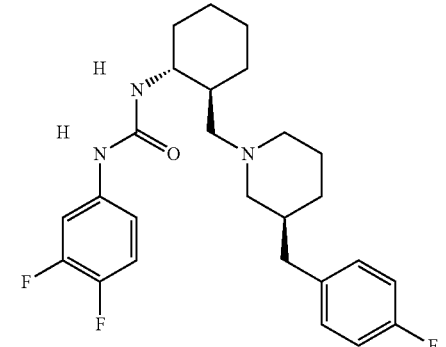
CCCXIII
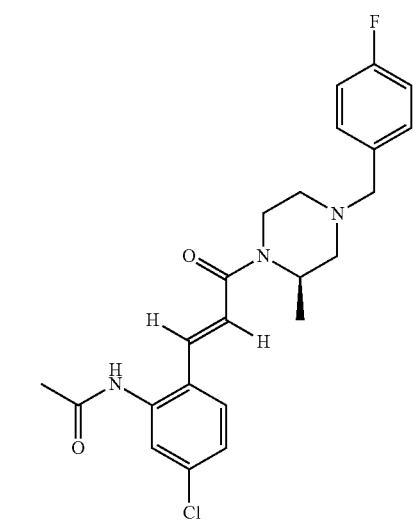

CCCXIV
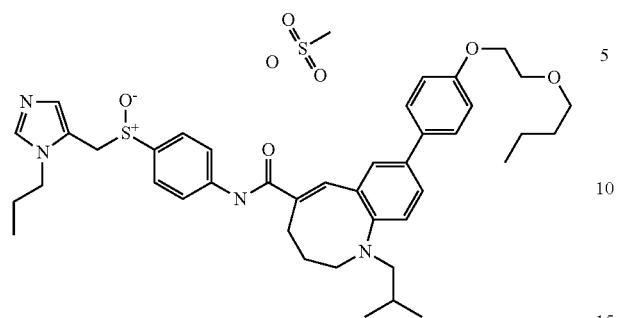
CCCXVIII
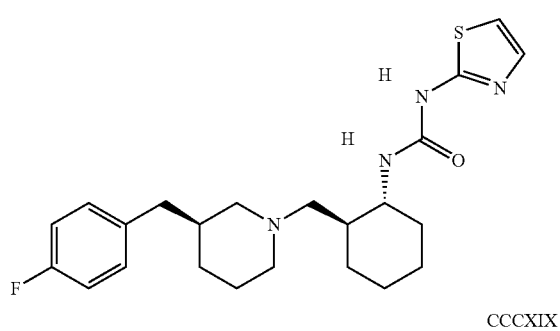
CCCXV
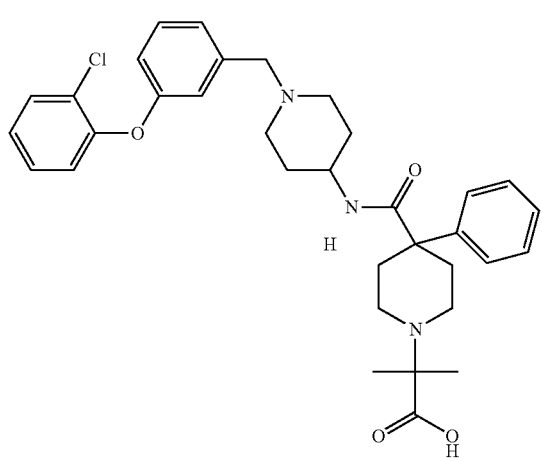
CCCXIX
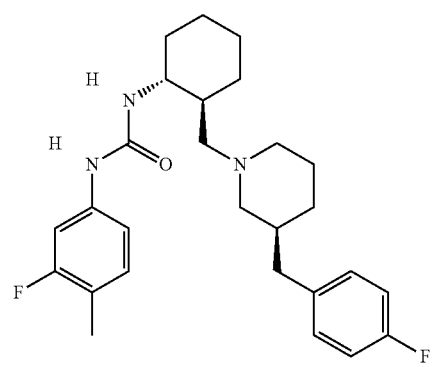
CCCXX
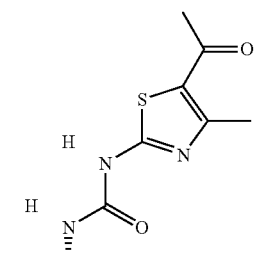
CCCXVI
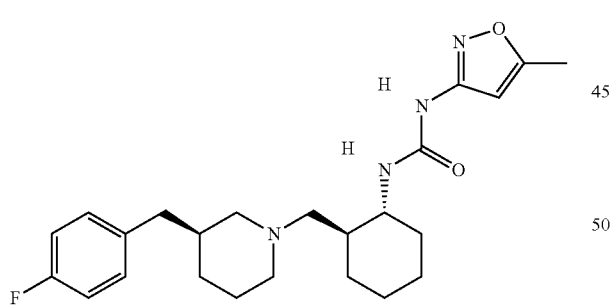
CCCXXI
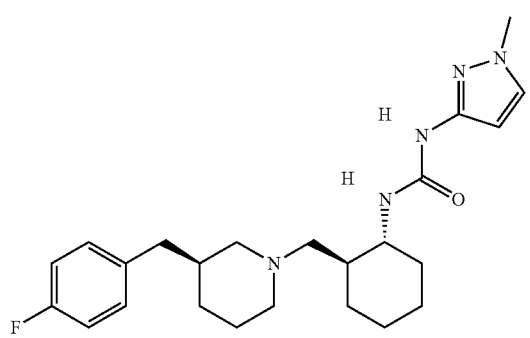
CCCXVII
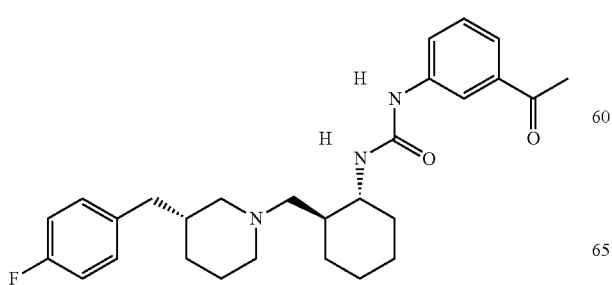

CCCXXII
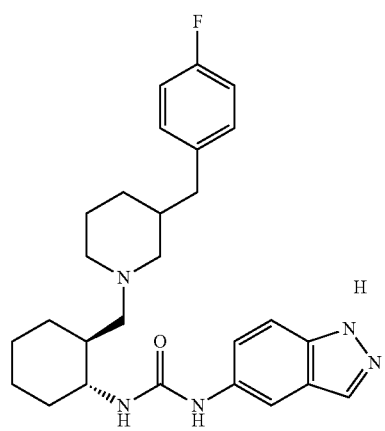
CCCXXV
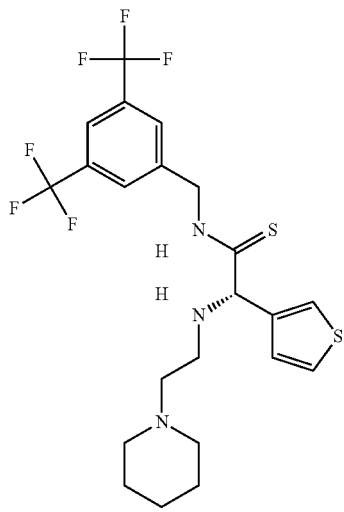
CCCXXIII
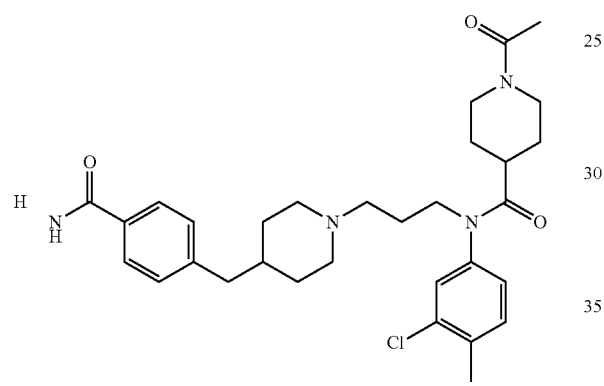
CCCXXIV
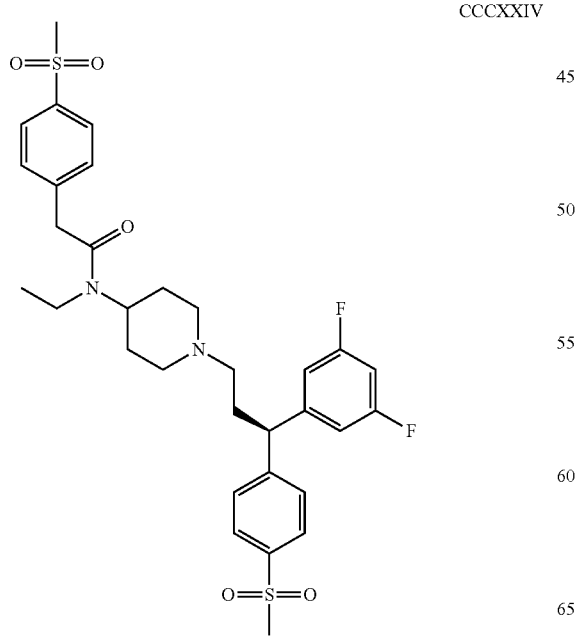
CCCXXVI
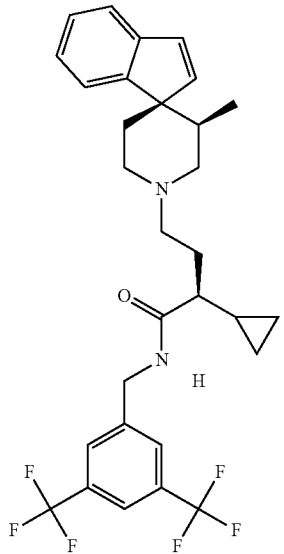

CCCXXVII
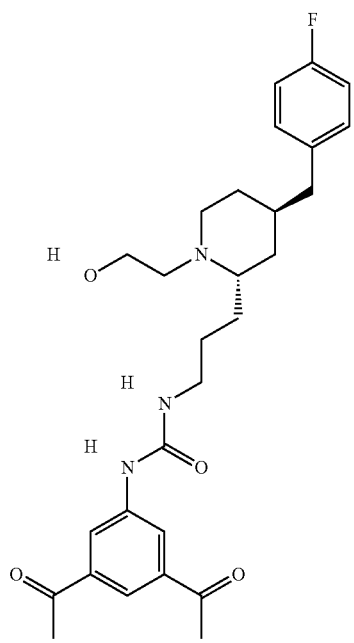
CCCXXVIII
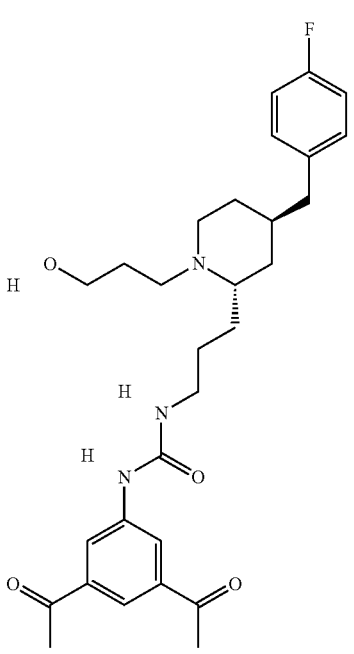
CCCXXIX
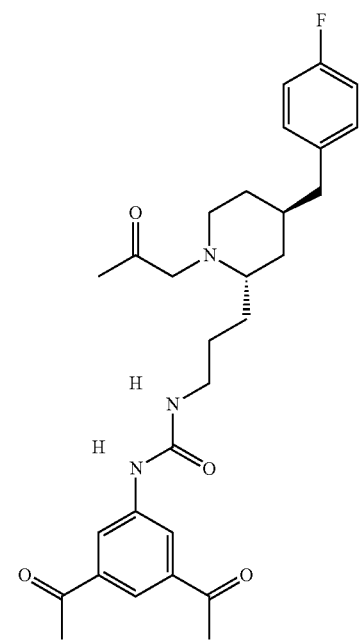
CCCXXX
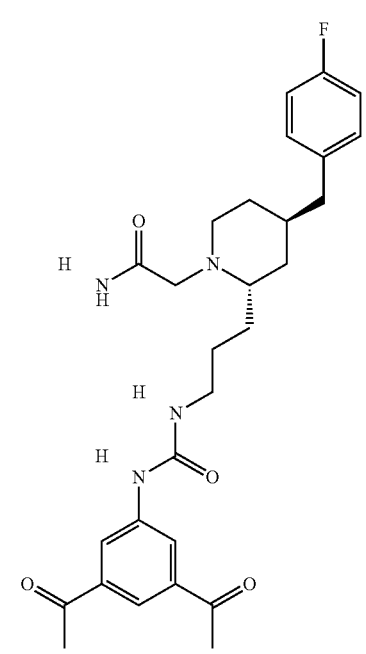

CCCXXXI
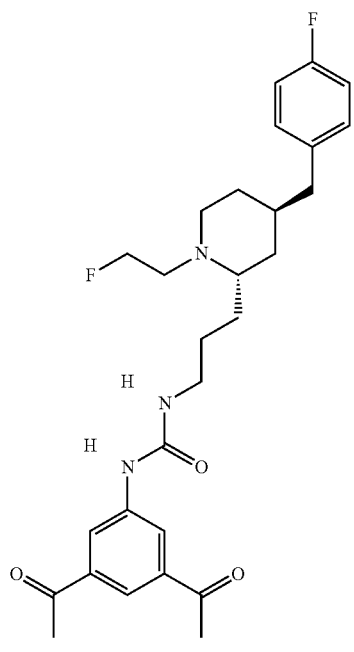
CCCXXXIII
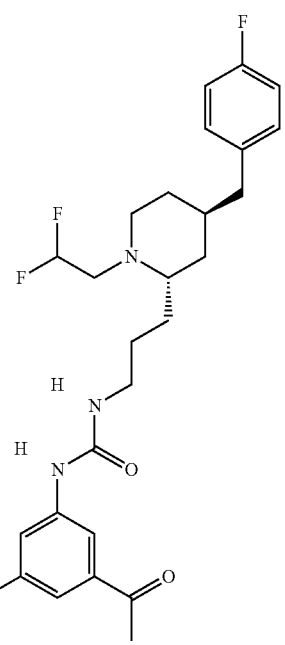
CCCXXXII
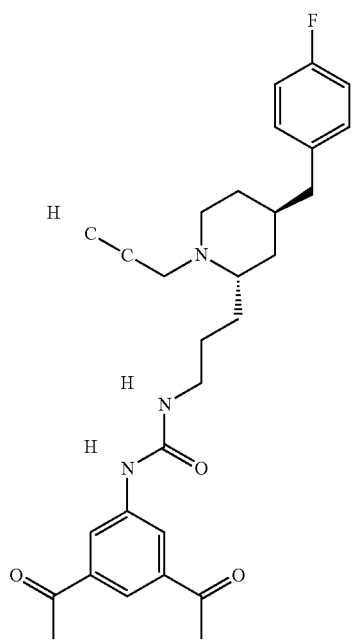
CCCXXXIV
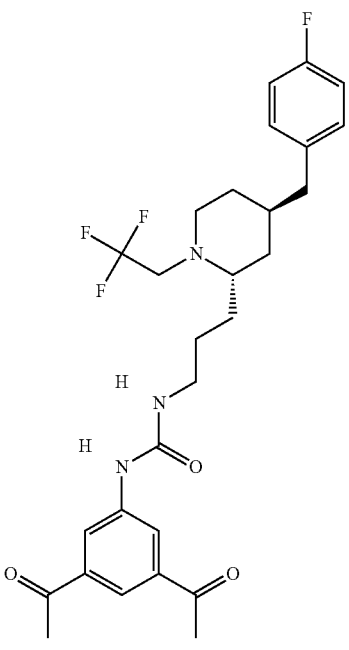

CCCXXXV
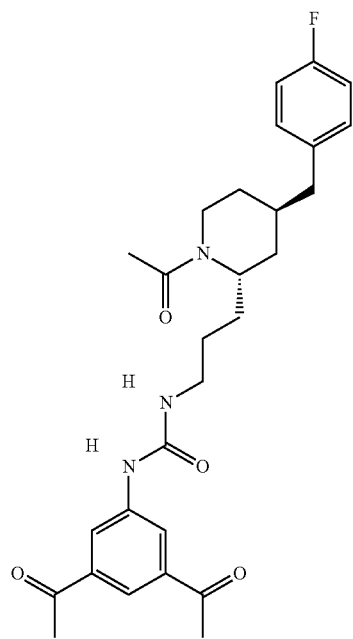
CCCXXXVI
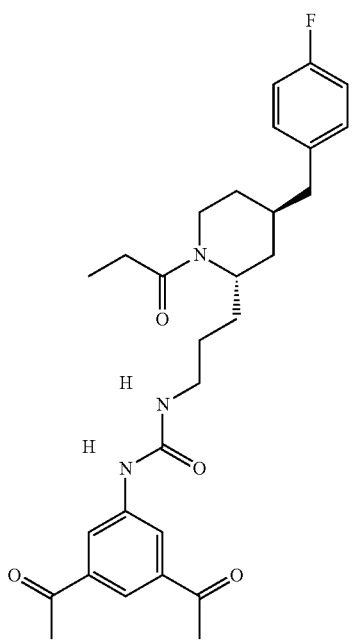
CCCXXXVII
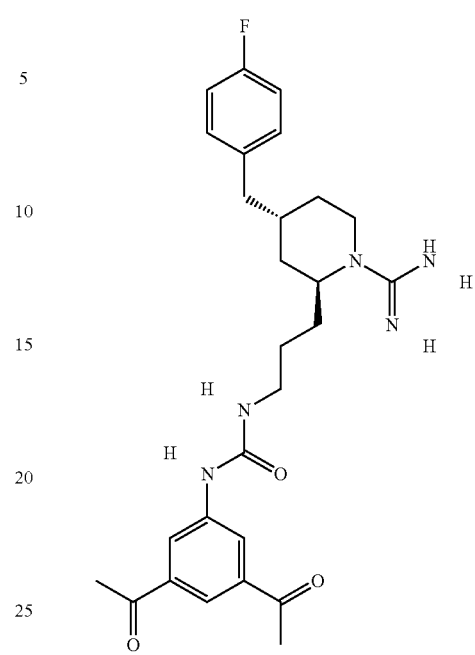
CCCXXXVIII
CCCXXXIX
CCCXL
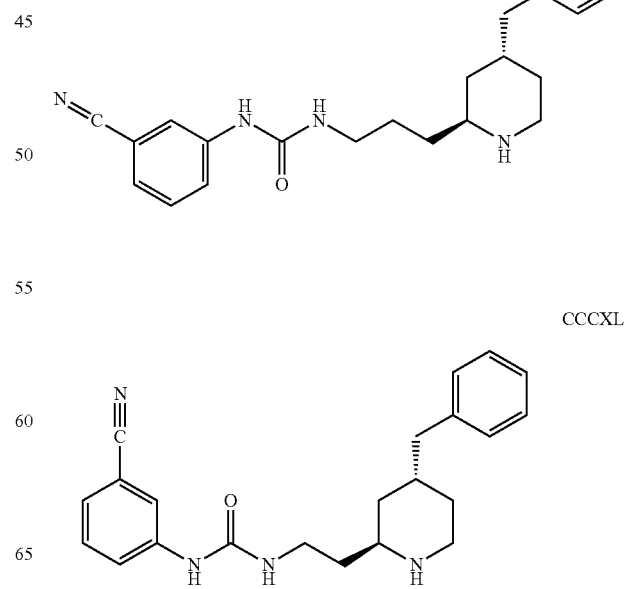

CCCXLI
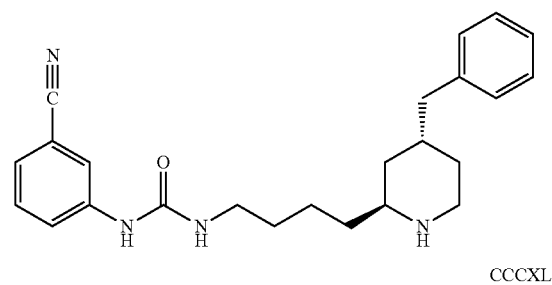
CCCXLII
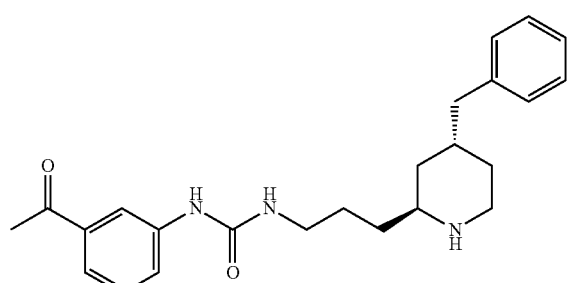
CCCXLIII
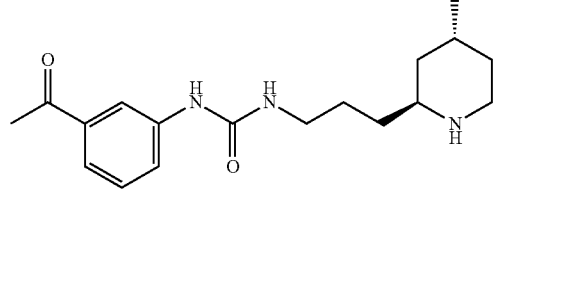
CCCXLIV
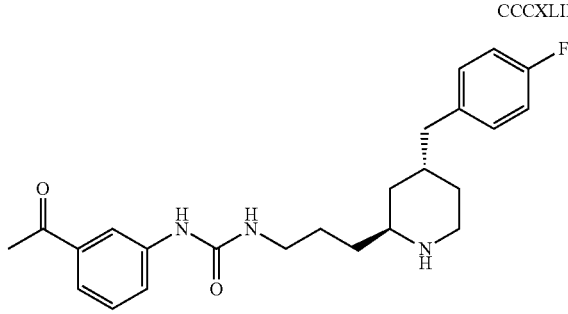
CCCXLV
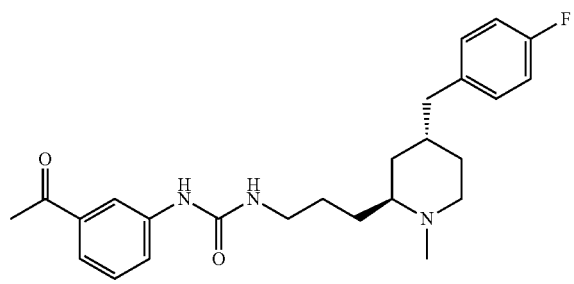
CCCXLVI
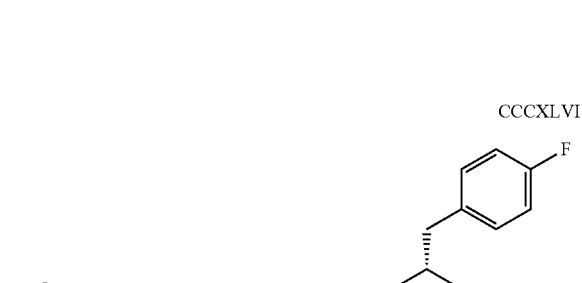
CCCXLVII
CCCXLVII
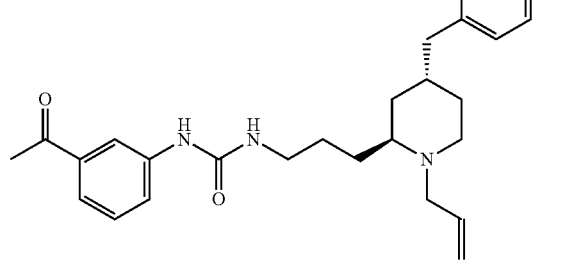

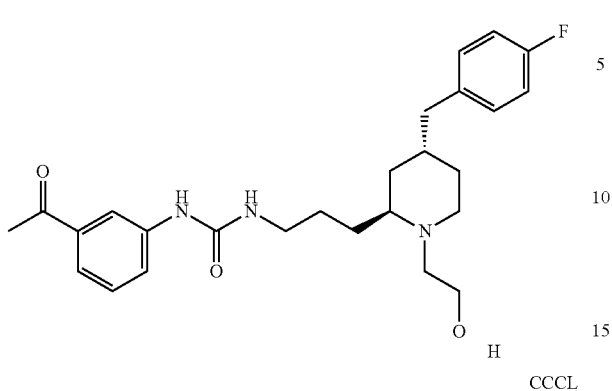
CCCXLIX
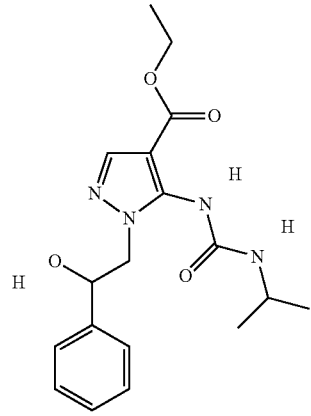
CCCLII
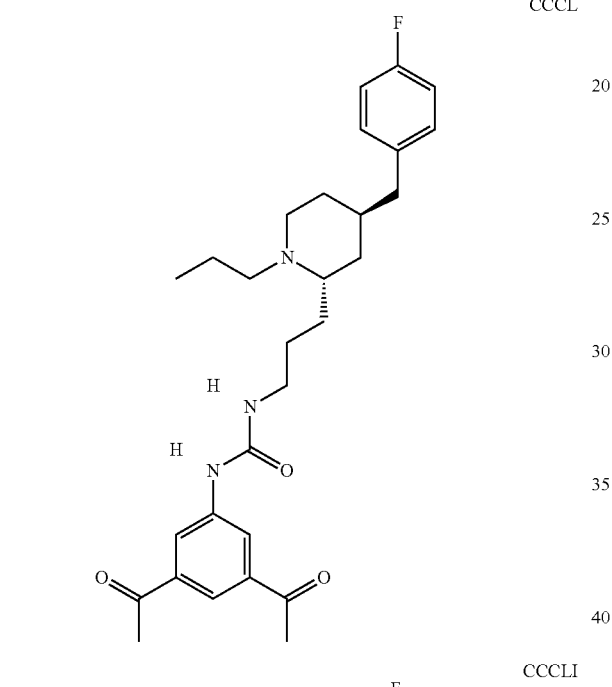
CCCL
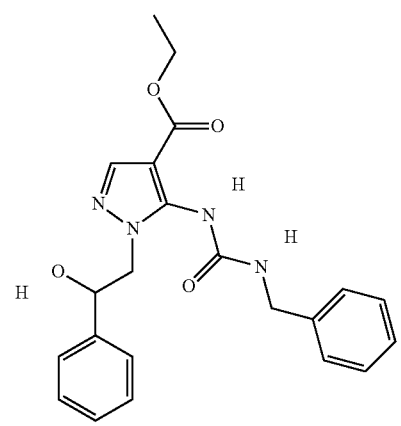
CCCLIII
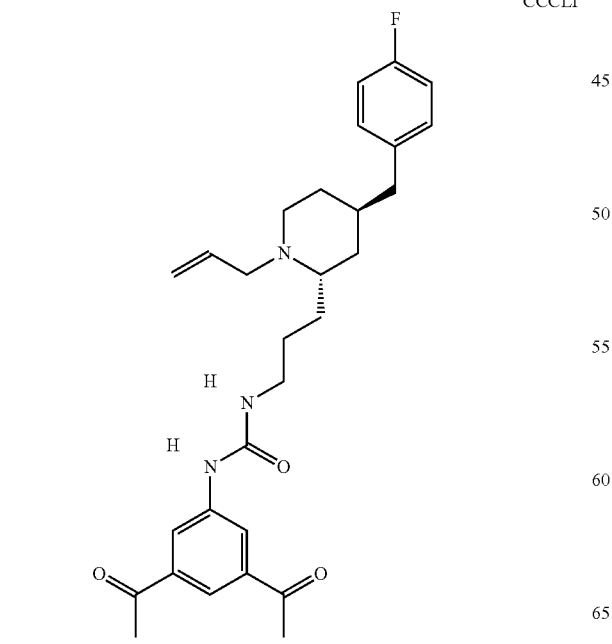
CCCLI
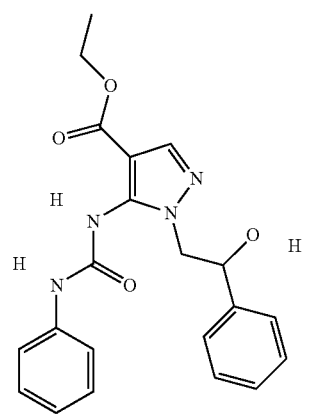
CCCLIV CCCLV
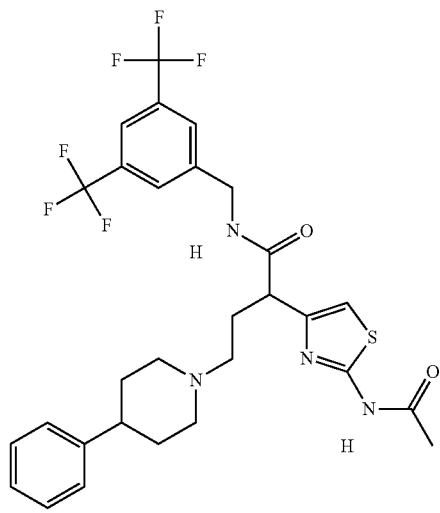
CCCLVI
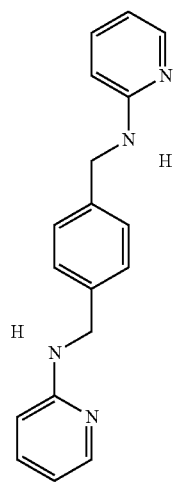
CCCLVII
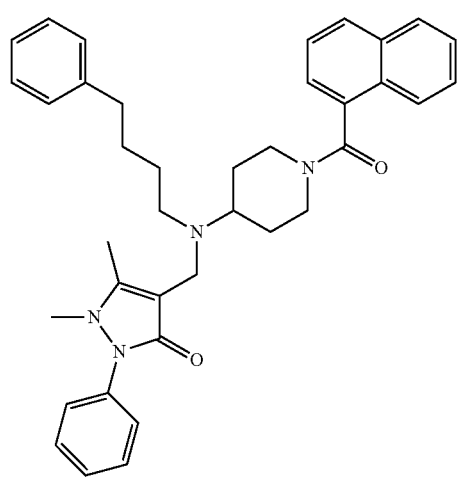
CCCLVIII
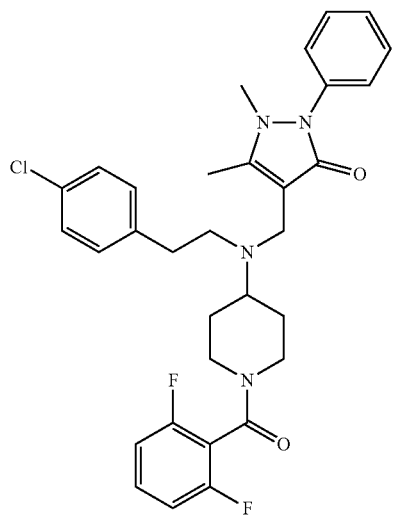
CCCLIX
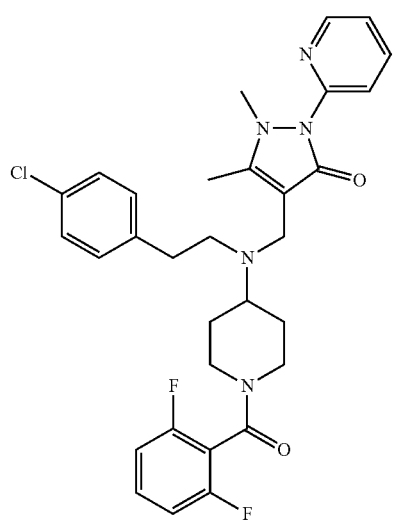
CCCLX
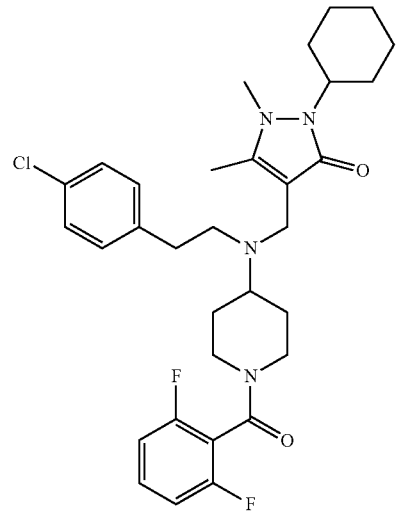

CCCLXI
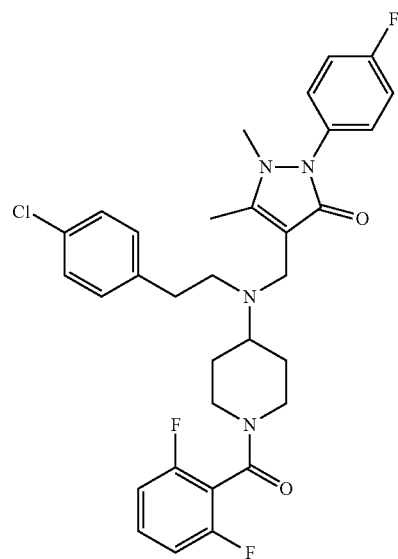
CCCLXII
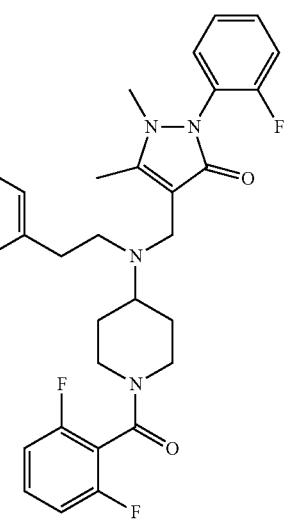
CCCLXIII
CCCLXIV
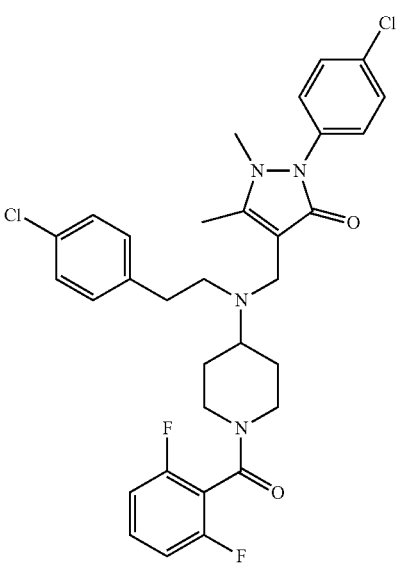
CCCLXV
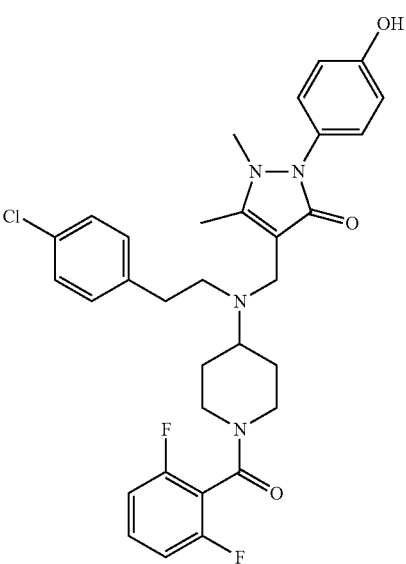

CCCLXVI
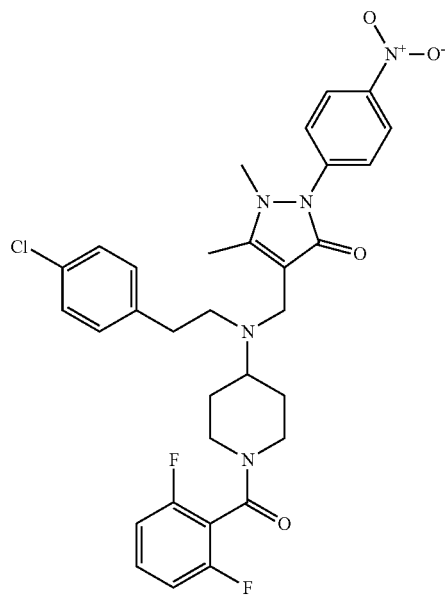
CCCLXVII
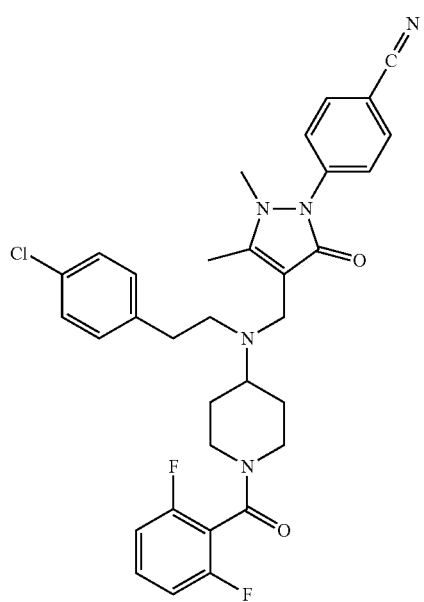
CCCLXVIII
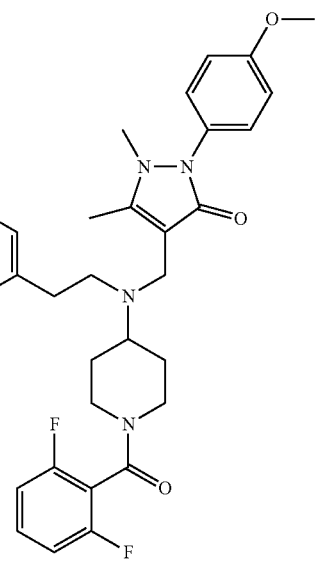
CCCLXIX
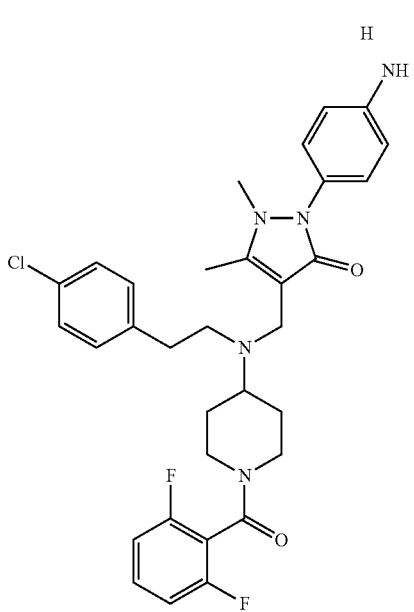

-continued
CCCLXX
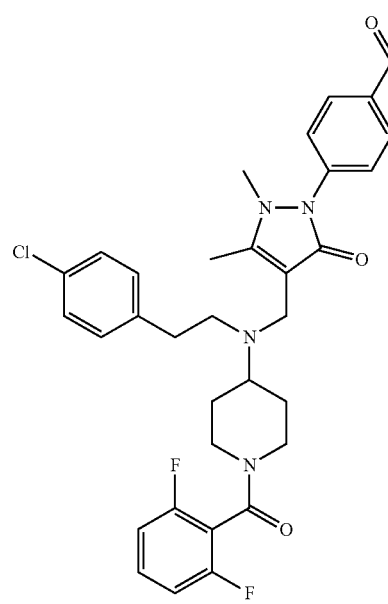
CCCLXXI
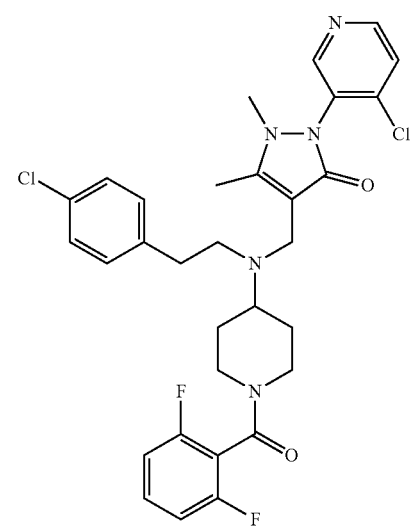
-continued
CCCLXXII
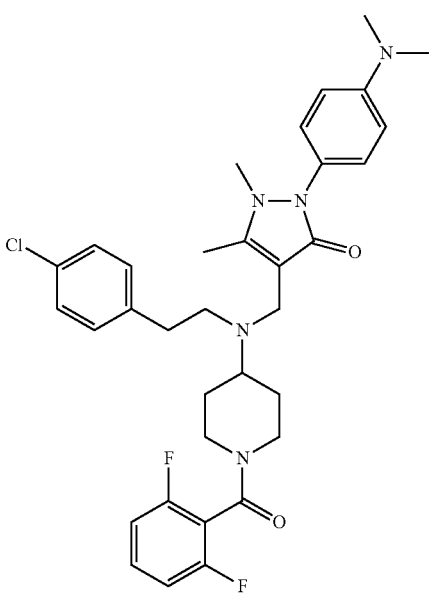
CCCLXXIII
CCCLXXIV CCCLXXV
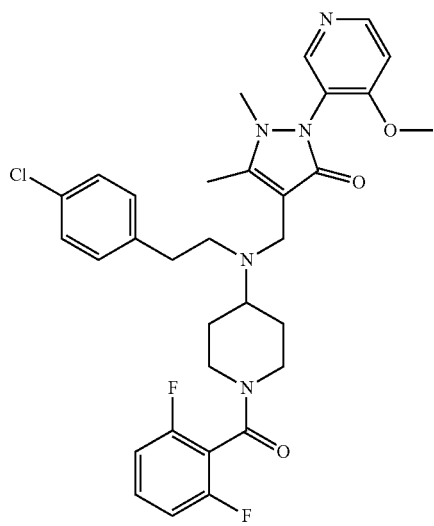
CCCLXXVIII
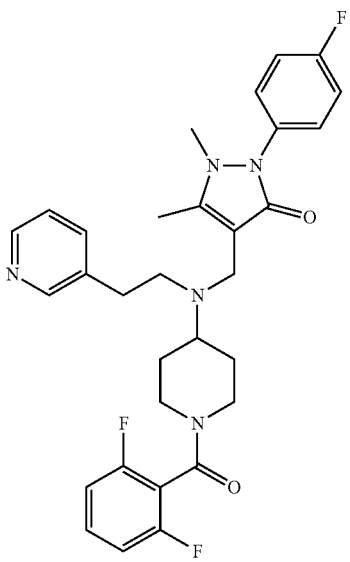
CCCLXXVI
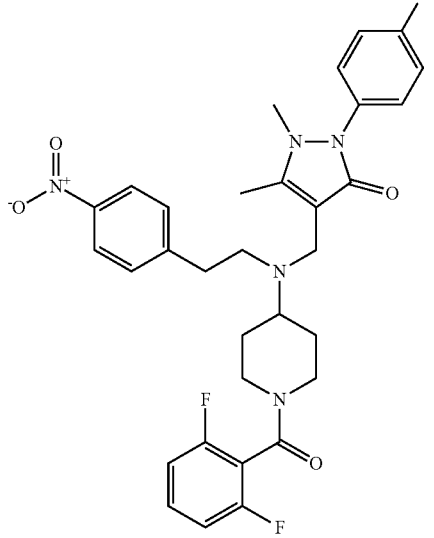
CCCLXXVII
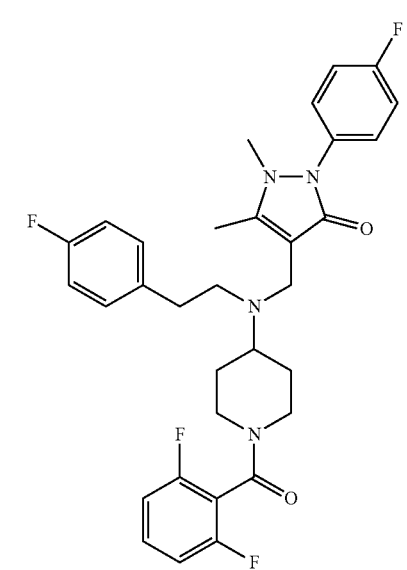
CCCLXXIX
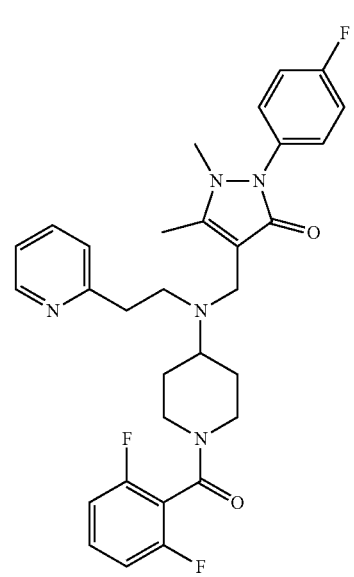

127
-continued
CCCLXXX
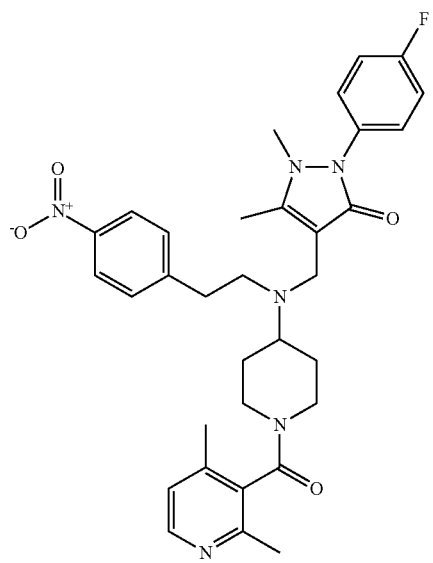
128
-continued
CCCLXXXII
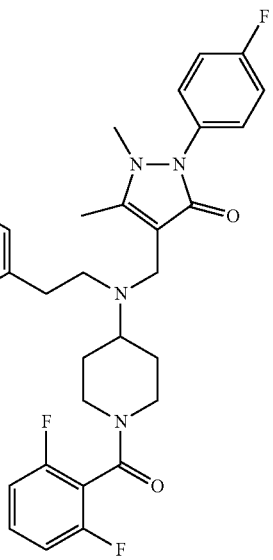
CCCLXXXI
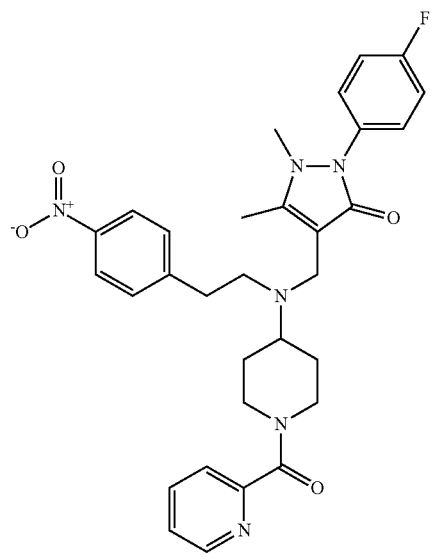
CCCLXXXIII
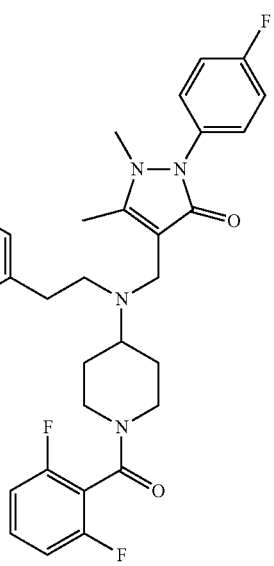

129
-continued
CCCLXXXIV
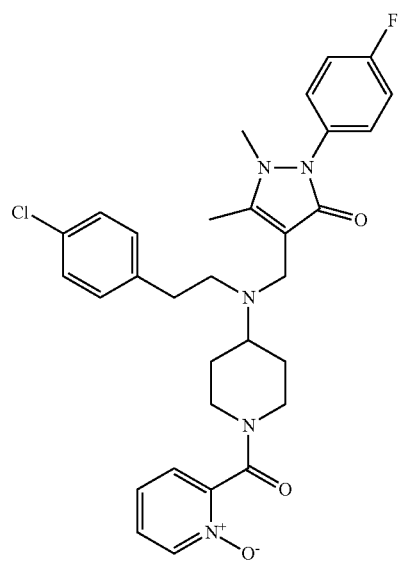
130
-continued
CCCLXXXVI
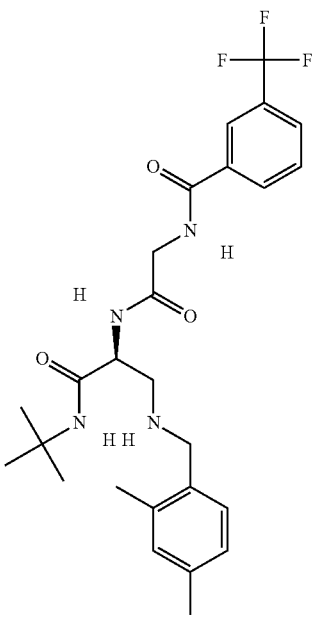
CCCLXXXV
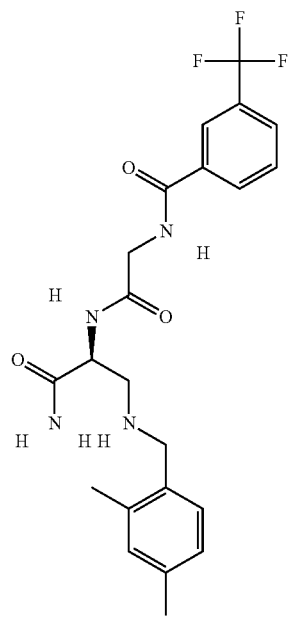
CCCLXXXVII
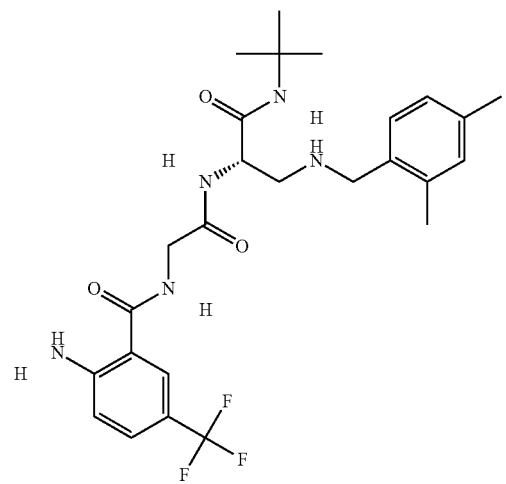

-continued
CCCLXXXVIII
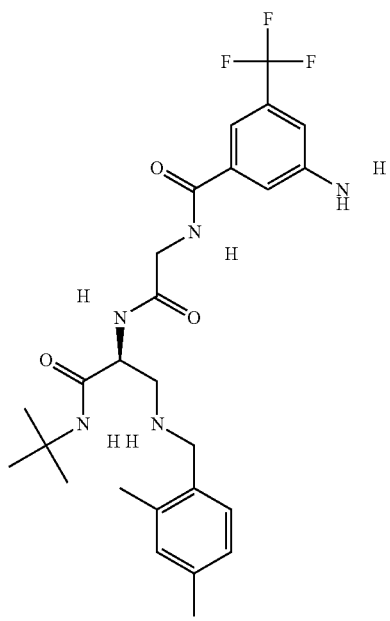
CCCLXXXIX
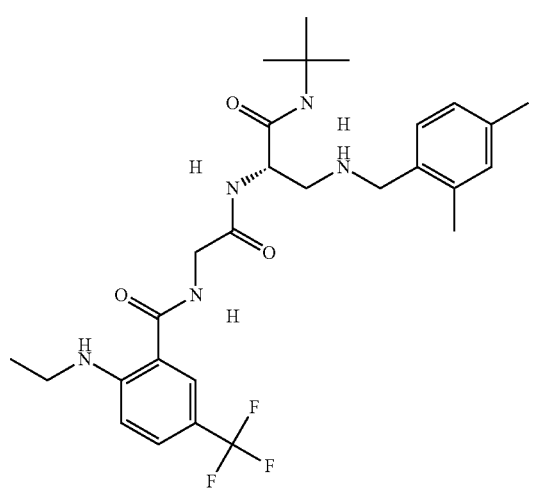
CCCXC
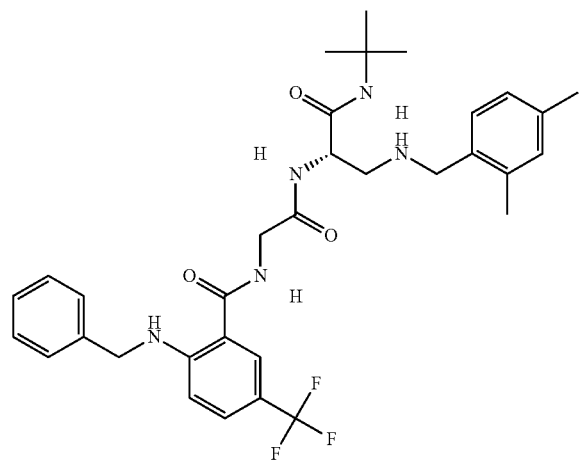
-continued
CCCXCI
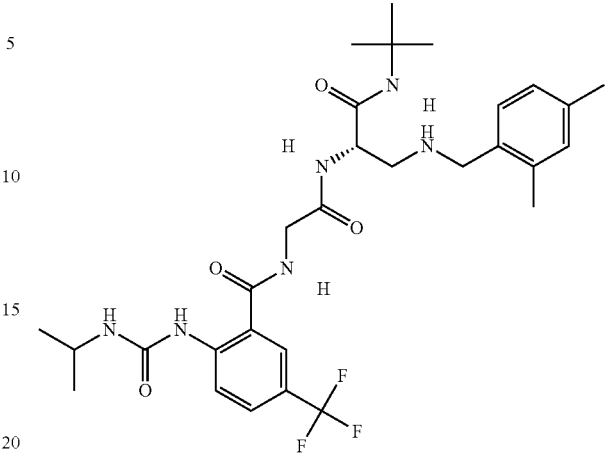
CCCXCII
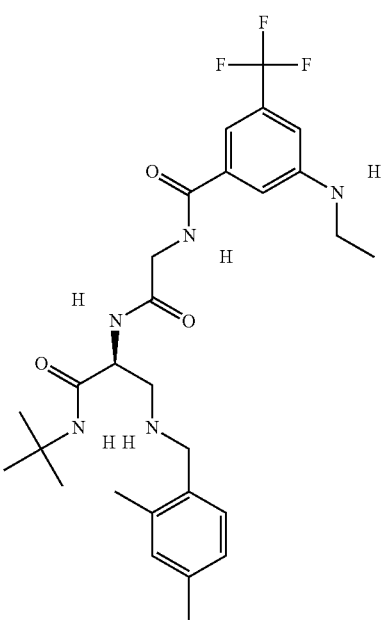
CCCXCIII
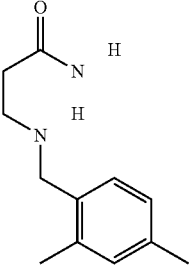

CCCXCIV
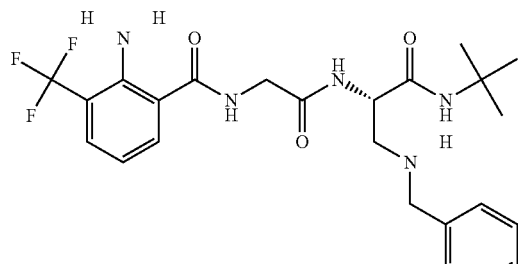
CCCXCVIII
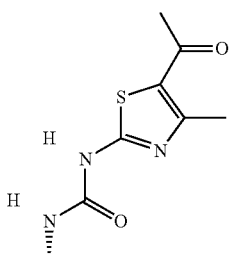
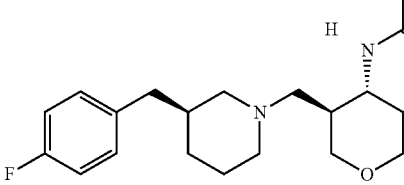
CCCXCV
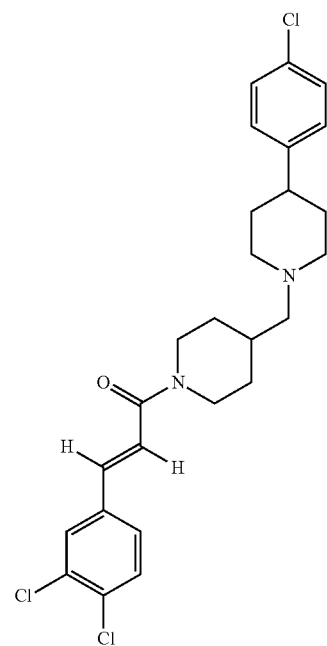
CCCXCIX
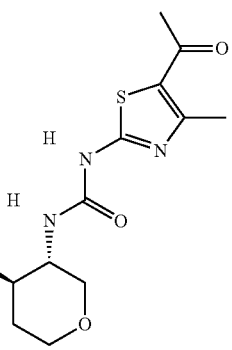
CCCXCVI
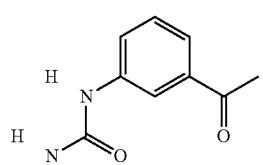
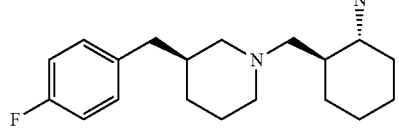
CD
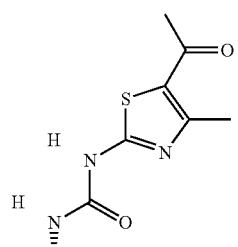
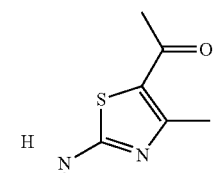
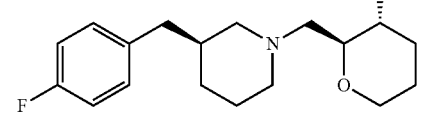
CCCXCVII

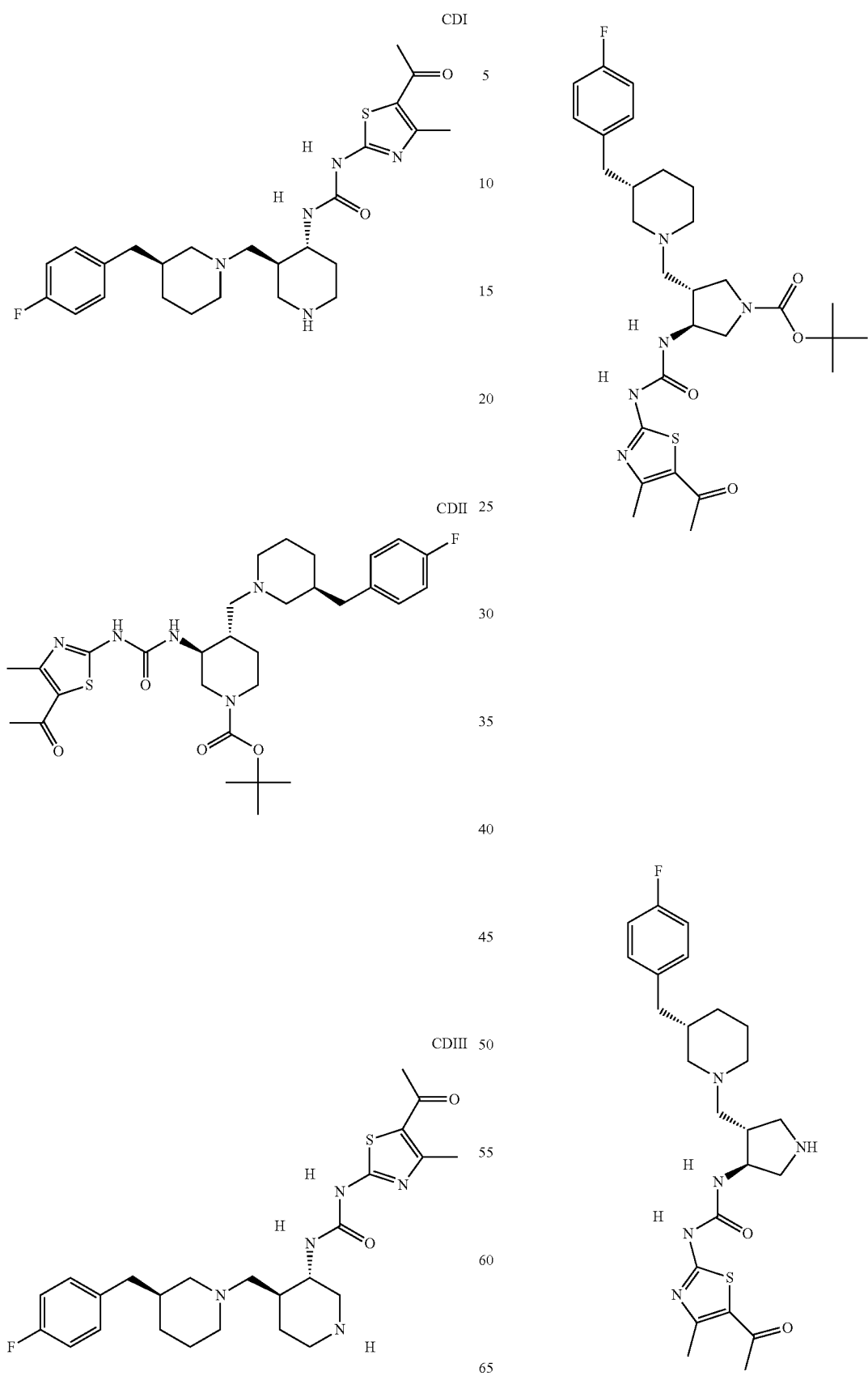

137
-continued
CDVI
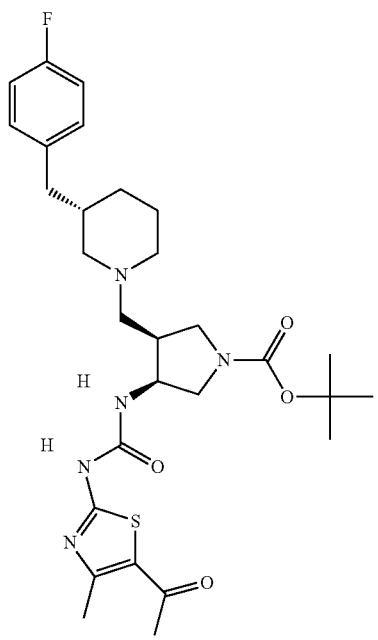
138
-continued
CDVIII
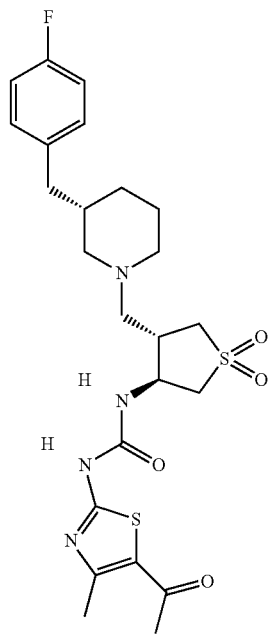
CDIX
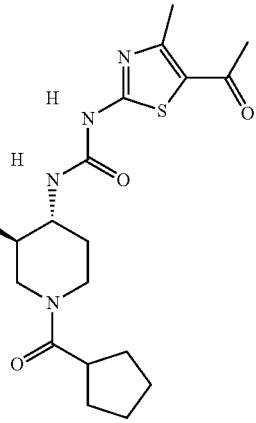
CDVII
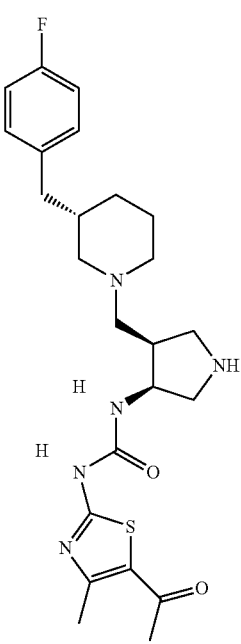
CDX CDXI
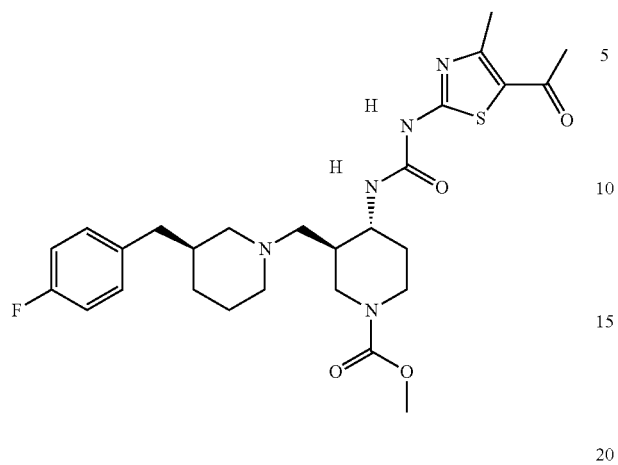
CDXIV
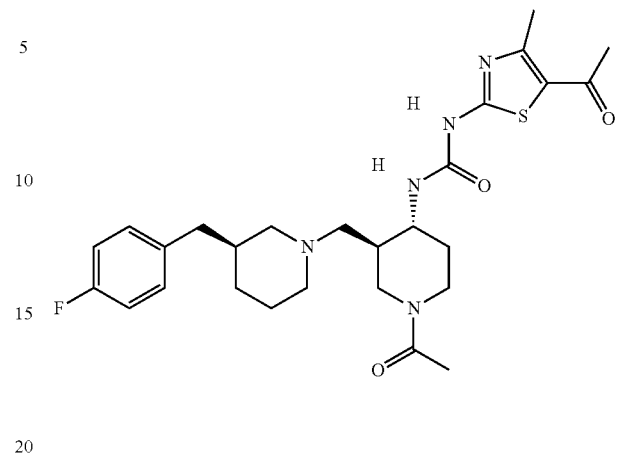
CDXII
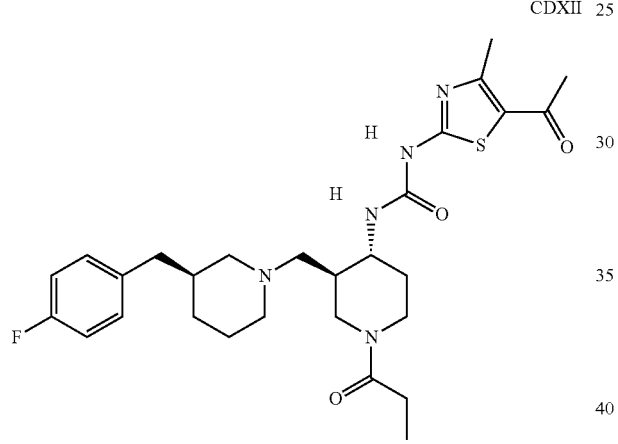
CDXV
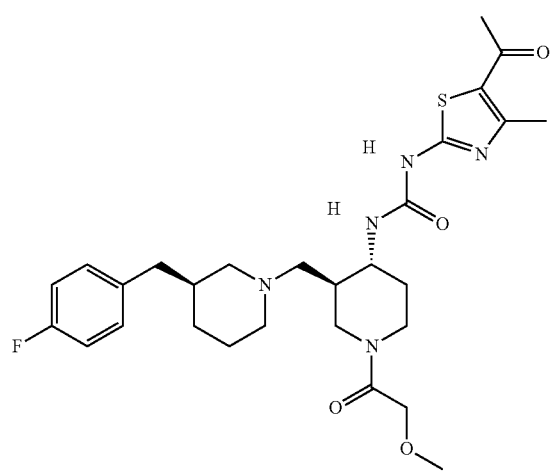
CDXIII
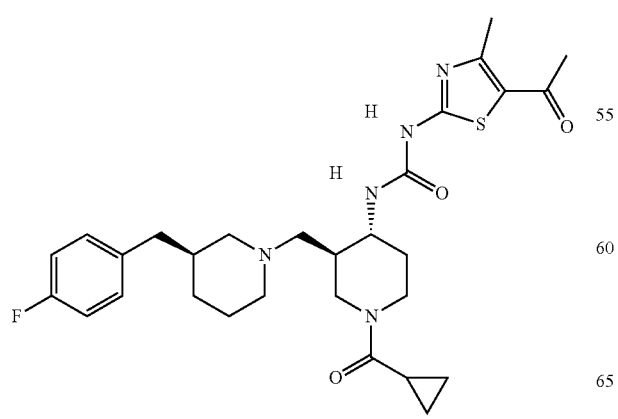
CDXVI
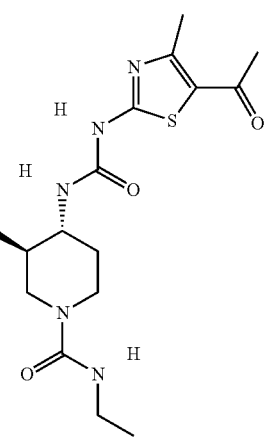

CDXVII
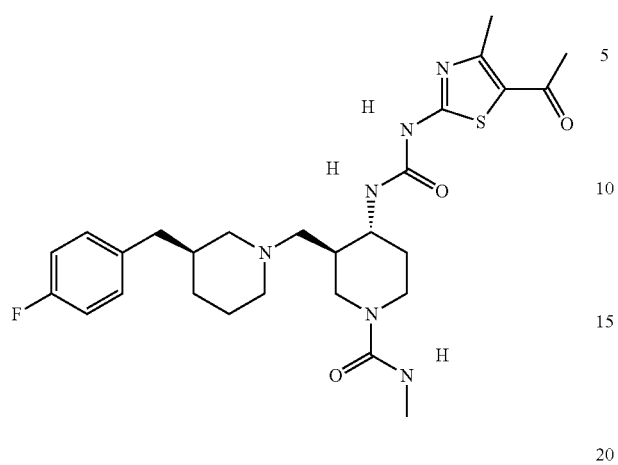
CDXX
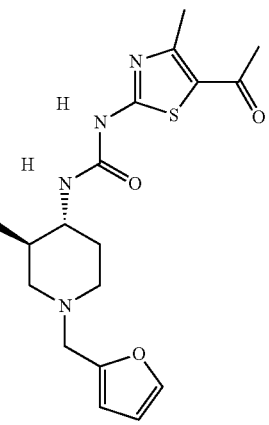
CDXVIII
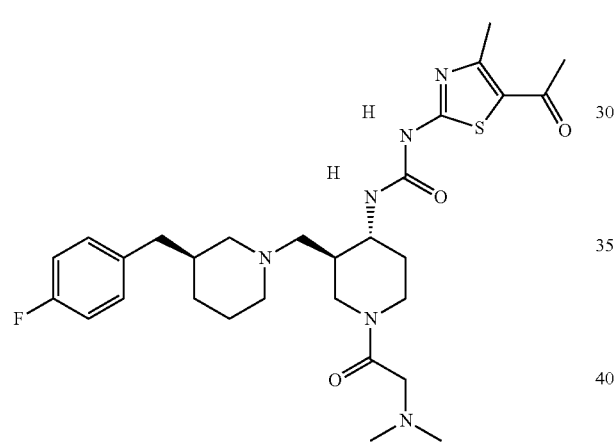
CDXXI
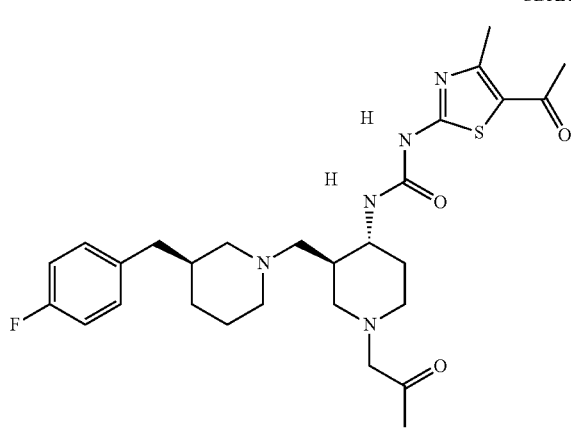
CDXIX
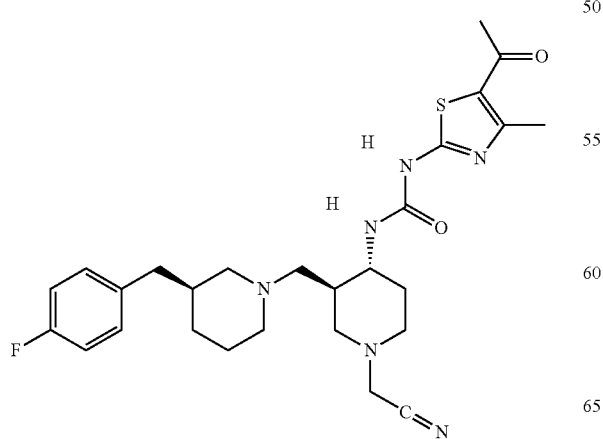
CDXXII
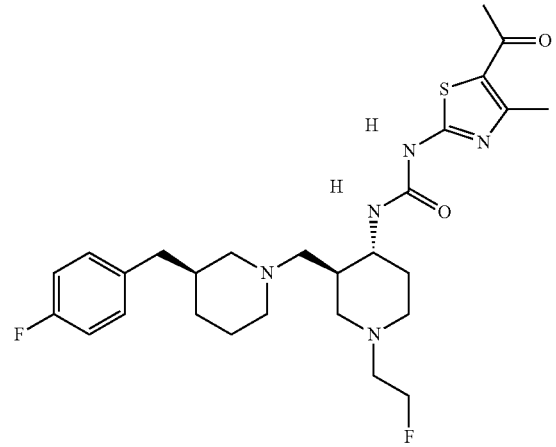

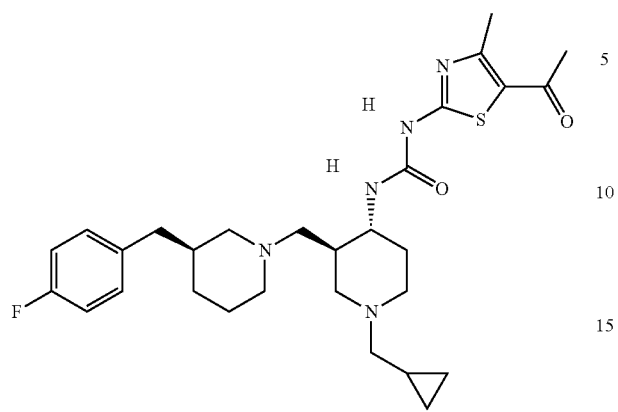
CDXXIII
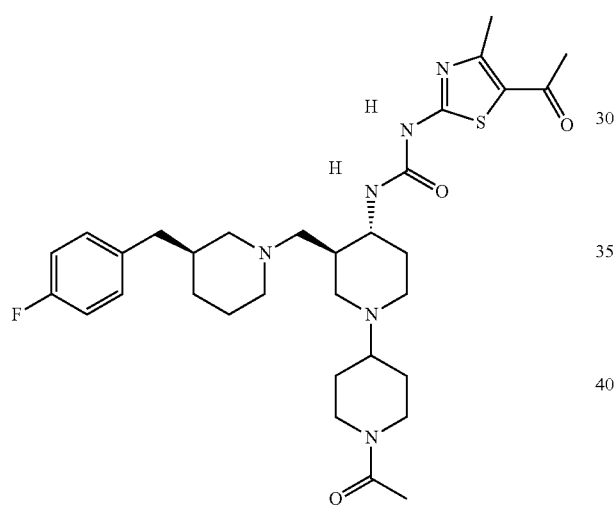
CDXXIV
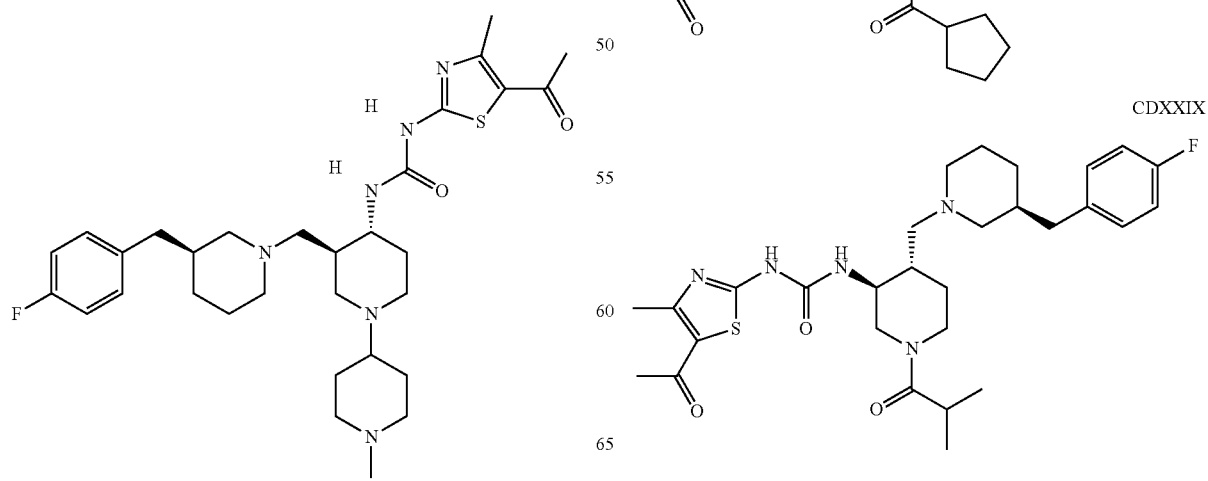
CDXXV
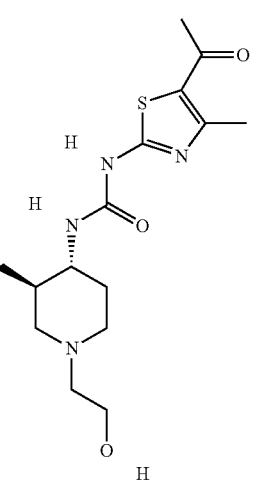
CDXXVI
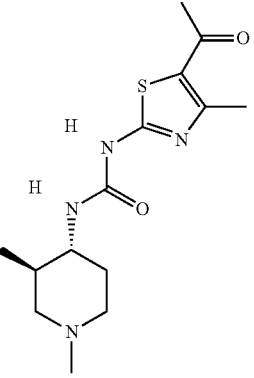
CDXXVII
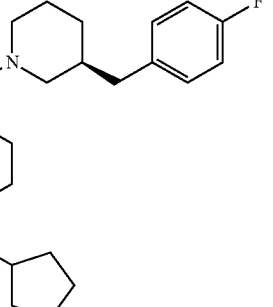
CDXXVIII
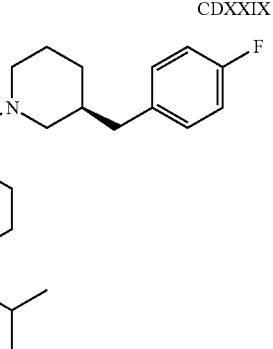
CDXXIX CDXXX
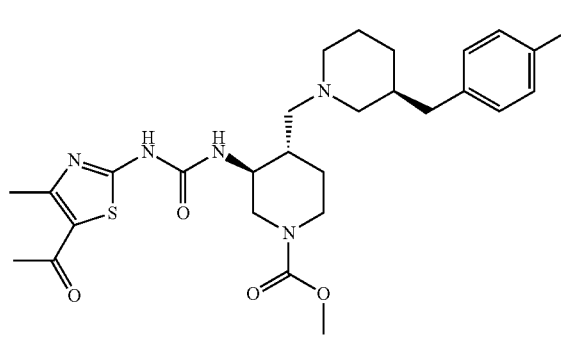
CDXXXIV
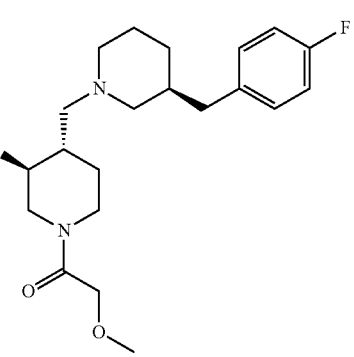
CDXXXI
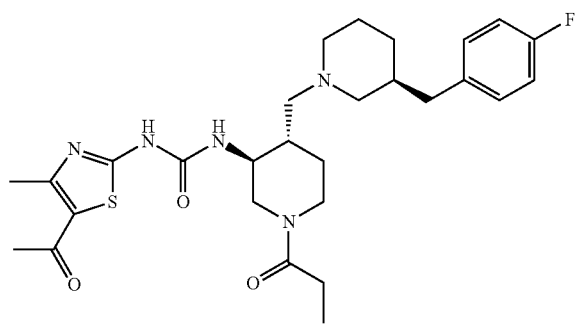
CDXXXV
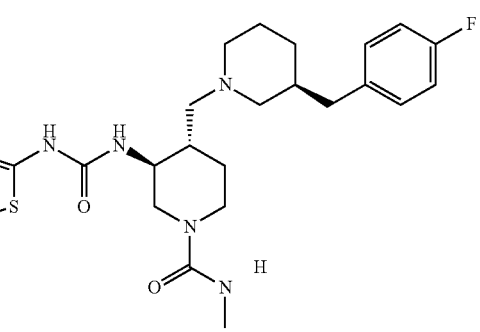
CDXXXII
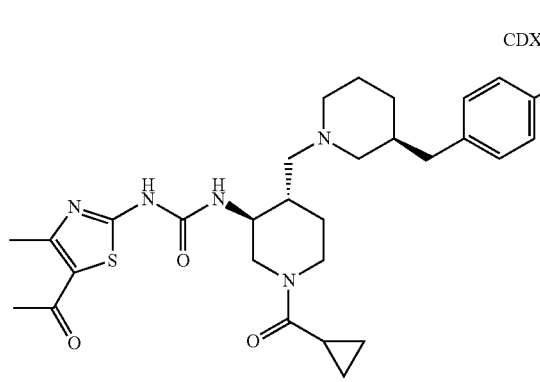
CDXXXVI
CDXXXIII
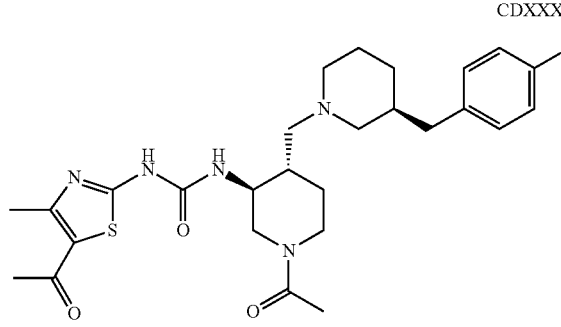
CDXXXVII
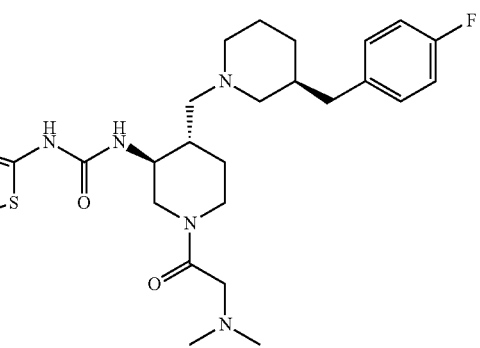

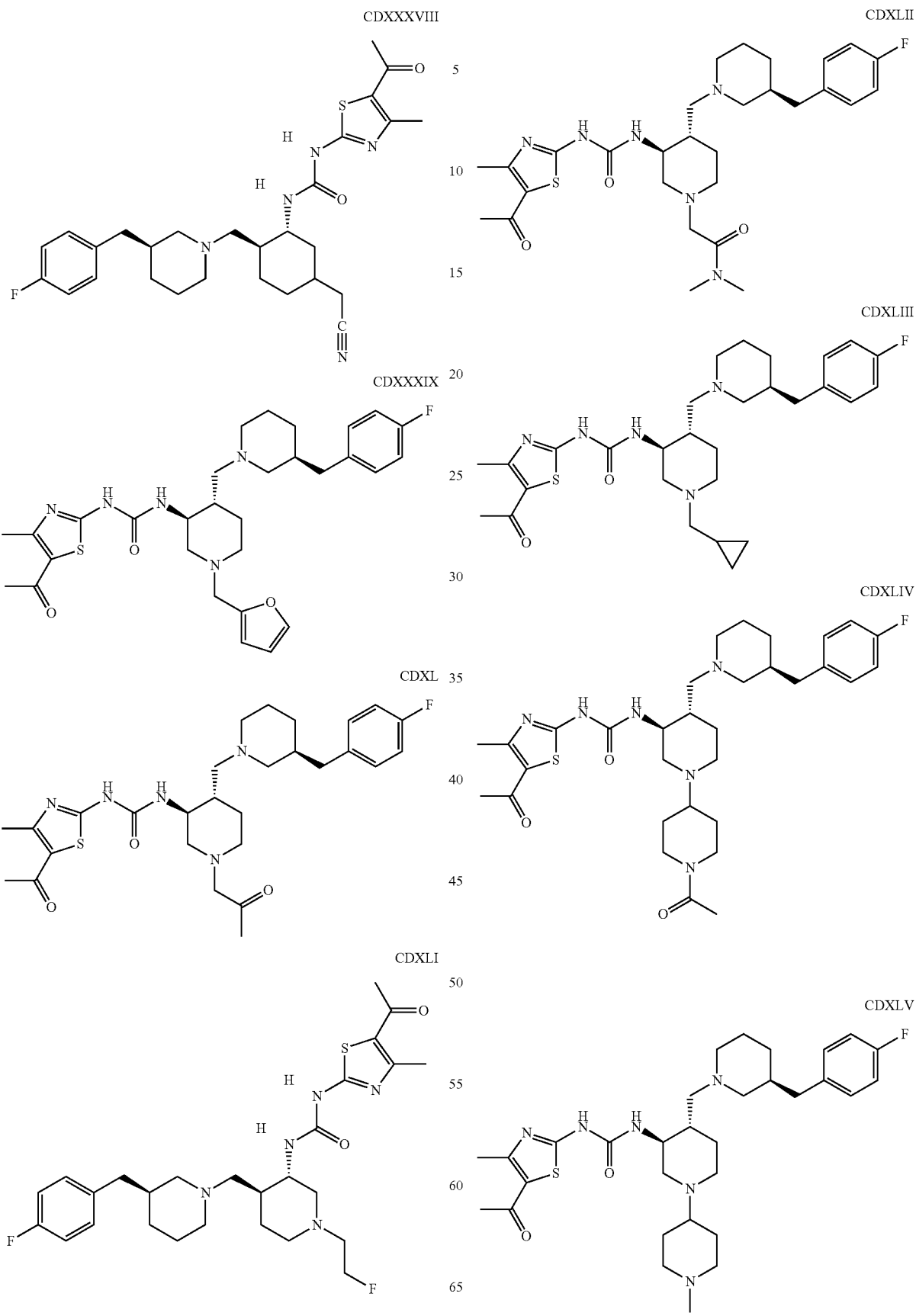

149
-continued
CDXLVI
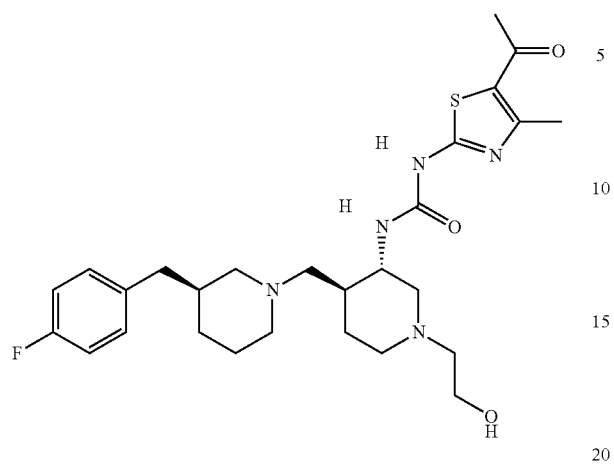
CDXLVII
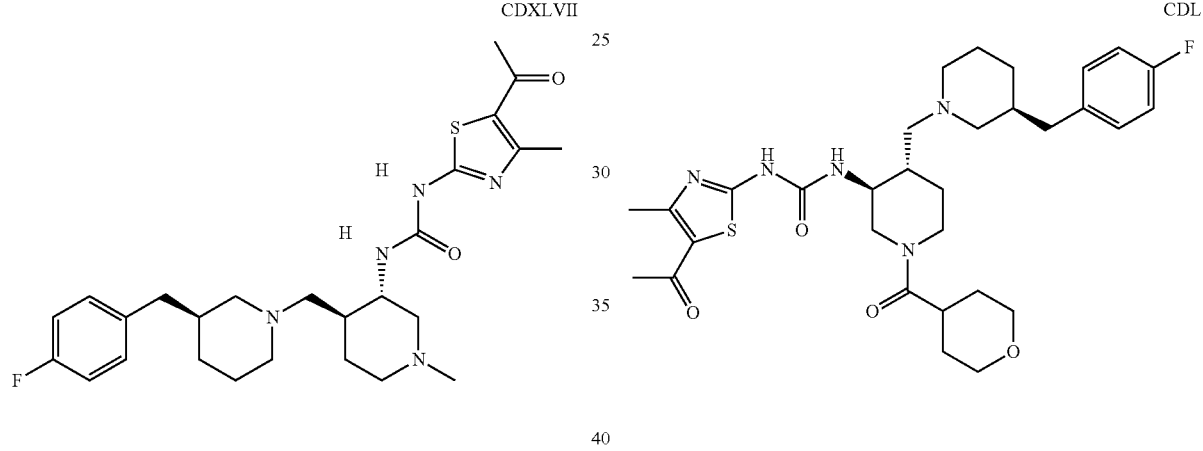
CDXLVIII
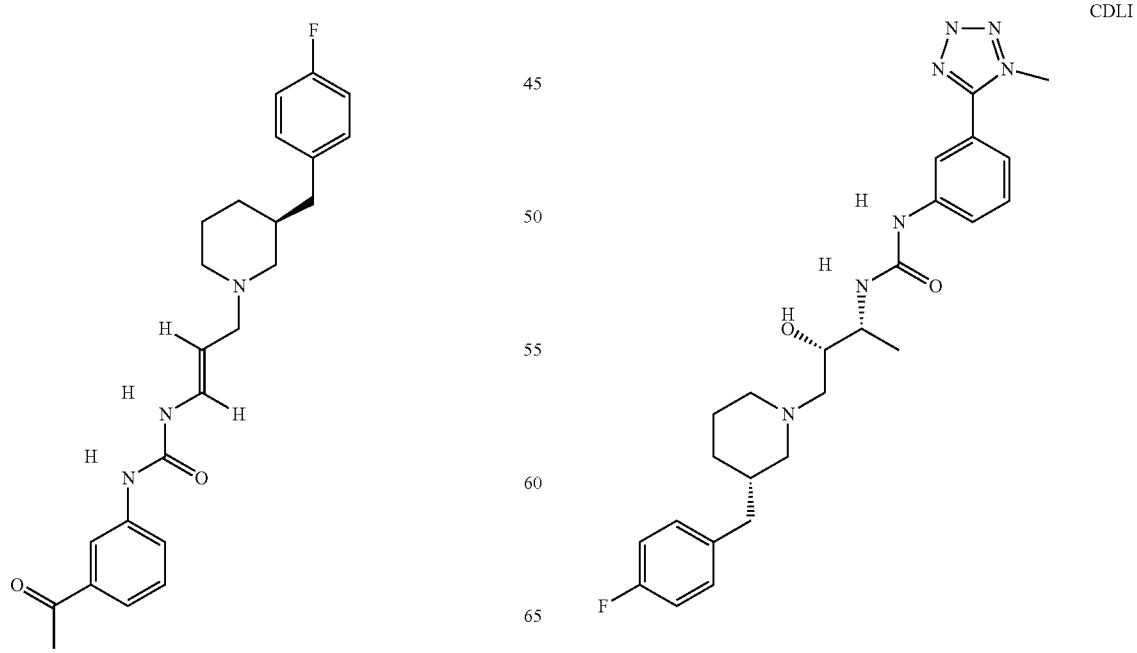
150
-continued
CDXLIX
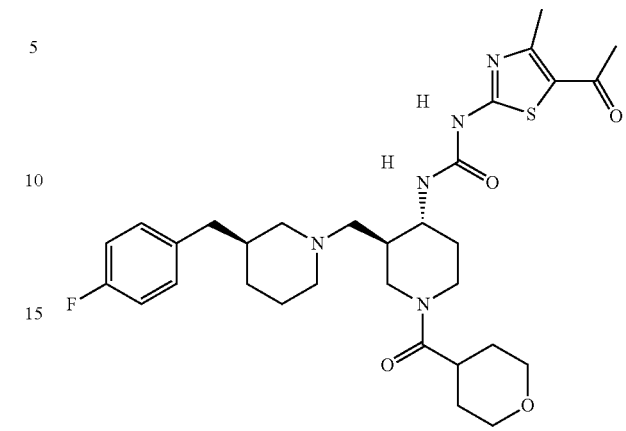
CDL
CDLI -continued
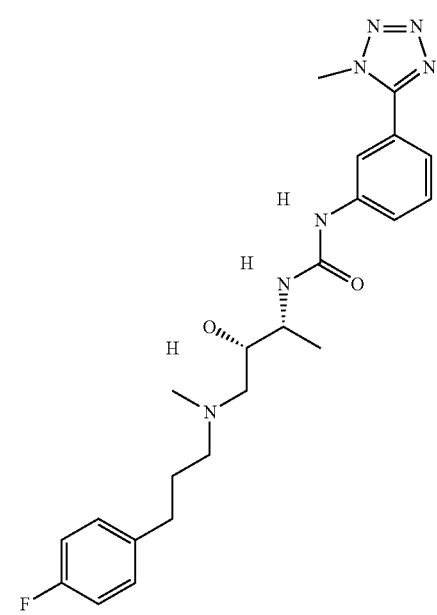
CDLII
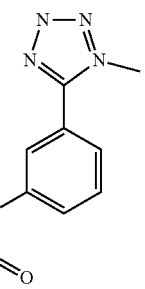
CDLIII
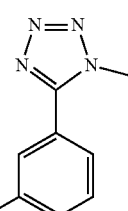
CDLIV
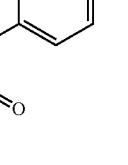
CDLV
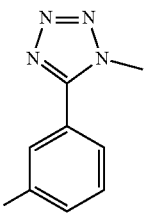
CDLVI
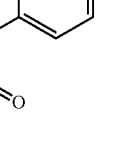

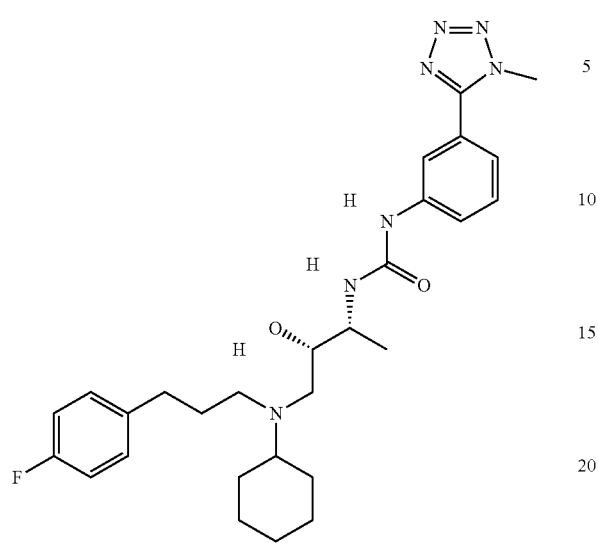
CDLVII
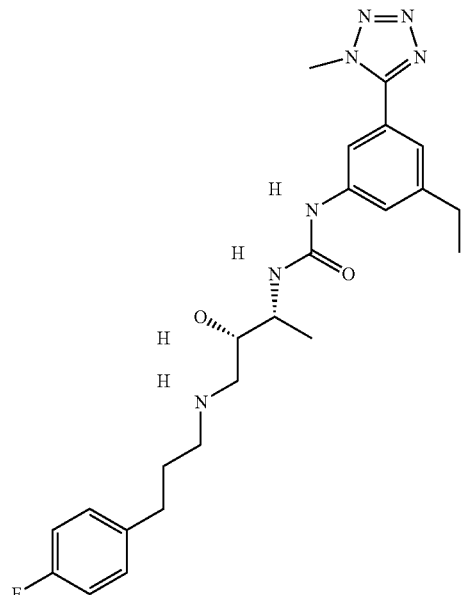
CDLX
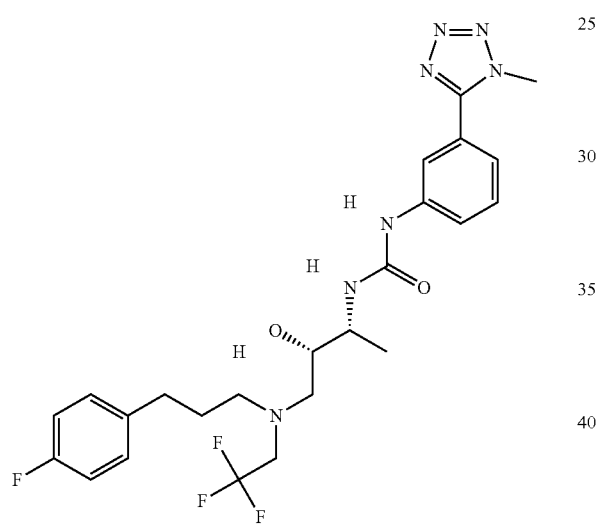
CDLVIII
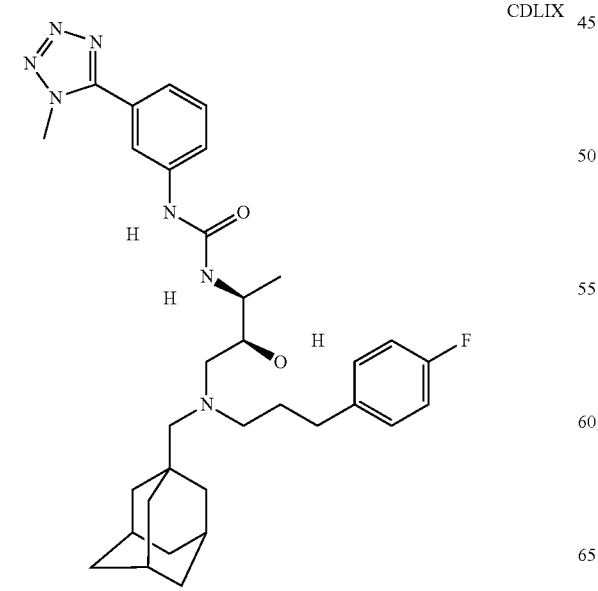
CDLIX
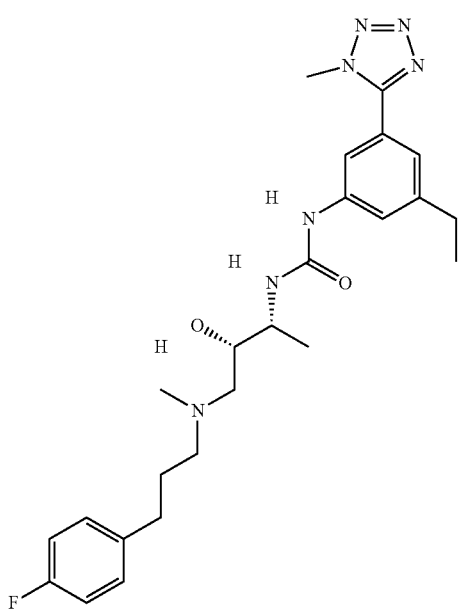
CDLXI CDLXII
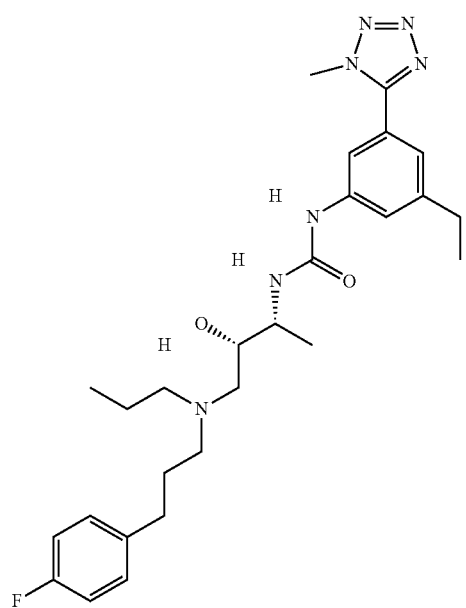
CDLXIII
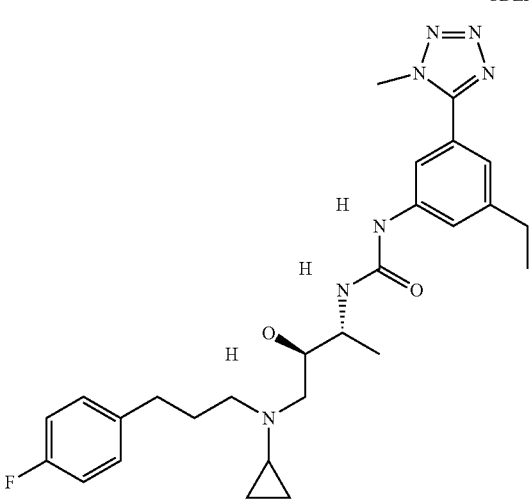
CDLXIV
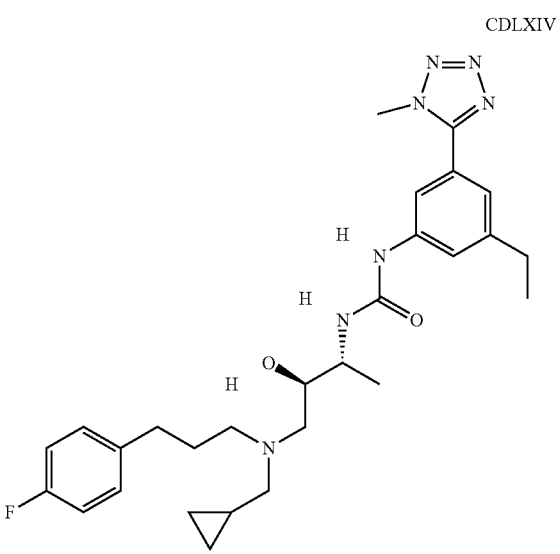
CDLXV
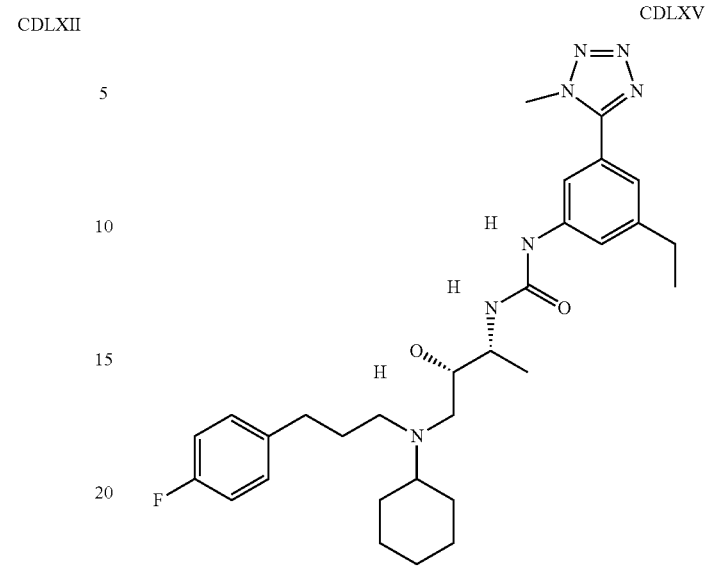
CDLXVI
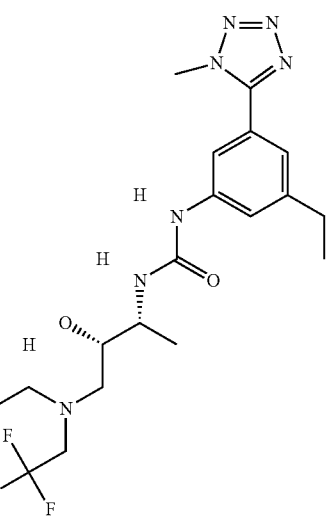
CDLXVII
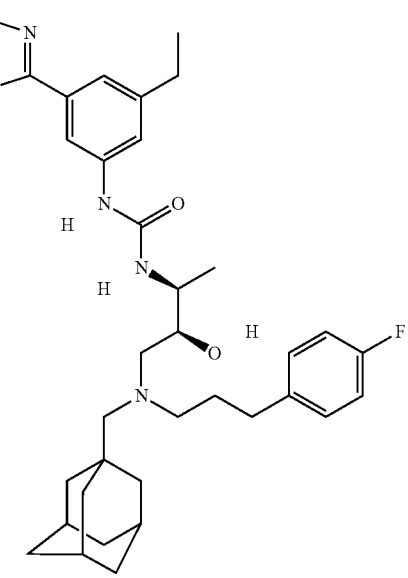

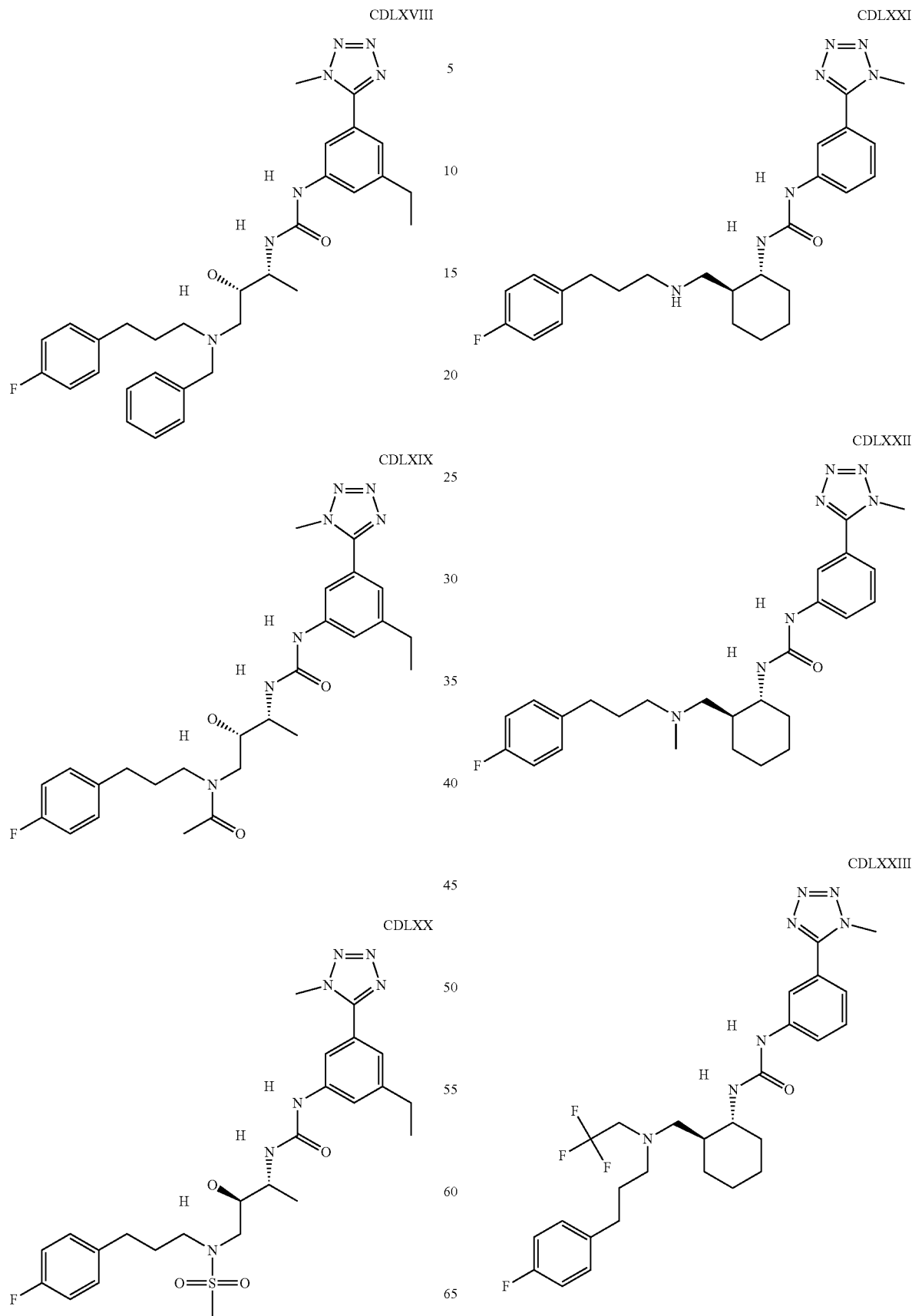

159
-continued
CDLXXIV
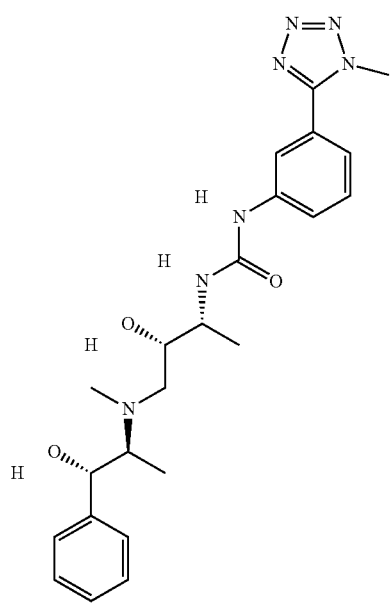
CDLXXV
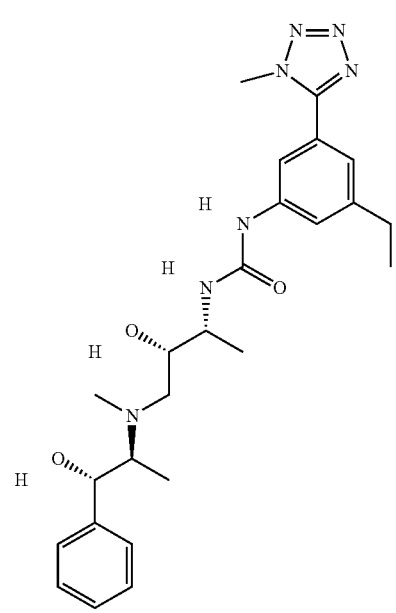
160
-continued
CDLXXVI
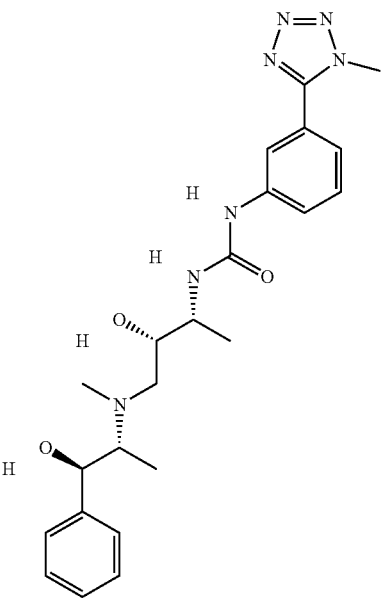
CDLXXVII
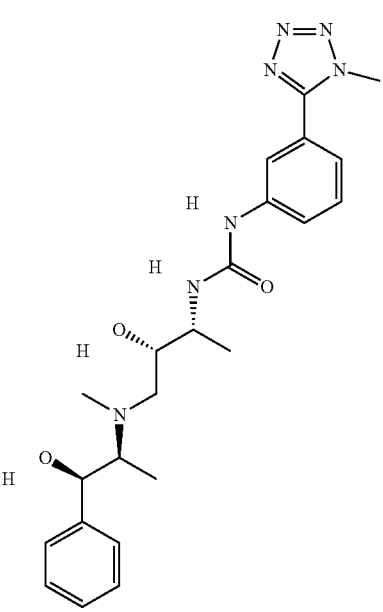

161
-continued
CDLXXVIII
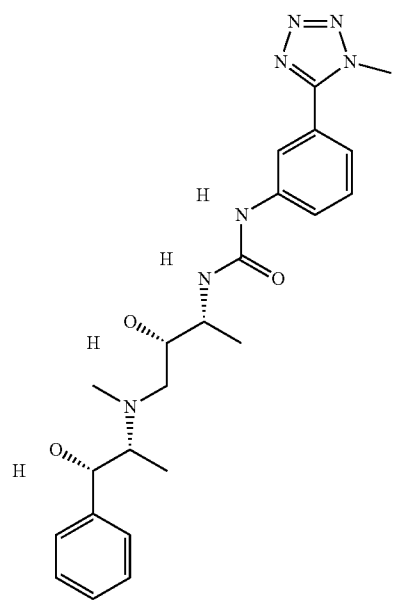
CDLXXIX
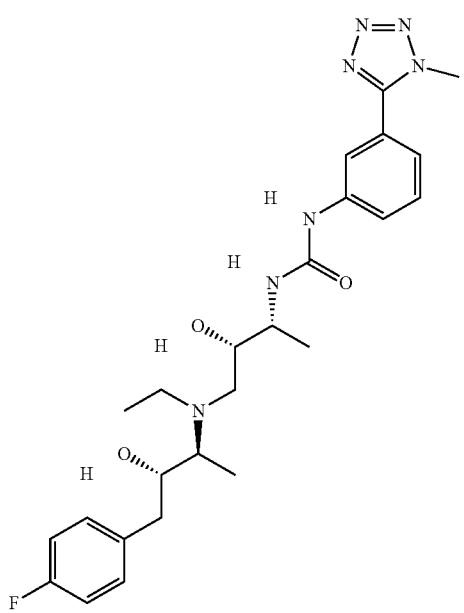
162
-continued
CDLXXX
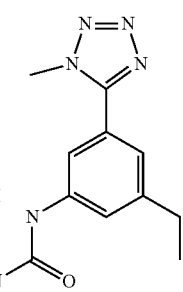
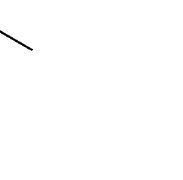
CDLXXXI
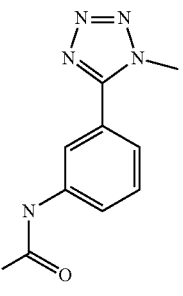

CDLXXXII
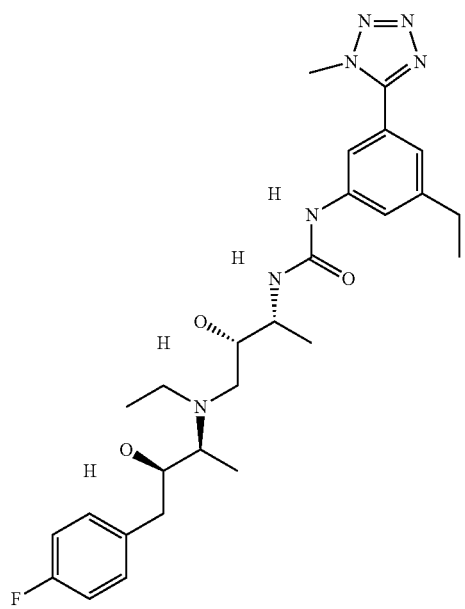
CDLXXXIV
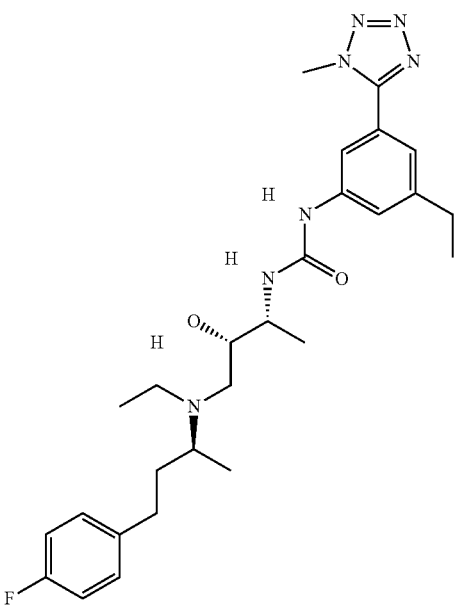
CDLXXXIII
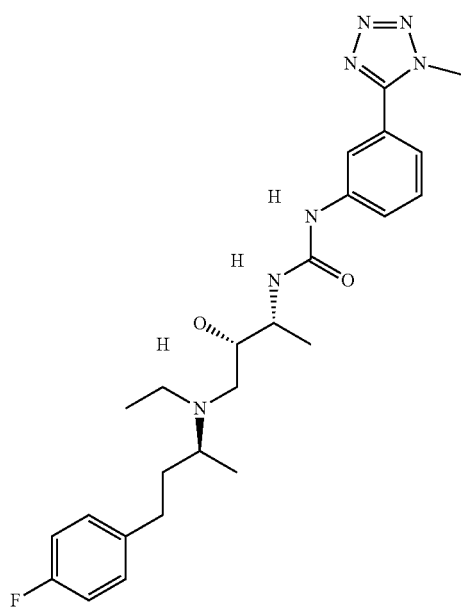
CDLXXXV
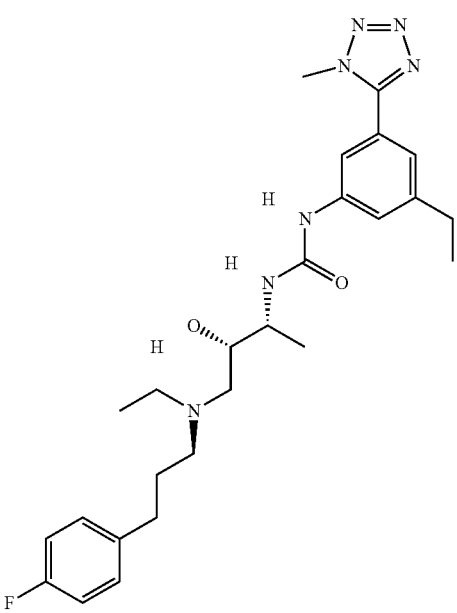

CDLXXXVI
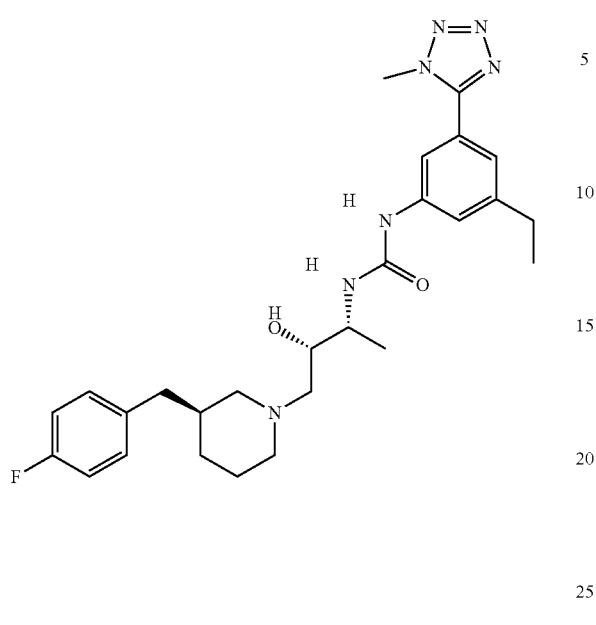
CDLXXXVII
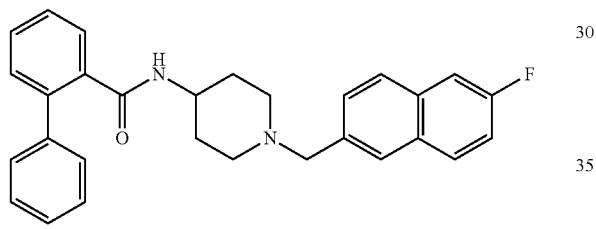
CDLXXXVIII
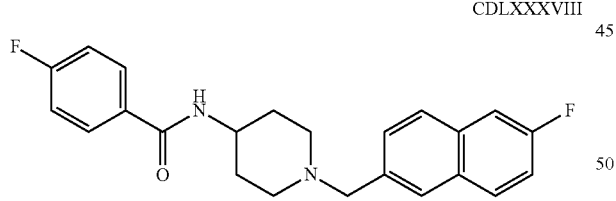
CDLXXXIX
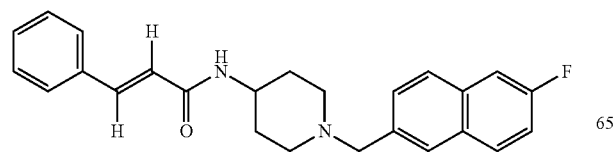
CDXC
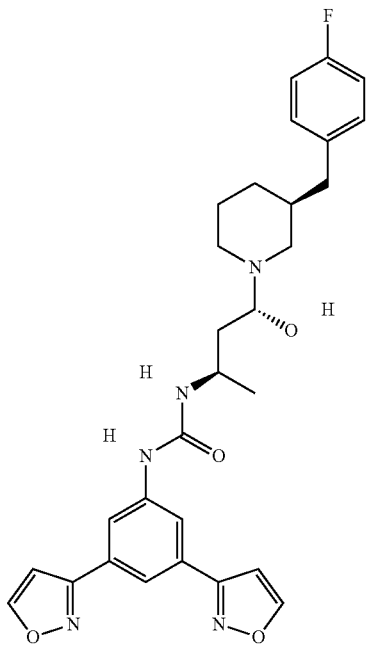
CDXCI
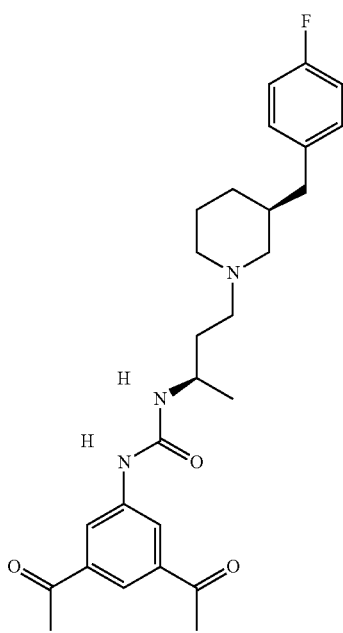

167
-continued
CDXCII
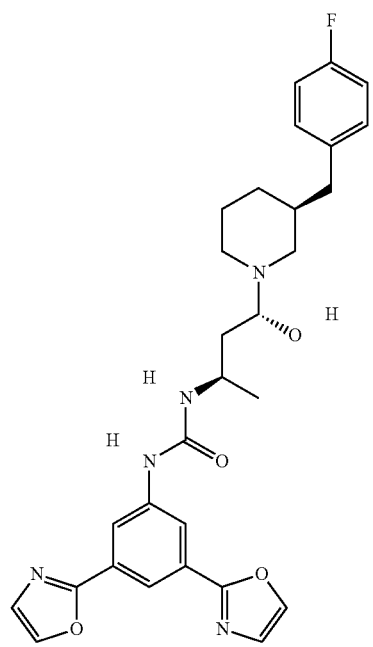
CDXCIII
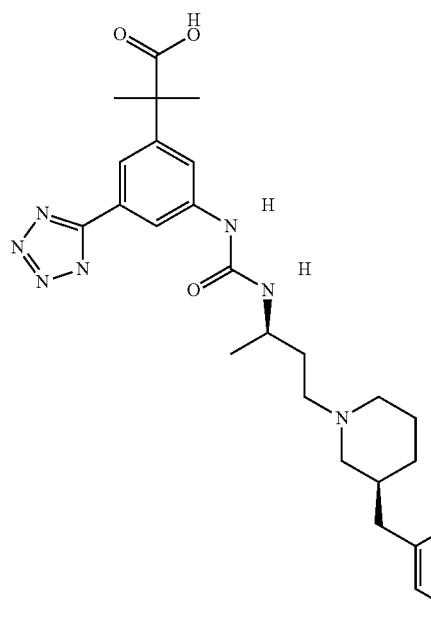
168
-continued
CDXCIV
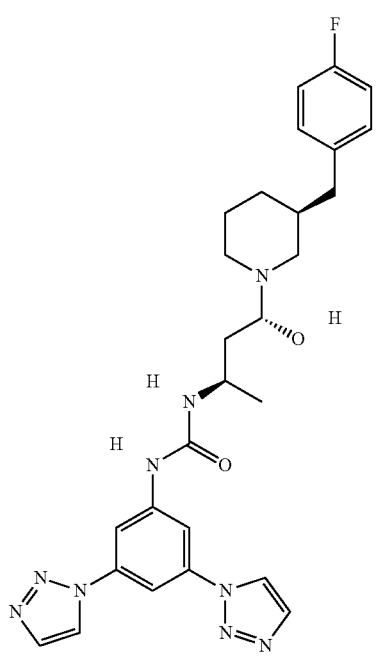
CDXCV
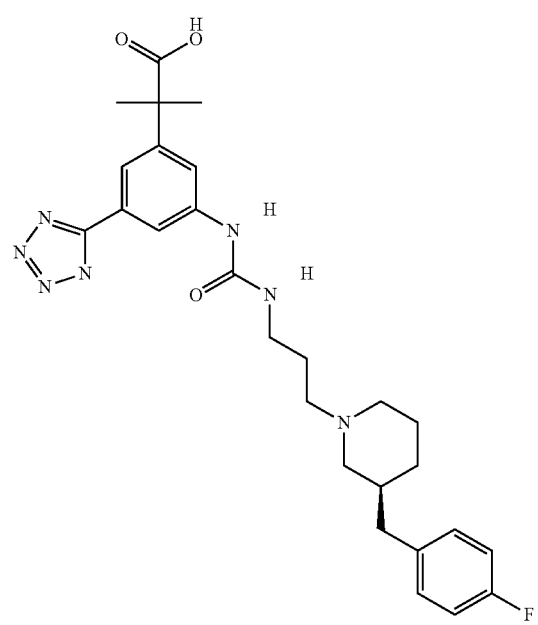

-continued
CDXCVI
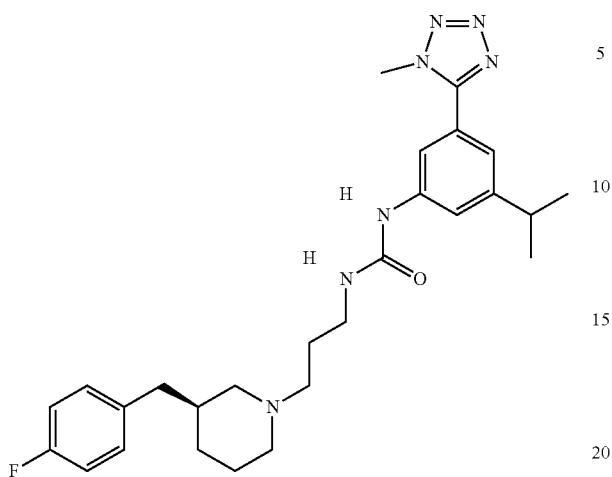
CDXCVII
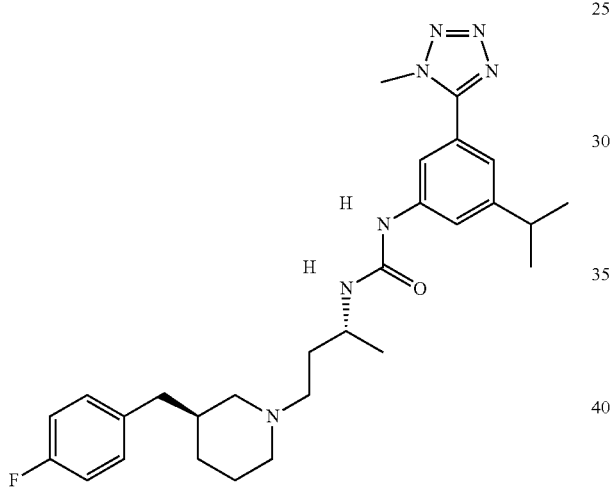
CDXCVIII
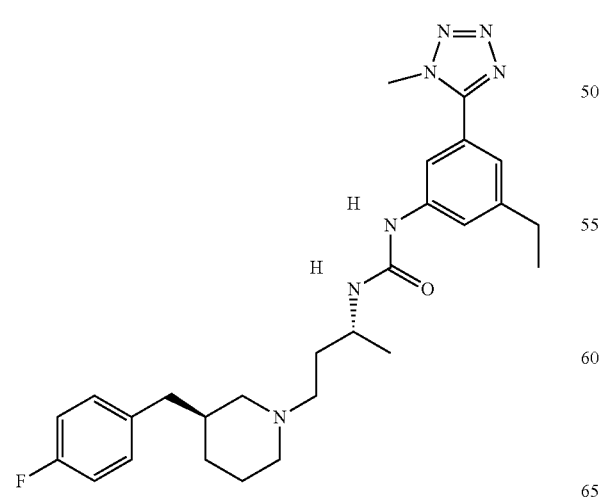
-continued
CDXCIX
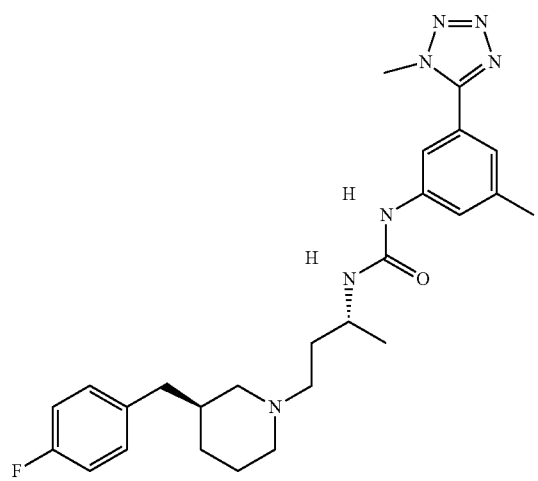
D
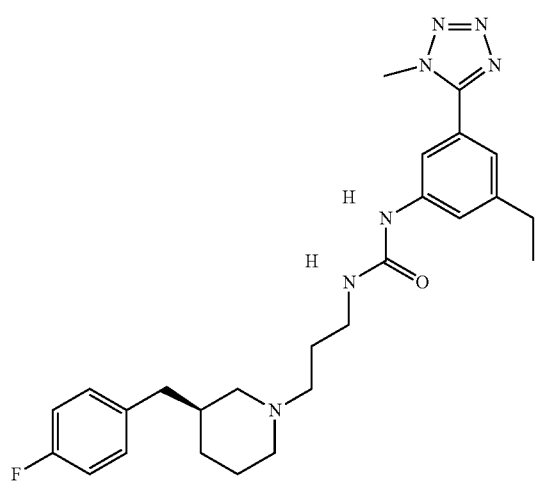
DI
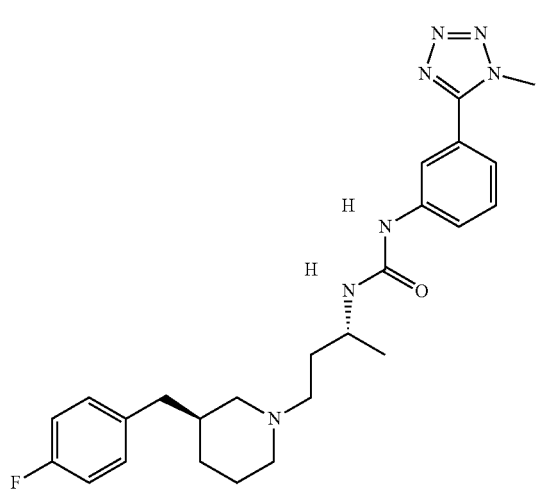

171
-continued
172
-continued
DII
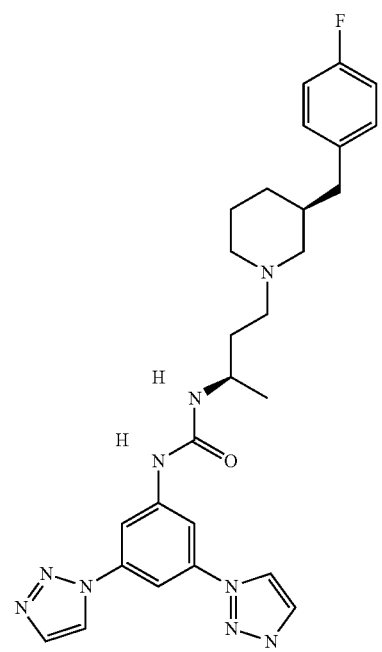
DIII
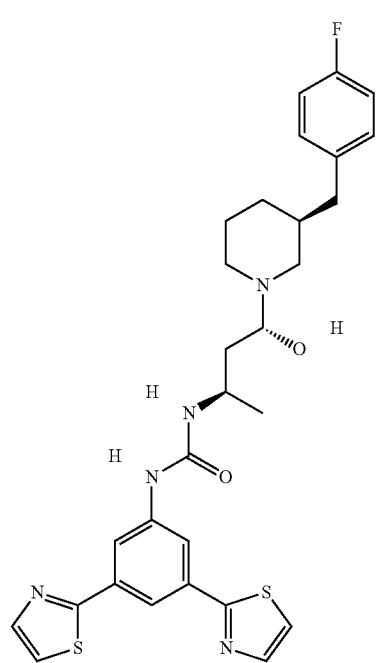
DIV
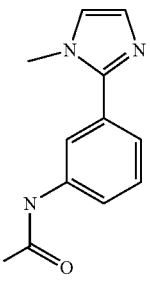
DV
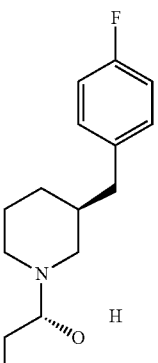
DVI
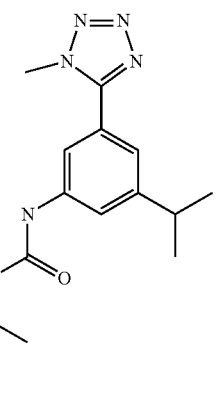

DVII
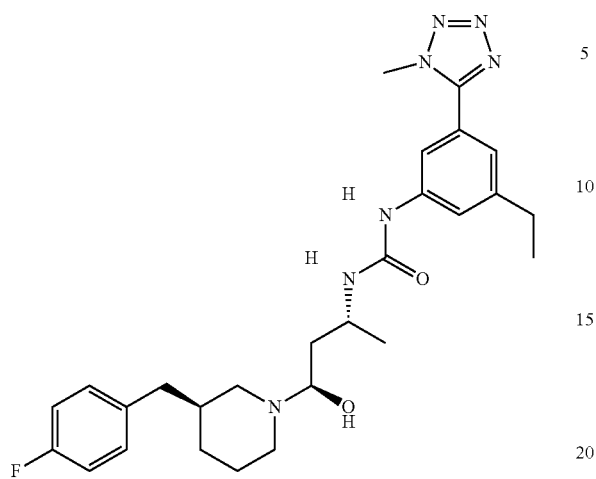
DVIII
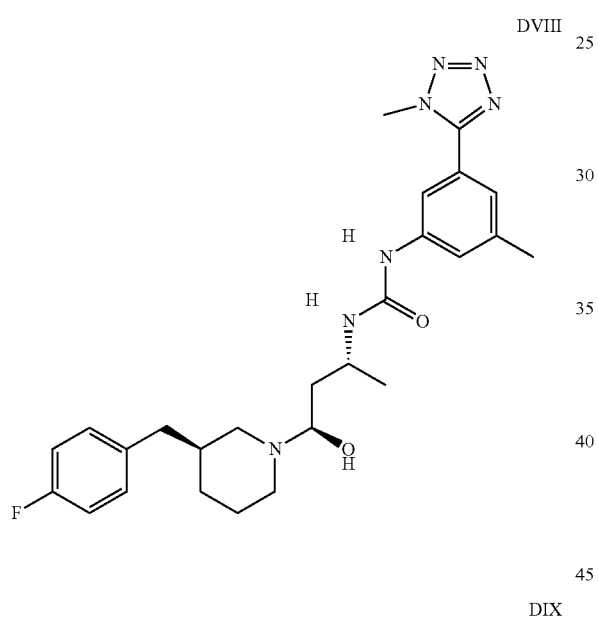
DIX
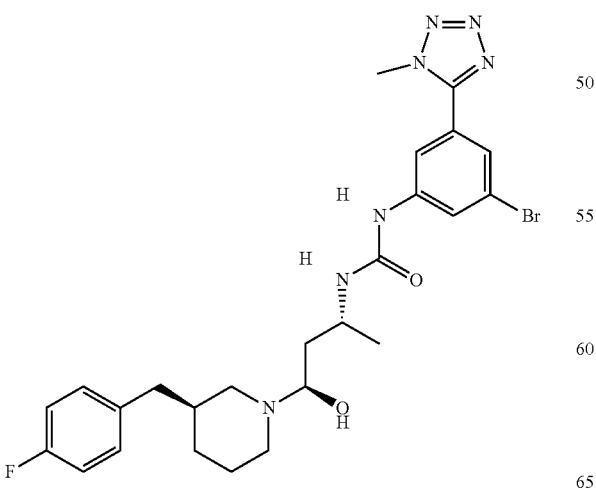
DX
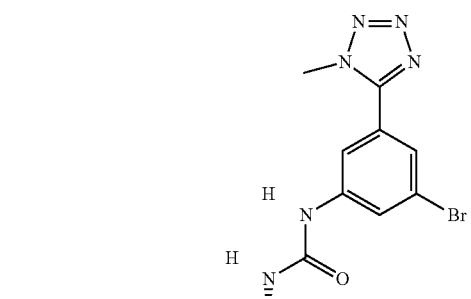
DXI
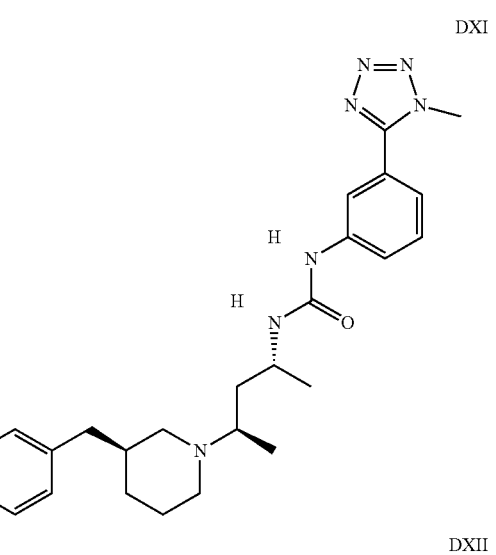
DXII
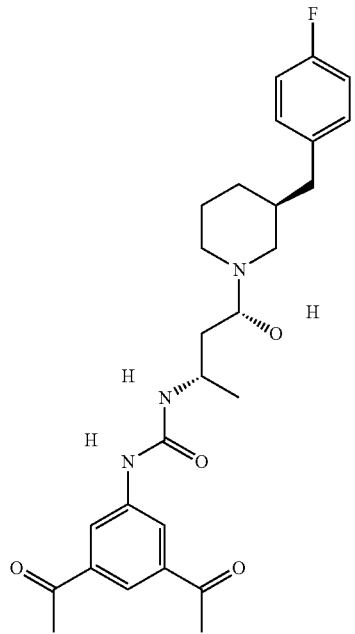

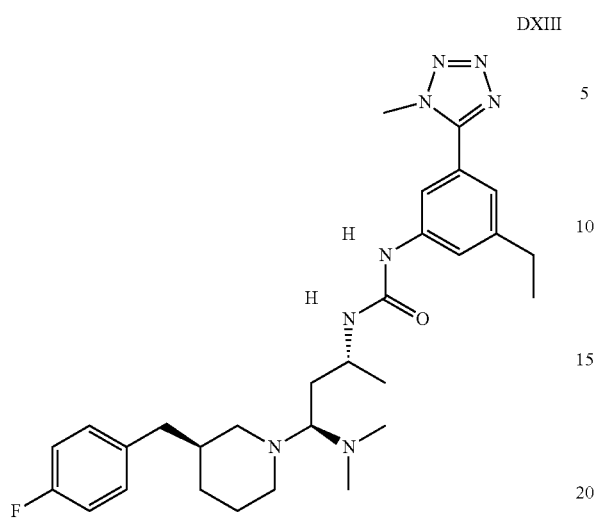
DXIII
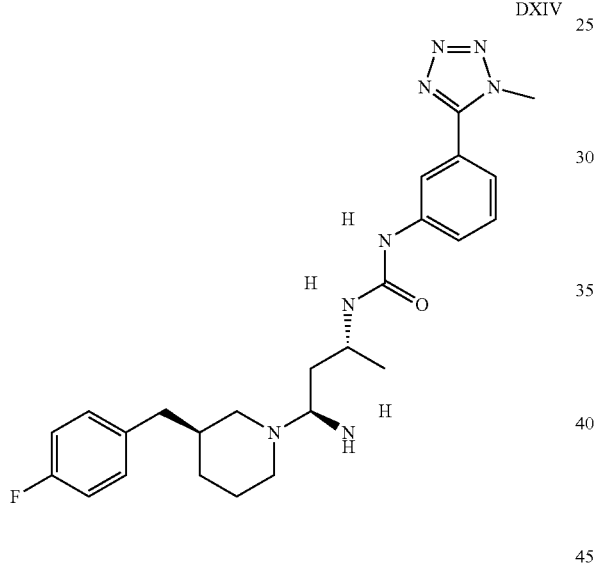
DXIV
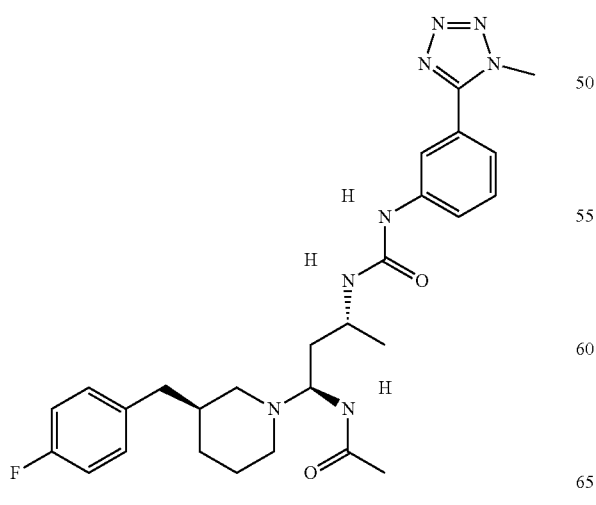
DXV
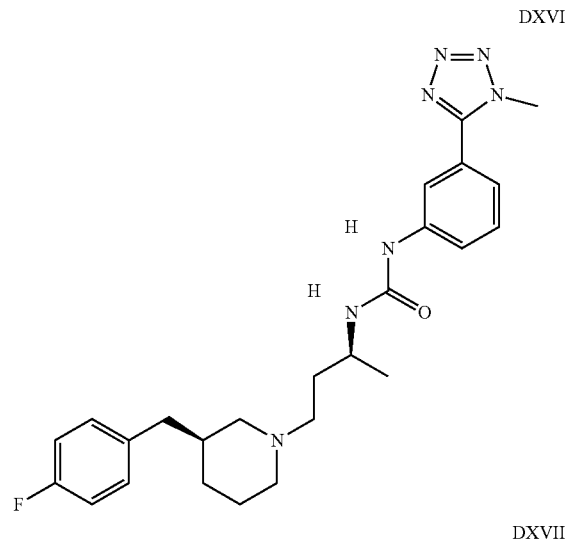
DXVI
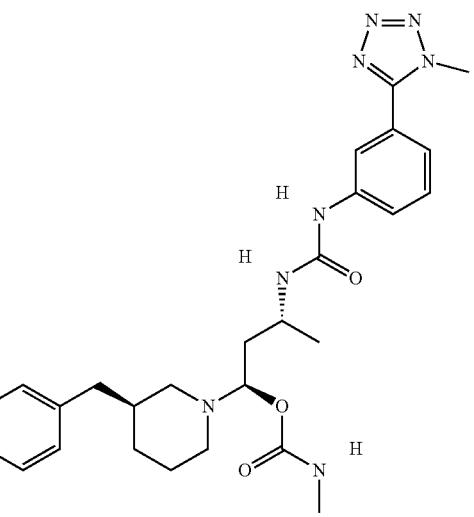
DXVII
DXVIII -continued
DXIX
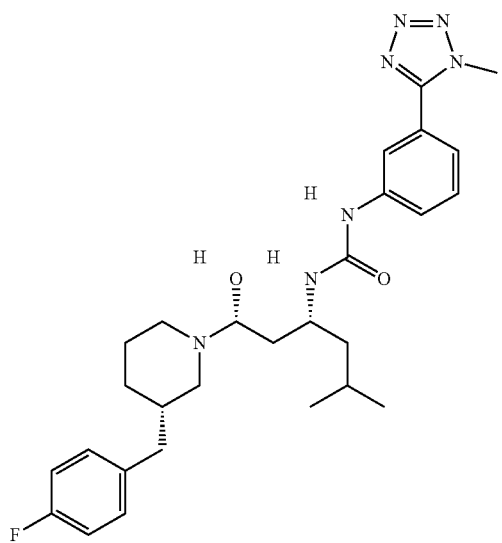
DXXII
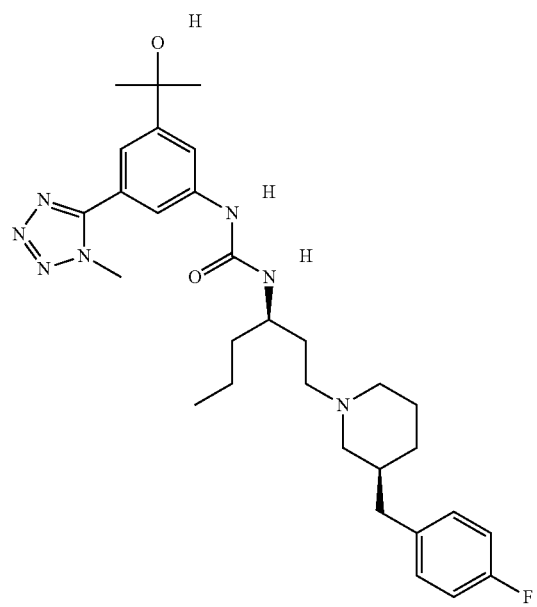
DXX
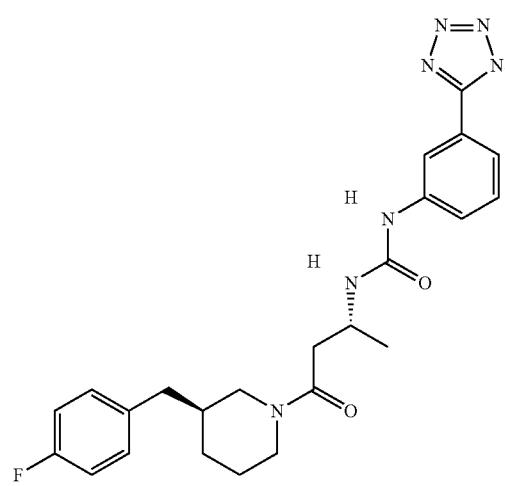
DXXIII
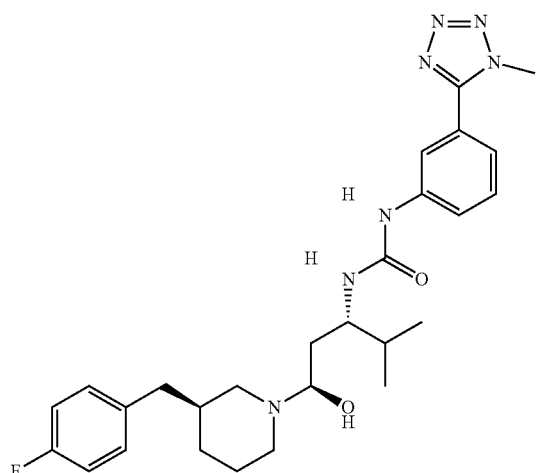
DXXI
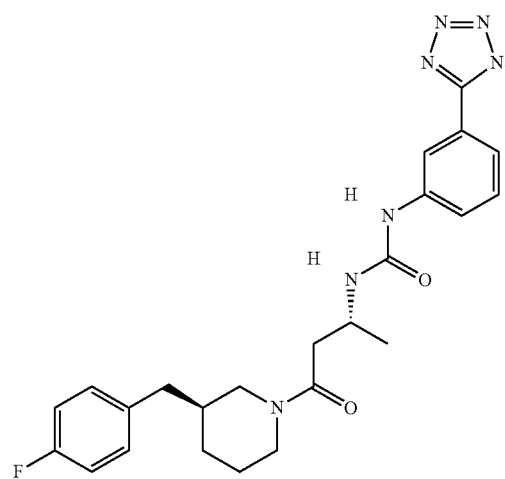
DXXIV
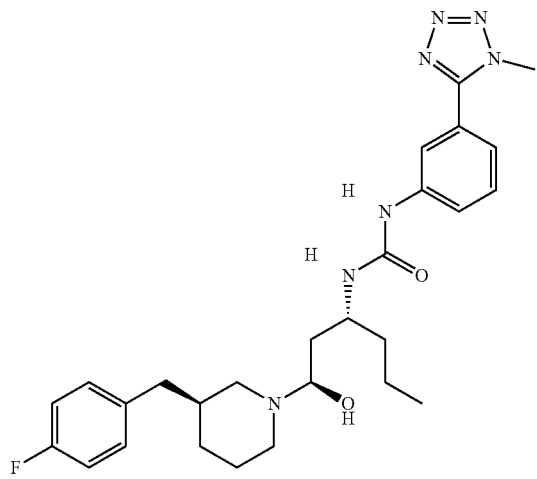

179
-continued
DXXV
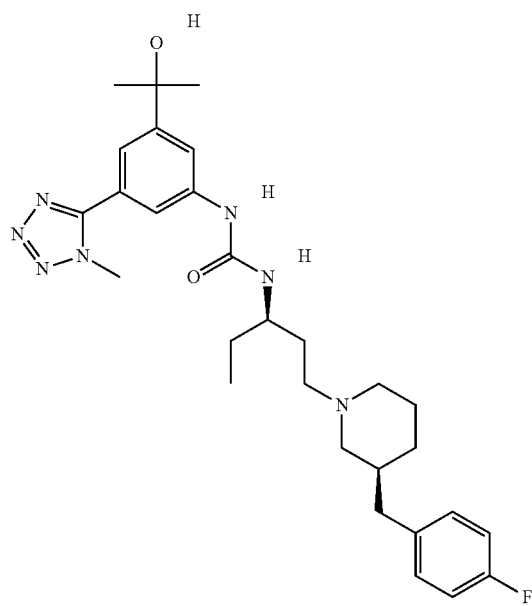
DXXVI
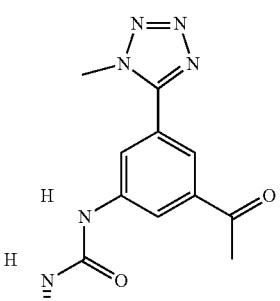
180
-continued
DXXVII
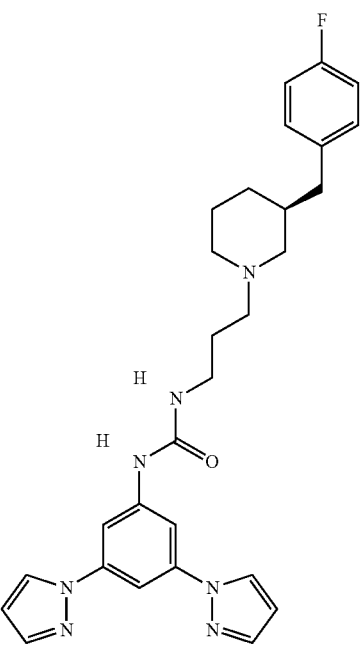
DXXVIII
DXXIX
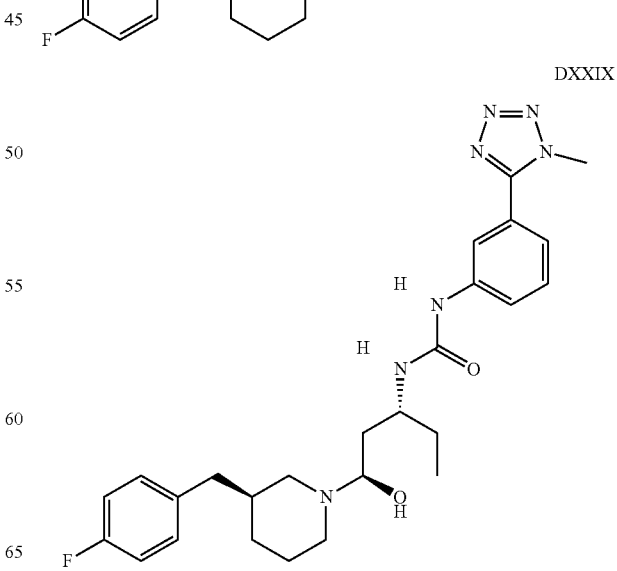

DXXX
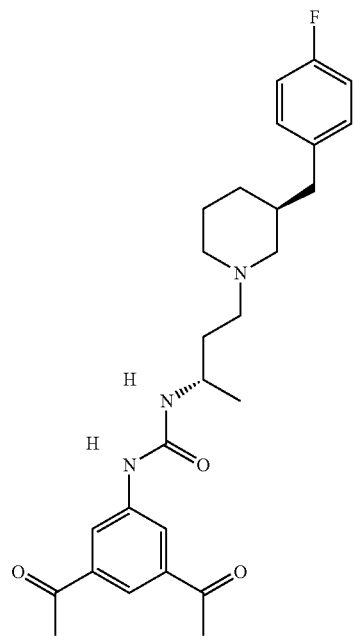
DXXXI
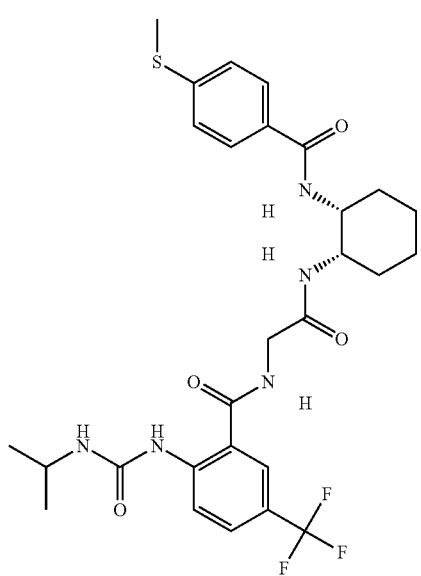
DXXXII
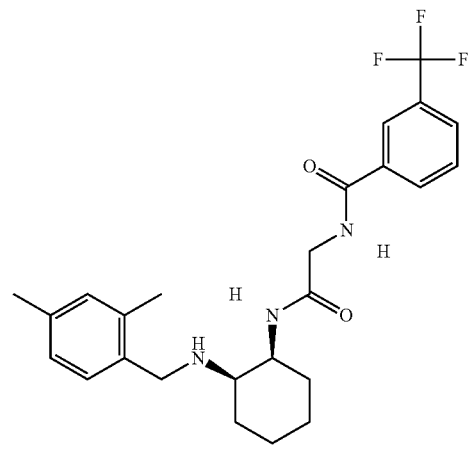
DXXXIII
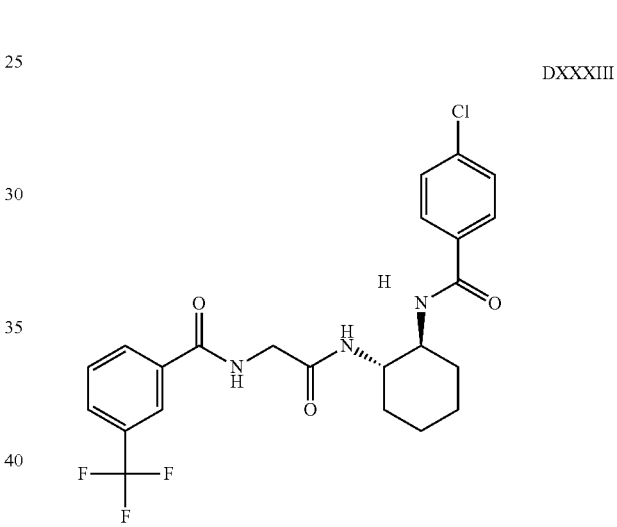
DXXXIV
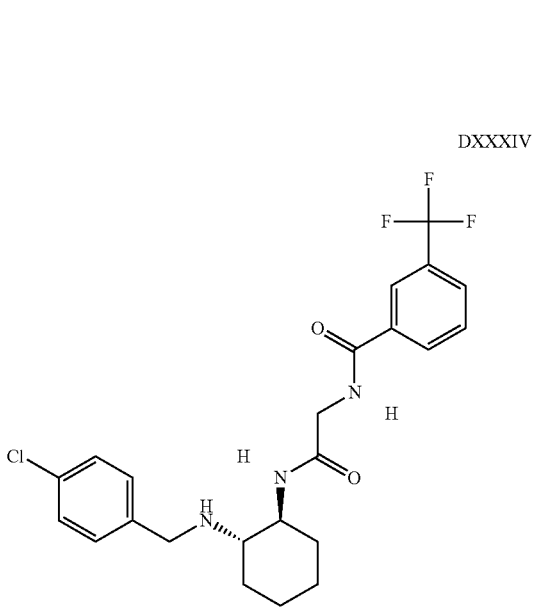

DXXXV
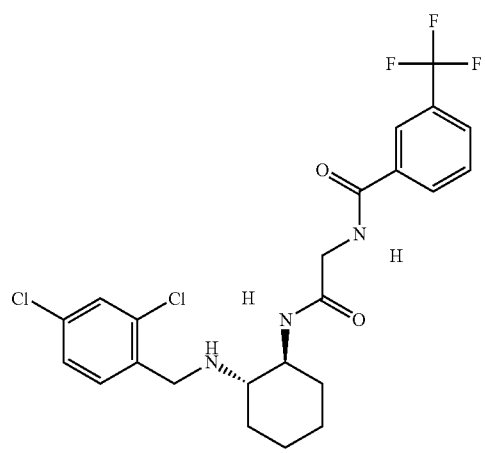
DXXXVIII
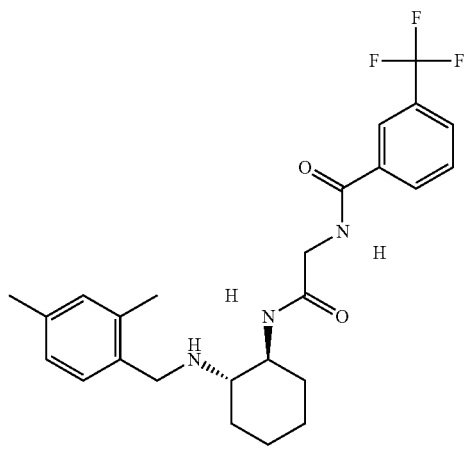
DXXXVI
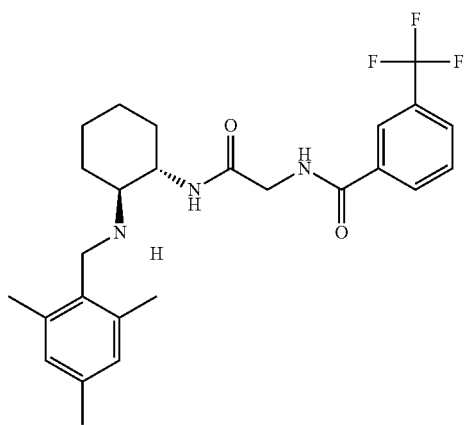
DXXXIX
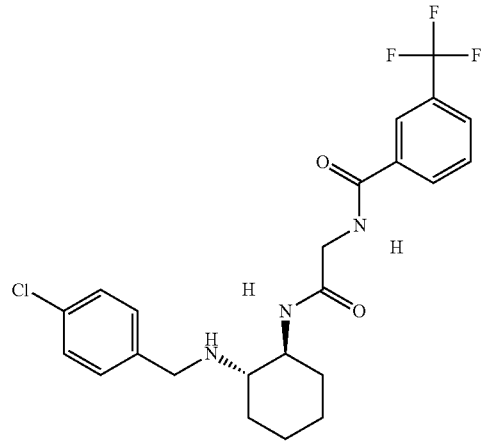
DXXXVII
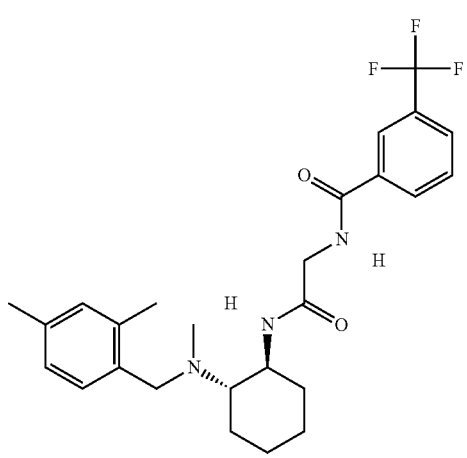
DXL
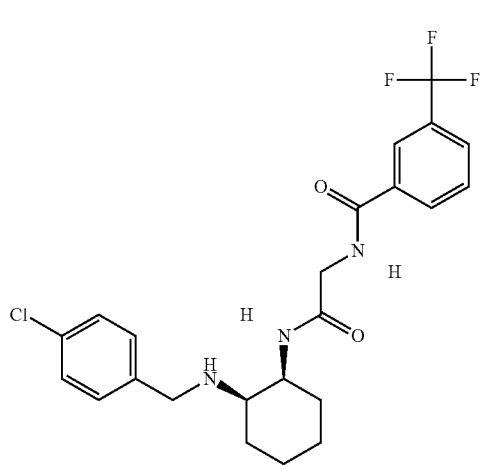

DXLI
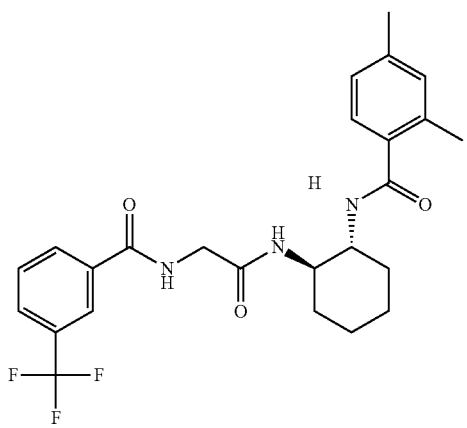
DXLII
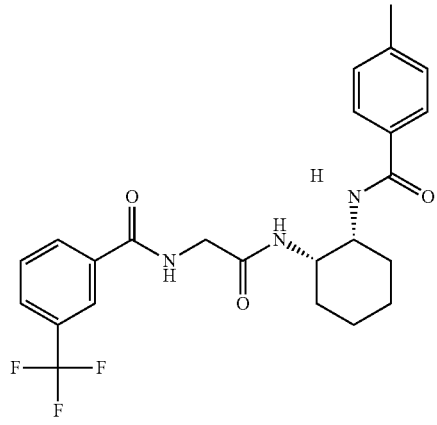
DXLIII
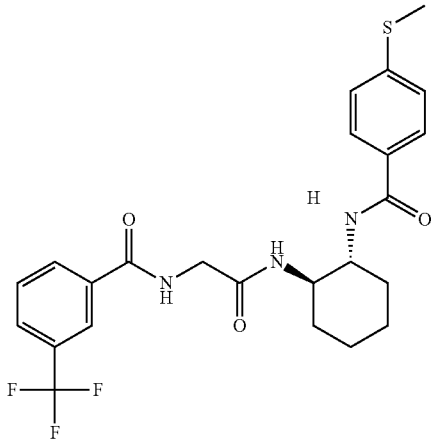
DXLIV
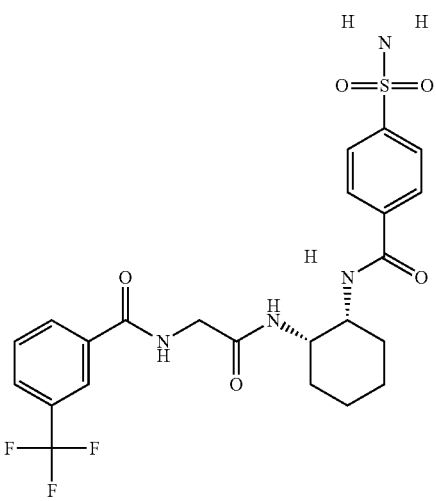
DXLV
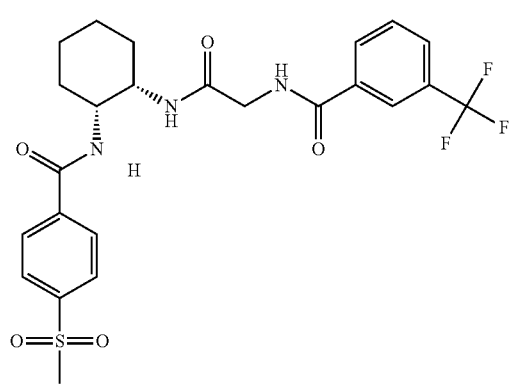
DXLVI
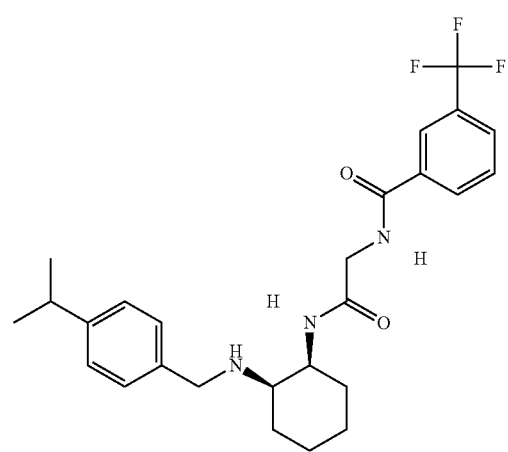

187
-continued
DXLVII
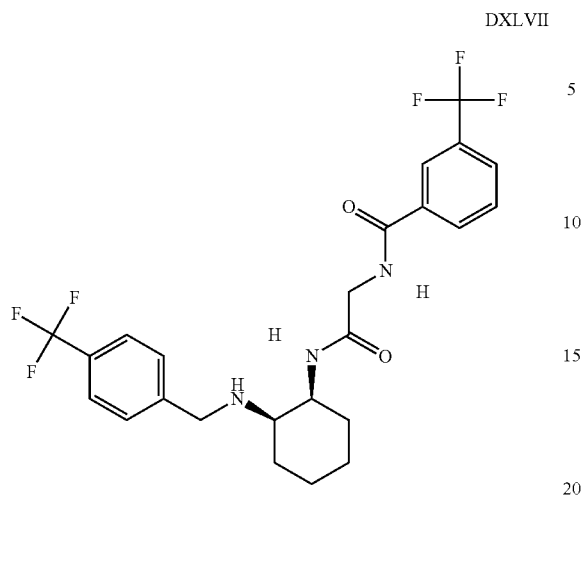
DXLVIII
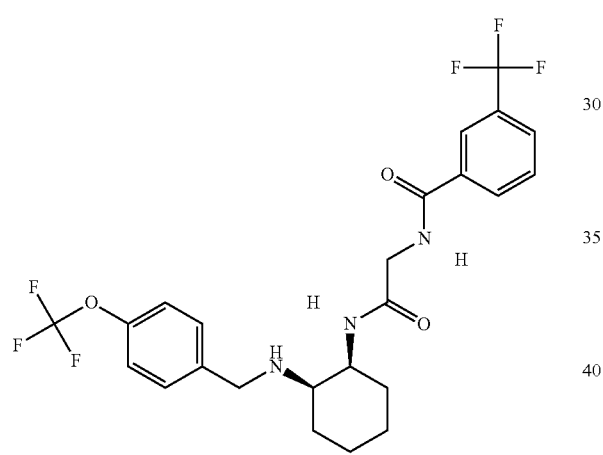
DXLIX
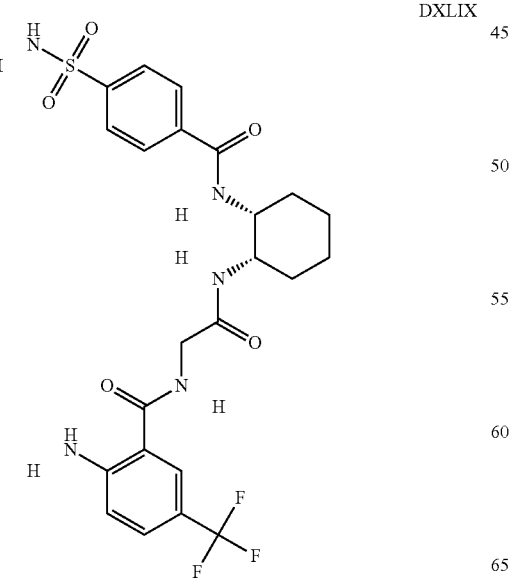
188
-continued
DL
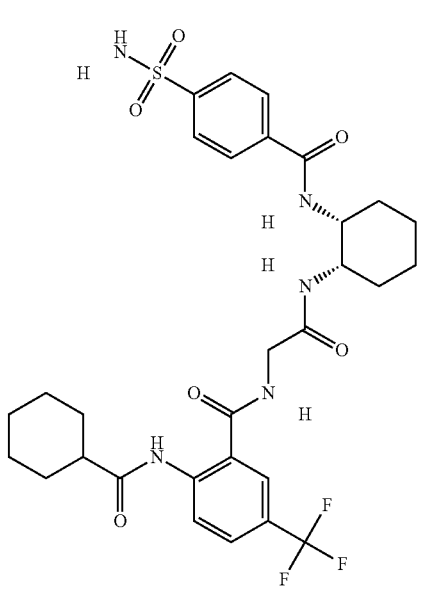
DLI
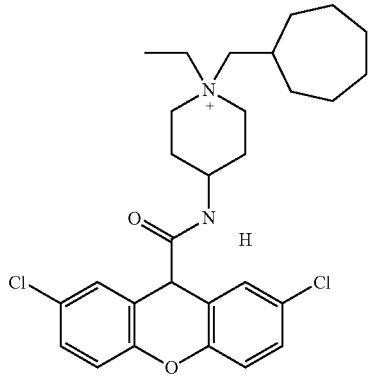
DLII
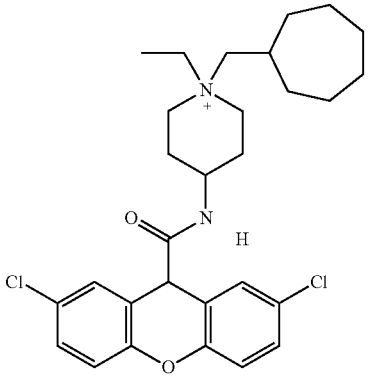

189
-continued
DLIII
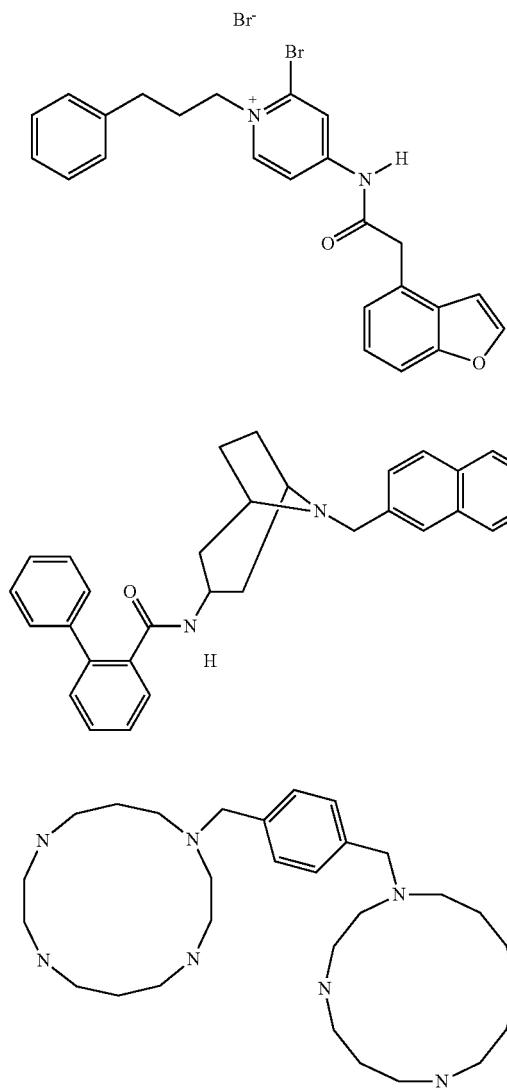
DLIV
DLV
DLVI
DLVII
190
-continued
DLVIII
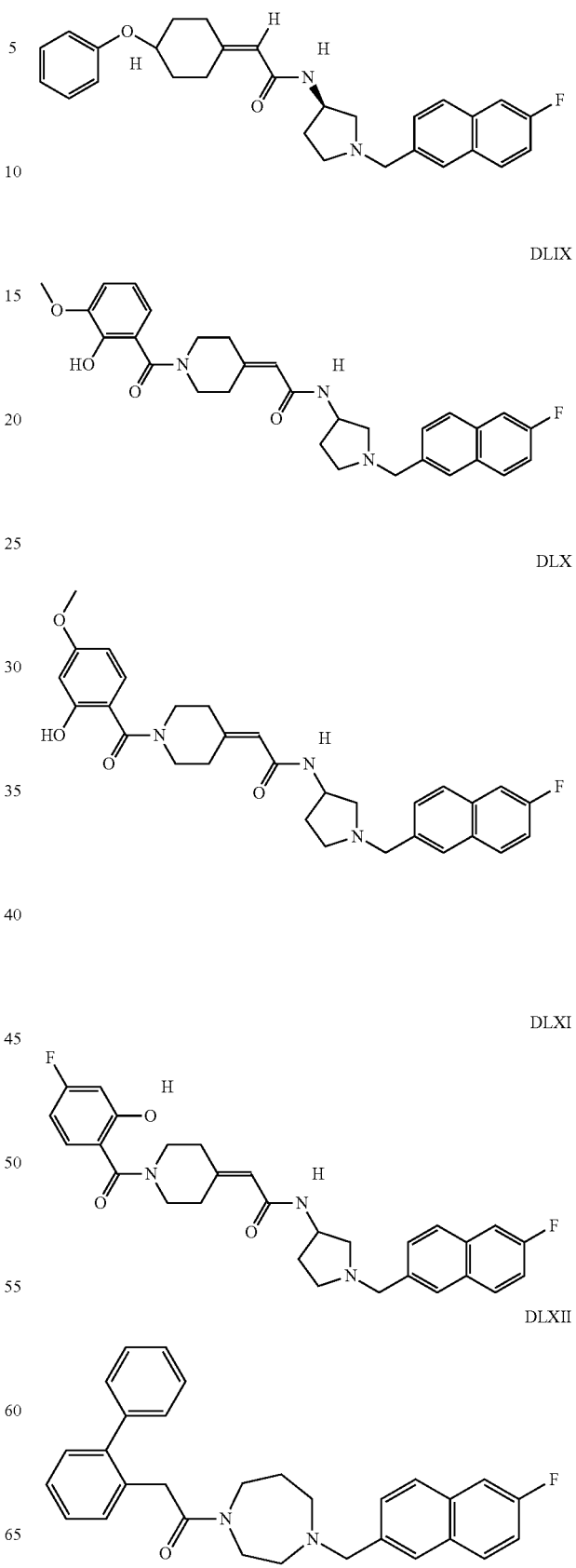
DLIX
DLX
DLXI
DLXII DLXIII
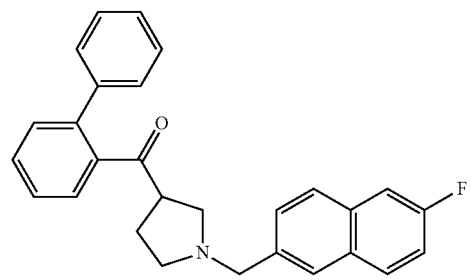
DLXIX
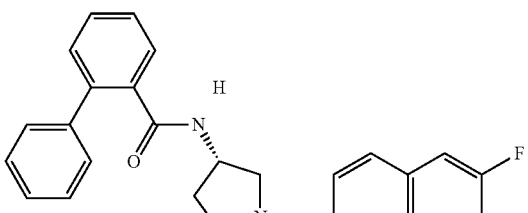
DLXIV
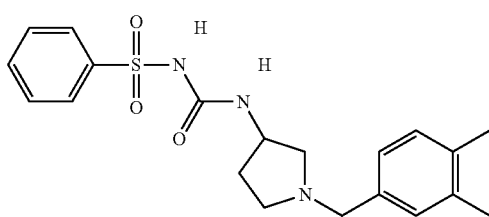
DLXX
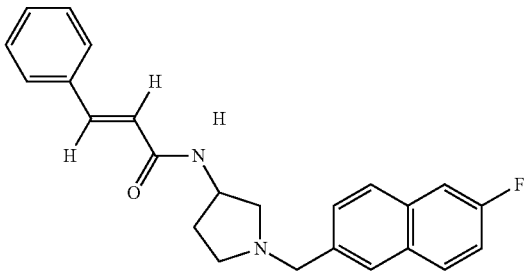
DLXV
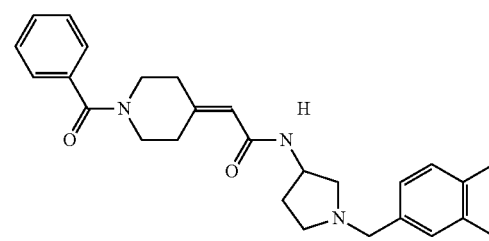
DLXXI
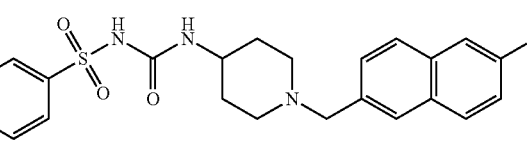
DLXVI
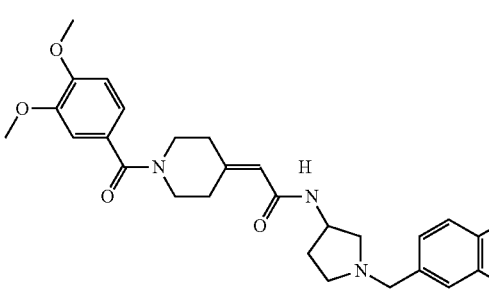
DLXXII
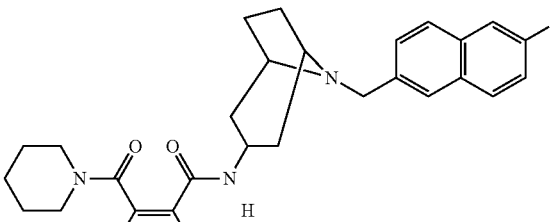
DLXVII
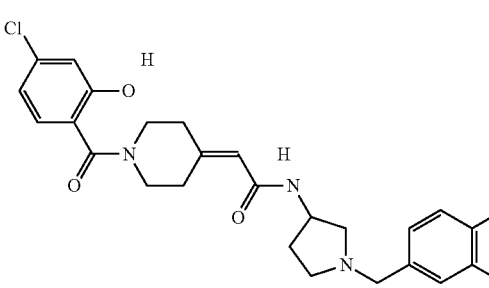
DLXXIII
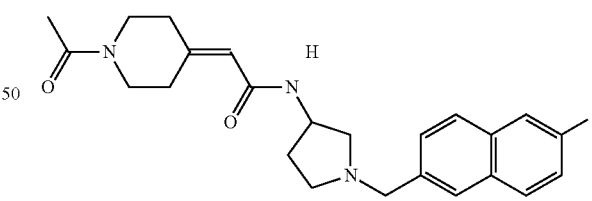
DLXVIII
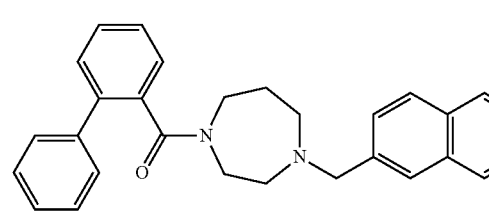
DLXXIV
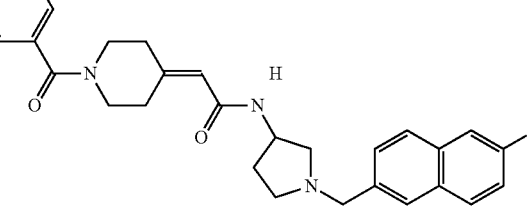

DLXXV
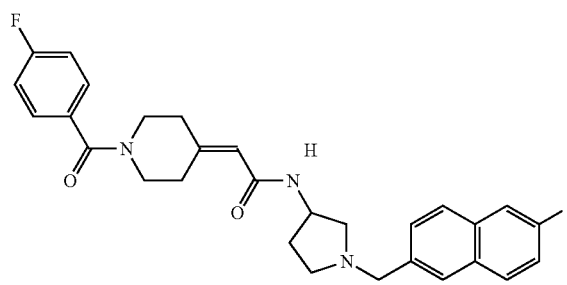
DLXXX
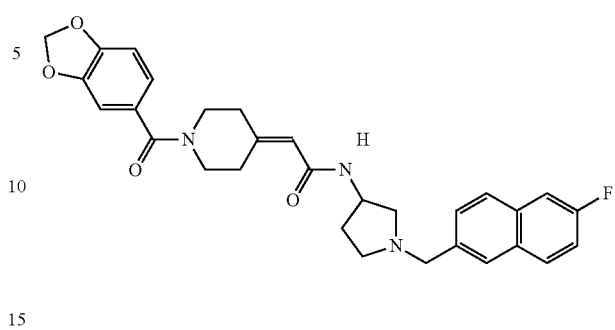
DLXXVI
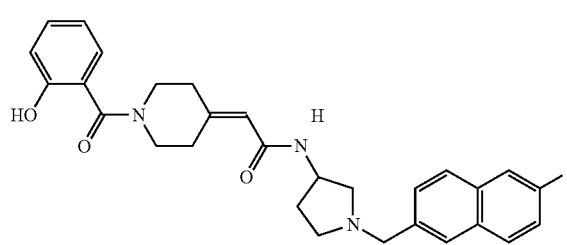
DLXXXI
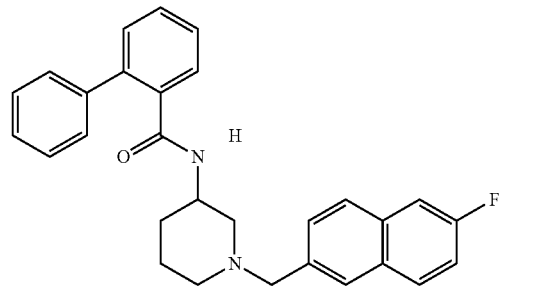
DLXXVII
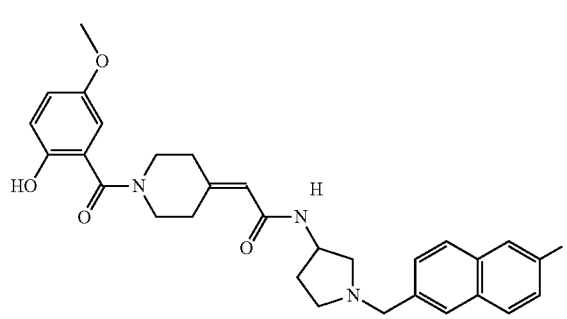
DLXXXII
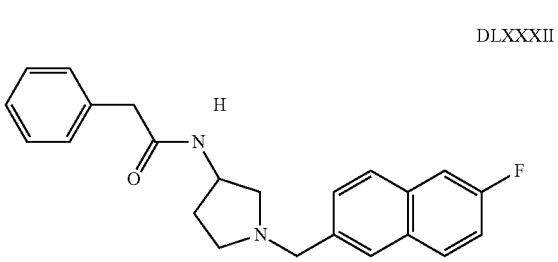
DLXXVIII
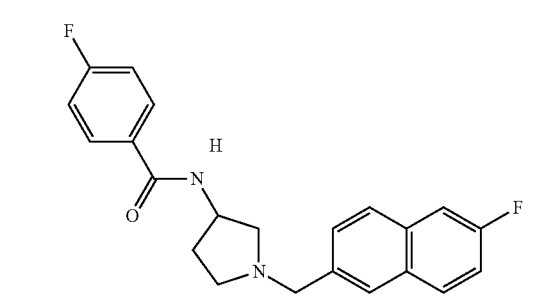
DLXXXIII
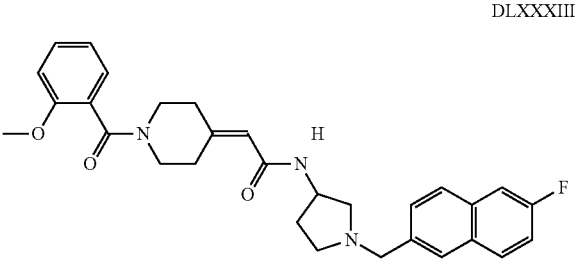
DLXXIX
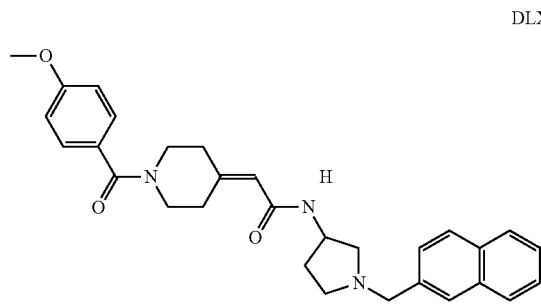
DLXXXIV
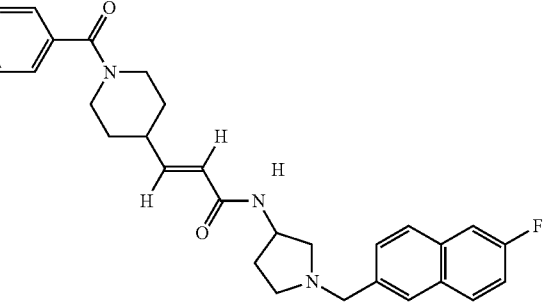

DLXXXV
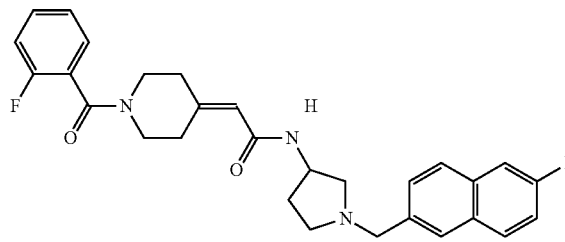
DXC
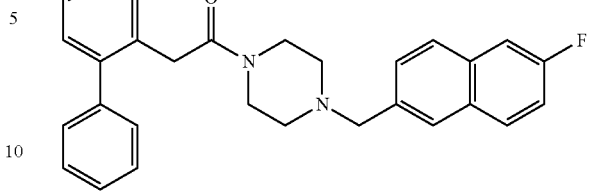
DLXXXVI
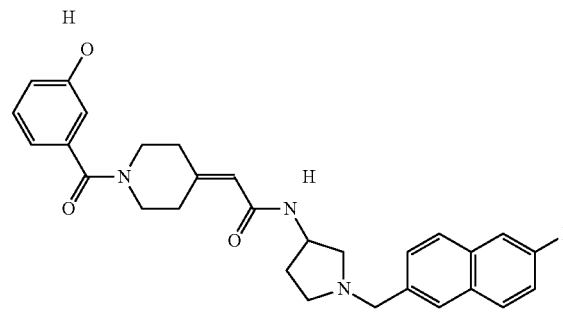
DXCI
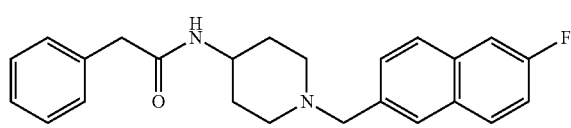
DLXXXVII
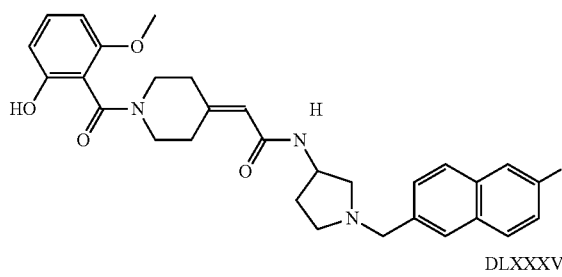
DXCII
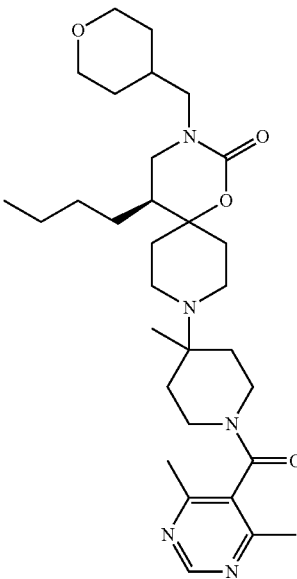
DLXXXVIII
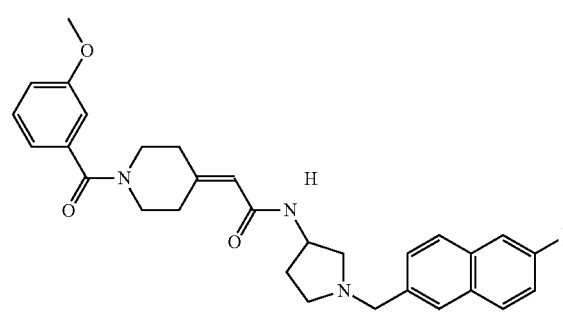
DLXXXIX
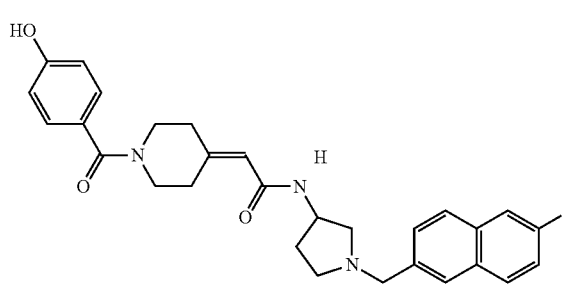
DXCIII
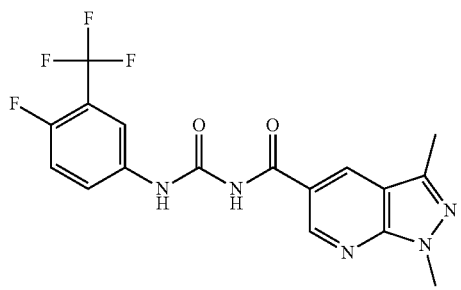

DXCIV
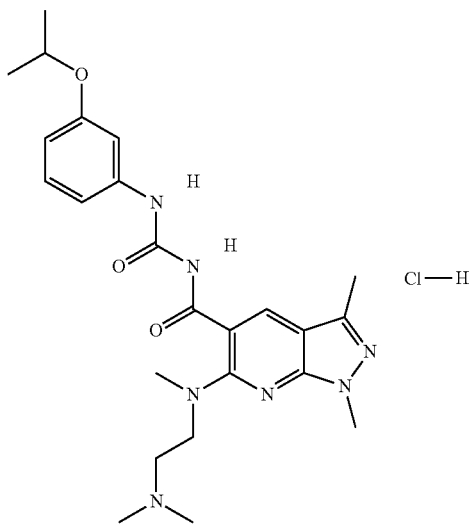
Cl—H
DXCVII
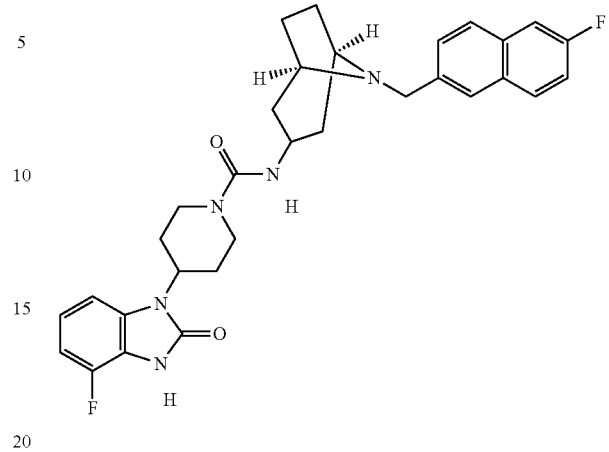
DXCV
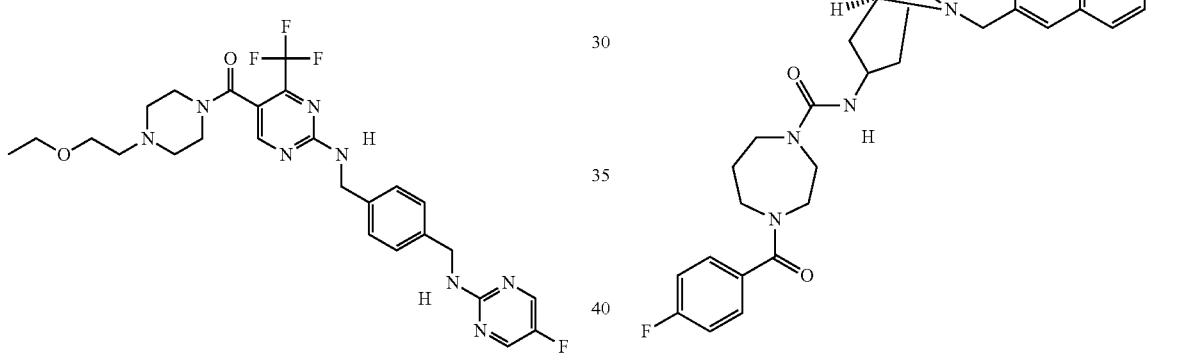
DXCVIII
DXCVI
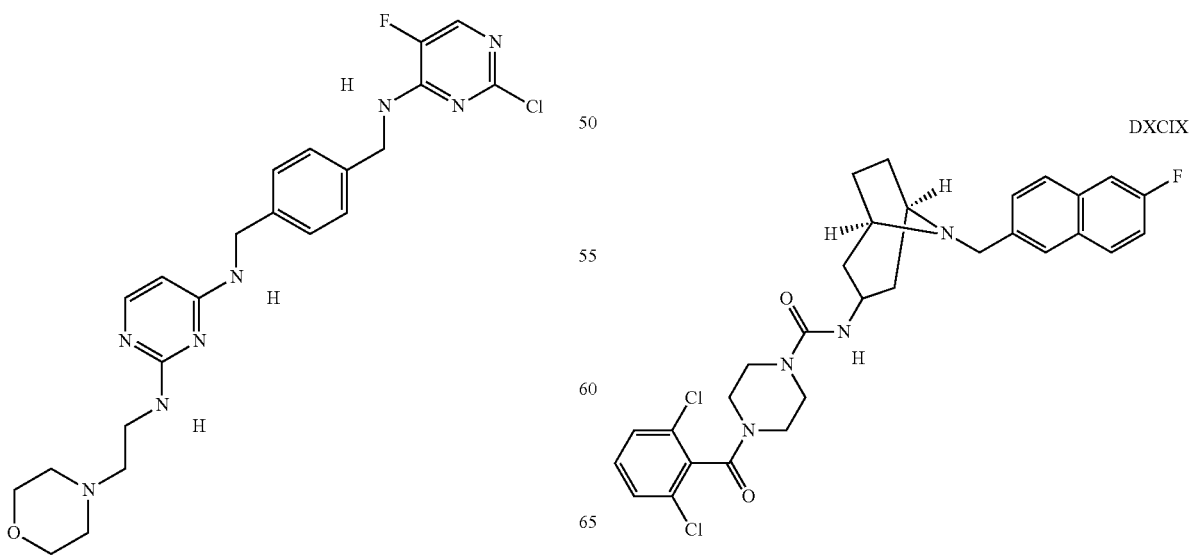
DXCIX 199
-continued
DC
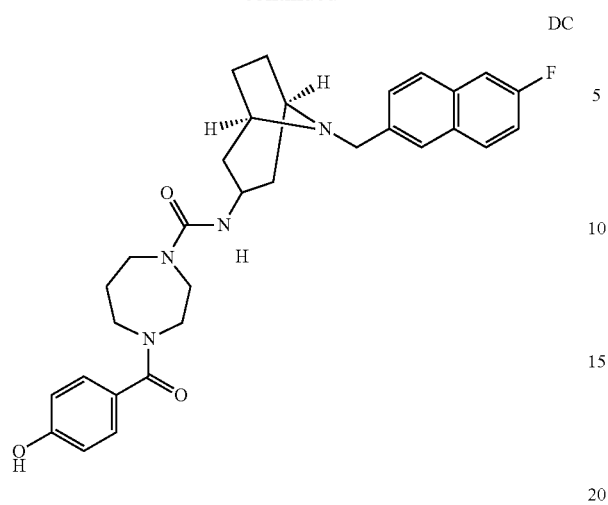
DCI
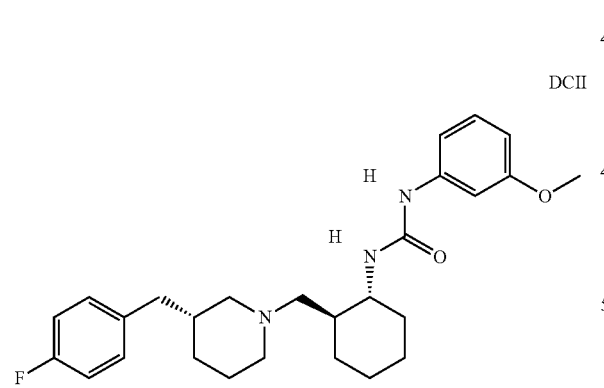
DCII
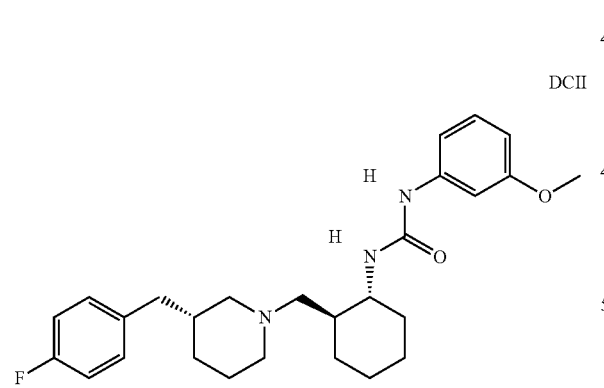
DCIII
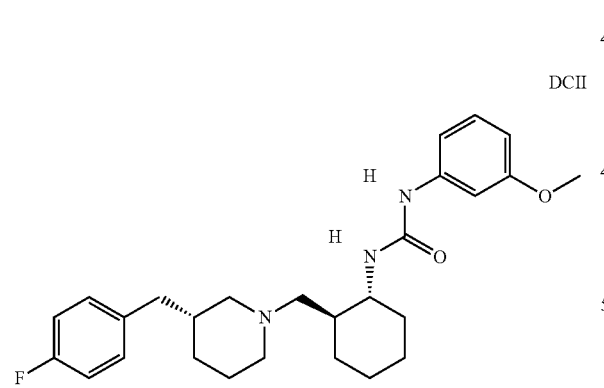
200
-continued
DCIV
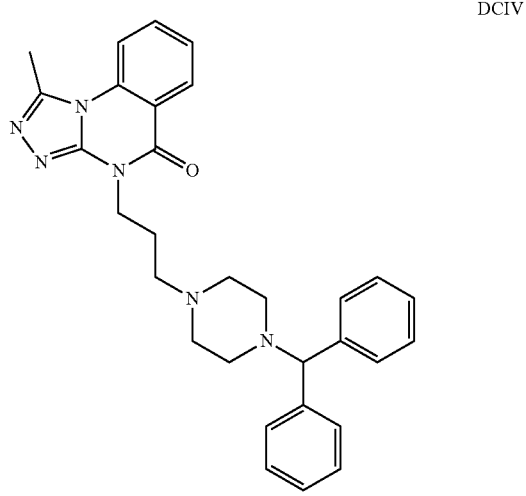
DCV
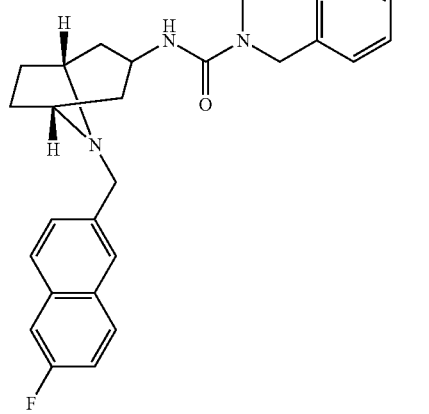
DCVI
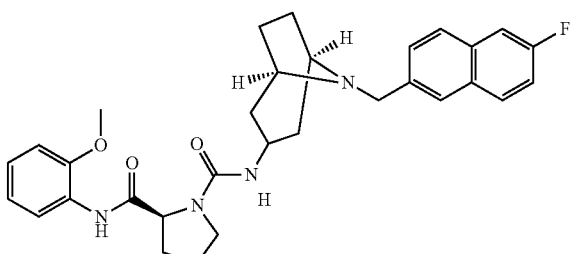
DCVII
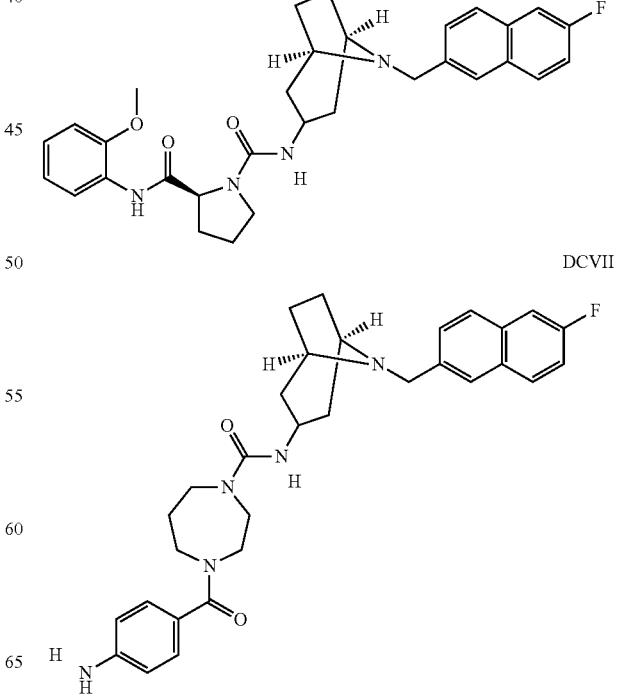

201
-continued
DCVIII
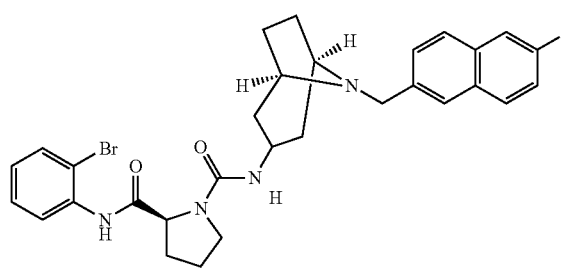
DCIX
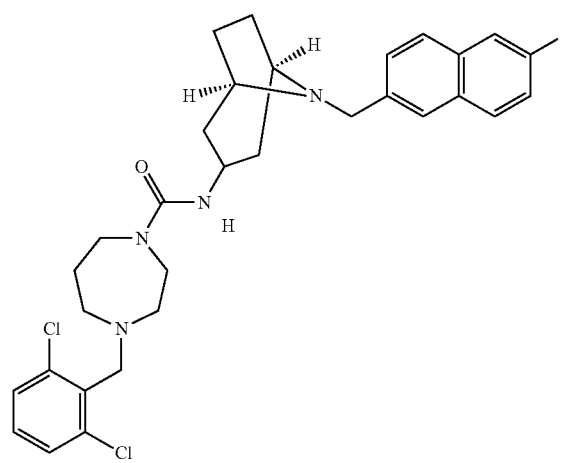
DCX
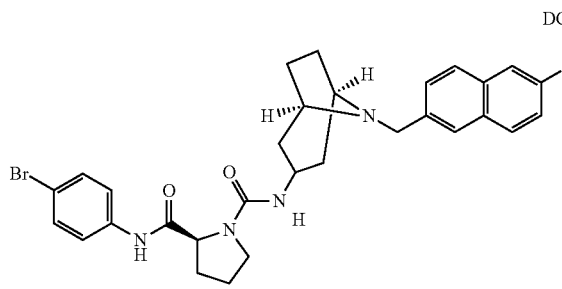
DCXI
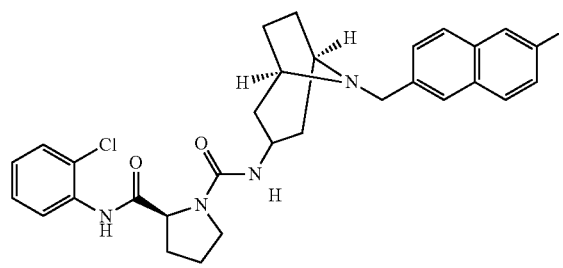
DCXII
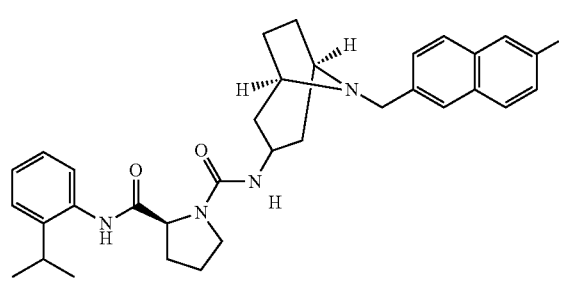
202
-continued
DCXIII
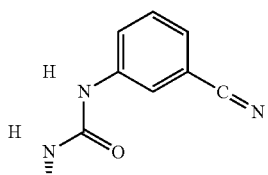
DCXIV
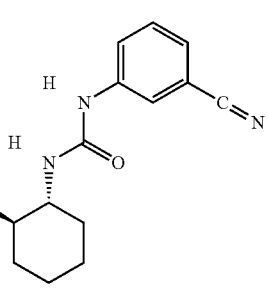
DCXV
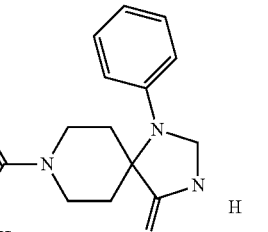
DCXVI
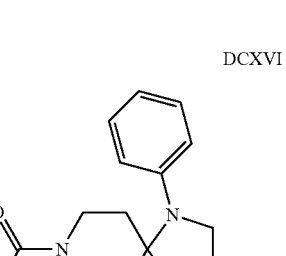

203
-continued
DCXVII
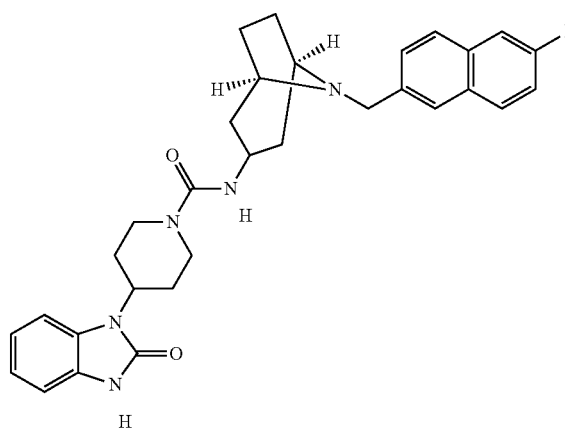
DCXVIII
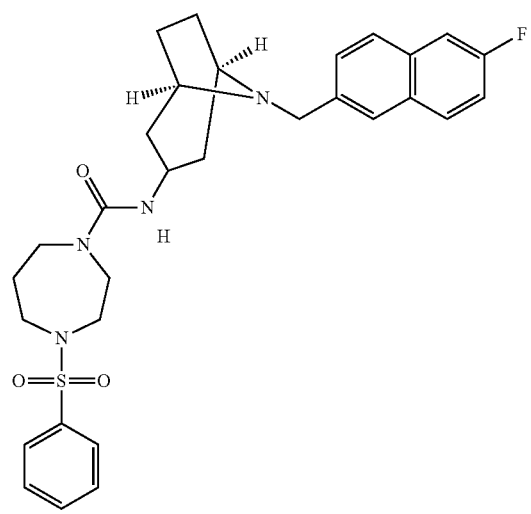
DCXIX
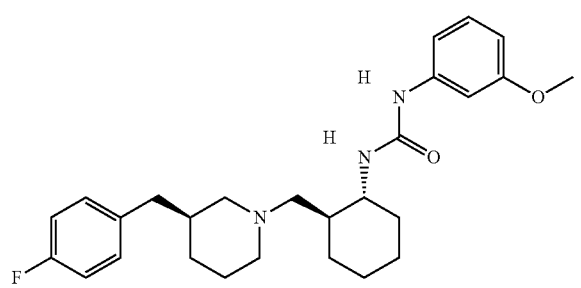
DCXX
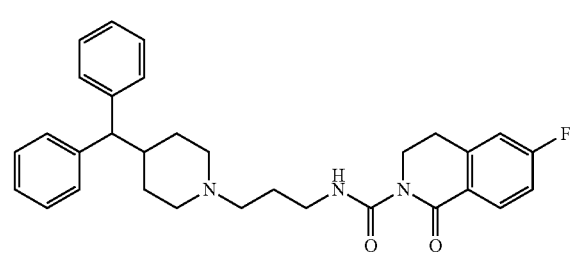
204
-continued
DCXXI
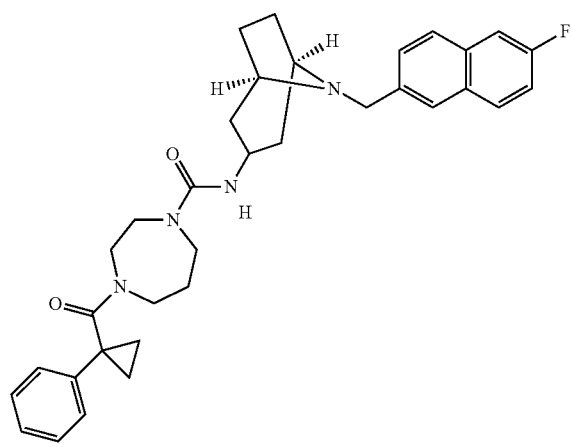
DCXXII
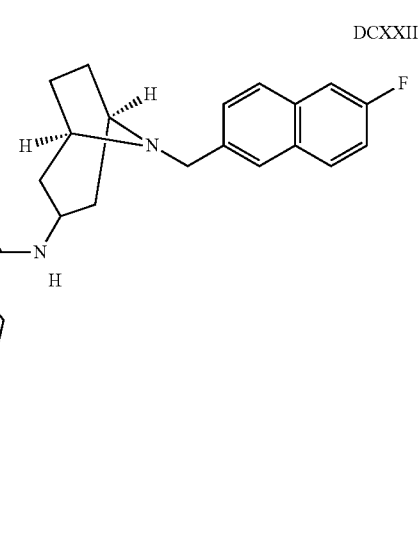
DCXXIII
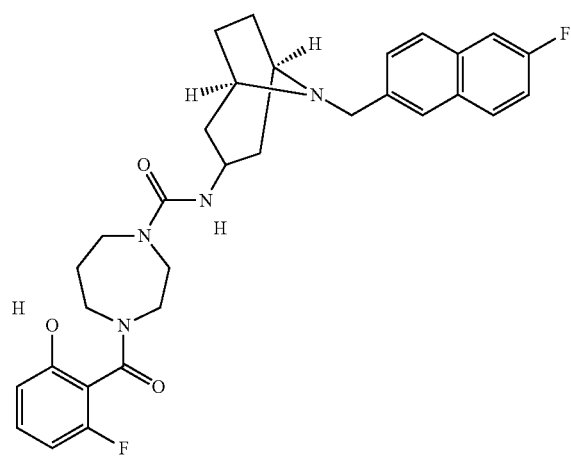

| 205 -continued | 206 -continued |
|---|---|
| DCXXIV 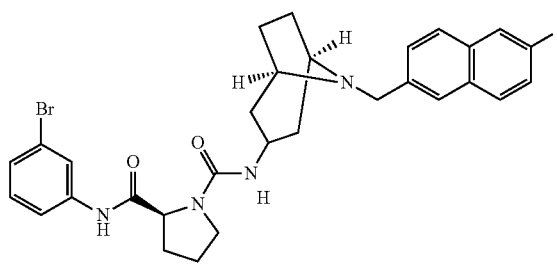 | DCXXVIII 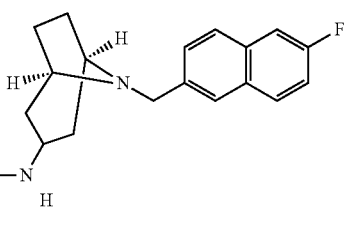 |
| DCXXV 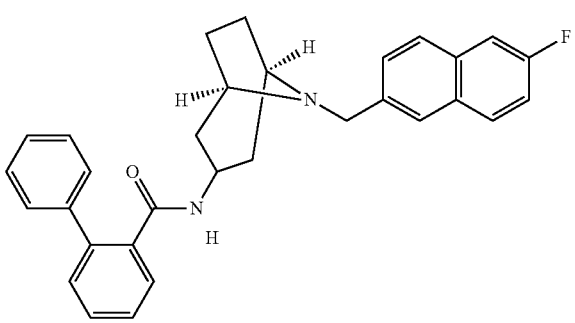 | DCXXIX |
| DCXXVI 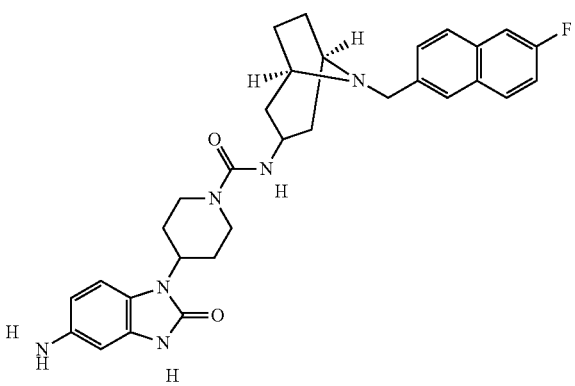 | DCXXX |
| DCXXVII 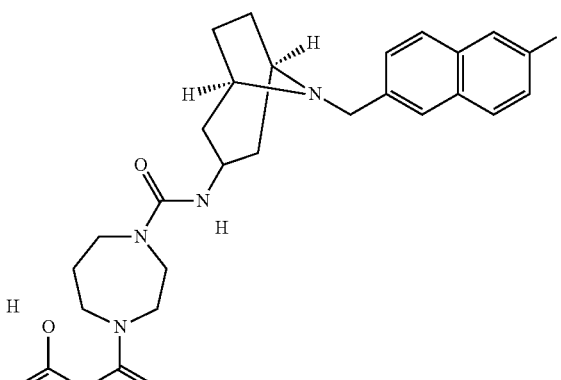 | DCXXXI 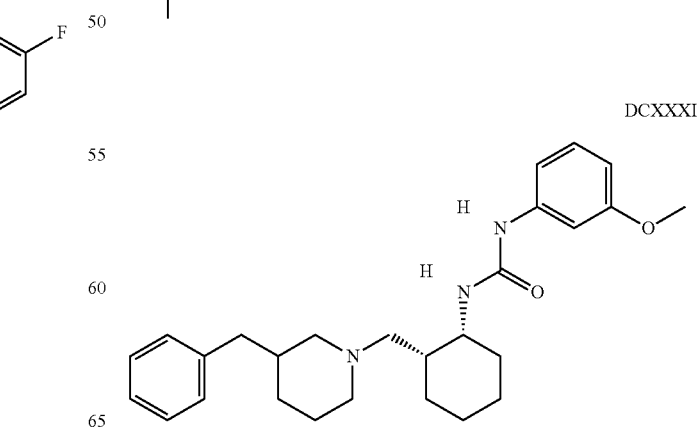 |

207
-continued
DCXXXII
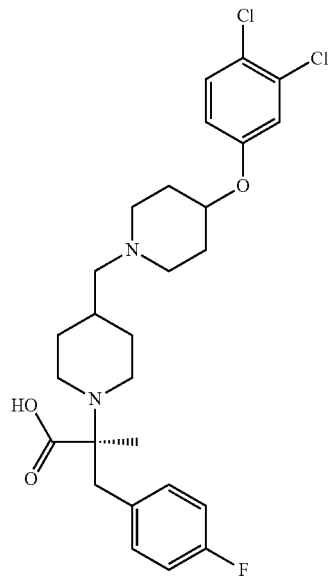
DCXXXIII
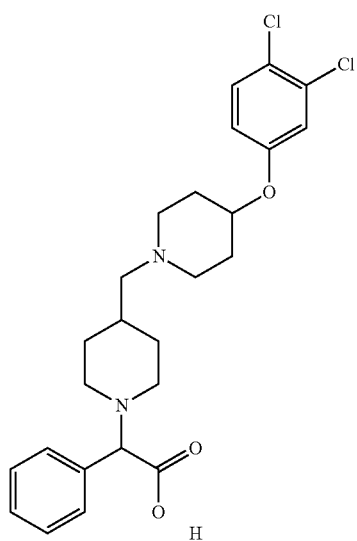
208
-continued
DCXXXIV
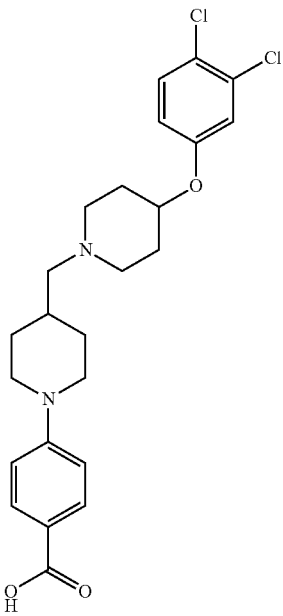
DCXXXV DCXXXVI
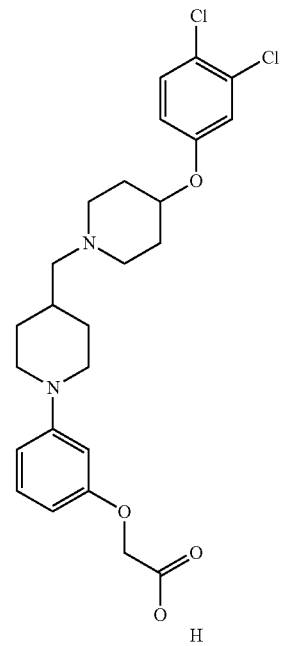
DCXXXVII
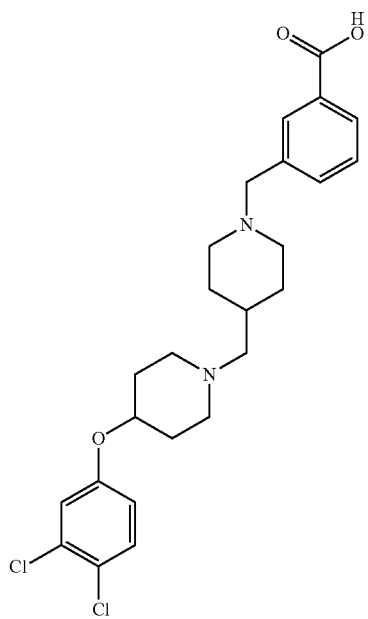
DCXXXVIII
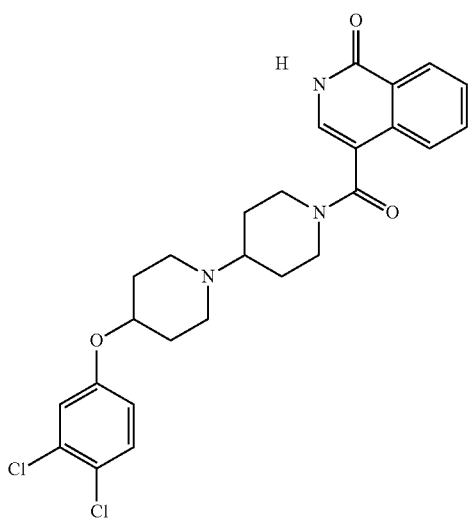
DCXXXIX
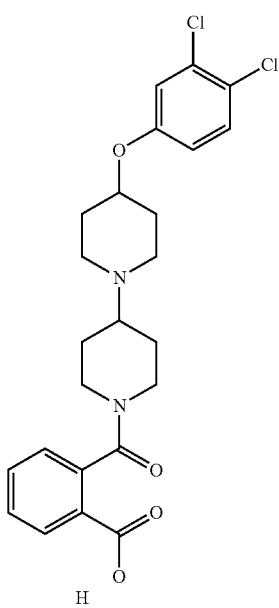

211
-continued
212
-continued
DCXL
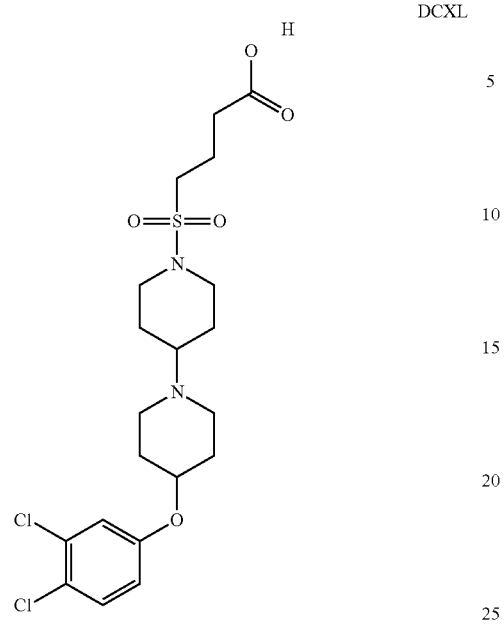
DCXLII
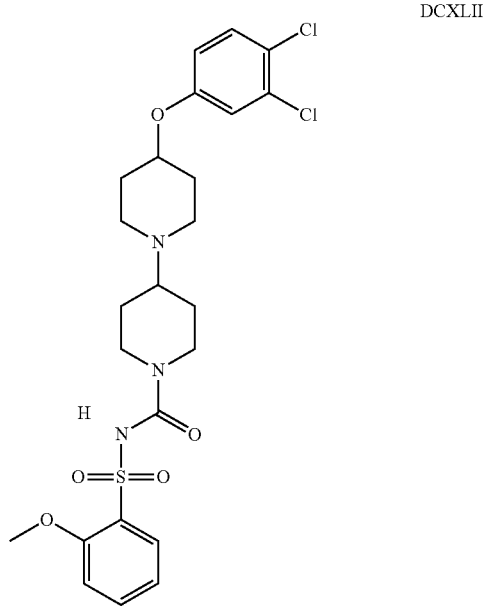
DCXLI
DCXLIII
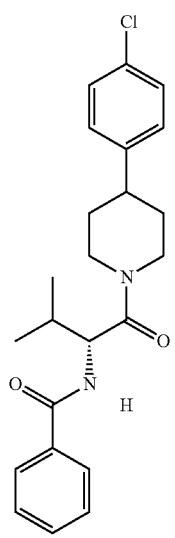

213
-continued
DCXLIV
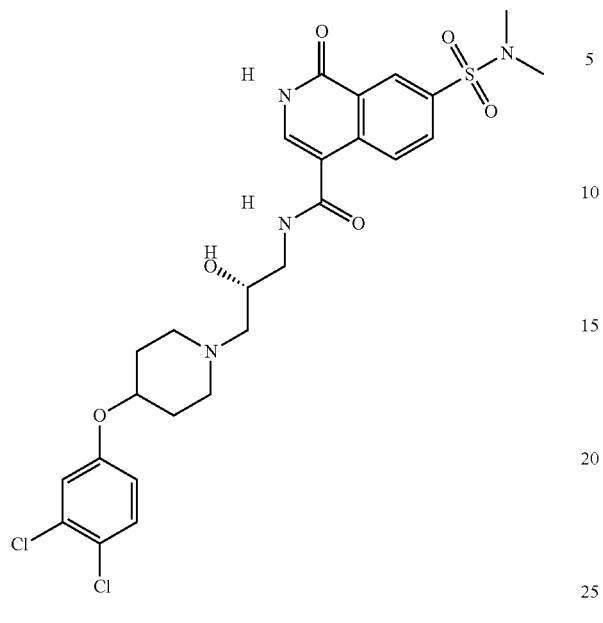
DCXLV
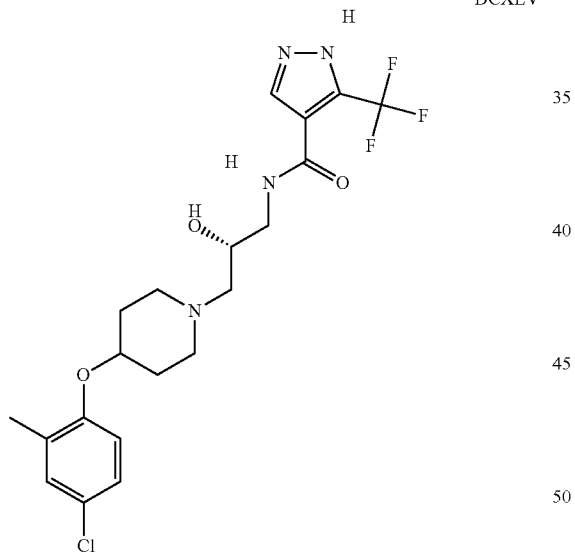
DCXLVI
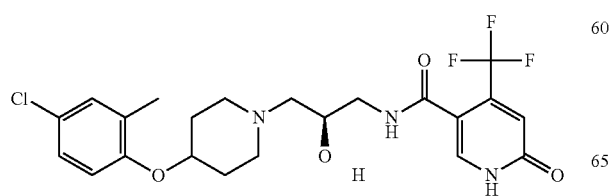
214
-continued
DCXLVII
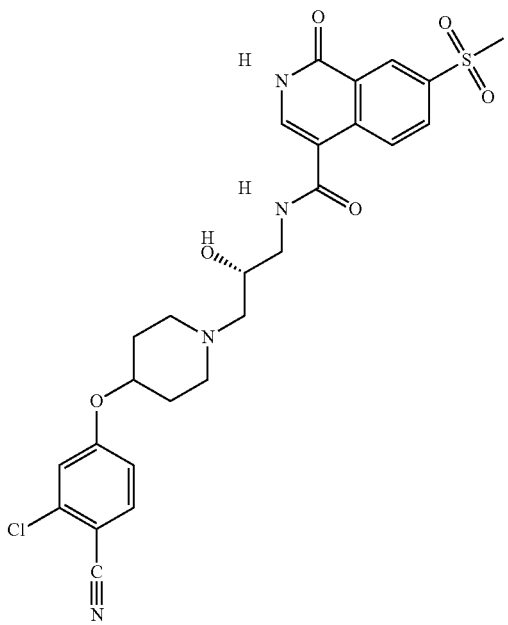
DCXLVIII
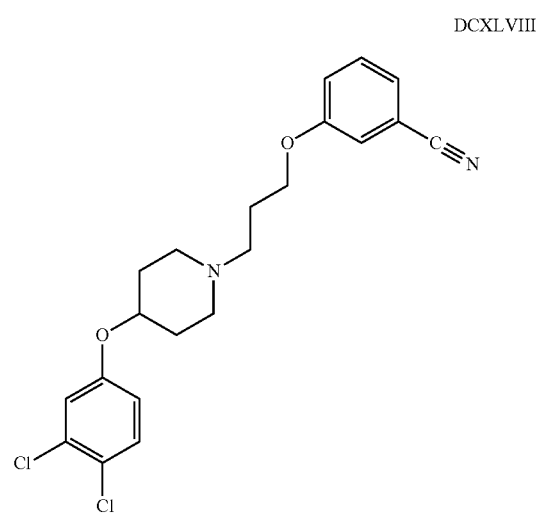

215
-continued
DCXLIX
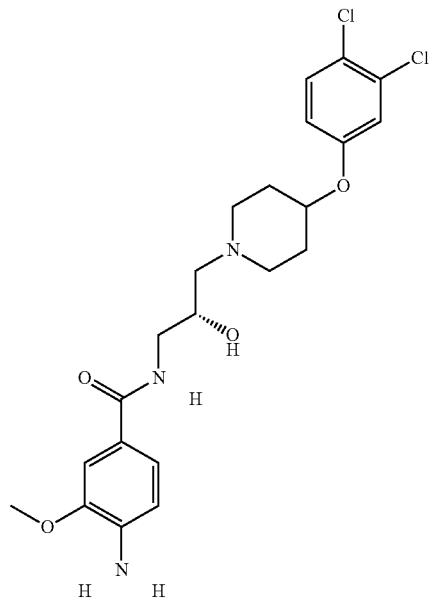
216
-continued
DCLI
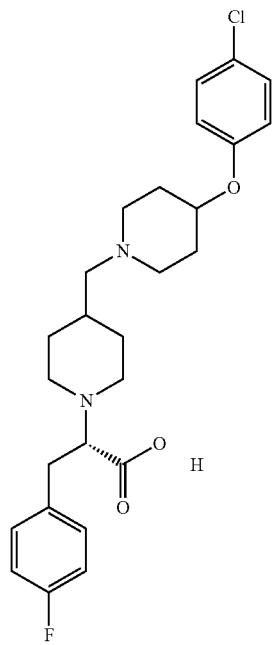
DCL
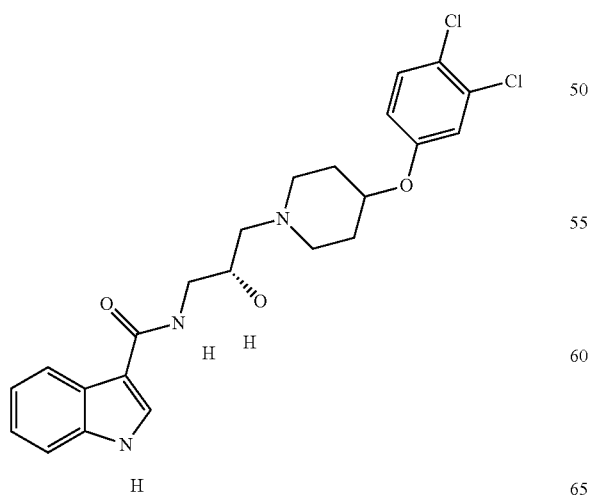
DCLII
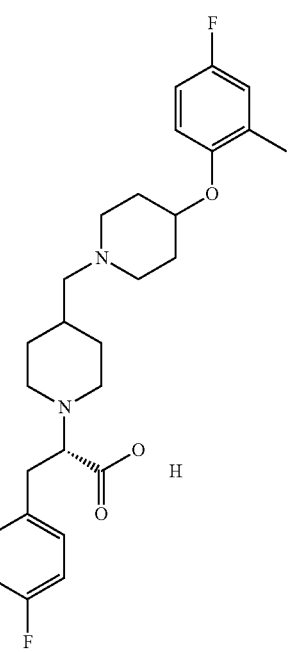

DCLIII
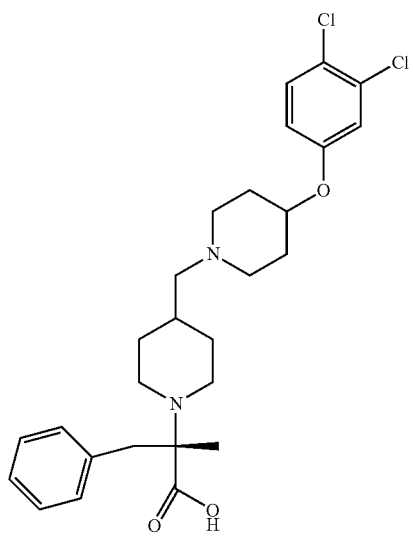
DCLIV
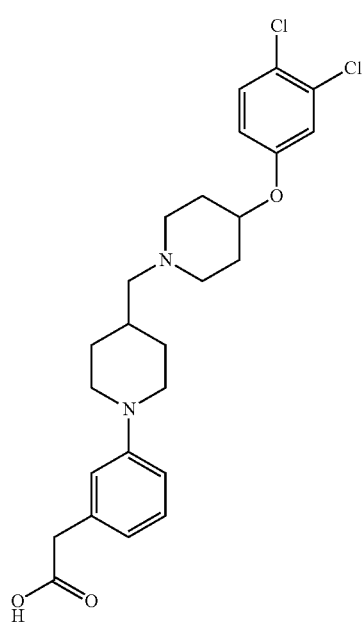
DCLV
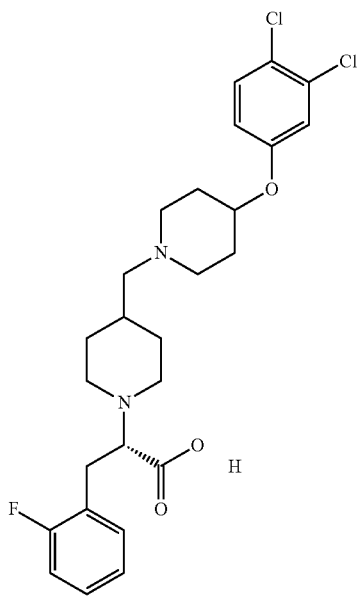
DCLVI
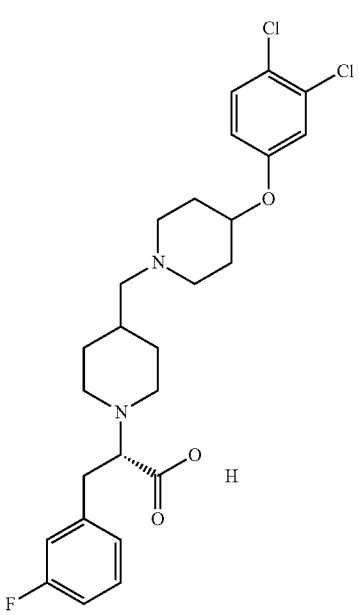

-continued
DCLVII
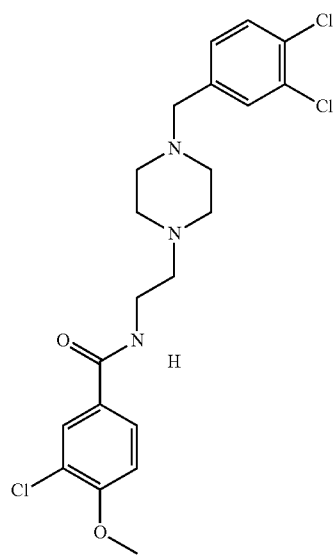
DCLVIII
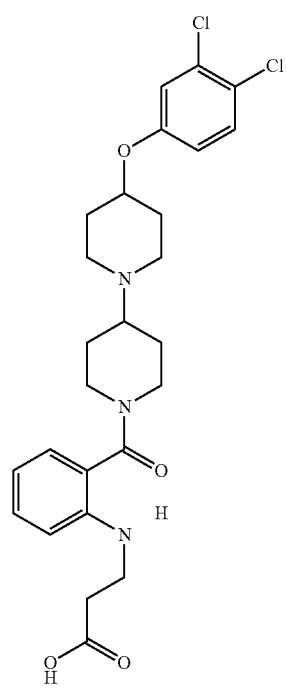
-continued
DCLIX
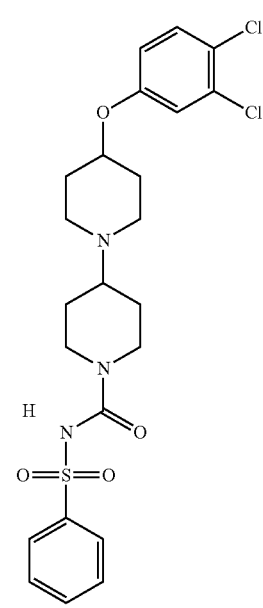
DCLX
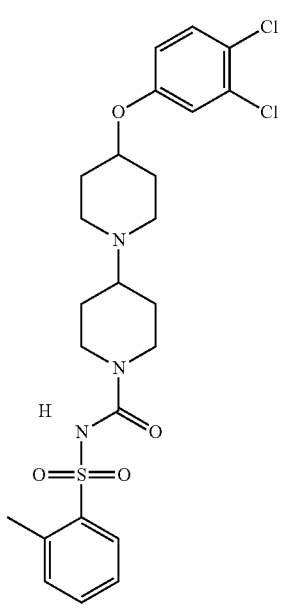

221
-continued
DCLXI
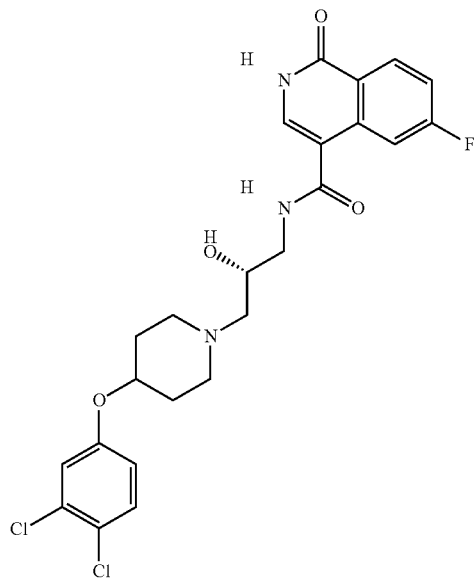
222
-continued
DCLXIII
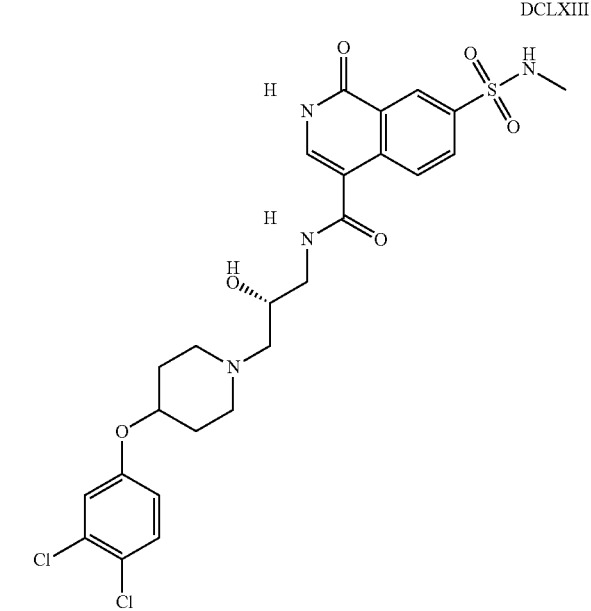
DCLXII
DCLXIV
DCLXV
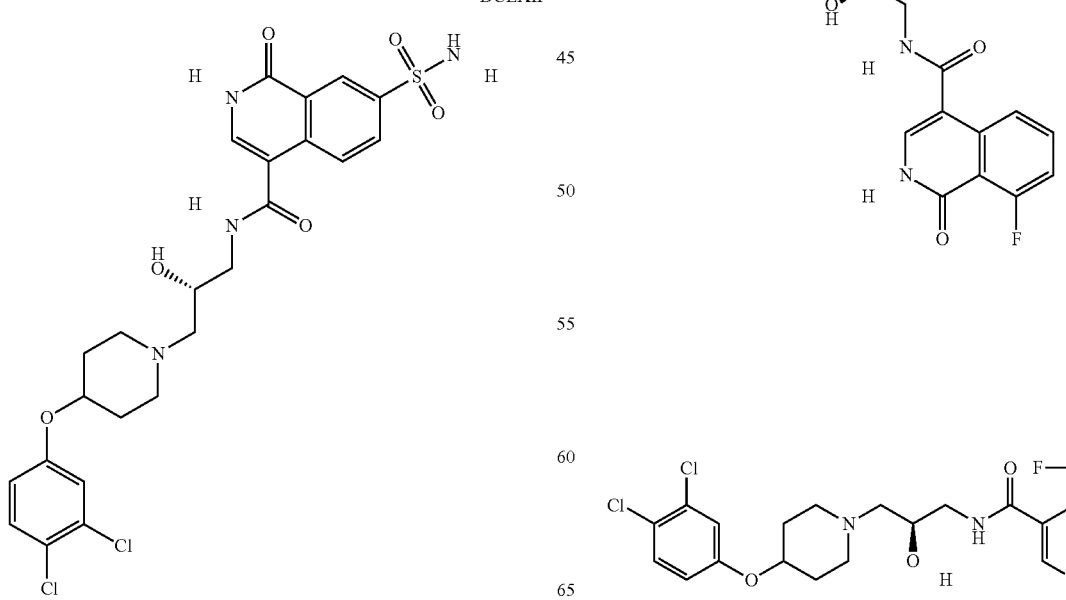

223
-continued
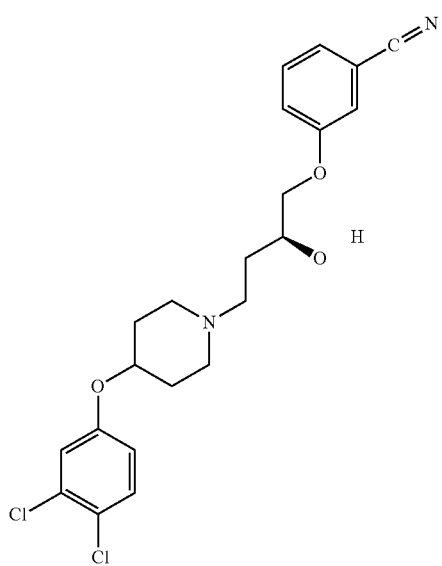
DCLXVI
224
-continued
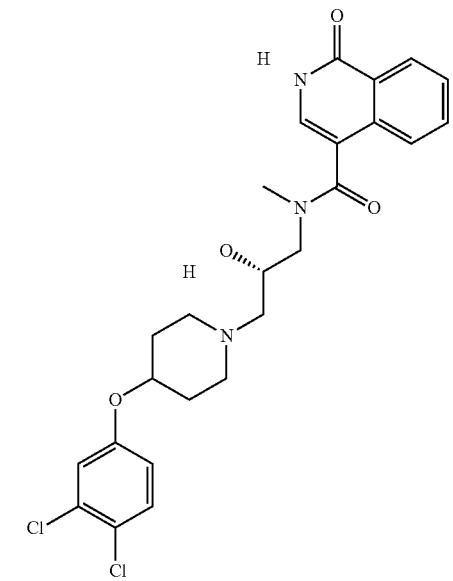
DCLXVIII
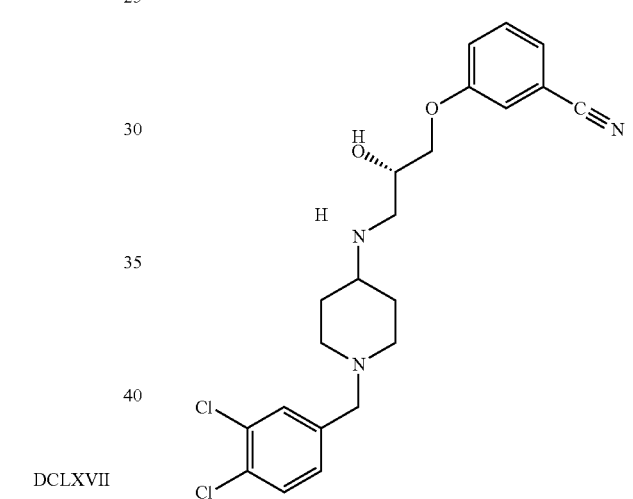
DCLXIX
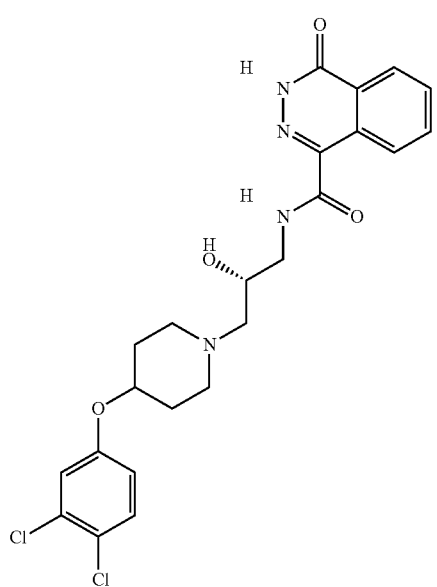
DCLXVII
DCLXX DCLXXI
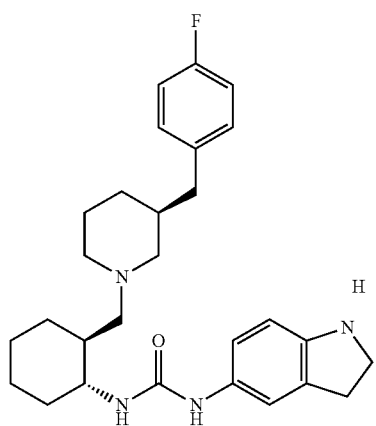
DCLXXIII
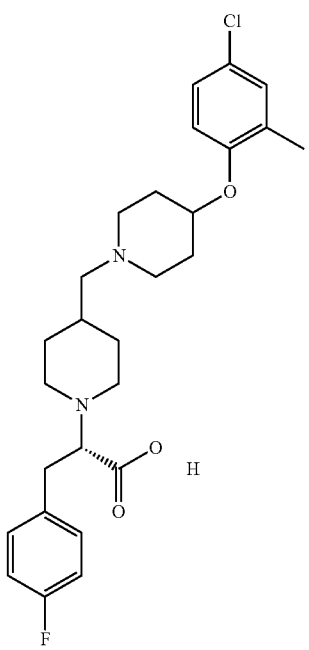
DCLXXII
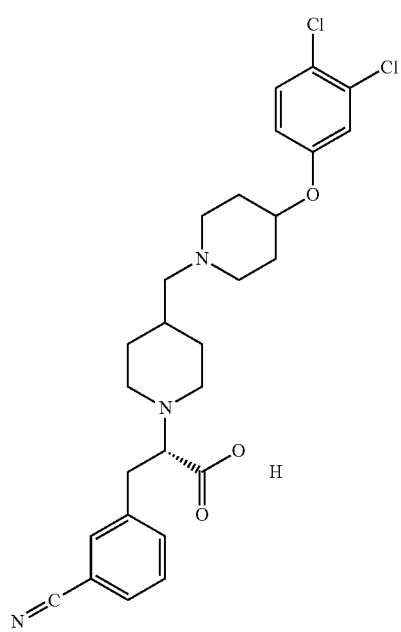
DCLXXIV DCLXXV
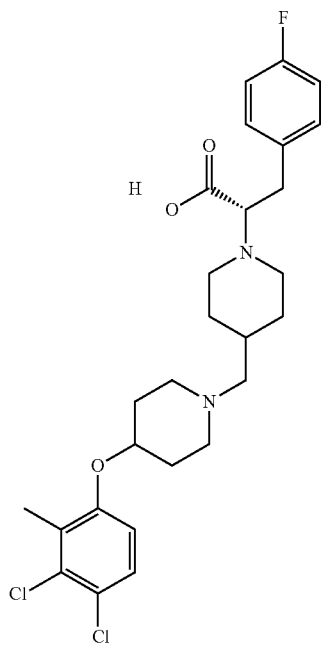
DCLXXVI
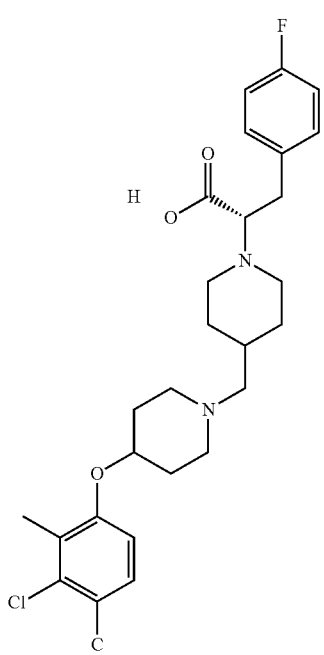
DCLXXVII
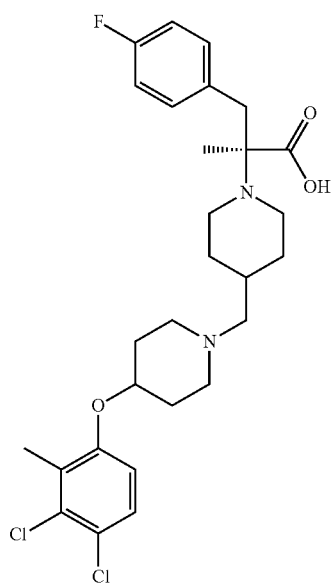
DCLXXVIII
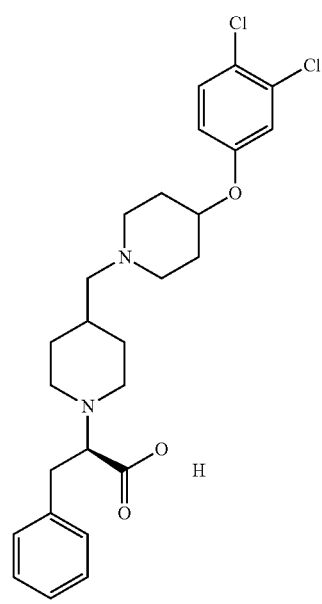

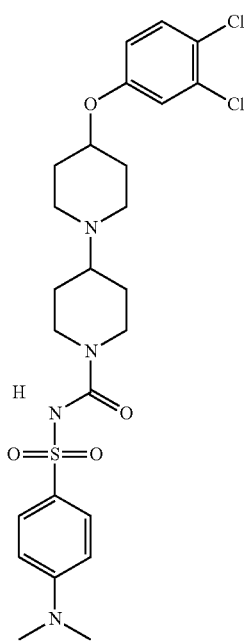
DCLXXIX
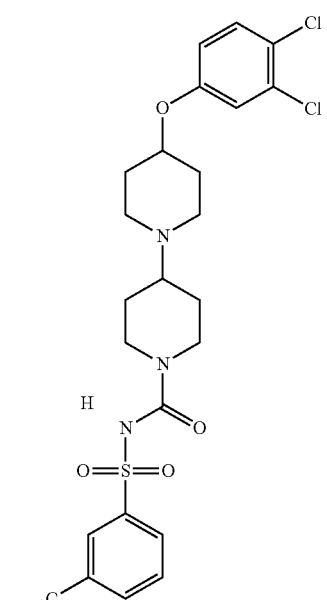
DCLXXXI
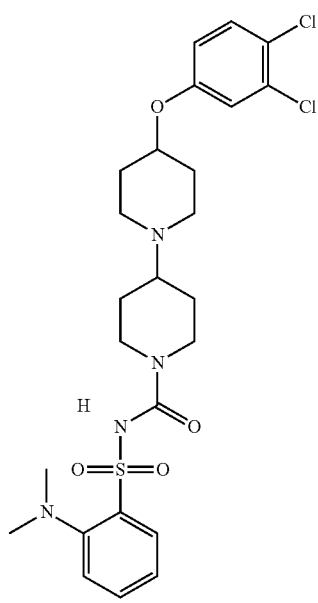
DCLXXX
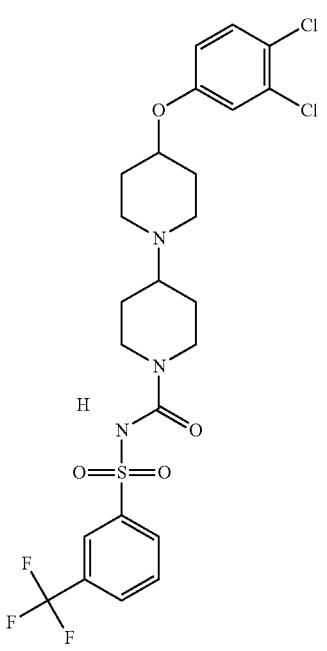
DCLXXXII

DCLXXXIII
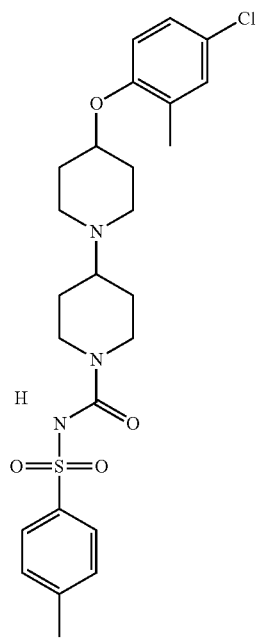
DCLXXXV
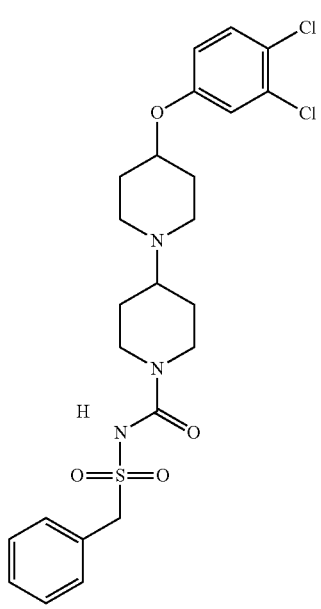
DCLXXXIV
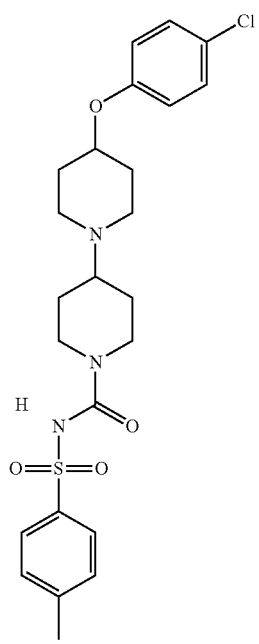
DCLXXXVI
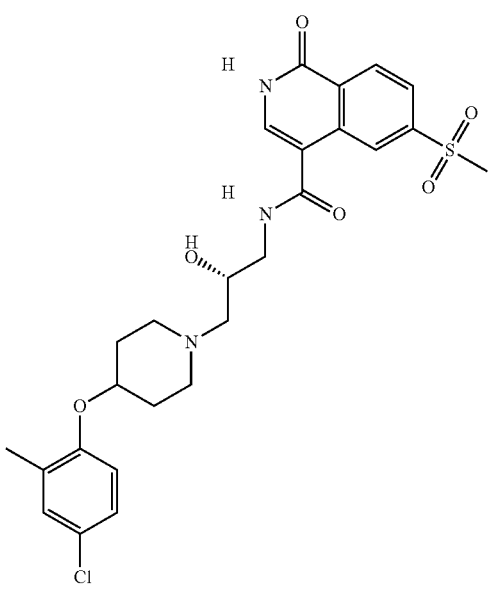

233
-continued
DCLXXXVII
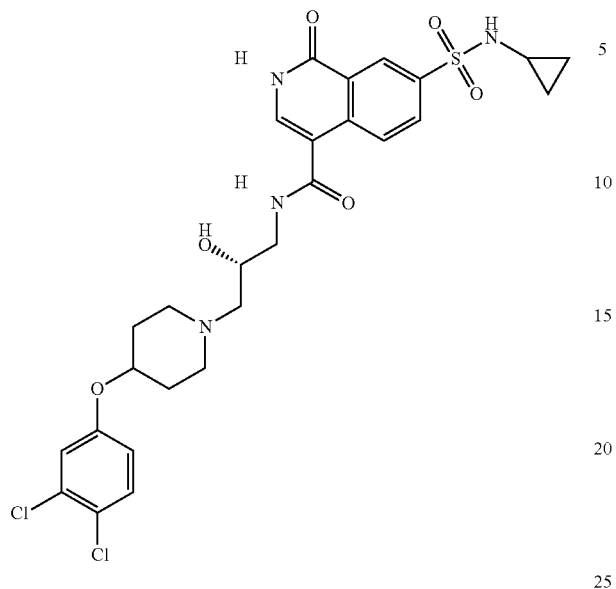
DCLXXXVIII
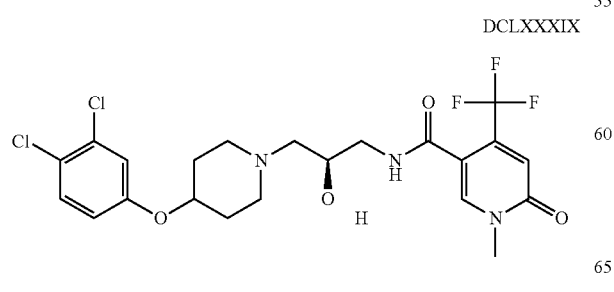
DCLXXXIX
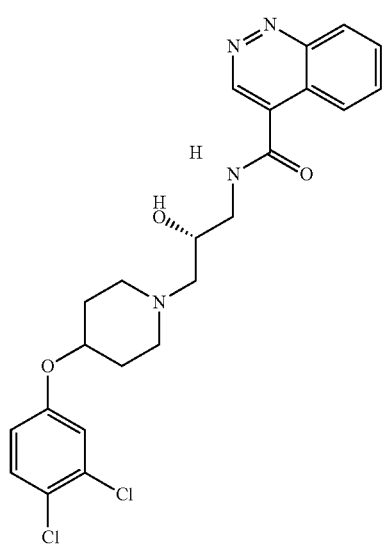
234
-continued
DCXC
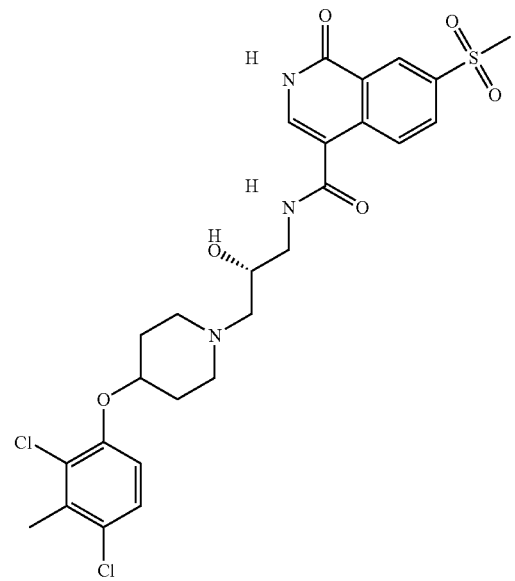
DCXCI
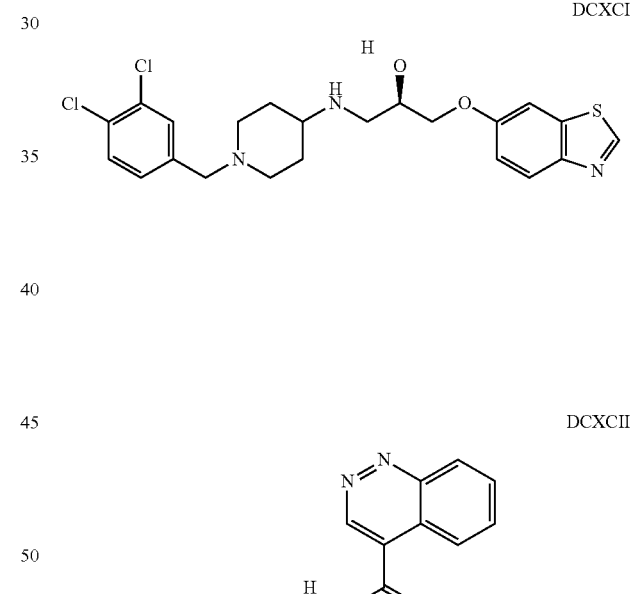
DCXCII

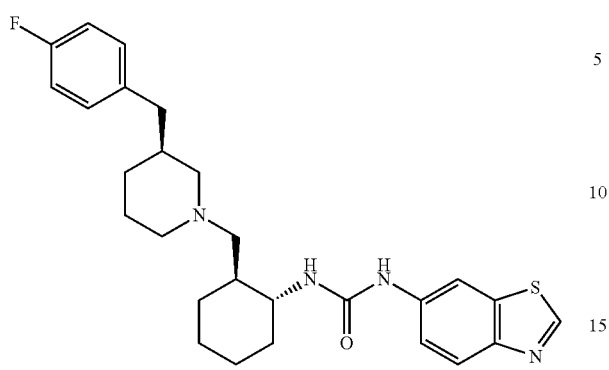
DCXCIII
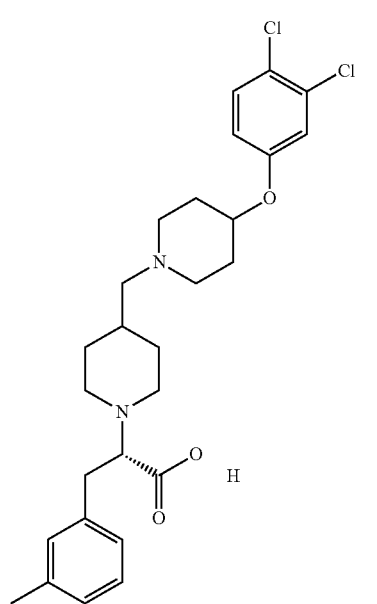
DCXCIV
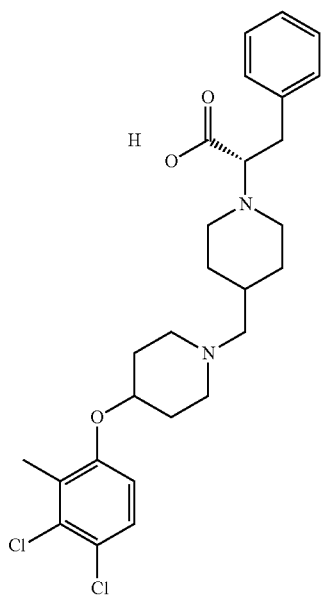
DCXCV
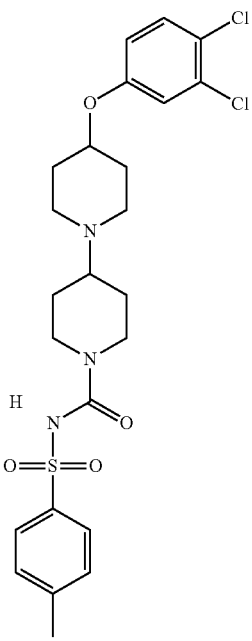
DCXCVI
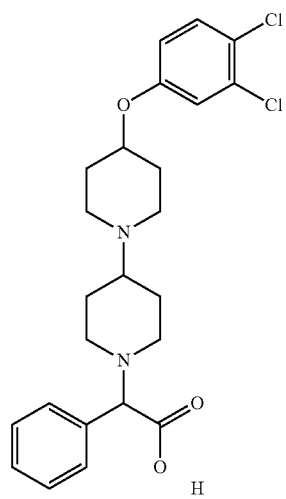
DCXCVII
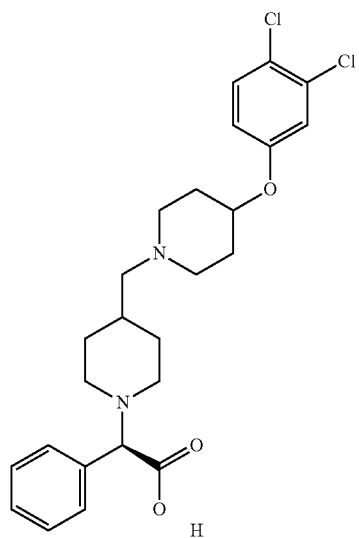
DCXCVIII 237
-continued
DCXCIX
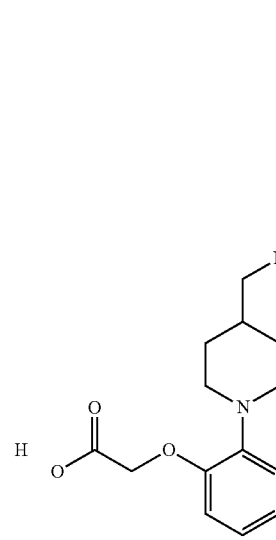
238
-continued
DCCI
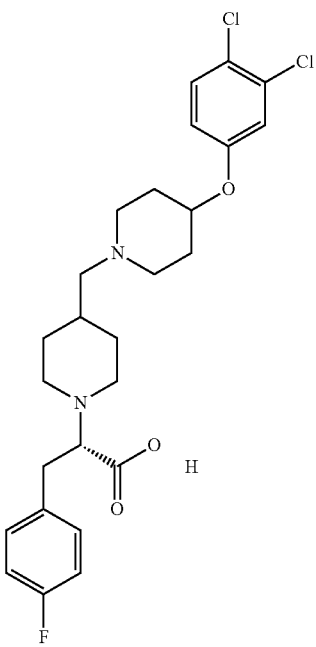
DCC
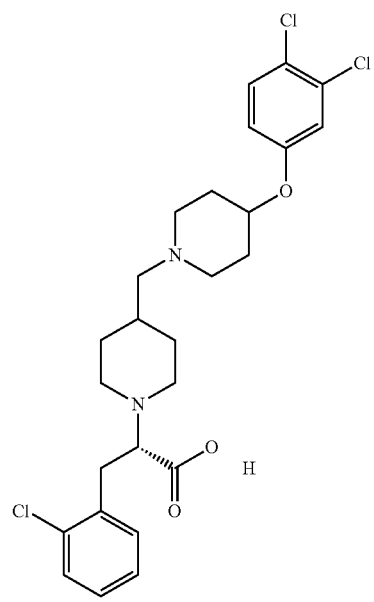
DCCII
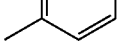

239
-continued
DCCIII
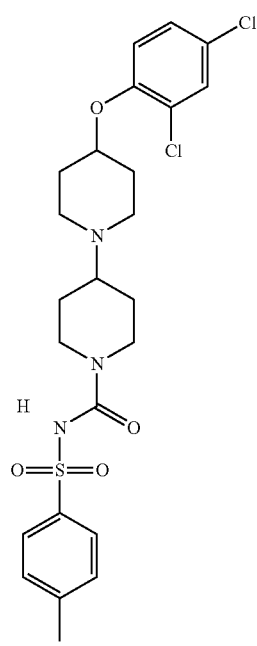
240
-continued
DCCV
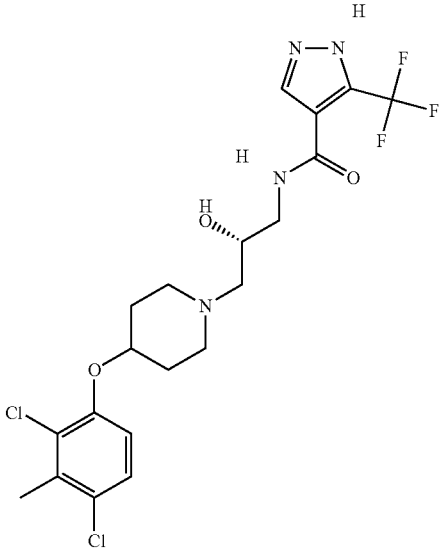
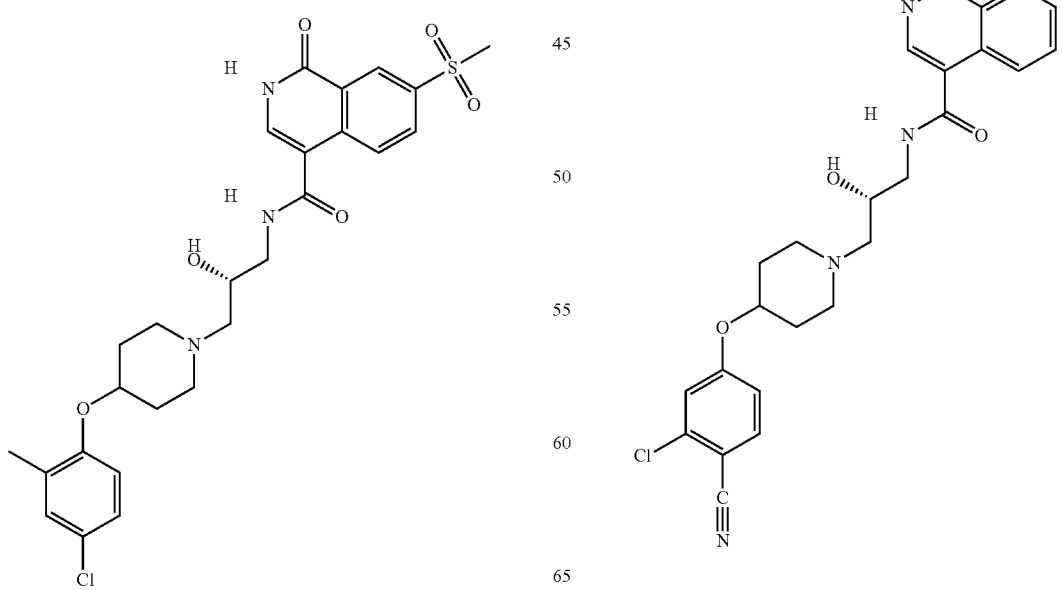

241
-continued
DCCVII
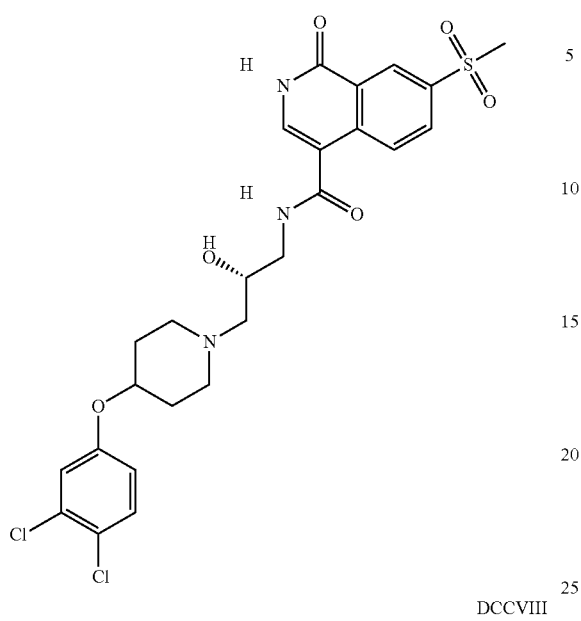
DCCVIII
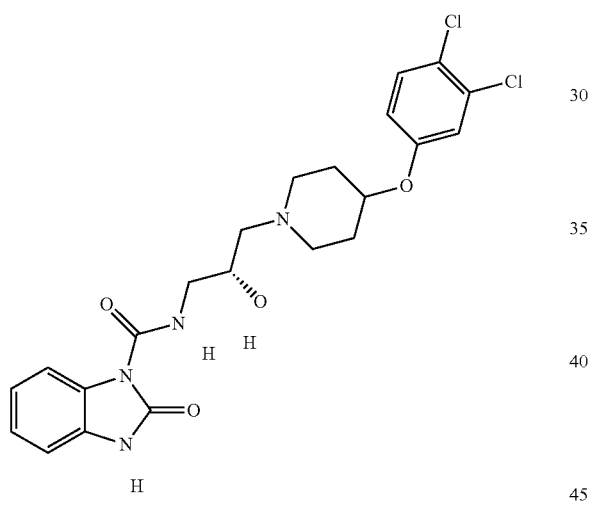
DCCIX
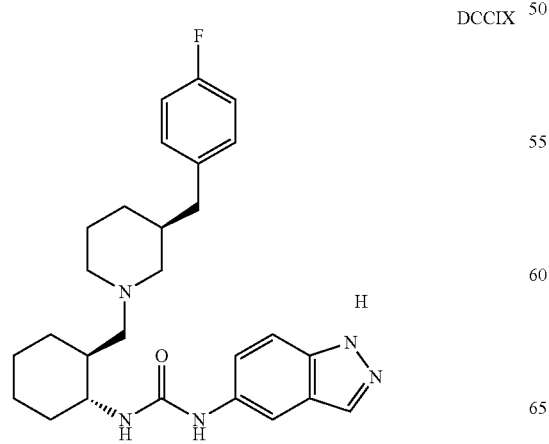
242
-continued
DCCX
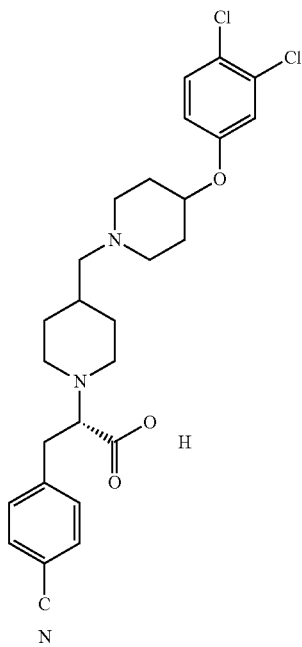
DCCXI
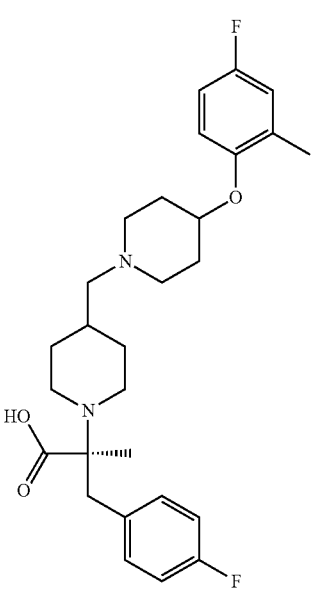

DCCXII
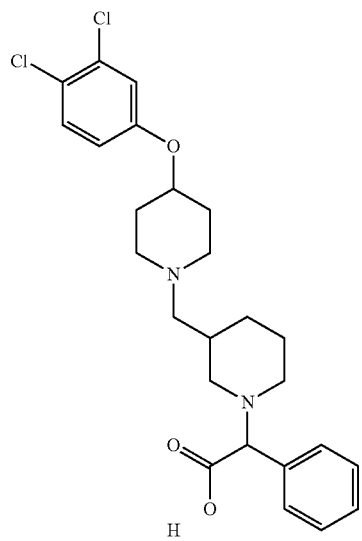
DCCXIII
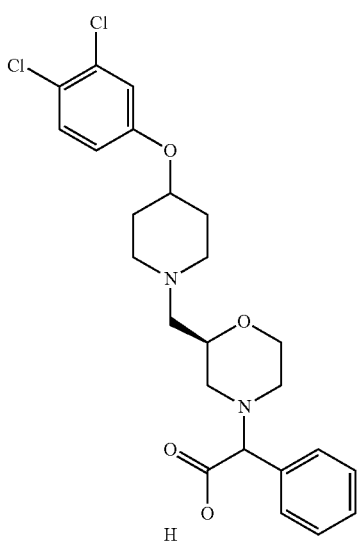
DCCXIV
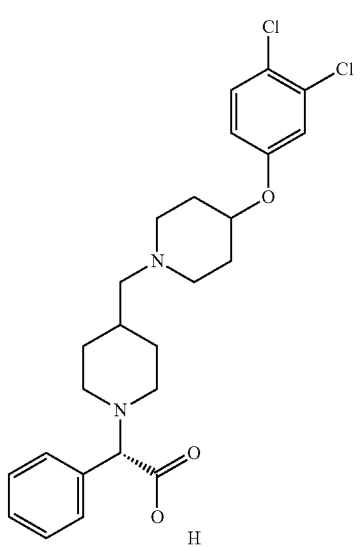
DCCXV
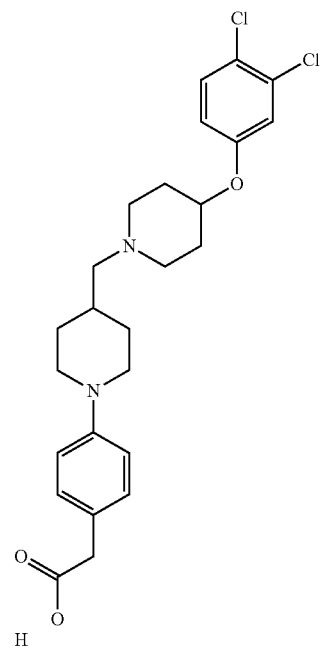
DCCXVI
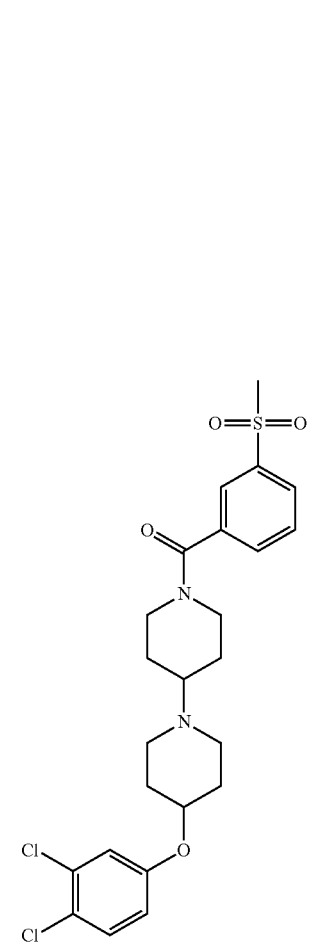

DCCXVII
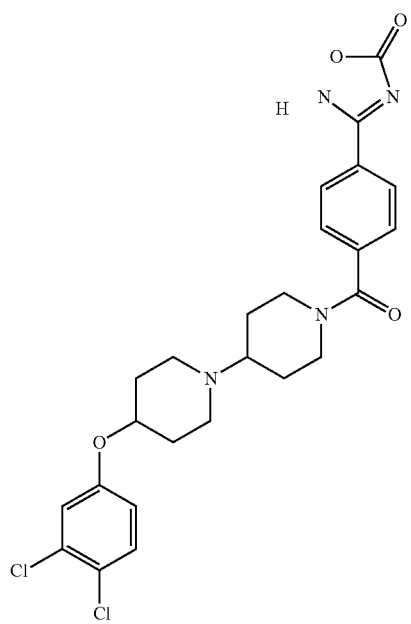
DCCXIX
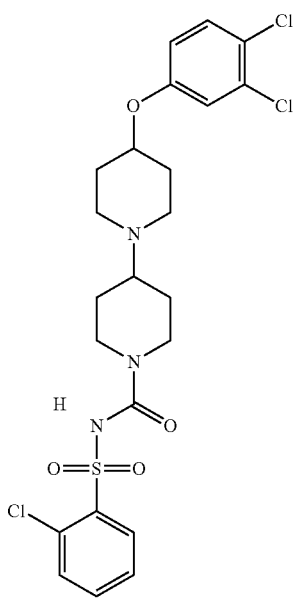
DCCXX
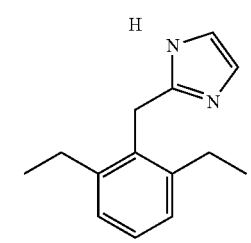
DCCXVIII
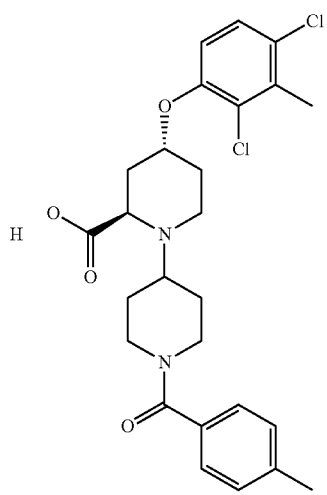
DCCXXI
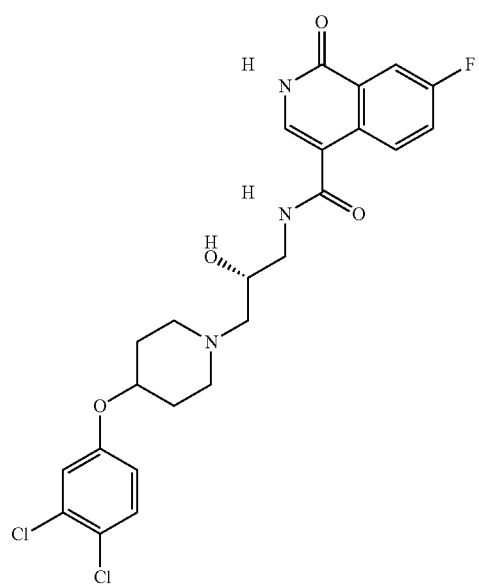

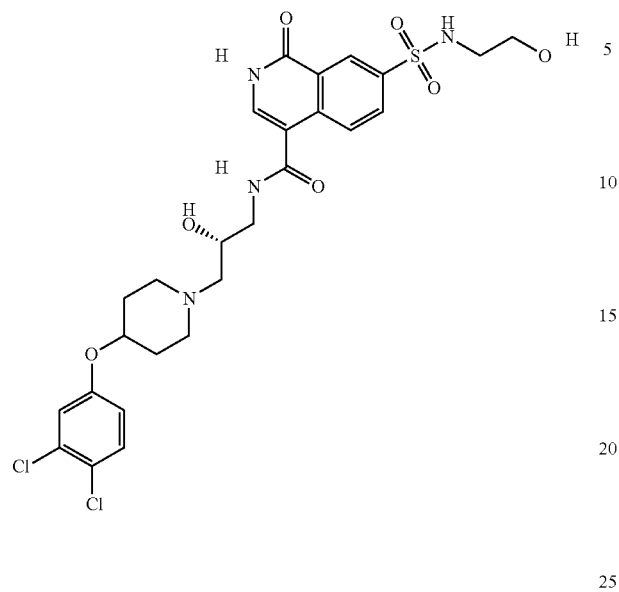
DCCXXII
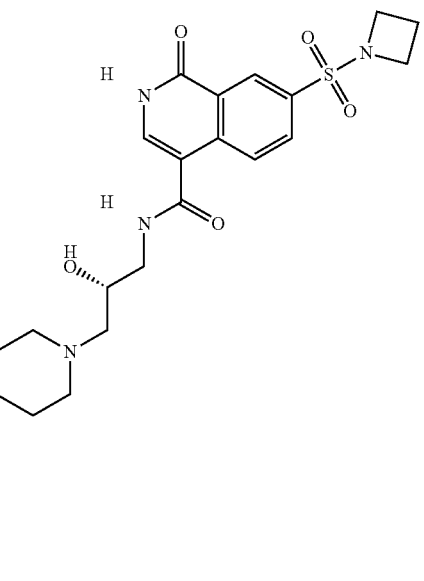
DCCXXIV
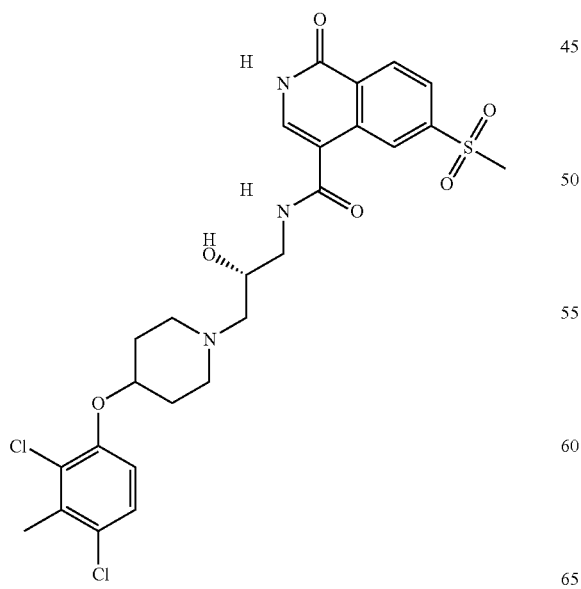
DCCXXIII
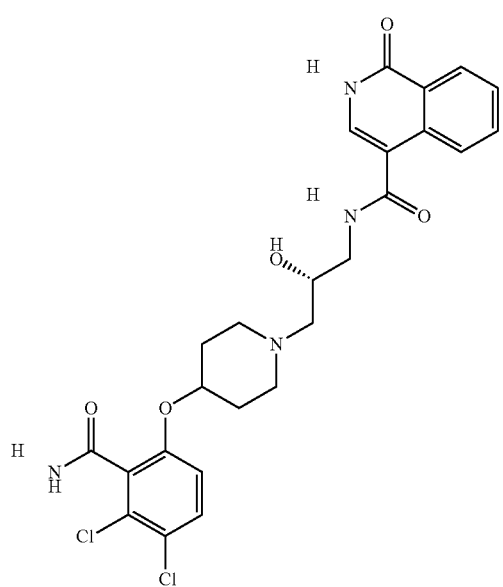
DCCXXV

-continued
DCCXXVI
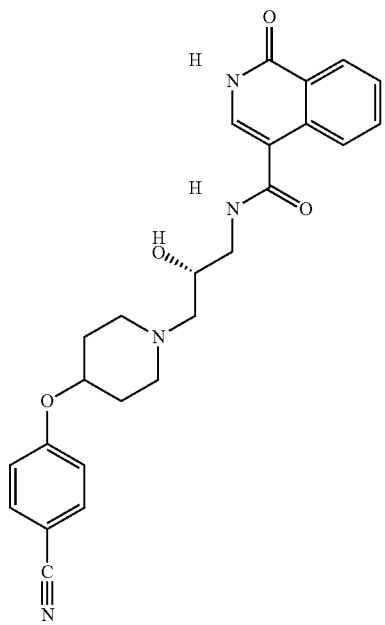
DCCXXVII
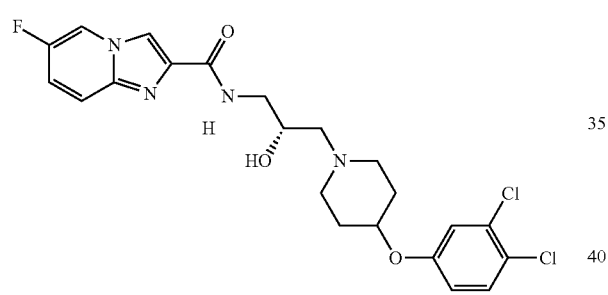
DCCXXVIII
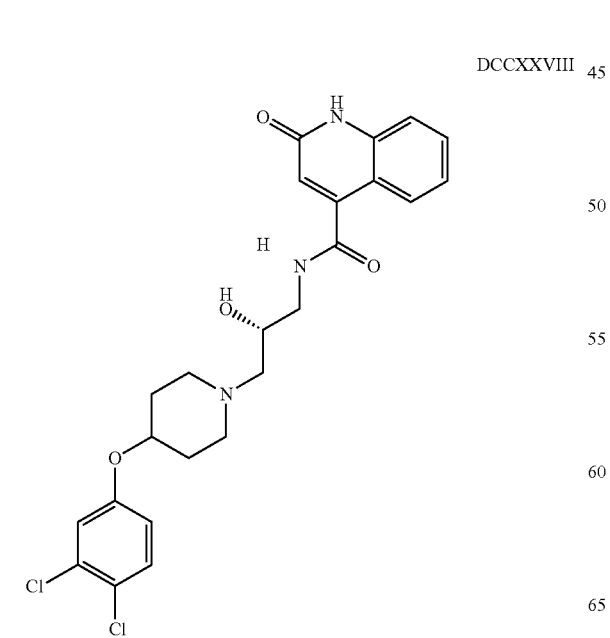
-continued
DCCXXIX
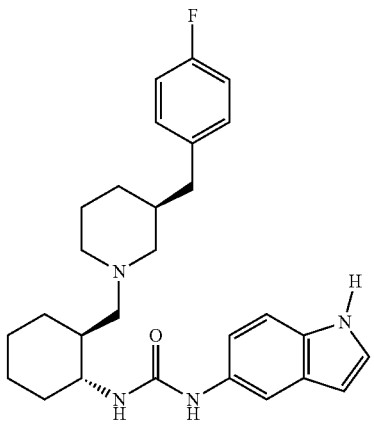
DCCXXX
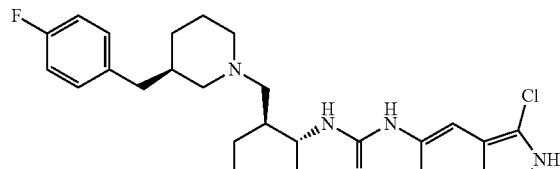
DCCXXXI
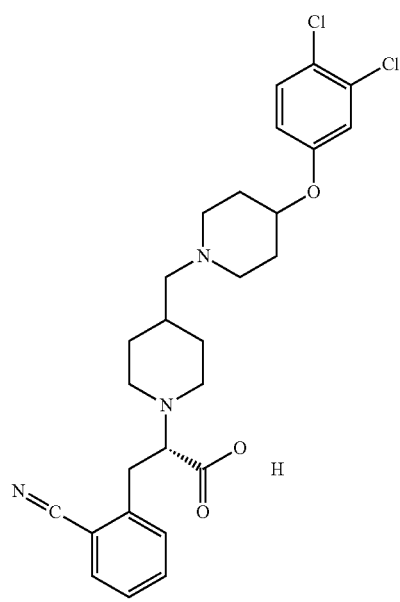

DCCXXXII
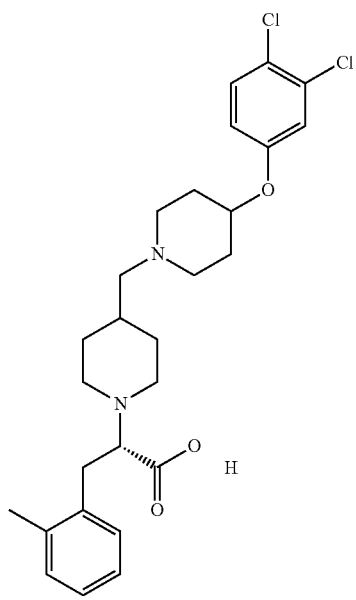
DCCXXXIII
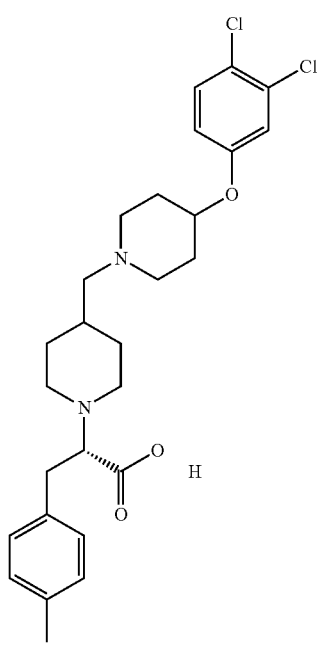
DCCXXXIV
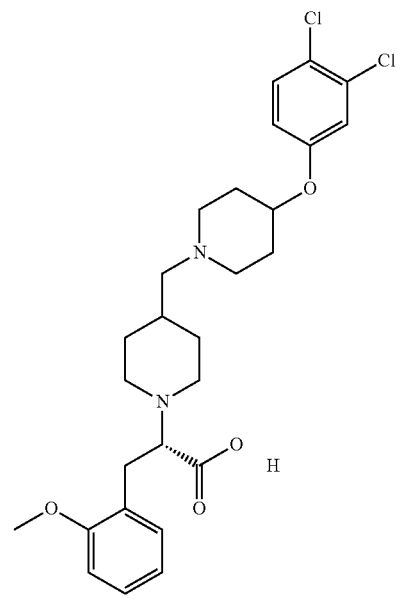
DCCXXXV
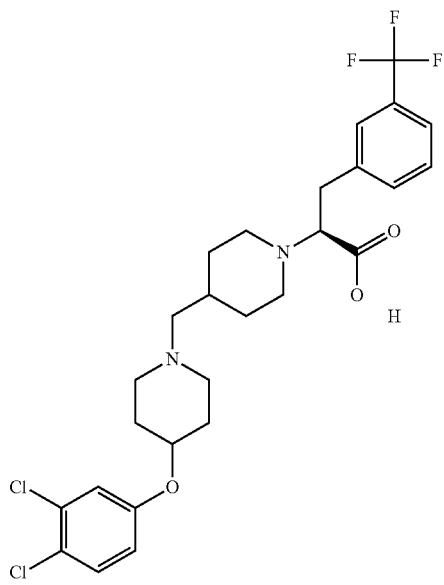

-continued
DCCXXXVI
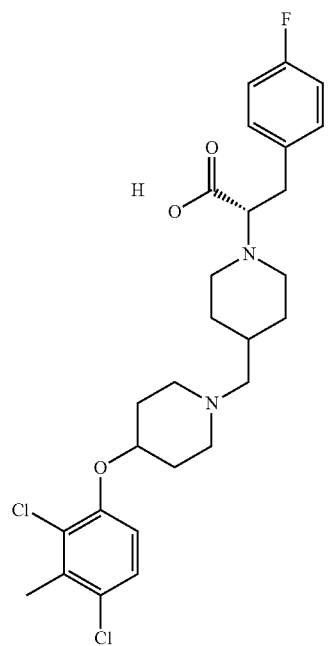
DCCXXXVII
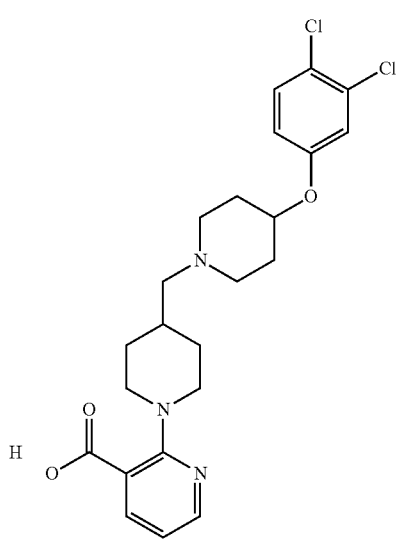
DCCXXXVIII
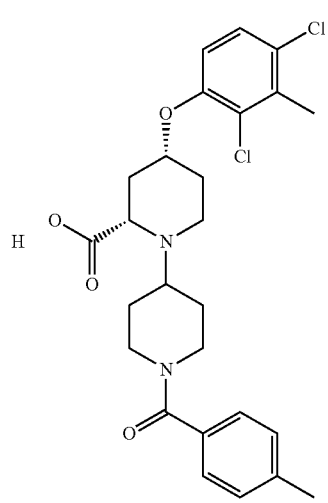
-continued
DCCXXXIX
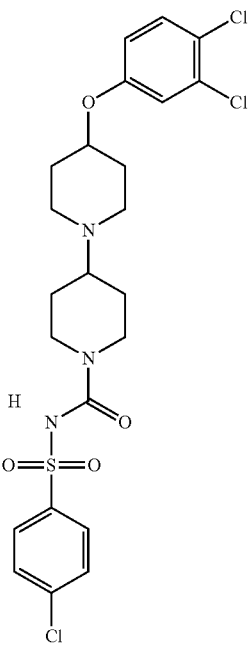
DCCXL
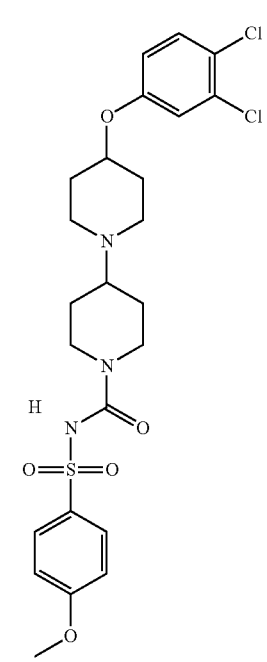

DCCXLI
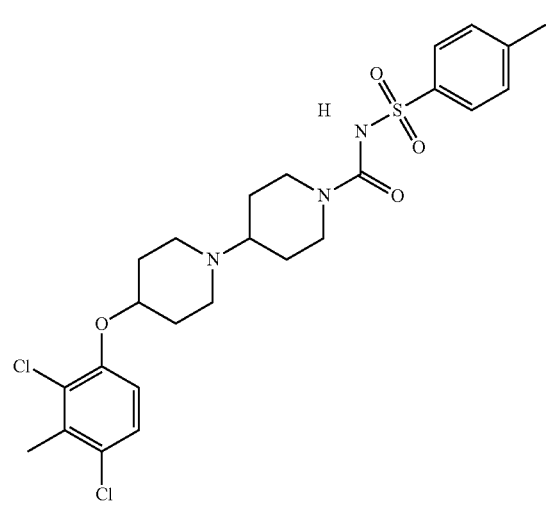
DCCXLII
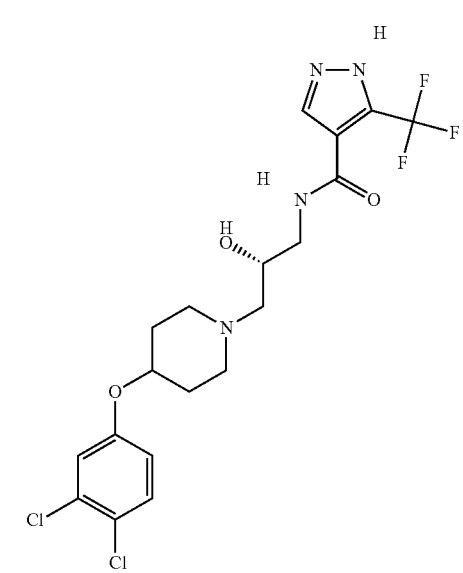
DCCXLIII
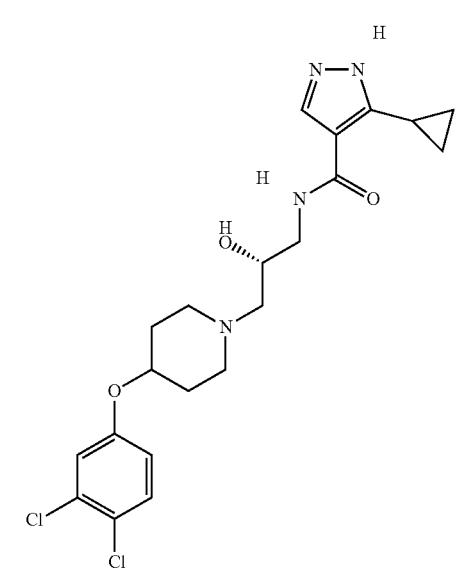
DCCXLIV
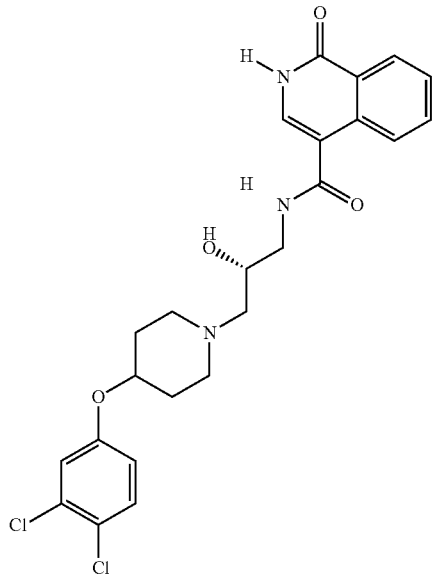
DCCXLV
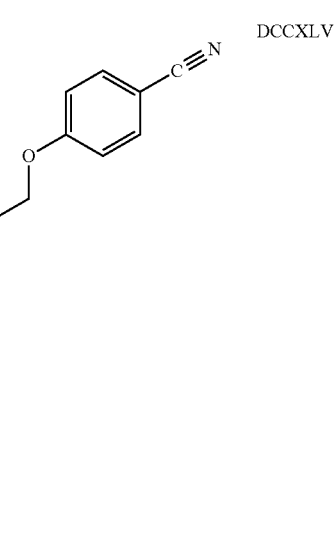
DCCXLVI
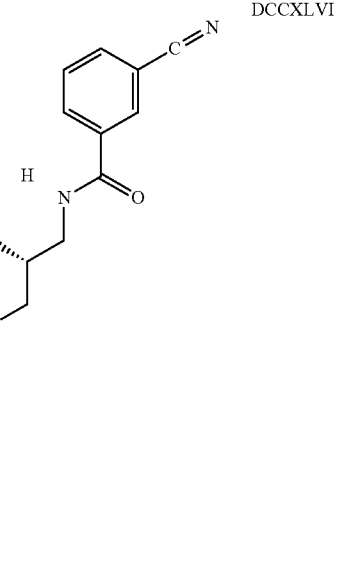

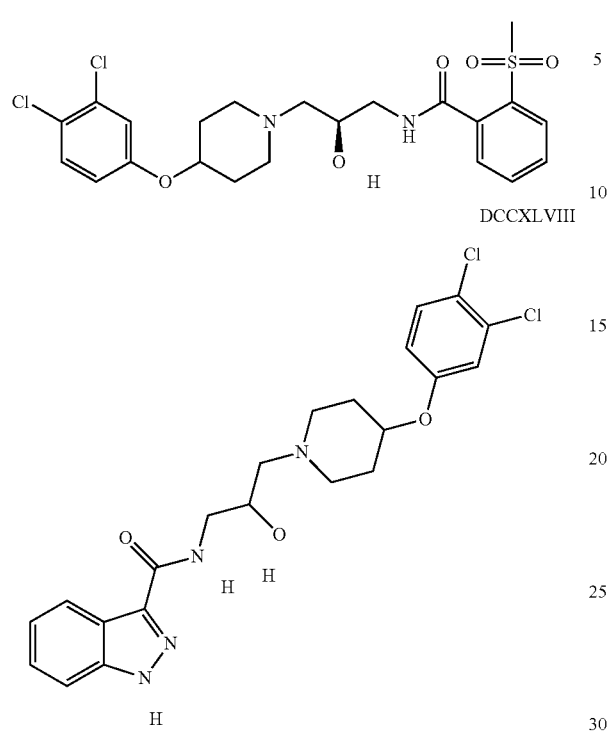
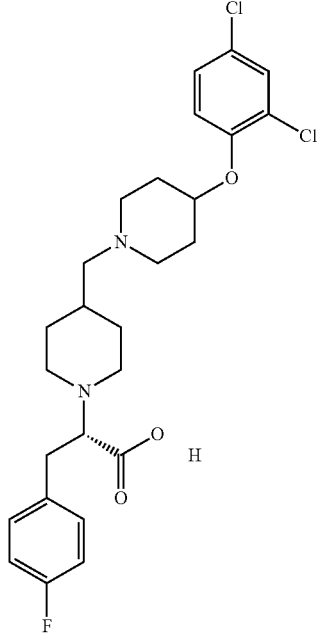
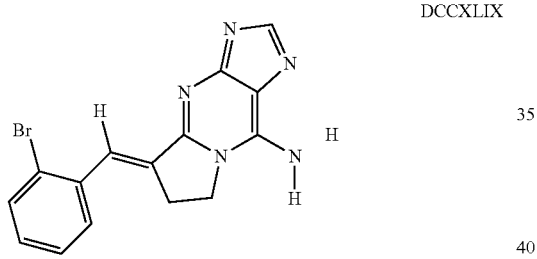
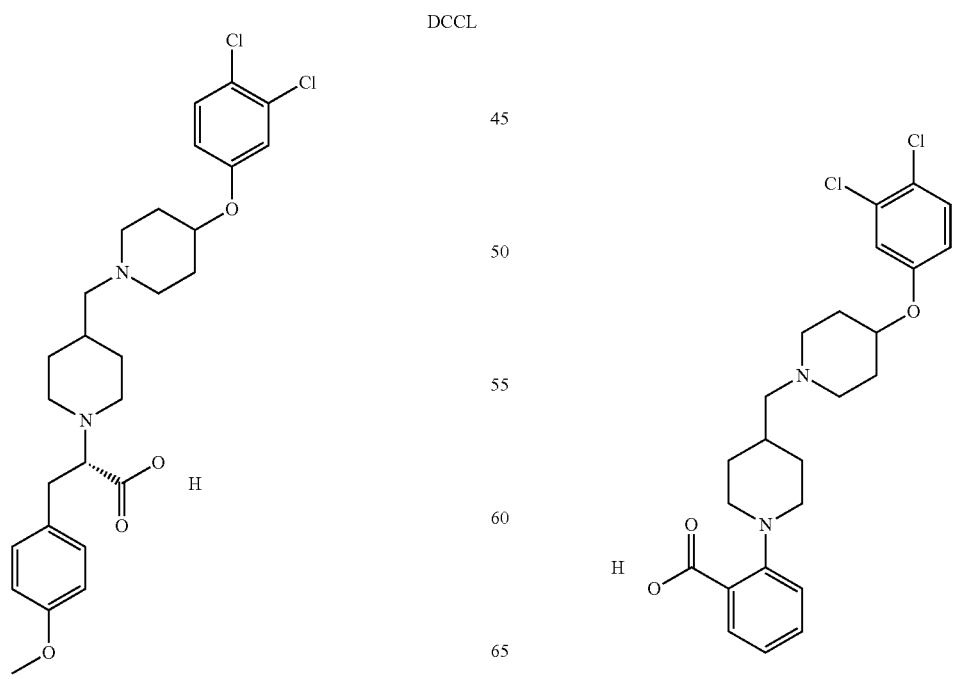

DCCLIII
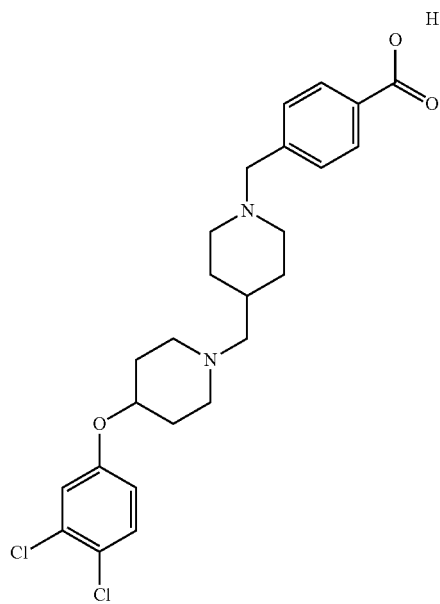
DCCLIV
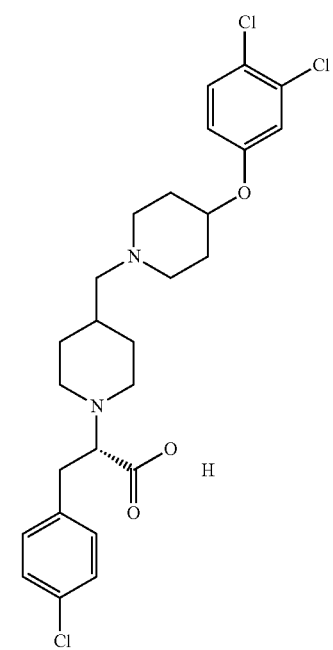
DCCLV
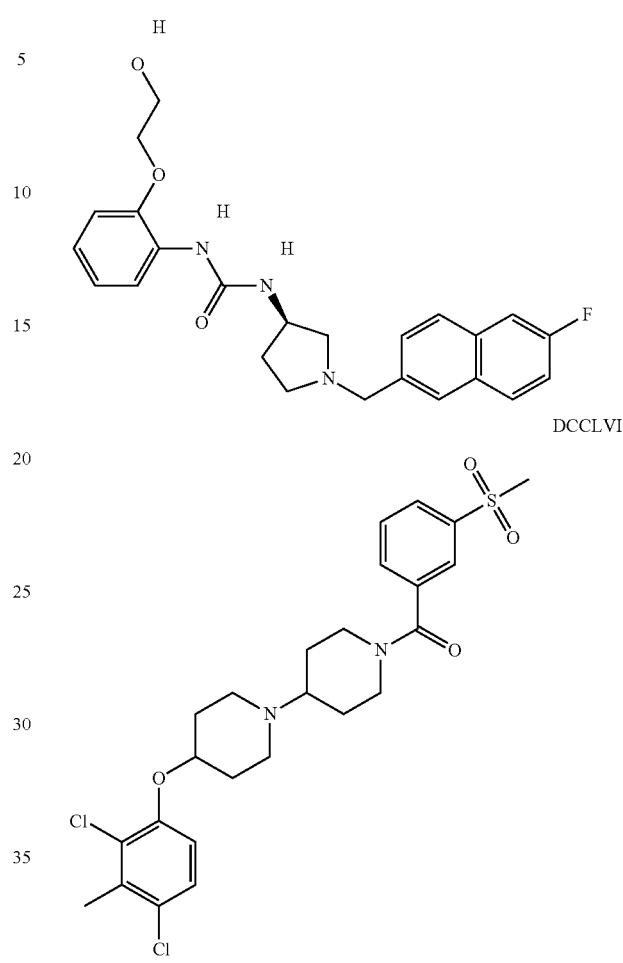
DCCLVI
DCCLVII
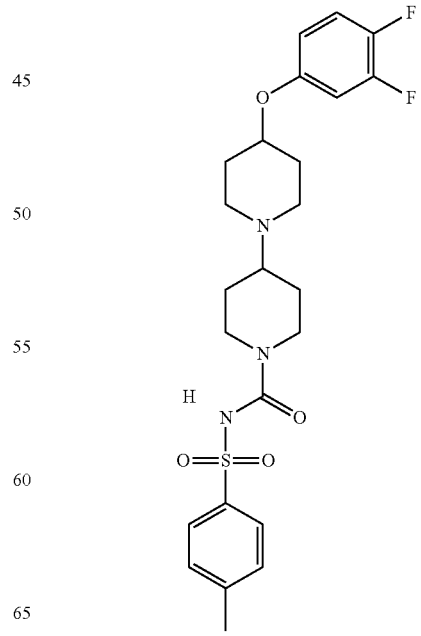

-continued
DCCLVIII
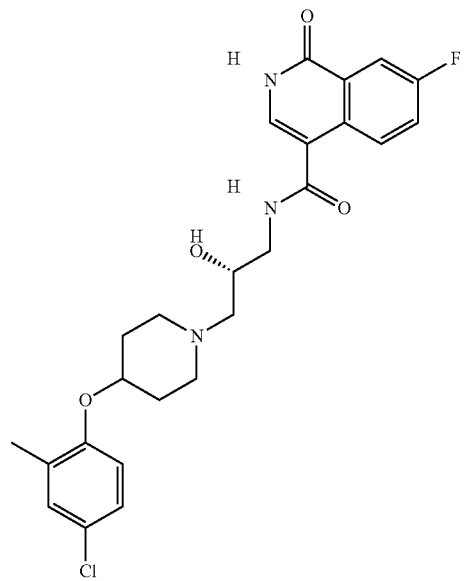
DCCLIX
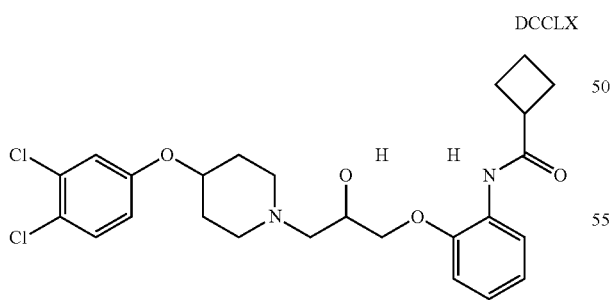
DCCLX
DCCLXI
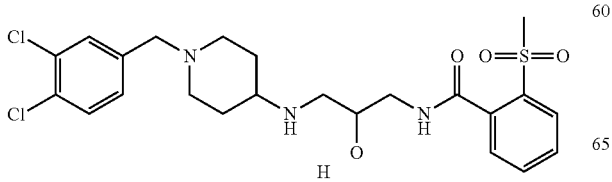
-continued
DCCLXII
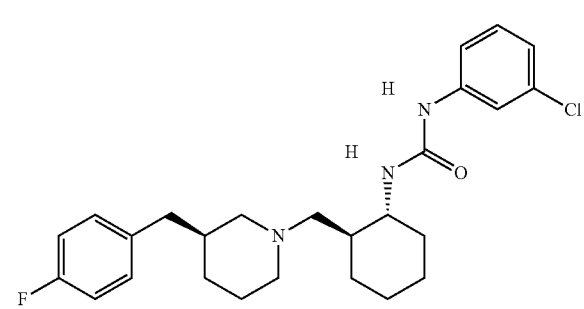
DCCLXIII
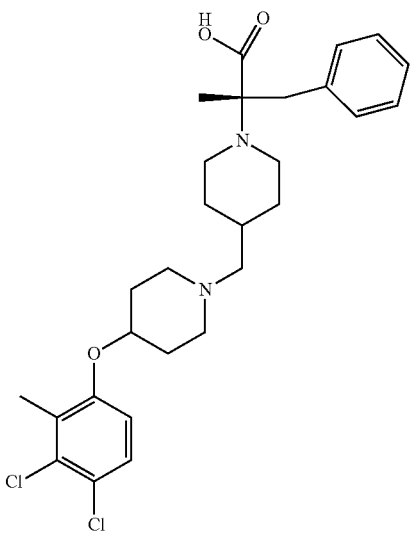
DCCLXIV
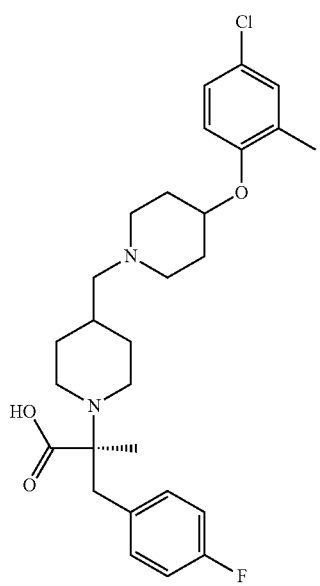

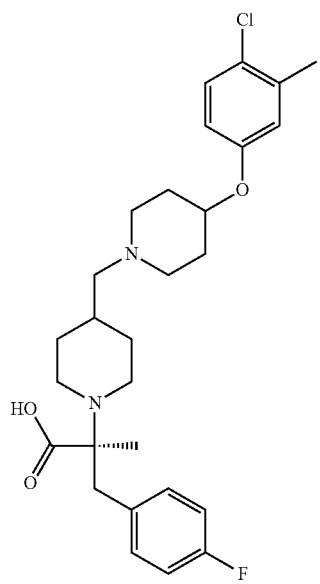
DCCLXV
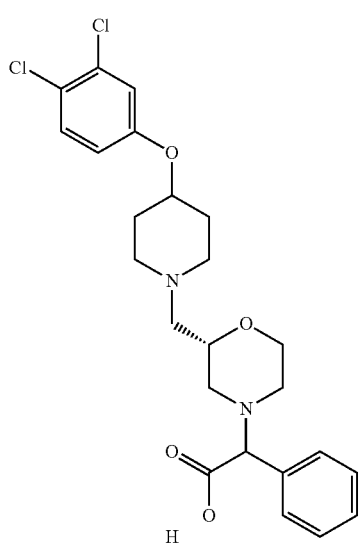
DCCLXVI
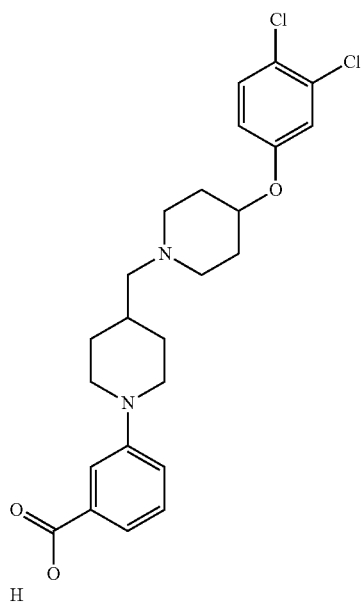
DCCLXVII
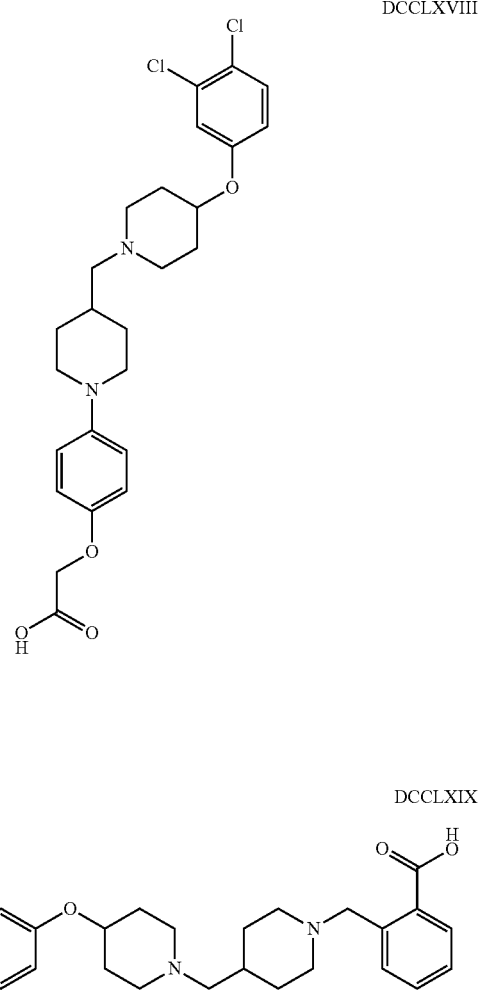
DCCLXVIII
DCCLXIX

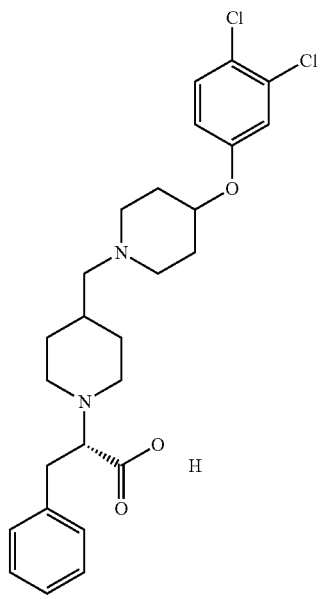
DCCLXX
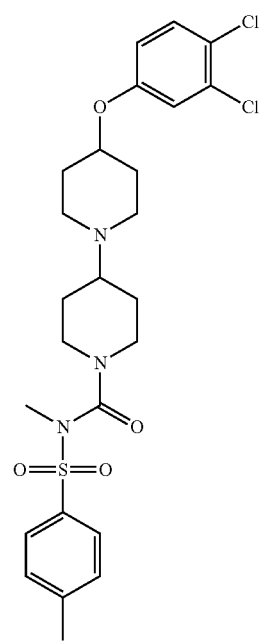
DCCLXXI
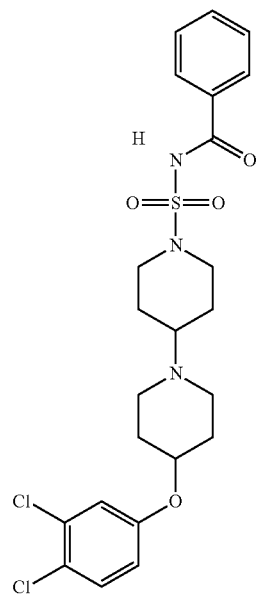
DCCLXXII
DCCLXXIII
DCCLXXIV

DCCLXXV
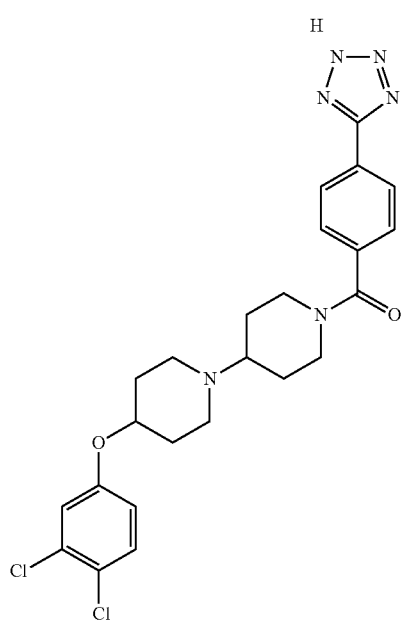
DCCLXXVI
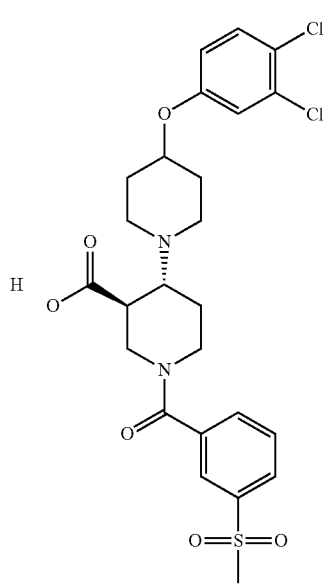
DCCLXXVII
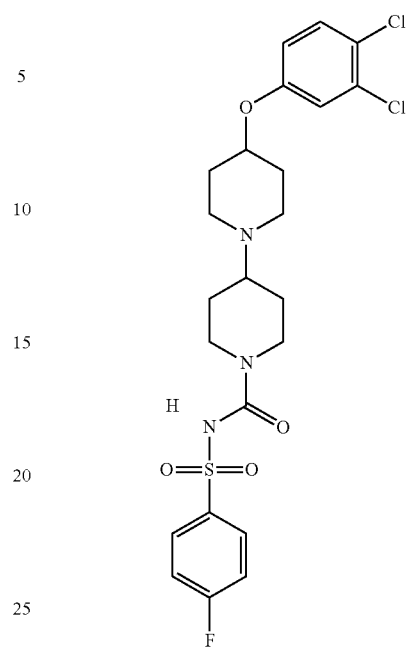
DCCLXXVIII
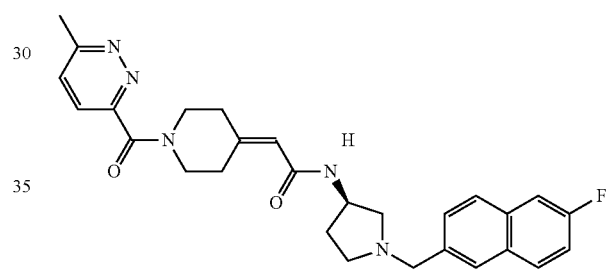
DCCLXXIX
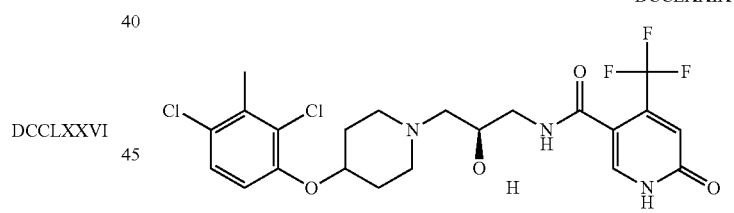
DCCLXXX
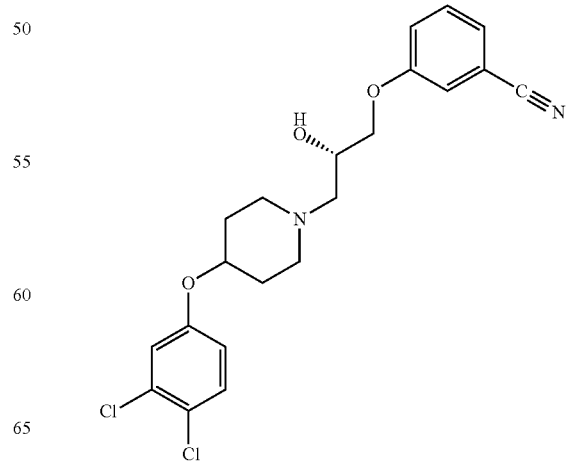

DCCLXXXI

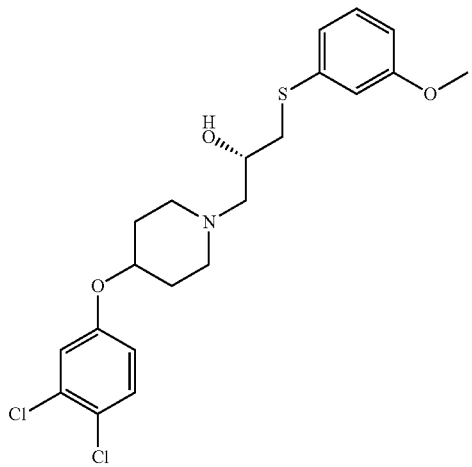

DCCLXXXII

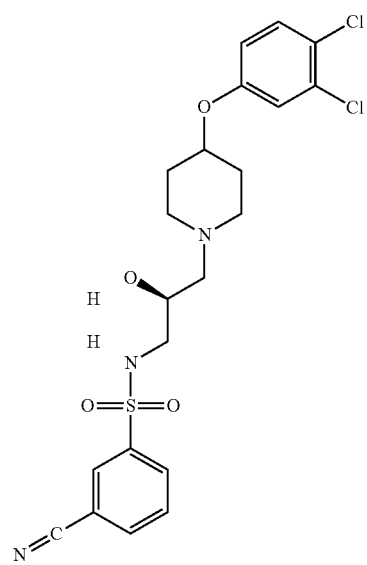

DCCLXXXIII

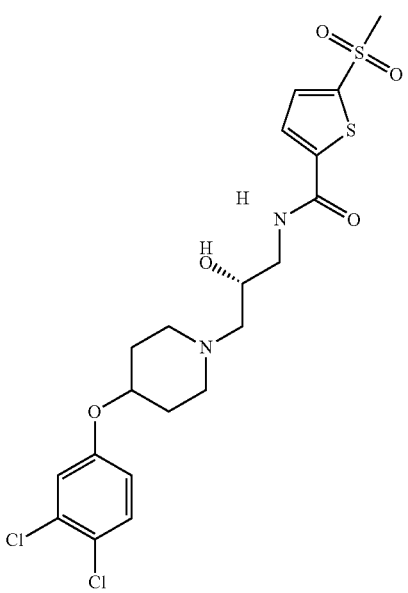

DCCLXXXIV

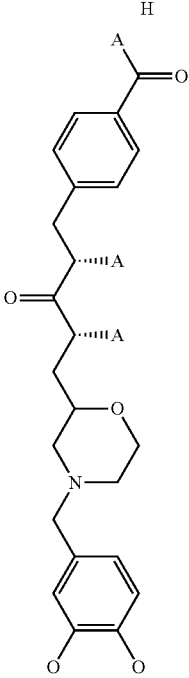

By way of examples of organic molecules inhibiting CCL7/CCR3 interaction, mention may also be made of irreversible CCR3 inhibitors such as the compounds morpholine-acetamide and morpholine urea, in particular those described in the Applications WO 2002/26723 and WO 03/082293, and the U.S. Pat. Nos. 7,101,882, 7,157,457, 7,531,651 and 7,560,548.

The inhibitors of CCL7/CCR3 interaction also include peptides. By way of example of peptides inhibiting CCL7/CCR3 interaction, mention may be made of the peptide met-RANTES (Kiss, Longden et al. 2009), or further peptides described in Houimel and Mazzucchelli 2013; Elsner, Escher et al. 2004; Kiss, Longden et al. 2009; Elsner, Petering et al. 1997; Loetscher, Pellegrino et al. 2001 and International Application WO2000073327.

The inhibitors of CCL7/CCR3 interaction also include antibodies targeted against CCR3 or CCL7, preferably blocking antibodies, which may be polyclonal or monoclonal.

The term "antibody" also includes functional antibody fragments, including chimeric, humanized, single-chain antibody fragments or fragments thereof (e.g. fragments Fv, Fab, Fab' and F(ab')$_2$). Preferred antibodies are those which are targeted against CCL7 or CCR3. Advantageously, the antibody is a monoclonal antibody or a fragment thereof. The methods for preparing monoclonal antibodies are well-known to those skilled in the art. The monoclonal antibodies may be prepared by immunizing a mammal (for example, a mouse, a rat, a rabbit, a camelid or humans) with the chemokine CCL7 or the receptor CCR3 or purified fragments thereof. By way of example of antibodies inhibiting CCL7/CCR3 interaction and by way of example anti-CCR3 monoclonal blocking antibody (reference D083-3, clone 444-11, MBL international, Houimel and Mazzucchelli 2013) or anti-CCL7 polyclonal blocking antibody (reference AF-282-NA, R&D systems, Szymczak and Deepe 2009).

The inhibitors of CCL7/CCR3 interaction also include peptidomimetics.

The term "peptidomimetic" denotes a molecule which is not a peptide but which imitates aspects of the structure of peptides (Elsner, Petering et al. 1997). By way of example of peptidomimetics inhibiting CCL7/CCR3 interaction, mention may be made of those described in the U.S. Pat. No. 7,488,717.

The inhibitors of CCL7/CCR3 interaction also include aptamers recognizing CCL7 or CCR3. Aptamers are molecules with a single strand of nucleic acid (DNA or RNA) which are selected for the ability thereof to bind with a target molecule.

Further inhibitors of CCL7/CCR3 interaction may be identified, for example, by screening a collection of candidate compounds for the ability thereof to inhibit the activation of CCR3 in the presence of CCL7. Methods for measuring the activation of RCPG receptors which are known per se, and which are for example used routinely in high-speed screening tests, may be used to evaluate the activation of CCR3. By way of example of methods for identifying inhibitors of CCL7/CCR3 interaction, mention may be made of in vitro ligand/receptor interaction tests (Loetscher, Pellegrino et al. 2001), time-resolved fluorimetric assays (Kuri-Harcuch and Green 1978) or surface Plasmon resonance screening (Ohori, Iacono et al. 1994).

The inhibitors used according to the invention may be administered to a subject alone, or in a mixture with at least one pharmaceutically acceptable excipient which may be any excipient known to those skilled in the art. The pharmaceutically acceptable excipients vary according to the inhibitor used and the method of administration chosen.

The methods and routes of administration of the inhibitors used according to the invention may be adapted by those skilled in the art according to the subject and the inhibitor used. By way of example, the inhibitors may be formulated for administration by the oral or nasal route, or by injection by the intravenous, intramuscular or subcutaneous route.

The determination of the dose at which said inhibitor is used according to the invention may be performed using techniques known to those skilled in the art, for example during clinical trials. This dose will be dependent on various factors comprising in particular the activity of the inhibitor, the method of administration, the duration of administration, the duration of the treatment, other medicinal products or compounds used in conjunction with the inhibitor, age, sex, weight, general health and previous medical history of the subject treated.

The present invention also relates to a method for preventing or treating the extension of prostate cancer outside the prostatic capsule, comprising the administration of an effective quantity of at least one inhibitor of the expression of the chemokine CCL7 or an inhibitor of the expression of the receptor CCR3 or an inhibitor of CCL7/CCR3 interaction, to a subject requiring this treatment. Obviously, the specifications described above also apply to this aspect of the invention.

The term effective quantity denotes a quantity of inhibitor used according to the invention to produce the biological result sought.

The present invention also relates to an ex vivo method for determining the degree of aggressiveness of a prostate cancer tumor in a subject suffering from prostate cancer, or for determining the risk of biological recurrence of prostate cancer in a subject, comprising the following steps:

a) determining the concentration or level of expression of the receptor CCR3 in a sample of prostate tumor cells obtained from said subject, b) comparing the concentration or level of expression of the receptor CCR3 determined in step a) with the reference concentration or level of expression of the receptor CCR3 in healthy prostate epithelium, a concentration or a level of expression of the receptor CCR3, in said sample of prostate tumor cells from said subject, greater than said reference concentration or level of expression being the indication of an aggressive prostate cancer tumor with a high extraprostatic dissemination potential or of a risk of biological recurrence of prostate cancer.

A sample of prostate tumor cells may be obtained according to methods known to those skilled in the art. For example, prostate biopsies, optionally targeted with a radiological examination, are the standard examination for establishing the diagnosis of prostate cancer (Ohori, Wheeler et al. 1994). These samples may also be obtained from endoscopic resection of the prostate or from total prostate resection specimens (Ohori, Wheeler et al. 1994).

A sample of healthy prostate epithelium may be obtained according to methods known to those skilled in the art. For example, this may consist of normal prostate epithelium present outside the cancer sites in prostate biopsies, healthy prostate tissue present next to cancer sites on specimens from endoscopic resection and/or total prostate resection (Ohori, Wheeler et al. 1994).

The term "aggressive prostate cancer tumor with high extraprostatic dissemination potential" denotes localized cancers wherein the progression is marked rapidly by local dissemination. These cancers at a high risk of progression have been defined using the D'Amico classification, as tumors having a TNM≥T2c (involvement of both lobes) or a Gleason score≥8 or PSA value (ng/ml)>20.

Said subject is preferably an adult male who is obese and/or has abundant PPAT.

The measurement of the concentration of the receptor CCR3 in a sample of cells (prostate cells or prostate epithelium cells) may be performed using a suitable immunological method (e.g. immunofluorescence, immunohistochemistry) by means of at least one specific antibody for the receptor CCR3.

The specific antibody for the receptor CCR3 may be polyclonal or monoclonal. It may be of human or non-human origin (for example mouse), humanized, chimeric. It may be recombinant or synthetic. It may also be an antibody fragment (for example Fab'$_2$ or Fab fragments) comprising a domain of the initial antibody recognizing the target antigen of said initial antibody. This may be for example the clone Y31, (Abcam Cambridge, Mass., USA; Lee, Kim et al. 2010).

The reference concentration of the receptor CCR3 in the healthy prostate epithelium is dependent on the method used for measuring the concentration.

By way of example, the reference concentration of the receptor CCR3 in the healthy prostate epithelium may be obtained by immunohistochemical analysis of prostate epithelium. The immunolabeling may be the subject of a semi-quantitative visual evaluation. Four intensity levels may be distinguished: no labeling (0), weak labeling (1+), intermediate labeling (1++) and strong labeling (1+++), as described in the publications (Ohori and Scardino 1994) and (Saitoh, Miura et al. 1994). The reference concentration of the receptor CCR3 in the healthy prostate epithelium is then between zero and 1+.

The method according to the present invention may comprise an additional step (c) after the comparison step (b), comprising the classification of said subject suffering from prostate cancer according to the degree of aggressiveness of the prostate cancer tumor, based on the level of concentration or expression of the receptor CCR3.

The present invention also relates to the use of a specific antibody for the receptor CCR3, as defined above, for determining the degree of aggressiveness of a prostate cancer tumor in a subject suffering from prostate cancer.

Figure 1B:
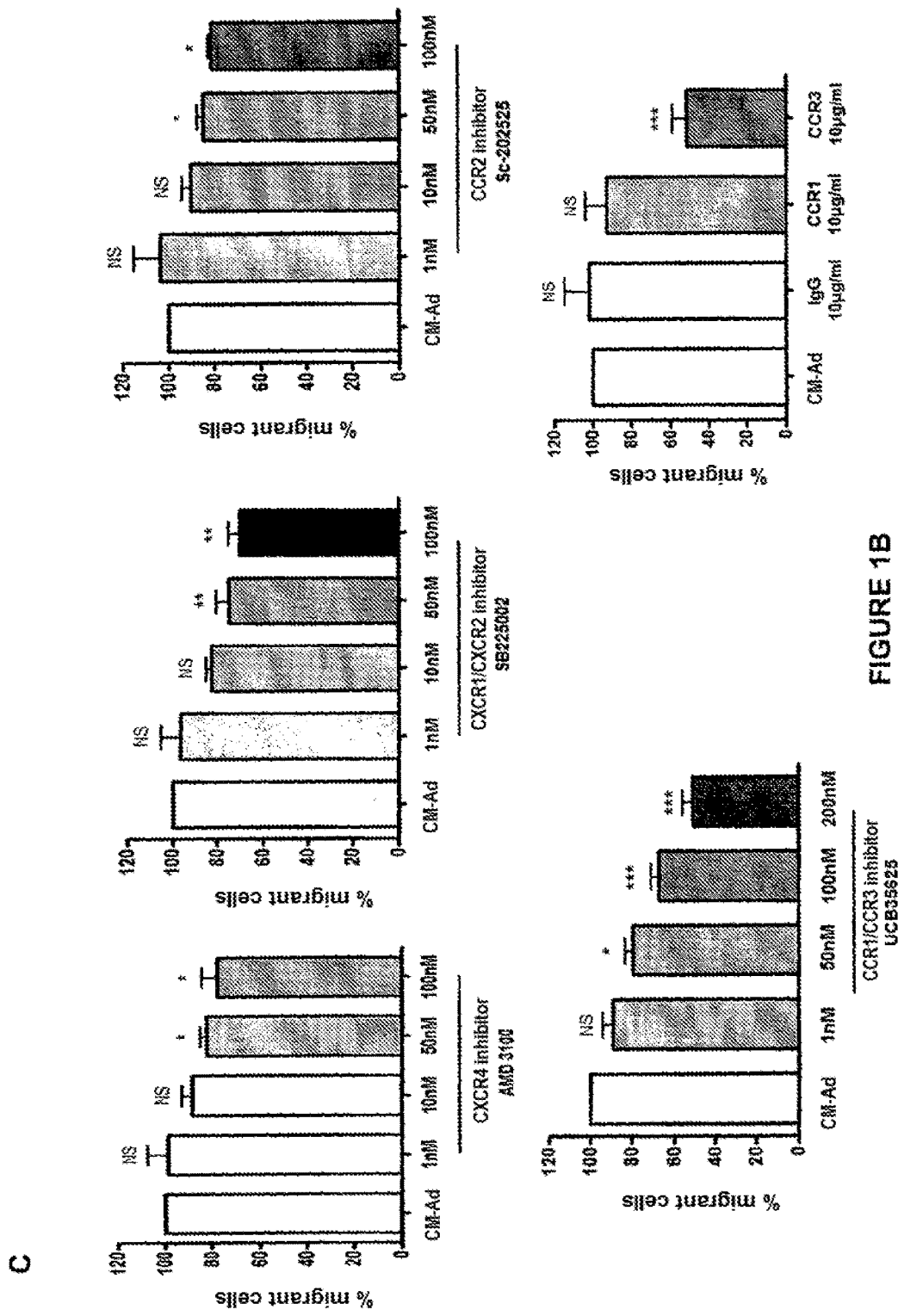

Besides the preceding arrangements, the invention comprises further non-limiting arrangements, which will emerge from the experimental examples hereinafter, along with the appended figures:

FIG. 1: Identification of chemokine receptors and role in the migration of prostate tumor cells. (A) Migration of LNCaP, C4-2B, Du-145 and PC-3 human prostate tumor cells against serum-free medium, medium containing 10% serum, or conditioned medium from mature adipocytes (CM-Ad). (B) Expression of the chemokine receptors CXCR1, CXCR2, CXCR4, CCR1, CCR2 and CCR3 by flow cytometry in Du-145 and PC-3 cells. (C) Migration of PC-3 against conditioned medium of adipocytes (CM-Ad) in the presence of CXCR4 inhibitor (AMD3100), CXCR1 and CXCR2 inhibitor (SB25002), CCR2 inhibitor (SB202525), CCR1 and CCR3 inhibitor (UCB35625) and 10 µg/ml of control IgG1, anti-CCR1 or anti-CCR3 antibody. (D) Expression of the receptor CCR3 by flow cytometry in human prostate (Du-145 and PC-3), breast (T47D and MDA-MB231), melanoma (501Mel and Lu1205), pancreas (CAPAN and PANC-1) and colon (sw620 and sw480) tumor cells) against conditioned medium from mature adipocytes (CM-Ad) in the presence of CCR1 and CCR3 inhibitor (UCB35625).

Figure 2:
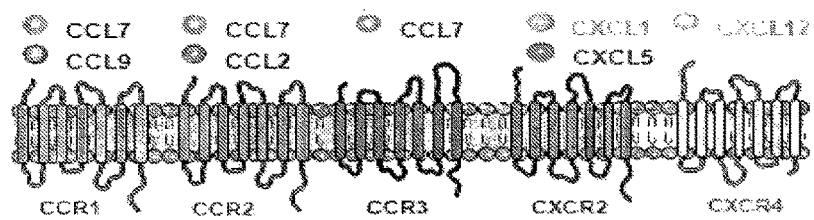
Figure 2:
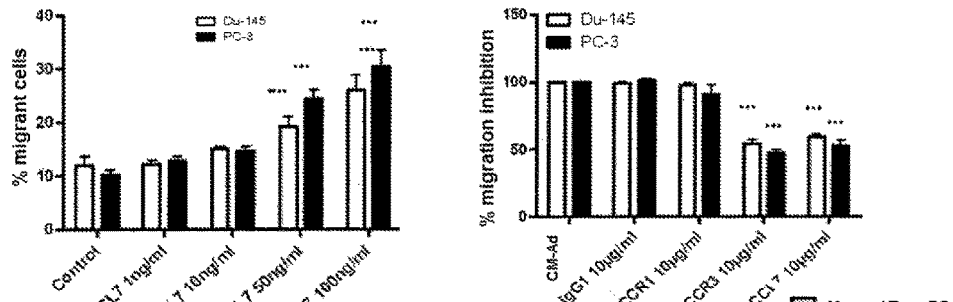
Figure 2:
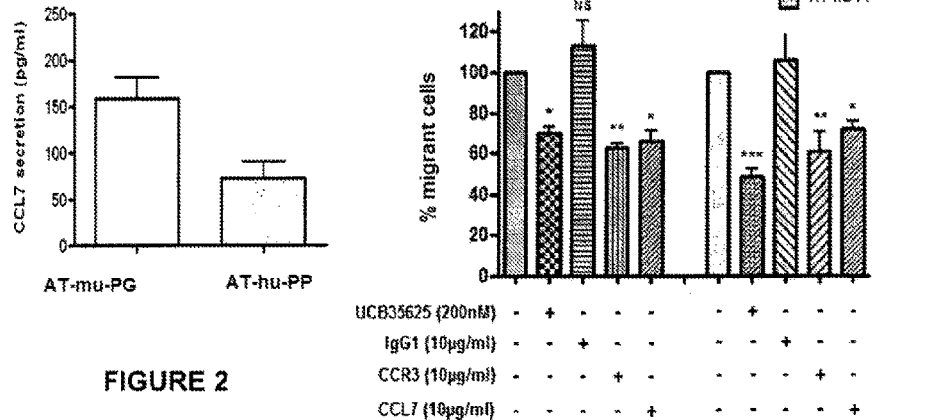

FIG. 2: Identification of adipocyte chemokines and role in the migration of prostate tumor cells. (A) analysis of adipocyte secretome (adipocytes 3T3-F442A) by mass spectrometry and identification of adipocyte chemokines. (B) Migration of Du-145 and PC-3 cells against medium (serum-free) optionally supplemented with the human recombinant chemokine CCL7 (1-100 ng/ml). Migration of Du-145 and PC-3 cells against CM-Ad after treatment with anti-CCL7, CCR1 and CCR3 blocking antibodies. (C) Analysis of secretion of CCL7 in conditioned media of mouse perigonadal (AT-mu-PG) and human periprostatic (AT-hu-PP) adipose tissues by ELISA. Migration of the cells PC-3 against conditioned medium from mouse perigonadal (AT-mu-PG) and human periprostatic (AT-hu-PP) adipose tissues after treatment with CCR1/CCR3 inhibitor (200 nM UCB35625) or with 10 µg/ml of control IgG1, anti-CCR3 or anti-CCL7 antibody.

Figure 3A:
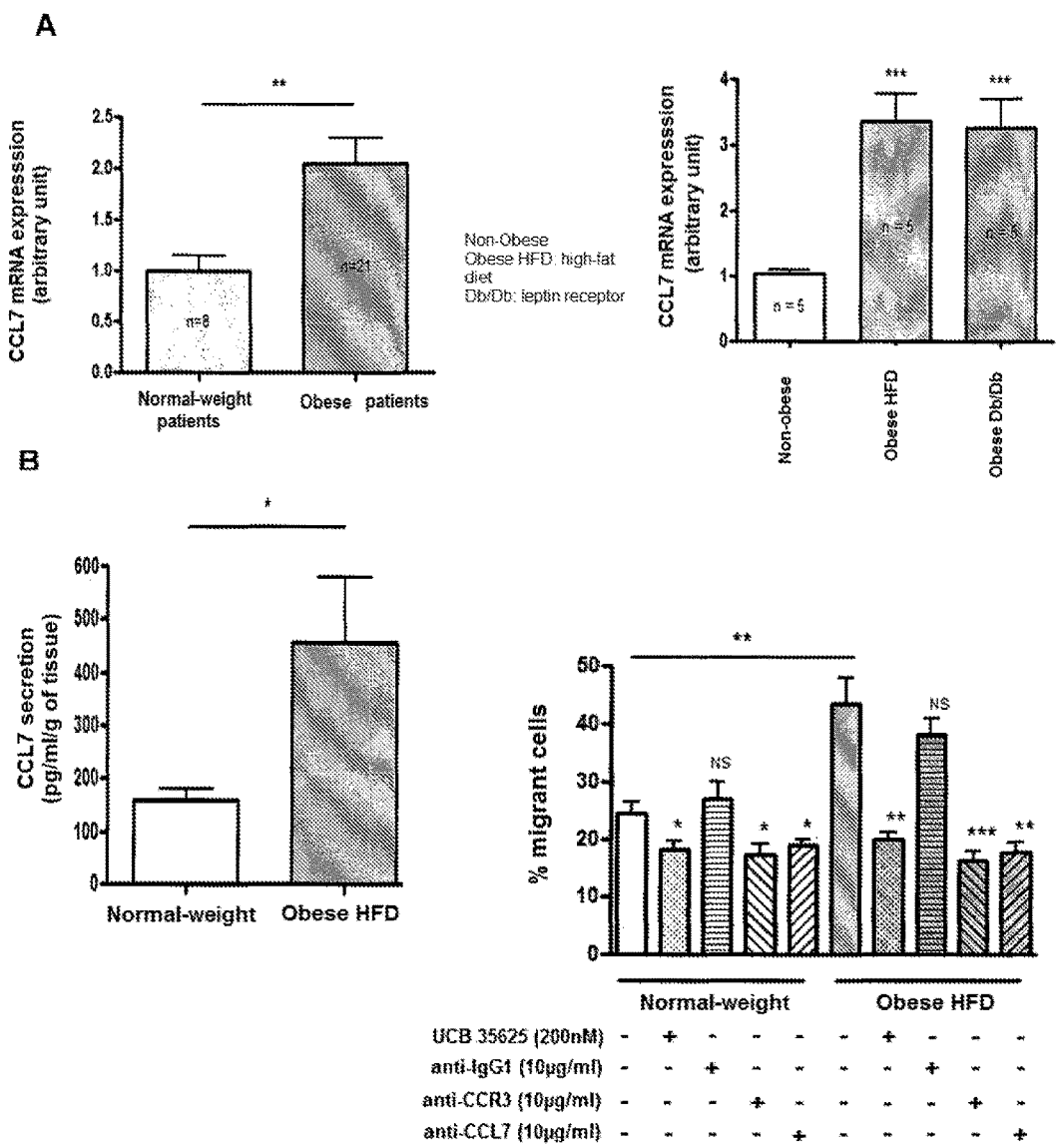

FIG. 3: The expression of the chemokine CCL7 is positively regulated in the adipose tissue and adipocytes of obese subjects. (A) Analysis of the mRNA of CCL7 by qPCR in human visceral adipose tissue of normal-weight or obese patients. Analysis of the mRNA of CCL7 by qPCR in perigonadal adipose tissue of normal-weight mice, on a high-fat diet, and of obese Db/Db mice. (B) Measurement by ELISA assay of the quantity of CCL7 secreted by perigonadal adipose tissue explants from normal-weight or obese C57BL/6 mice (high-fat diet). Migration of PC-3 cells against conditioned medium from adipose tissue explants from normal-weight or obese mice optionally in the presence of CCR1/CCR3 inhibitor (200 nM UCB35625) or 10 µg/ml of control IgG1, anti-CCR1 or anti-CCR3 antibody. (C) Measurement by ELISA assay of the quantity of CCL7 secreted by primary adipocytes or by Stromal Vascular Fraction (SVF) cells isolated from perigonadal adipose tissue from normal-weight or obese C57BL/6 mice (high-fat diet). Migration of PC-3 cells against conditioned medium from primary adipocytes or SVF cells isolated from adipose tissues from obese or normal-weight mice. Migration of PC-3 cells against CM-Ad from isolated primary adipocytes optionally in the presence of CCR1/CCR3 inhibitor (200 nM UCB35625) or 10 µg/ml of control IgG1, anti-CCR1 or anti-CCR3 antibody.

Figure 4A:
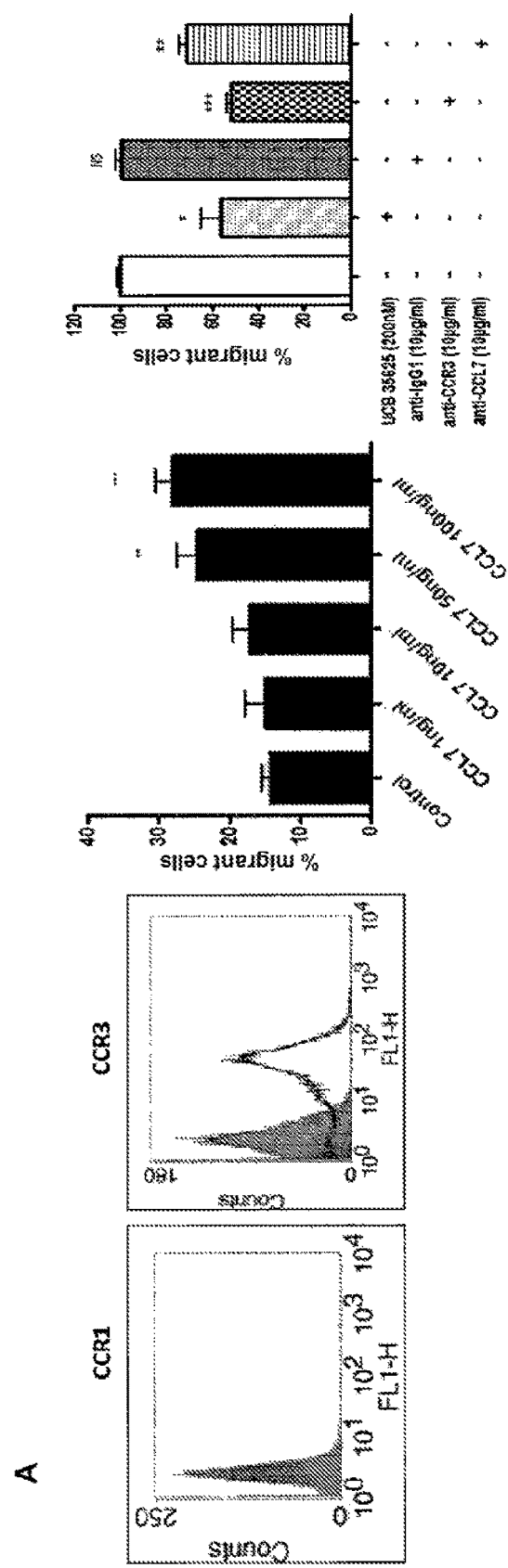

FIG. 4: Role of the receptor CCR3 in the migration of TRAMP-C1P3 cells. (A) Expression of the receptors CCR1 and CCR3 by TRAMP-C1P3 cells by flow cytometry. Migration of TRAMp-C1P3 cells against medium (serum-free) optionally supplemented with the human recombinant chemokine CCL7 (1-100 ng/ml). Migration of TRAMP-C1P3 cells against CM-Ad (3T3-F442A) after treatment with CCR1 and CCR3 inhibitor (200 nM UCB35625) and with 10 µg/ml of control IgG1, anti-CCR1 or anti-CCR3 antibody. (B) Expression of the receptor CCR3 by TRAMP-C1P3 cells non-transfected (WT) or transfected with a control plasmid (sh Ctrl), with 3 independent shRNA targeting the receptor CCR3 (m4, m5 and m6CCR3) by flow cytometry (with quantification of the mean fluorescence intensity). (C) Migration of transfected TRAMP-C1P3 cells (shCtrl, shRNA m4CCR3, shRNA m6CCR3) against CM-Ad (3T3-F442A) optionally in the presence of UCB35625 (200 nM). Migration of transfected TRAMP-C1P3 cells (shCtrl, shRNA m6CCR3) against conditioned medium of adipose tissue of obese or normal-weight mice optionally in the presence of 10 µg/ml of control IgG1, anti-CCR1 or anti-CCR3 antibody.

Figure 5:
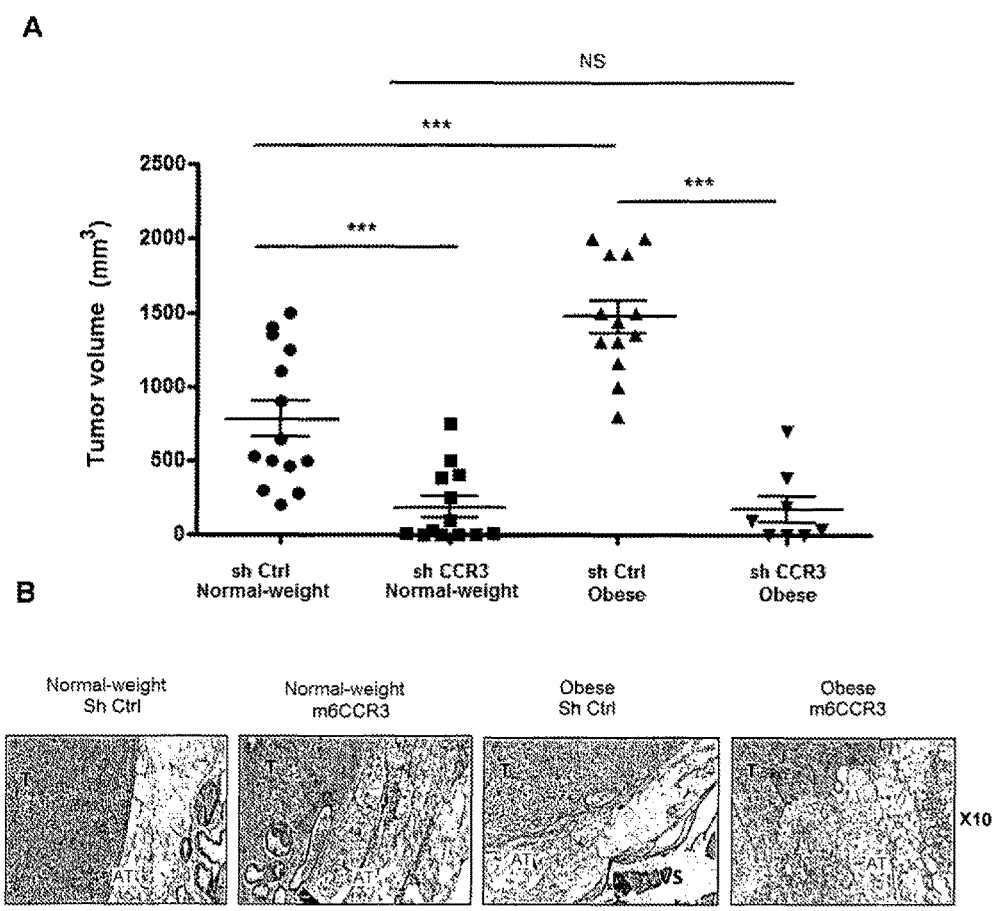

FIG. 5: Role of the receptor CCR3 in tumor progression in vivo. (A) Measurement of the tumoral growth of TRAMP-C1P3 cells (shCtrl and shCCR3) 20 days after intraprostatic injection of 2 million cells in normal-weight and obese C57BL/6 mice. (B) Observations of cross-sections of these tumors after labeling with hematoxylin/eosin (H&E) at different magnification factors (10× zoom).

Figure 6:
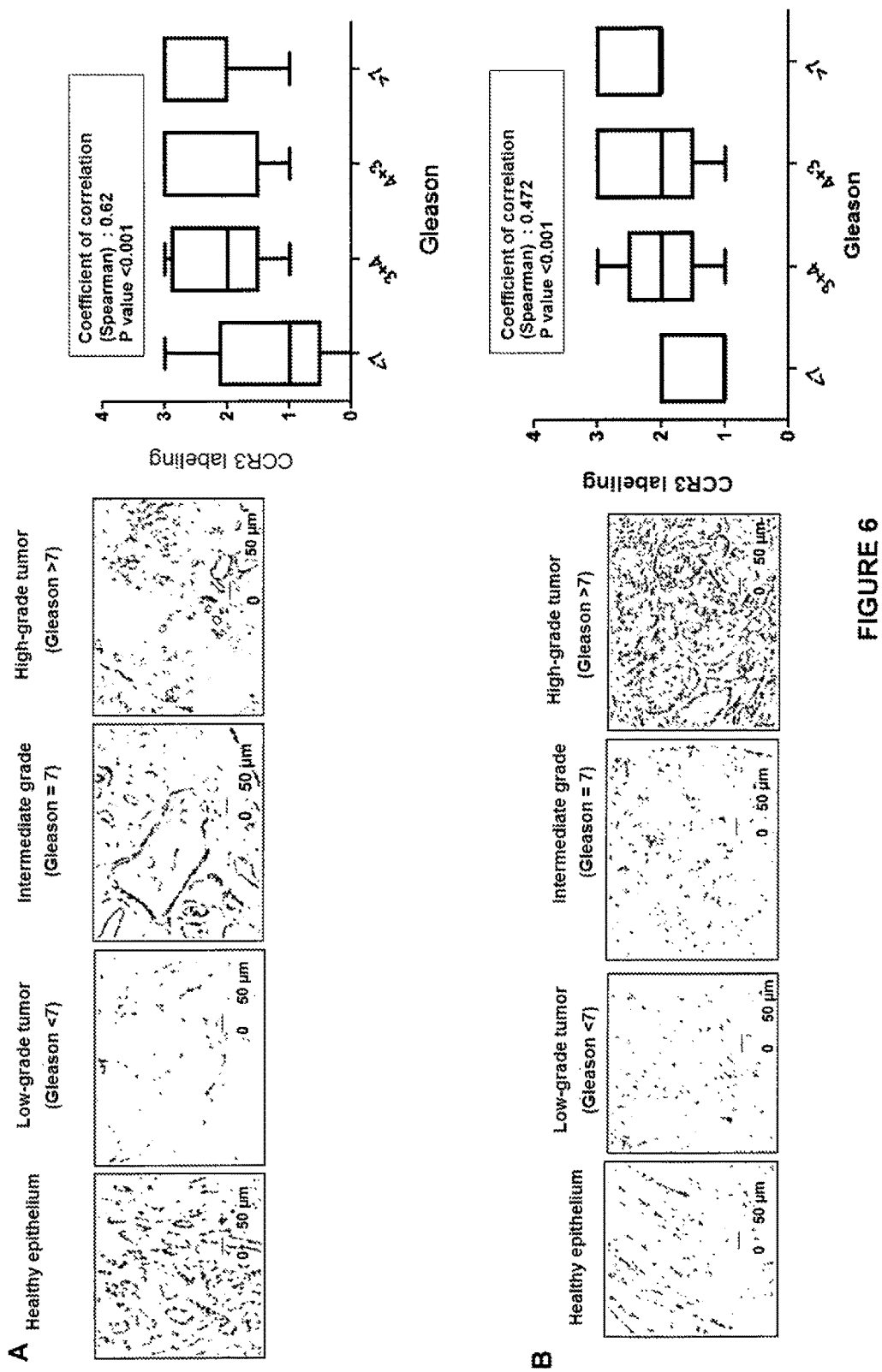

FIG. 6: The expression of the receptor CCR3 is correlated with the aggressiveness of human prostate tumors. Study conducted using two series of prostate cancer TMA, a first collection including 92 tumors (A) and a second annotated collection containing 101 tumors (B). The expression of CCR3 was measured by immunohistochemistry and a representative result for the healthy epithelium and each group of tumors: low-grade (Gleason <7), intermediate-grade (Gleason 3+4 and 4+3) and high-grade (Gleason >7) tumor, is shown (A and B, left-hand panels). In both series, the expression of CCR3 is strongly correlated with the Gleason scores which reflects the aggressiveness of the prostate cancer. For each cohort analyzed, a representation in quartile form is featured along with a correlation test (Spearman test).

FIG. 7: Role of the CCR3/CCL7 pathway in the migration of prostate tumor cells in response to mouse medullary adipocyte secretions (bone metastasis context). (A) Development of two medullary adipocyte models: one in vitro model with the 14F1.1 line and one ex vivo model obtained from the differentiation of mouse mesenchymal medullary stem cells. During the treatment with the selection and differentiation medium, these cells change appearance and are charged with lipids until medullary adipocytes are obtained after 6 weeks of ex vivo differentiation. (B) Comparison of the secretion of CCL7 between visceral primary adipocytes of C57B16 mice, 3T3-F442A adipocytes differentiated in vitro, 14F1.1 cells differentiated in vitro and mouse medullary adipocytes differentiated ex vivo. Migration of PC-3 cells against conditioned medium from adipocytes obtained from the different models: differentiated F442A, differentiated 14F1.1 and mature mouse medullary adipocytes (ex vivo). Migration of PC-3 against conditioned medium from mature mouse medullary adipocytes (ex vivo) optionally in the presence of CCR1/CCR3 inhibitor (200 nM UCB35625) or 10 µg/ml of control IgG1, anti-CCR1 or anti-CCR3 antibody. (C) Expression of the chemokine receptors CCR1 and CCR3 by flow cytometry in RM1-BM cells. Migration of RM1-BM against CM-Ad from F442A optionally in the presence of CCR1/CCR3 inhibitor (200 nM UCB35625) or 10 µg/ml of control IgG1, anti-CCR1 or anti-CCR3 antibody. Migration of RM1-BM cells against serum-free medium optionally supplemented with the recombinant chemokine CCL7 (100 µg/ml). Migration of RM1-BM against conditioned medium from mouse medullary adipocytes differentiated ex vivo (ex vivo) optionally in the presence of CCR1/CCR3 inhibitor (200 nM UCB35625) or 10 µg/ml of control IgG1, anti-CCR1 or anti-CCR3 antibody.

Figure 8:
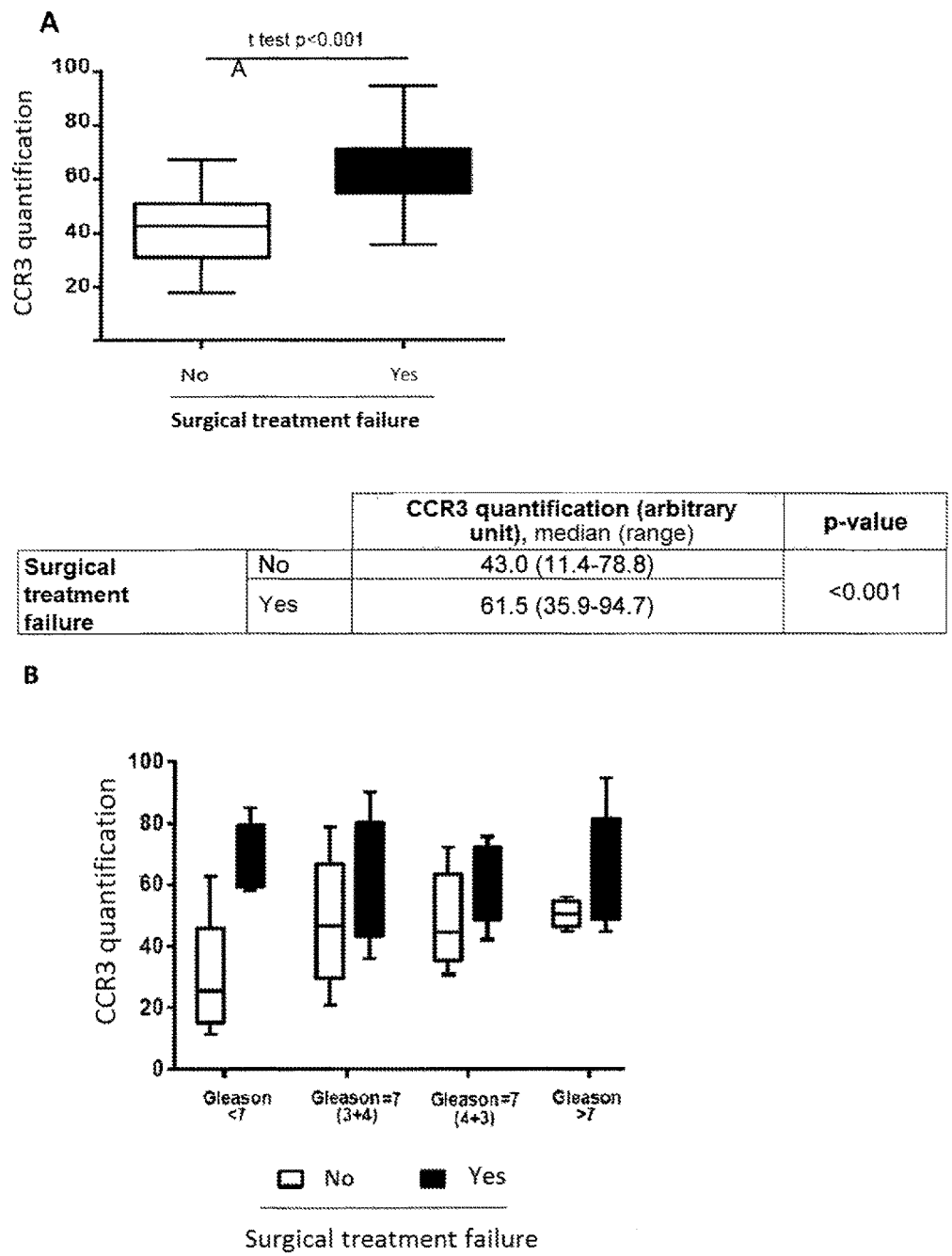

FIG. 8: The expression of CCR3 is higher in tumors of patients presenting with surgical treatment failure regardless of the Gleason score. (A) Scatchard diagram comparing the expression values of CCR3 in tumors from patients presenting with surgical treatment failure or not. We used a Student's test to correlate the expression of CCR3 with the occurrence or not of surgical treatment failure (which is a non-ordinal variable representing a category). The median values of the expression of CCR3 for both categories are demonstrated. (B) Scatchard diagram comparing the expression values of CCR3, after one year of follow-up, with the 4 Gleason score classes. The CCR3 values are systematically higher in patients presenting with surgical treatment failure regardless of the Gleason score class. The deviation tends to be greater for tumors having a low Gleason score (<7).

Figure 9:
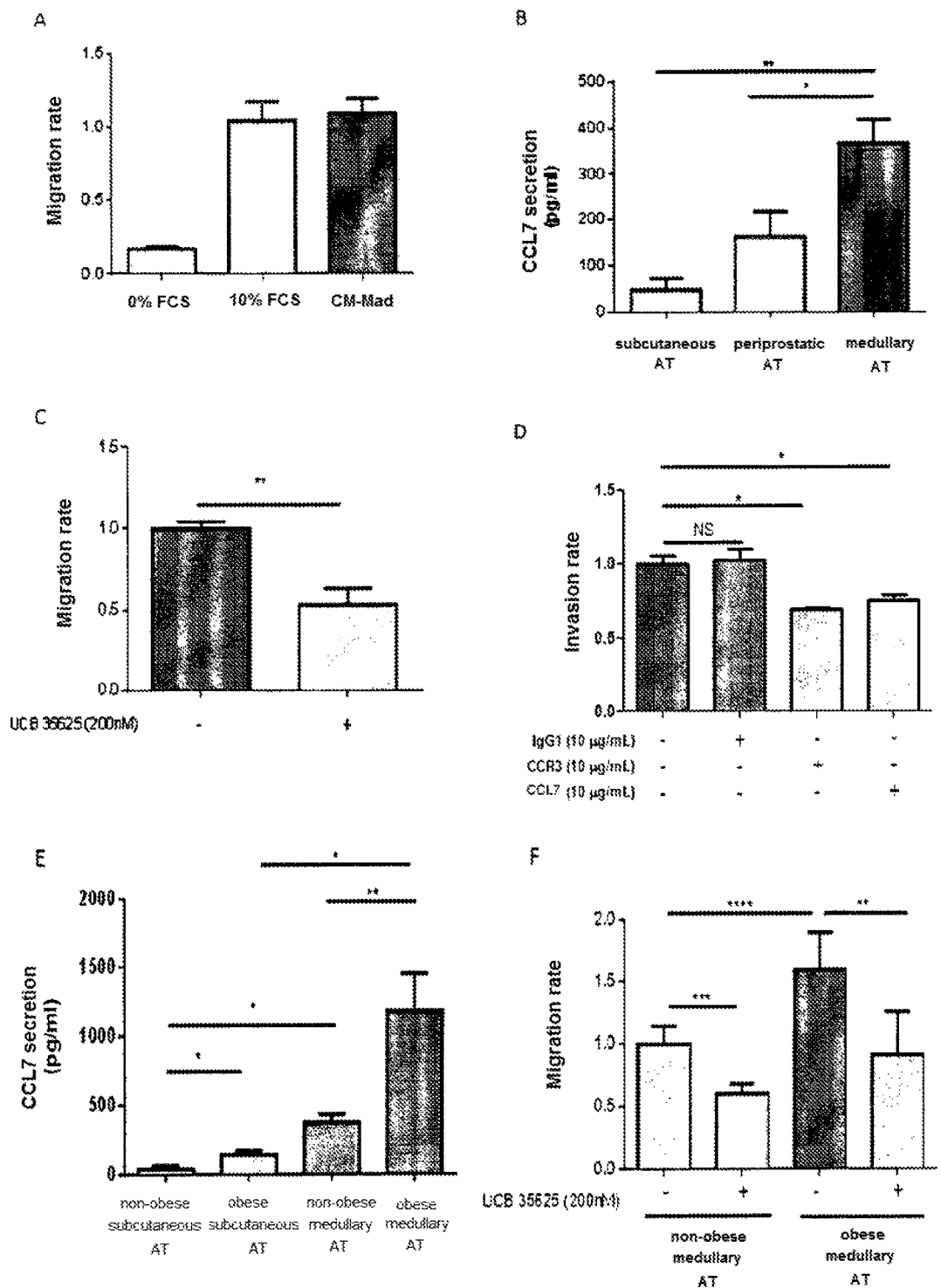

FIG. 9: Human medullary adipocytes have the ability to chemoattract human prostate tumor cells, this effect is dependent on the CCR3/CCL7 pathway and is regulated by obesity. (A) Migration of PC-3 human prostate tumor cells against serum-free medium, containing 10% serum, or conditioned medium from human medullary adipocytes obtained from yellow marrow samples (CM-MAd). (B) Analysis of the secretion of CCL7 in conditioned media from subcutaneous, periprostatic and human medullary adipose tissues by ELISA (1 g of tissue in 8 ml of medium for 24 hr). (C) Migration of PC-3 cells against conditioned medium of human medullary adipocytes obtained from yellow marrow samples (CM-MAd) in the presence of CCR1/CCR3 inhibitor (200 nM UCB35625). (D) Migration of PC-3 cells against conditioned medium from human medullary adipocytes obtained from yellow marrow samples in the presence of IgG1 and blocking antibodies targeted against CCR3 and CCL7. (E) Analysis of the secretion of CCL7 in conditioned media of human subcutaneous and medullary adipose tissues obtained from non-obese (BMI<25 mg/m$^2$) or obese (BMI>30 mg/m$^2$) by ELISA (1 g of tissue in 8 ml of medium for 24 hours). (F) Migration of PC-3 cells against conditioned medium of human medullar adipocytes obtained from yellow marrow samples (CM-MAd) from obese or normal-weight patients in the presence of CCR1/CCR3 inhibitor (200 nM UCB35625).

EXAMPLE: INHIBITION OF CHEMOKINE RECEPTOR CCR3 IN PROSTATE CANCER DISSEMINATION

Materials and Methods
Antibodies, Inhibitors and Product Used

The monoclonal antibodies targeted against CCR1 (D063-3 clone 141-2) and CCR3 (D083-3, clone 444-11) are obtained from MBL International (Worburn, Mass., USA). The anti-CCR2 (clone E68) and anti-CCR3 (clone Y31) monoclonal antibodies are obtained from Abcam (Cambridge, Mass., USA). The monoclonal antibodies against CXCR2 (clone 48311), CXCR4 (clone 44716) and CCR1 (clone 53504) are obtained from R&D Systems (Minneapolis, Minn., USA).

The inhibitor targeting the receptor CXCR4, AMD3100 (Rosenkilde, Gerlach et al. 2004) is obtained from Sigman Aldrich and is used at final concentrations of 1, 10, 50 and 100 nM. The inhibitor targeting the receptors CXCR1 and CXCR2, SB225002 (White, Lee et al. 1998)) is obtained from Tocris (Bristol, United Kingdom) and is used at final concentrations of 1, 10 and 100 nm. The inhibitor targeting the receptor CCR2, sc-202525 (Cherney, Mo. et al. 2008) is obtained from Santa Cruz Biotechnology (Dallas, Tex., USA) and is used at final concentrations of 1, 10 and 50 and 100 nm. The inhibitor targeting the receptor CCR1 and CCR3, UCB35625 (Sabroe, Peck et al. 2000) is obtained from Tocris (Bristol, United Kingdom) and is used at final concentrations of 1, 50, 100 and 200 nM.

Cell Culture

The prostate cell lines LNCaP (ATCC® CRL-1740™), DU-145 (ATCC® HTB-81™), PC-3 (ATCC® CRL-1435™), and the human carcinoma cell lines from the colon sw480 (ATCC® CCL-228™) and sw620 (ATCC® CCL-227™), pancreas CAPAN (ATCC® HTB-79™) and PANC-I (ATCC® CRL-2547™), breast ZR-75-1 (ATCC® CRL-1500™) and MDA-MB321 (ATCC® CRM-HTB-26™) and melanomas SK-Mel-28 (ATCC® HTB-72™) and Lu1205 (donated by Dr. Herlyn, Wistar Institute, Philadelphia, USA) are cultured in RPMI culture medium (Invitrogen, Auckland, NZ) supplemented with 10% FCS (Fetal Calf Serum), 2 mM L-glutamine, 125 µg/ml of streptomycin, 125 U/ml of penicillin. All the lines used in this study are cultured in a wet atmosphere with 5% $CO_2$.

The mouse tumor line TRAMP-C1P3 derived from the line TRAMP-C1 (ATCC® CRL-2730™) is cultured in DMEM medium supplemented with 10% FCS, 125 µg/ml of streptomycin, 125 U/ml of penicillin, 5 mg/ml of insulin and 10 nM of dihydrotestosterone (18).

The RM1-BM line is cultured in DMEM medium (Invitrogen, Auckland, NZ) containing 4.5 g/l of glucose, supplemented with 10% FCS, 125 µg/ml of streptomycin and 125 U/ml of penicillin. The RM1-BM line was supplied by Dr. Carl Power (Eastern Virginia Medical School). It consists of a syngeneic mouse cell line having a C57BL/6 genetic background and derived from the RM1 line and which is characterized by the high bone metastatic potential thereof. Indeed, following an intracardial injection to C57BL/6 mice, bone metastases are thus obtained in 86% of cases (Kanno, Amakasu et al. 1994).

The mature adipocytes are obtained from the in vitro differentiation of the mouse pre-adipocyte line 3T3-F442A (00070654 Sigma Aldrich) (Kuri-Harcuch and Green 1978). These cells are cultured in DMEM culture medium (Invitrogen, Auckland, NZ) containing 10% FCS, 125 µg/ml of streptomycin and 125 U/ml of penicillin (complete DMEM medium). To induce adipocyte differentiation, $6 \times 10^4$ cells are inoculated in a 6-well plate. After 3 days of culture, the confluent cells are incubated in the presence of complete DMEM medium containing 50 mM of insulin (referred to as adipocyte differentiation medium) for a period of 10 to 14 days. After 10 days of culture under these conditions, 80% of the cells exhibit lipid droplets specific for adipocyte differentiation. Conditioned medium from adipocytes (CM- Ad) (1% BSA, 0% FCS) is obtained during the culture of the mouse adipocytes differentiated in vitro under the conditions described above.

During this study, an in vitro medullary adipocyte model was used: the line 14F1.1. This line is derived from immortalized bone marrow cells selected for the ability thereof to differentiate either into endothelial cells, or into medullary adipocytes (Yamamura, Salomon et al. 2011) and (Menzies and Salomon 2011). These cells are cultured in DMEM culture medium (Invitrogen, Auckland, NZ) containing 10% FCS, 125 µg/ml of streptomycin and 125 U/ml of penicillin (complete DMEM medium). Adipocyte differentiation is obtained 28 days after the cells have reached confluence.

Ex Vivo Differentiated Medullary Adipocyte Model

In order to obtain medullary adipocytes ex vivo, a protocol was developed for the differentiation of the stromal vascular fraction bone marrow cells into medullary adipocytes in C57BL/6 mice. In order to isolate these cells, the tibias and femurs of C57BL/6 mice are isolated and then placed in DMEM (1% BSA) at 4° C. The bones are then cut at both ends and, using a syringe, the cells contained in the bone marrow are retrieved by injecting cold medium inside the bone. The cellular solution obtained is treated with a 2.5 µg/ml solution at a rate of 5 µL per 2 mL of cellular suspension. The mixture is left to incubate in a water-bath at 37° C. for 5 minutes. This step makes it possible to remove any traces of extracellular matrix. The liberase is then neutralized with a volume-by-volume addition of DMEM (10% FCS), and the cellular solution is filtered to remove debris and blood clots. The cellular suspension is centrifuged at 2000 RPM for 20 minutes and the sediment containing the stromal fraction cells is resuspended in DMEM medium containing 10% FCS, 125 µg/ml of streptomycin and 125 U/ml of penicillin. The cells are inoculated in 24-well plates at a density of $1-2\times10^7$ cells/mL and placed in culture at 37° C. with 5% of $CO_2$. The cells are left in culture in this way for 4 days and the culture medium is then changed so as only to retain the cells having adhered. Once the cells have reached confluence, the medium is replaced by a differentiation medium. This medium is composed of DMEM (10% FCS) supplemented with 1 µM dexamethasone, 0.45 mM IBMX, 60 µM indomethacin and 10 µg/ml insulin. The medium is changed every 4 days for 30 to 35 days. After this period, the mesenchymal precursors have differentiated into medullary adipocytes and contain lipid droplets visible under microscopy. Conditioned medium from ex vivo medullary adipocytes (CM-Ad med) (1% BSA, 0% FCS) is obtained as described above.

Human Medullary Adipocyte Samples

The samples of human yellow bone marrow and human subcutaneous adipose tissue were collected during the implantation of hip or knee prostheses carried out in the Traumatology department at Hôpital Pierre Paul Riquet (Toulouse university hospital, France). Samples were collected in line with the recommendations of the Midi-Pyrénées (France) ethics and patient protection committee. Non-opposition to sample collection was obtained from each patient, prior to the operation, in accordance with article L. 1211-2 of the French Public Health Code. These adipose tissues are immediately placed at 37° C. in DMEM (serum-free) medium supplemented with 1% Bovine Serum Albumin, at a rate of 1 g of tissue per 8 mL of medium. The tissues are left to secrete for 24 hours and the medium containing the secretions is retrieved and frozen.

Human Visceral Adipose Tissue Samples for Analysis of the Expression of CCL7 by Q-PCR The human visceral adipose tissues (AT-Visc) were collected according to the guidelines of the ethics committees of the Toulouse-Rangueil and Nancy-J. d'Arc hospitals (France). All the patients gave their informed consent to take part in the study and the research was conducted in accordance with the Declaration of Helsinki revised in 2000 (http://www.wma.net/e/policy/b3.htm). The human samples of AT-Visc (intra-abdominal) from normal-weight subjects were obtained from 8 patients (aged 40.3±2.2 years and body mass index (BMI) of 23.3±1.2 kg/m2) having undergone an intra-abdominal surgical procedure. The samples of AT-Visc from obese subjects were obtained from 21 patients suffering from grade III morbid obesity (aged from 41.3±2.2 years and BMI of 45.7±2.9 kg/m2) prior to bariatric surgery. The tissue samples were immediately frozen in liquid nitrogen after sampling and stored at −80° C.

Human Periprostatic Adipose Tissue Samples

The periprostatic adipose tissue samples were collected from radical prostate resection in accordance with the recommendations of the ethics committee of Rangueil university hospital (Toulouse, France). All the patients gave their informed consent to take part in this study which was conducted in accordance with the Declaration of Helsinki revised in 2000. The periprostatic adipose tissue samples are sampled in the vicinity of the tumor and do not exhibit visible fibrosis. This adipose tissue is immediately placed at 37° C. in DMEM medium (serum-free) supplemented with 1% Bovine Serum Albumin.

Human Yellow Marrow and Subcutaneous Adipose Tissue Samples

The samples of human yellow bone marrow and human subcutaneous adipose tissue were collected during the implantation of hip or knee prostheses carried out in the Traumatology department at Hôpital Pierre Paul Riquet (Toulouse university hospital, France). Samples were collected in line with the recommendations of the Midi-Pyrénées (France) ethics and patient protection committee. Non-opposition to sample collection was obtained from each patient, prior to the operation, in accordance with article L. 1211-2 of the French Public Health Code. These adipose tissues are immediately placed at 37° C. in DMEM (serum-free) medium supplemented with 1% Bovine Serum Albumin, at a rate of 1 g of tissue per 8 mL of medium. The tissues are left to secrete for 24 hours and the medium containing the secretions is retrieved and frozen.

Mouse Perigonadal Adipose Tissue Samples

Male C57BL/6 mice supplied by Janvier (Le Genest St-Isle, France) aged 8 weeks and accommodated in ventilated Plexiglas cages (3 mice per cage) were used. These C57BL/6 mice are either placed on a normal diet consisting of 5% fat (PicoLab Rodent Diet 20; Purina Mills Inc., Brentwood, Mo., USA), or, on a high-fat diet (60% fat, 22% carbohydrates and 18% protein) for 10 weeks. All the procedures were validated by the Midi-Pyrénées (France) animal ethics committee. At the end of the diet, the animals are sacrificed by cervical dislocation, weighed and the perigonadal adipose tissue (AT-PG) is sampled and immediately placed at 37° C. in DMEM (serum-free) medium supplemented with 1% Bovine Serum Albumin.

Measurement of Genic Expression by Q-PCR

The total RNA are extracted using the RNeasy® Mini kit (Qiagen GmbH, Hilden, Germany). A total RNA microgram is transcribed to cDNA by Superscript II reverse transcriptase (Invitrogen, Auckland, NZ). Incubation is conducted in parallel under the same conditions for each sample in the absence of Superscript II to ensure that there is no contamination with the genomic DNA. The real-time PCR reaction is performed with 50 ng of cDNA, 5 µl of an oligonucleotide solution targeting the mouse gene of CCL-7 and 10 µl of SYBR Green TaqMan Universal PCR master mix (Applied Biosystems, Foster City, Calif.). The PCR reaction is first conducted on the genes of mixtures (GAPDH and HPRT) in order to normalize the genic expression (use of GeNorm software). Analyses then related to the expression of CCL7 gene (human or mouse). The nucleotide sequences of the primers and the optimal concentrations for use are compiled in table 1 below.

TABLE 1 primers used for Q-PCR

| Gene studied | Species | Sense primer (SEQ ID NO:) | Antisense primer (SEQ ID NO:) | Concentration used |
|---|---|---|---|---|
| CCL7 | Human | AAACCTCCA ATTCTCATG TGGAA (4) | CAGAAGTGC TGCAGAGGC TT (5) | 900 Nm |
| CCL7 | Mouse | AAGATCCCC AAGAGGAAT CTCAA (6) | CTTCCCAGG GACACCGAC TA (7) | 900 Nm |
| GADPH | Human/ Mouse | TGCACCACC AACTGCTTA GC (8) | GGCATGGAC TGTGGTCAT GAG (9) | 500 Nm |
| HPRT | Human/ Mouse | TGACACTGG CAAAACAAT GCA (10) | GCTTGCGAC CTTGACCAT CT (11) | 900 Nm |
| HPRT | Mouse | TGGCCATCT GCCTAGTAA AGC (12) | GGACGCAGC AACTGACAT TTC (13) | 300 nM |

Digestion of Adipose Tissue with Collagenase

The human or mouse adipose tissue is digested with liberase (Roche Applied Science, Meylan, France) for approximately 30 minutes at 37° C. under stirring. After digestion, liberase is inhibited by adding serum in the medium containing the cells. Adipocytes, due to the lipid content thereof, float whereas stromal vascular fraction (SVF) cells sink and are found at the bottom of the tube. The isolated primary adipocytes and the SVF cells are then cultured in DMEM (serum-free) medium containing 1% BSA for 24 hours. Conditioned medium is sampled after 24 hours of secretion. The cells are counted at the end of the experiment to refer the various secretions to the number of cells.

Human and Mouse CCL7 Assay Using ELISA Test

The human and mouse CCL7 assays were conducted using the ELISA kit supplied by Peprotech and R&D system respectively in accordance with the protocols provided by these manufacturers.

Analysis of Expression of Chemokine Receptors in Tumor Lines by Flow Cytometry

The tumor cells (from prostate, breast, colon, pancreas, or melanoma) were washed three times in FACS buffer (PBS supplemented with 0.5% BSA and 2% FCS) and fixed with a 3.7% paraformaldehyde solution for 20 min at 4° C. The tumor cells were suspended with anti-CXCR4 (10 µg/ml), anti-CXCR1 (10 µg/ml), anti-CXCR2 (1:25), anti-CCR1 (10 µg/ml), anti-CCR2 (20 µg/ml), anti-CCR3 (10 µg/ml) antibodies or isotypical mouse anti-IgG control antibodies at 4° C. for 2 hours. The tumor cells were incubated with a mouse anti-IgG secondary antibody (dilution to 1:200) coupled with Alexa Fluor 488 or coupled with Cyanine 5 (for cells expressing GFP) for 30 minutes at 4° C. Finally, $2 \times 10^4$ cells were analyzed by flow cytometry using a FACScan and FACScalibur flow cytometer (analysis on CellQuest™ software (BD-PharMingen)).

Boyden Chamber Migration Tests

In order to evaluate the ability of tumor cells to migrate according to the culture medium, Boyden chamber migration tests were conducted using 8 µm porosity Greiner bio-one inserts. In the lower compartment either culture medium with or without serum, or conditioned medium from F442A adipocytes (CM-Ad), human periprostatic adipose tissue (CM-PPAT), mouse perigonadal adipose tissue (CM-PGAT), adipocytes or vascular fraction cells (SVF) isolated from PPAT or PGAT is introduced. These conditioned media may be pretreated for 30 minutes by adding antibodies blocking the chemokine CCL7. Experiments with the recombinant chemokine CCL7 were also conducted, in this case the chemokine is added to serum-free culture medium to verify the chemoattractant potential thereof on a cell line. In the upper chamber $1 \times 10^5$ cells, previously depleted for 6 hours of serum are deposited in serum-free culture medium. For the migration tests in the presence of blocking antibodies specific for CCR1 or CCR3 or inhibitors of CCR1/CCR3, CCR2, CXCR1/CXCR2 and CXCR4, the tumor cells are previously incubated in a tube with the blocking antibody or the inhibitor for 30 min at 37° C. The migration of the tumor cells is evaluated after 12 hrs of migration at 37° C. and 5% $CO_2$ by 1% toluidine blue staining supplemented with 0.1M borax (Sigma, St Louis, Mo., USA) and quantification of the absorbance (measured at 570 nm).

Adipocyte Secretome Analysis (Mass Spectrometry)

The conditioned media from adipocytes (CM-Ad) are sampled after 24 hours of secretion (medium free from serum and phenol red) centrifuged and filtered to remove the cell debris and supplemented with protease inhibitor. The concentration of 5 ml of adipose CM-Ad medium was conducted with StrataClean resin (Agilent Technologies, Santa Clara, Calif., USA) according to the manufacturer's instructions.

After reduction and alkylation of cysteine, the sample was separated by SDS-PAGE (12% acrylamide). The proteins were visualized by Coomassie blue staining and each track was divided into 13 homogeneous bands and digested (digestion of gel by trypsin). The digestion product was analyzed by nanoLC-MS/MS via the Ultimate3000 system (Dionex, Amsterdam, Netherlands) coupled with an LTQ-Orbitrap mass spectrometer (Thermo Fisher Scientific, Bremen, Germany) as described above (Contreras, Ferrero Guadagnoli et al. 2010), except that the peptides were eluted using a 5 to 50% gradient of solvent B for 60 min at a flow rate of 300 nL/min. Mascot was used to automatically extract the "peak lists" from the raw files. The MS/MS data were compared to all the entries in the mouse databases (*Mus musculus*) and the identification of the peptides was validated using a computer system as described above (Santini, Salomon et al. 2010), except that 1% FDR was used for the validation peptides and proteins.

Inhibition of the Expression of CCR3 Using shRNA

In order to inhibit the expression of the receptor CCR3 (NM_009914) in a stable manner in TRAMP-C1P3 cells, an shRNA approach was used enabling stable negative regulation even after several months of culture. The interfering sequences were generated using the Dharmacon "Center siDesign" tool. The sequences of the sense strands of shRNA generated are as follows:

```
m4CCR3 (SEQ ID NO: 1):
5'-cgcgtccccAGACCACACCCTATGAATAttcaagagaTATTCAT
AGGGTGTGGTCTtttttggaaat-3, m5CCR3 (SEQ ID NO: 2):
5'-cgcgtccccGACCACACCCTATGAATATttcaagagaATATTCA
TAGGGTGTGGTCtttttggaaat-3
and m6CCR3 (SEQ ID NO: 3)
5'-cgcgtccccGGTGAGAGGTTCCGGAAAttcaagagaGTTTCCG
GAACCTCTCACCtttttggaaat-3.
```

The nucleotides targeting the sequence of CCR3 are shown in upper case, whereas the sequence responsible for the hairpin structure and the sequences required for directional cloning are represented in lower case letter. The lentiviral vector LVTHM® is a lentiviral vector (LV) coding for the shRNA CCR3 sequences under the control of the H1 promoter also expressing GFP. The TRAMP-C1P3 cells were then transfected in the presence of m4, m5 or m6-LVTHM for 24 hours at a multiplicity of infection (MOI) of 1:10. The transfected population is selected by GFP expression (cell sorting). These cells were then analyzed by flow cytometry to validate the loss of expression of the CCR3 gene. The control used is the pLVTHM plasmid which expresses an ineffective shRNA sequence.

Intraprostatic Injection of TRAMP-C1P3 Cells in C57BL/6 Mice

Male C57BL/6 mice aged 18 weeks on a normal or high-fat diet were anesthetized with isoflurane. A transverse incision was made at the lower part of the abdomen. The muscles of the abdominal wall were incised, and the bladder and the seminal vesicles were released so as to expose the dorsal lobe of the prostate. A suspension of $2\times10^6$ cells (in 30 μl of PBS) was then carefully injected under the prostate capsule by means of a gauge 30 needle. The incision was closed using 4-0 suture and clips. The animals were then placed in cages and regular monitoring is conducted in order to monitor macroscopically the general condition of the mouse. After 20 days of tumor establishment, the mice are sacrificed, the primary tumor is thus removed, measured and weighed, and an acquisition in white light and GFP is carried out. The tumors are then placed in a paraformaldehyde solution (4%) and included in paraffin.

Sampling of Human Prostate Tumor Samples and Tissue Micro-Arrays TMA

The first database includes a cohort of 92 patients all operated on for prostate adenocarcinoma in the Urology Department of Toulouse university hospital (France).

For the second database, it consists of a single-center, prospective study. The patients included were all operated on for prostate adenocarcinoma, between Feb. 1, 2010 and Dec. 1, 2011, in the Urology Department of Toulouse university hospital (France). The surgical treatment consisted of a radical prostate resection by the robot-assisted laparascopic route or by the open retropubic route. The prostate resection was associated in some cases with bilateral ilio-obuturator lymph node dissection (standard or extended). All the patients included in the study presented with localized disease with no metastatic site during the procedure. For all the patients, a form in respect of non-opposition to the use of their tissue samples for scientific purposes was collected and signed prior to the procedure in order to be included in a study. The fresh specimen, accompanied by the certificate of non-opposition, is processed within 15 minutes following the surgical exeresis in order to obtain the shortest possible interval between devascularization and freezing to ensure preservation of the labile molecules. The tissue samples collected are placed in cryotubes and frozen in nitrogen and stored at −80° C.

In order to facilitate the study, a multiplex histological analysis was possible due to the performance of "tissue microarrays" (TMA) on regions of interest selected on prostate sample slides. The regions of interest retained for TMA preparation were selected by two pathologists in double-blind mode: the aim was to select a region rich in carcinomatous tissue. The tumor regions selected corresponded morphologically to sectors having a comparable histological differentiation to the Gleason score of the tumor or to the least favorable Gleason score in the case of a multifocal tumor. After having chosen the blocks to be sampled, core samples of 0.2 mm in diameter were included on an orthonormal basis along a predefined plane in a receiving block. The receiving block could then be cut on a standard microtome.

Analysis of the Expression of CCR3 by Tissue Immunohistochemistry

Immunohistochemistry experiments on human prostate tumor biopsies were conducted in order to detect the expression of CCR3. Immunolabeling was conducted using EnVision™ FLEX Mini Kit, High pH (Dako Autostainer/Autostainer Plus) (Dako France, Trappes, FR). The TMA (Tissue Micro-Arrays) are immersed in xylene to remove the paraffin and then rehydrated with successive graduated alcohol baths (100 to 70% followed by distilled water), followed by a treatment with antigen unmasking solution for antigen retrieval (Dako1X pH 6 citrate buffer with 95° C. waterbath). After an endogenous peroxidase saturation step (Peroxidase blocking, Dako), the samples are incubated with the anti-CCR3 primary antibody (diluted to 1:100). The TMA are then incubated with the biotinylated secondary antibody, then with HRP-conjugated streptavidin (Dako). They are then rinsed, and treated with liquid DAB (BioGenex, San Ramon, Calif.), and washed with distilled water. Finally, counterstaining was performed with hematoxylin (Dako), and the various TMA are finally mounted using EUKITT reagent. The slides are digitally scanned using the Hamamatsu Nanozoomer 2.0RS apparatus and analyzed using the software supplied by the manufacturer. The TMA readings were conducted by an anatomopathologist.

Measurement of Surface Area of Periprostatic Adipose Deposits

The measurement of the surface area of the periprostatic adipose deposits was conducted on 15 patients from the main cohort used in our study. The measurements were conducted using preoperative CT-scan or MRI imaging data of each of these patients. For this, images of cross-sections at the femur were used, at the point where the fusion of the symphysis pubis starts. The adipose deposit which was studied is situated between the anterior part of the prostate and the symphysis pubis. It is easily recognizable by the difference in attenuation between the bone, the prostate and the adipose tissue. The thickness and width of the deposit were measured using these images. The area of this deposit was then approximated for each patient, by calculating an elliptical area based on the data collected.

Statistical Analysis

The statistical significance of the differences between the means (at least three independent experiments) was evaluated using Student tests, performed using Prism software (GraphPad Inc.). For the analyses on the patient, Spearman rank correlation tests were conducted. The correlations are described as strong for values greater than 0.7, moderate for values between 0.3 and 0.7 and weak for values less than 0.3. The values of p less than 0.05 (*), <0.01 () and <0.001 (*) are considered to be significant whereas "NS" signifies non-significant.

Results

The Receptor CCR3 is Involved in the Migration of Prostate Tumor Cells Against Conditioned Medium from Adipocytes Boyden chamber migration tests were performed with prostate cancer lines of increasing aggressiveness (LNCaP, C4-2B, Du-145 and PC-3). The lower chamber contains different media: RPMI free from fetal calf serum (negative control), RPMI containing 10% fetal calf serum (positive control), conditioned medium from mature adipocytes (CM-Ad) (obtained from the in vitro differentiation of the mouse pre-adipocyte line 3T3-F442A (Kuri-Harcuch and Green 1978). The percentage of migrant cells against a medium containing 10% serum is dependent on tumoral aggressiveness. The percentage of migration in the presence of CM-Ad is similar to the migration induced by medium containing 10% serum for the LNCaP and C4-2B lines and is greater for the Du-145 and PC-3 lines (p<0.05), demonstrating that this medium contains chemokines (see FIG. 1A).

As described above (Vindrieux, Escobar et al. 2009), the receptors CCR2, CXCR1, CXCR2 and CXCR4 are expressed by the prostate cancer lines Du-145 and PC-3, the expression detected by flow cytometry. The receptor CCR3 is expressed in the prostate cancer lines Du-145 and PC3 unlike the receptors CCR1 (see FIG. 1B).

The functionality of these receptors in the migration of PC-3 cells against CM-Ad was tested using known specific inhibitors used at the inhibitory doses described in the literature. The results (see FIG. 1C) are as follows:

AMD3100 (specific inhibitor of CXCR4; Rosenkilde et al., 2004) significantly reduces by approximately 20% (p<0.05) the migration of PC-3 cells against CM-Ad medium only at the maximum dose of 100 nM;

SB225002 (inhibitor of CXCR2 and CXCR1 at a lower affinity; White et al., 1998) significantly inhibits by approximately 30% the migration induced by CM-Ad at the dose of 50 nM (p<0.01);

sc-202525 (specific antagonist of CCR2; Cherney et al., 2008) inhibits by merely 10% the migration of tumor cells (p<0.05);

UCB35625 (inhibitor of CCR1 and CCR3; Sabroe et al., 2000) induces a significant dose-dependent decrease in the migration of PC-3 tumor cells induced by CM-Ad from 50 nM (p<0.05). The maximum effect is observed at 200 nM (approximately 50% inhibition, p<0.001). These results were confirmed by a more specific approach based on the use of antibodies blocking CCR1 (reference D063-3, clone 141-2, MBL international Corp, (Iacono, Masciangelo et al. 1994)) or CCR3 (D083-3, clone 444-11, MBL international, (Iacono, Masciangelo et al. 1994)). The incubation of the tumor cells with a blocking antibody targeted against CCR3 (10 µg/ml) induces a significant inhibition of the migration induced by CM-Ad (approximately 50%, p<0.01) with respect to the isotypical control. On the other hand, no inhibition effect is observed with the use of blocking antibody targeted against CCR1, which is not expressed by the tumor cells.

The specificity of the role of CCR3 in the migration of prostate cells against conditioned medium from mature adipocytes was studied. The results are shown in FIG. 1D.

Various epithelial tumors were used, for which adipose tissue (AT) is situated anatomically in the vicinity when they become invasive. It consists of breast cancer (mammary AT), pancreatic and colon cancer (visceral AT). Furthermore, melanoma lines were included; this tumor when invading finding itself in contact with the AT of the hypodermis. Two pairs of lines were chosen for each tumor type. As shown in FIG. 1D (left-hand panel), breast (T47D and MDA-MB231), colon (sw480 and sw620), pancreatic (CAPAN and PANC-1) cancer and melanoma (501Mel and SK28) lines express the receptor CCR3 (flow cytometry). All these lines migrate against CM-Ad, the percentage of migrant cells being correlated with the degree of aggressiveness thereof. The migration of pancreatic, colon cancer and melanoma tumor cells against CM-Ad medium is not affected by the presence of UCB35625 at a dose of 200 nM (right-hand panel). Only a very modest effect (inhibition of the order of 10%, p<0.05) is observed for the aggressive breast cancer line MDA-MB231, whereas the migration of the breast cancer line (T47D) is not affected. In this same series of experiments, significant inhibition of migration against CM-Ad medium of PC-3- and Du-145 prostate tumor cells by approximately 50% is detected (p<0.001).

Figure 1C:
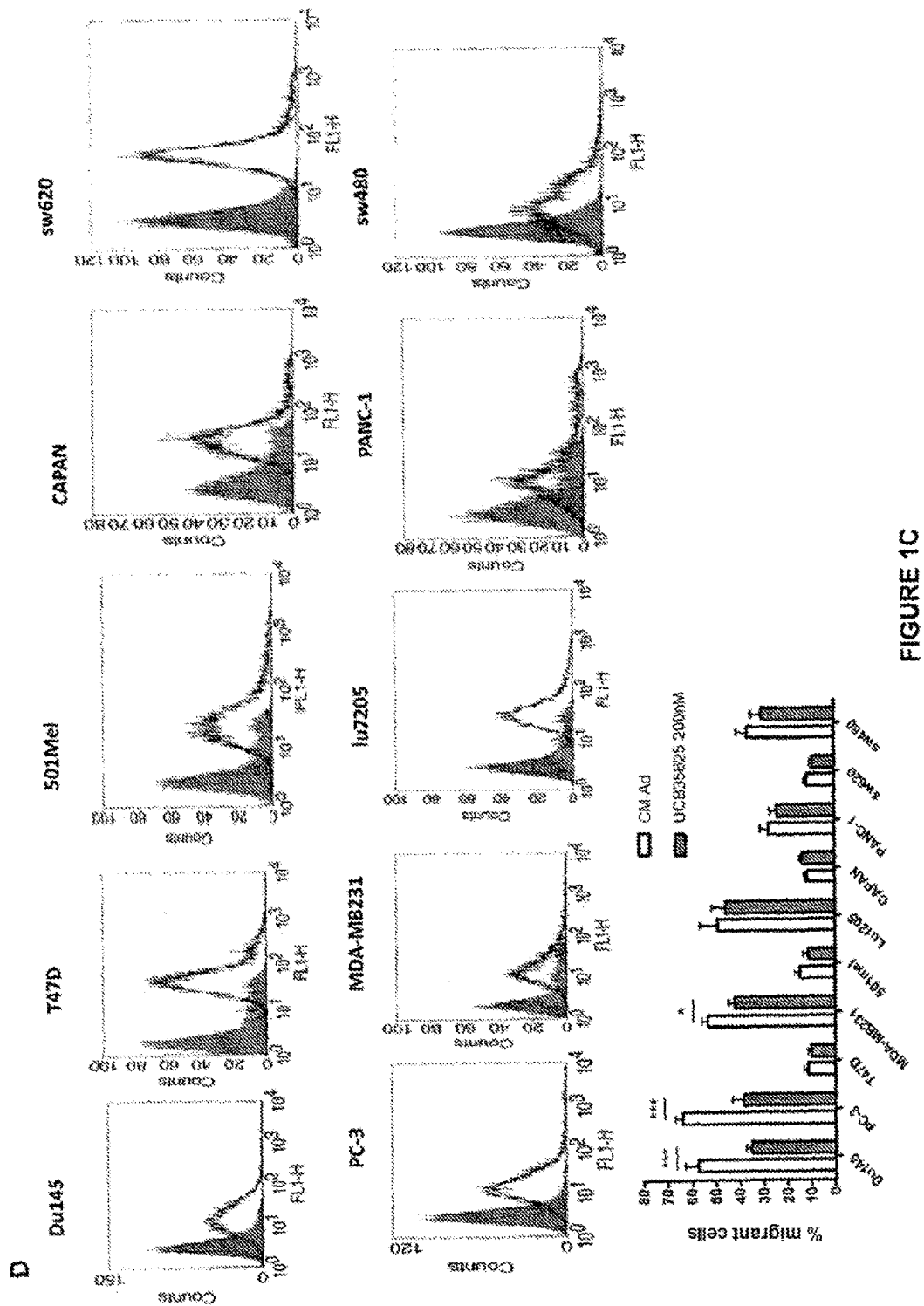

The Ligand of CCR3, CCL7 is Involved in the Migration of Prostate Tumor Cells Against Conditioned Medium of Adipocytes A proteomic analysis was conducted on CM-Ad (Proteomics Department, IPBS, CNRS UMR5089, Toulouse France). This analysis was conducted on 3 independent media. Six chemokines were detected reproducibly: CXCL1, CXCL5, CXCL12, CCL2, CCL7 and CCL9 (right-hand panel). The chemokines, CXCL1 and CXCL5, can interact with the receptor CXCR2, CXCL12 with CXCR4 and CCL2 with CCR2 (left-hand panel). These results (see FIG. 2A) could explain why the inhibitors of CXCR1/CXCR2, CXCR4 and CCR2 partially reduce the chemotaxis induced by CM-Ad (FIG. 1C). Of the ligands of CCR3, only CCL7 is detected. It should also be noted that no ligand of CXCR1 was detected in the adipocyte secretions analyzed.

The recombinant chemokine CCL7 is capable of inducing the migration of PC-3 and Du-145 prostate cells in a dose-dependent manner in a Boyden chamber migration test. The results (see FIG. 2B) are significant for both lines from 50 ng/mL compared to the medium alone (left-hand panel). In these two same cell lines, migration of the prostate cells is inhibited by approximately 50% by a blocking antibody targeted against CCR3 and by a blocking antibody targeted against CCL7 (AF-456-NA, R&D System) (p<0.001), whereas the antibody blocking CCR1 has no effect (right-hand panel).

Perigonadal adipose tissue (AT-mu-PG) was sampled from male mice (3 independent experiments conducted on 3 independent lots of mice, containing 3 to 10 mice). Similar experiments were conducted with periprostatic adipose tissue in humans (AT-hu-PP). This AT is obtained on prostate resection specimens, remote from the tumor. This tissue exhibits macroscopic characteristics of AT and does not contain tumor cells. These experiments were conducted on 5 patients having a BMI between 20 and 25. For these two types of AT, conditioned medium was prepared using a 24-hour culture. These experiments (see FIG. 2C) demonstrate that CCL7 is secreted by these two AT with a mean of 155±20 pg/mL/g of AT in mice and 75±15 pg/ml/g of AT in humans (left-hand panel). The conditioned media of human and mouse AT are capable of inducing in a similar manner the migration of tumor cells (approximately 20% migrant cells for both media). Finally, this migration is significantly inhibited by the use of inhibitors and antibodies blocking the CCR3/CCL7 pathway and by the inhibitor of CCR3 (200 nM UCB35625) (right-hand panel). The CCR3/CCL7 pathway is thus involved in the migration of prostate cells against secretions of mouse visceral and human periprostatic adipose tissue.

The Secretion of CCL7 by AT is Increased in an Obesity Context which Helps Amplify the Role of the CCR3/CCL7 Pathway in Prostate Cell Migration The genic expression of CCL7 was evaluated in a series of samples of human (intra-abdominal) visceral AT (VAT) from patients who were either normal weight (Body Mass Index (mean BMI 23.3±1.2 kg/m$^2$, 8 samples), or obese (mean BMI 45.7±2.9 kg/m$^2$, 21 samples). The results (see FIG. 3A) show an approximately 3-fold increase of the mRNA of CCL7 in the VAT of obese subjects compared to subjects of normal BMI ($p<0.01$) (left-hand panel). In mice, the level of expression of the mRNA of CCL7 is also increased by a factor of 3 in mice rendered obese by a "High-Fat Diet" (HFD) compared to mice of normal weight ("Normal Diet", ND) ($p<0.001$). Similar results were obtained with a mouse genetic obesity model exhibiting invalidation of the leptin receptor (db/db mice) compared to wild mice.

Figure 3B:
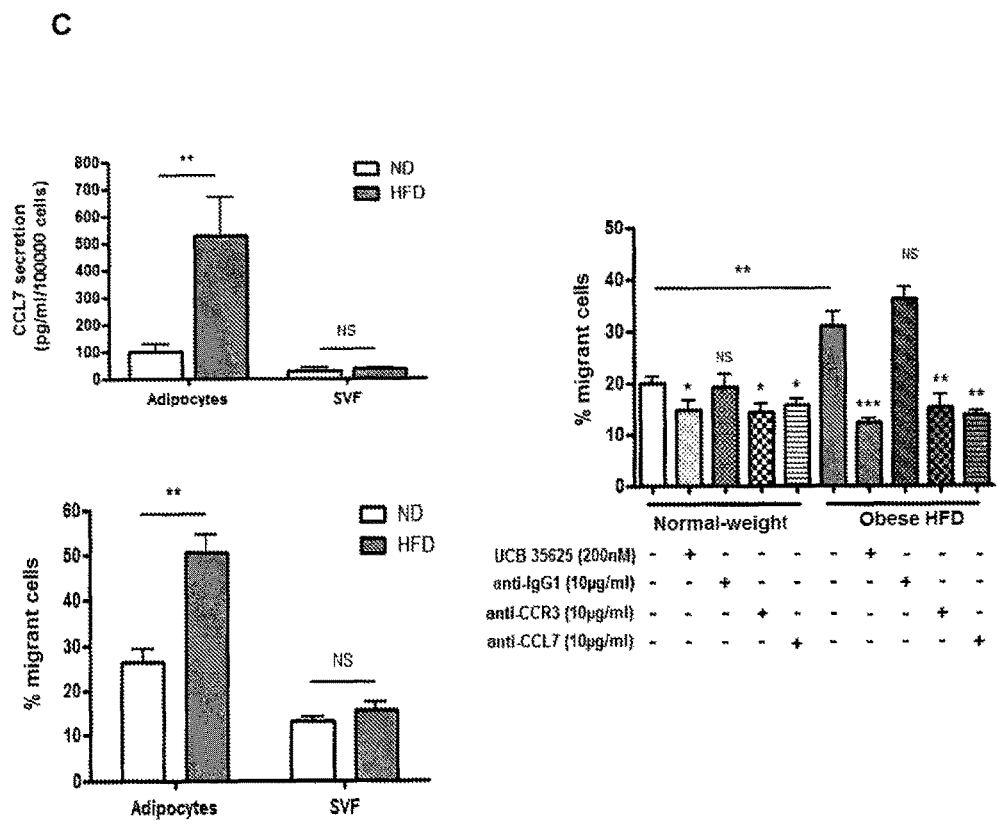

Perigonadal adipose tissue (AT-mu-PG) was sampled from mice subjected for 8 weeks, either to a normal diet (normal-weight mice) or a high-fat diet resulting in the onset of obesity (obese, HFD) (independent experiments conducted on 3 different lots of mice). The results are shown in FIG. 3B. In the conditioned medium prepared as above, a 2.7-fold increase in the level of secretion of CCL7 is observed in the tissue from obese mice compared to normal-weight mice ($p<0.05$) (left-hand panel). These conditioned media were used to conduct Boyden chamber migration experiments. The migration of PC-3 tumor cells against conditioned medium is significantly increased by obesity (28% migrant cells against CM of AT of normal-weight mice versus 40% against CM of AT of obese HFD mice, $p<0.01$) (right-hand panel). Under both conditions, the migration of tumor cells against CM is inhibited by the use of inhibitors and antibodies blocking the CCR3/CCL7 pathway, the effect being however more pronounced under obesity conditions. As such, UCB35625 or anti-CCR3 or CCL7 inhibit migration against CM of ND AT-mu-PG by 25%, whereas this effect is 60% for CM of HFD AT-mu-PG.

AT-mu-PG of ND or HFD mice were digested with collagenase in order to be able to separate, after a short centrifugation, the mature adipocytes (floating cells) from the stromal vascular fraction (containing the endothelial cell, macrophages, adipocyte stem cells and pre-adipocytes, etc.). These mature adipocytes were then incubated for 24 hours in a serum-free medium supplemented with 1% BSA in order to prepare CM. The assay of CCL7 in these media (3 independent media) was conducted by ELISA. The results (see FIG. 3C) demonstrate that the primary adipocytes secrete CCL7 and that this secretion is highly regulated in an obesity context (90±10 pg/mL/10$^5$ cells versus 720±80 pg/mL/10$^5$ cells, $p<0.001$). The migration of tumor cells against CM of adipocytes from obese animals is significantly increased with respect to the CM of normal-weight animals ($p<0.01$). Under both conditions, the migration of tumor cells against CM is inhibited by the use of inhibitors and antibodies blocking CCR3, the effect being however more pronounced using obesity conditions. As such, the inhibition of CCR3 by UCB35625 or by an antibody reduces by 60% the migration against CM of adipocytes from obese mice, whereas this effect is 30% for CM of adipocytes from normal-weight mice ($p<0.01$).

Validation of the Involvement of CCR3 in Migration in Response to Adipocyte Secretions in a Mouse Tumor Line Model (TRAMP-C1P3)

The TRAMP-C1P3 syngeneic mouse line for the mouse strain C57 BL/6 was used to produce orthotopic prostate tumor cell graft models in normal-weight or obese mice. This choice of line is justified in that the C57 BL/6 is a model sensitive to obesity induced by a high-fat diet with perfectly characterized reproducibility (Winzell and Ahren 2004). The results (see FIG. 4A) demonstrate that TRAMP-C1P3 cells, like human prostate tumor cells, express the receptor CCR3 but not the receptor CCR1 (left-hand panel). The recombinant chemokine CCL7 is capable of inducing dose-dependent chemotaxis as for the human lines from 50 ng/mL (center panel). Finally, the migration induced by CM-Ad is significantly inhibited by the use of UCB35625 (200 nM, $p<0.05$) of the blocking antibodies targeted against CCR3 (10 µg/mL, $p<0.001$) or CCL7 (10 µg/mL, $p<0.01$) whereas the blocking antibody targeted against CCR1 is ineffective (right-hand panel).

Figure 4B:
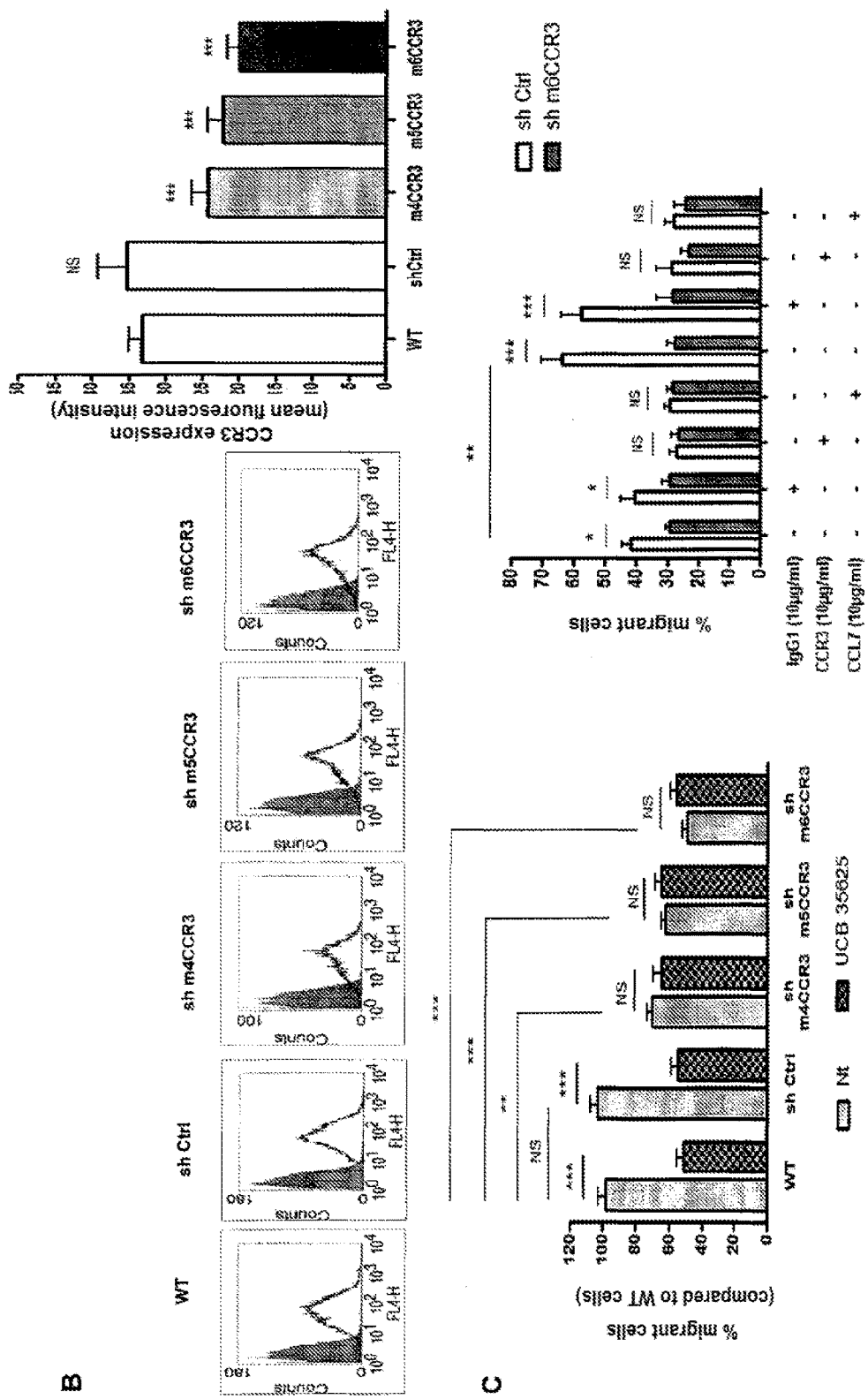

Three plasmids containing shRNA targeted against the coding sequence of CCR3 and against a non-coding sequence (control shRNA) were constructed. These plasmids were transfected by a lentiviral approach in the TRAMP-C1P3 line and 3 lines (m4CCR3, m5CCR3, m6CCR3) invalidated for the receptor CCR3 were obtained along with a control line (shCtrl). The results are represented in FIG. 4B. As shown in the left-hand panel (upper quadrant of FIG. 4B), the 3 lines invalidated for CCR3 exhibit a significant reduction in the expression of the receptor with respect to the control line (immunofluorescence). This inhibition of the expression of CCR3 is accompanied by a significant reduction in migration against CM-Ad for the three shCCR3 lines with respect to the control line (left-hand panel, lower quadrant). This reduction in the migration is also detected for the m6CCR3 line with respect to the control line when the conditioned medium of ND AT-mu-PG is used. Under these conditions, UCB35625 and the antibodies blocking CCR3 or CCL7 no longer have a significant effect on the migration of m6CCR3 tumor cells unlike the control line ($p<0.001$). Finally, the increase in migration observed in the presence of HFD AT-mu-PG is not significant for the m6CCR3 line unlike the shCtrl line and the effect of UCB35625 and the antibodies blocking CCR3 or CCL7 is not significant (right-hand panel, lower quadrant).

The Receptor CCR3 is Involved in Tumor Progression in Mouse Models In Vivo

The results are given in FIG. 5A. The injection of the TRAMP-C1P3 line into the prostate (dorsal lobe) of 16 week old C57BL/6 mice fed using a normal-fat diet (ND) (mean weight 32±3 g) results in the onset of tumors (measured at 3 weeks, mean tumor size 800±100 mm3, n=14). When the cells are injected into the prostate gland of mice under an 8-week high-fat diet (HFD) and which are obese (mean mouse weight: 45±3 g, injection at 16 weeks as for normal-weight mice), there is a significant increase in the tumor size of approximately 2-fold with respect to the non-obese mice (mean tumor size 1500±80 mm3, n=14, $p<0.001$). The same experiments conducted with the m6CCR3 line demonstrate a significant decrease in the tumor size with respect to the shCtrl line whether for mice fed with a normal-fat diet (mean weight 30±4 g [NS with respect to the shCtrl group], tumor size 220±30 mm3, n=11, $p<0.001$ [with respect to the shCtrl group]) or obese mice fed with a high-fat diet (mean weight 45±3 g) [NS with respect to the shCtrl group], tumor size 210±25 mm3, n=11, p<0.001 [with respect to the shCtrl group]. For mice injected with the m6CCR3 line, there is no longer a difference in tumor size between the normal-weight or obese mice (tumor size 220±30 mm$^3$ versus 200±50 mm$^3$), (left-hand panel in FIG. 5A). An anatomo-pathological analysis of the tumors was conducted (lower panel). The analysis of the histological sections of these tumors after hematoxylin-eosin (HE) staining confirms that the mice injected with the control line (C1P3 Ctrl) exhibit tumors of a large volume having completely invaded the dorsal lobe of the prostate. For these tumors, a disappearance of periprostatic adipose tissue is also observed in particular in the obese mice. Indeed, in contact with the tumor, the mature adipocytes are delipidized and dedifferentiated which results in the replacement thereof by a fibrous tissue. On the other hand, in the mice injected with the line invalidated for CCR3 (C1P3 m6CCR3), tumors of a smaller volume are observed, characterized by a much less extensive invasion of the dorsal lobe of the prostate than for the C1P3 Ctrl line. At the periphery of the tumor, intact adipose tissue is found, exhibiting hypertrophy and hyperplasia in the obese mice.

Expression of the Receptor CCR3 is Detected in Aggressive Prostate Tumors and the Expression Thereof is Correlated with the Extension of the Tumor Outside the Prostatic Capsule The expression of the receptor CCR3 in human tumors was analyzed in a first TMA (Tumor Micro-Array) containing 92 prostate tumors. The results demonstrate that CCR3 is expressed in human prostate tumors (figure representing the immunohistochemistry labeling result, left-hand panel in FIG. 6A) and that the level of expression thereof is correlated with the grade of the tumor defined by the Gleason score (coefficient of correlation of 0.62, p<0.001, Spearman test) (FIG. 6A, right-hand column). In low-grade tumors (Gleason score less than 7), a high expression of CCR3 is observed (quantitative immunohistochemical score+++) in 10% of tumors against 75% of tumors expressing a low CCR3 score (quantitative immunohistochemical score+). On the other hand, in more aggressive tumors having a Gleason score equal to and/or greater than 7, intense labeling of CCR3 is detected in 46.8% and 76% of tumors respectively against 12.8% and 4% exhibiting weak labeling respectively. Finally, it should be noted that the expression of CCR3 is low or absent in non-tumoral prostate glands.

A second series of experiments was conducted on an annotated collection of 101 patients. The patients included were all operated on for prostate adenocarcinoma in the Urology Department of Rangueil university hospital (France). The TMA were produced in duplicate using a region containing tumor from cryopreserved prostate resection specimens. In order to improve the quantification of CCR3, the tumor slides were acquired digitally and the expression of the protein was quantified using ImageJ software plugins to obtain more precise measurements than the convention evaluation based on manual notation (Systel et al., 2013).

Immunohistochemical Quantification of the Vitamin B12 Transport Protein (TCH), Cell Surface Receptor (TCH-R) and Ki-67 in Human Tumor Xenografts.

The clinical characteristics of the cohorts are given in table 2 hereinafter and the immunohistochemical characteristics in table 3 hereinafter.

TABLE 2

Clinical characteristics of cohort.

|  |  | Variables | Percentage of cohort |
|---|---|---|---|
| Cohort size (number of patients |  | 101 | 100 |
| Age at time of surgery (years), median (range) |  | 63 (47-75) |  |
| Body Mass Index (BMI) (kg/m$^2$), median (range) |  | 26.1 (19-34) |  |
| Post-surgery PSA (ng/mL), median (range) |  | 7 (2-37) |  |
| Latest PSA assay (ng/mL), median (range) |  | 0 (0-4.02) |  |
| Prostate resection specimen weight (g), median (range) |  | 48 (22-93) |  |
| Monitoring time (Day), median (range) |  | 765 (62-1736) |  |
| Post-surgery treatment (number of patients) | Monitoring only | 71 | 70.30 |
|  | Radiotherapy only | 16 | 15.84 |
|  | Hormone therapy only | 7 | 6.93 |
|  | Radiotherapy and hormone therapy | 7 | 6.93 |
| Post-surgery progression (number of patients) | Biochemical recurrence | 14 | 13.86 |
|  | Surgical treatment failure $^a$ | 30 | 29.70 |
|  | No recurrence | 70 | 69.31 |
|  | Death | 1 | 0.99 |

TABLE 3

Histolocrical and immunohistochemical characteristics of cohort.

|  |  | Variables | Percentage of cohort |
|---|---|---|---|
| Gleason score, number of patients | <7 | 18 | 17.82 |
|  | =7 (3 + 4) | 39 | 38.62 |
|  | +7 (4 + 3) | 36 | 35.64 |
|  | >7 | 8 | 7.92 |
| Percentage of undifferentiated contingent (grade 4 and 5), median (range) |  | 40 (0-100) |  |
| Tumor site, number of patients | Transition zone | 10 | 9.90 |
|  | Peripheral zone | 91 | 90.10 |
| Tumor stage, number of patients | pT2b | 6 | 5.94 |
|  | pT2c | 35 | 34.65 |
|  | pT3a | 44 | 42.57 |
|  | pT3b | 16 | 15.84 |
| Positive surgical margins, number of patients |  | 22 | 21.78 |
| Presence of lymphatic emboli, number of patients | No | 93 | 92.08 |
|  | Yes | 8 | 7.92 |
| Bilateral lymph node dissection, number of patients |  | 79 | 79.21 |
| Lymph node invasion, number of patients | Nx (No lymphnode dissection conducted) | 22 | 21.78 |
|  | N0 | 74 | 73.27 |
|  | N1 | 5 | 4.95 |
| Expression of CCR3 (arbitrary units), median (range) |  | 48.5 (11.4-94.7) |  |

As in the previous cohort, an expression of CCR3 is detected in the prostate tumors (figure representing the immunohistochemistry labeling result, left-hand panel in FIG. 6A), and the level of expression thereof is correlated with the grade of the tumor defined by the Gleason score (coefficient of correlation of 0.472, p<0.001, Spearman test) (FIG. 6A, right-hand column). An extensive analysis of the correlation between the level of expression of CCR3 and various clinical and biological parameters of the tumors was conducted (see results hereinafter).

As such, a correlation was demonstrated between the level of expression of CCR3 and
- the Gleason score (p<0.001),
- the percentage of poorly histologically differentiated tumor contingent (grade 4 and grade 5 combined) (p<0.01),
- the histological pT stage equivalent to the degree of extension of the tumor (p<0.03)
- the peripheral site of the tumor (p<0.04),
- the present of lymphatic emboli (p<0.02),
- biological recurrence defined by two successive PSA assays >0.2 mg/mL (P<0.001).

Furthermore, the level of expression of CCR3 is increased in obese patients (p=0.01).

The expression of the receptor of CCR3 is a factor of poor prognosis in prostate cancer. There is a significant correlation between the level of expression of CCR3 and surgical treatment failure (p<0.001). Surgical treatment failure is defined either by biological recurrence (two successive PSA levels greater than 0.2 ng/mL), or by locoregional recurrence or the onset of remote metastases, or by the use of hormone deprivation treatment and/or radiotherapy immediately after surgery, a criterion which was used in a previous study (Malavaud et al., 2010).

Sphingosine Kinase-1 Activity and Expression in Human Prostate Cancer Resection Specimens.

The CCR3 values were correlated with this criterion (see FIG. 8A). When the CCR3 values were compared in patients presenting with surgical treatment failure or not at one year of follow-up in the four Gleason score classes (i.e. <7, 7 [3+4 or 4+3], >7), they were systematically higher in patients presenting with surgical treatment failure (FIG. 8B). Furthermore, the differences were greater in the case of a low Gleason score (<7). The CCR3 level could thus represent a prognostic factor of recurrence.

In one subgroup of patients, the extent of periprostatic adipose tissue was measured. The clinical (table 4 hereinafter) and histological and immunohistochemical characteristics (table 5 hereinafter) of this subgroup are shown.

TABLE 4

Clinical characteristics of cohort for which prostatic fat was measured.

| | | |
|---|---|---|
| Total number of patients (percentage in column; %) | | 15 (100) |
| Age (Years), Median (range) | | 62 (48-71) |
| BMI (kg/m$^2$), Median (range) | | 28 (20-34) |
| Initial PSA prior to prostate resection (ng/ml), Median (range) | | 7 (2-34) |
| Prostate resection, specimen weight (g), Median (range) | | 48 (32-69) |
| Proposed post-surgery treatment | Monitoring only, n (percentage in column) | 10 (66.7) |
| | Radiotherapy, n (percentage in column) | 3 (20) |
| | Hormone therapy, n (percentage in column) | 3 (20) |

TABLE 4-continued

Clinical characteristics of cohort for which prostatic fat was measured.

| | | |
|---|---|---|
| Post-surgery progression | No biological recurrence | 12 (80) |
| | Biological recurrence | 3 (20) |
| | Death | 1 (10) |

TABLE 5

Histological and immunohistochemical characteristics of cohort for which prostatic fat was measured.

| | | |
|---|---|---|
| Total number of patients (percentage in column; %) | | 15 (100) |
| Tumor site | Transitional, n (percentage in column) | 1 (6.7) |
| | Peripheral, n (percentage in column) | 14 (93.3) |
| Gleason score on prostate resection specimen | 5, n (percentage in column) | 2 (13.3) |
| | 6, n (percentage in column) | 1 (6.7) |
| | 7, n (percentage in column) | 10 (66.7) |
| | 8, n (percentage in column) | 1 (6.7) |
| | 9, n (percentage in column) | 1 (6.7) |
| Percentage of poorly differentiated contingent (grade 4 and 5 combined), Median (range) | | 25 (0-95) |
| Tumor volume (prostate invasion percentage), Median (range) | | 13 (6-48) |
| Presence of emboli | yes, n (percentage in column) | 2 (13.3) |
| | no, n (percentage in column) | 13 (56.7) |
| pTNM stage | pT2a, n (percentage in column) | 1 (6.7) |
| | pT2b, n (percentage in column) | 4 (26.7) |
| | pT3a, n (percentage in column) | 7 (46.7) |
| | pT2a, n (percentage in column) | 3 (20) |
| | pT2a, n (percentage in column) | 0 (0) |
| Presence of metastatic lymph nodes **, n (percentage in column) | | 1 (6.7) |
| Expression of CCR3 | 0 = none, n (percentage in column) | 1 (6.7) |
| | 1 = low, n (percentage in column) | 2 (13.3) |
| | 2 = moderate, n (percentage in column) | 10 (66.67) |
| | 3 = high, n (percentage in column) | 3 (20) |

Abundant PPAT was defined by a surface area greater than 10 cm2, the surface area for which all patients exhibit a Gleason score greater than 7 (see table 6 hereinafter).

TABLE 6

Correlation between surface area of periprostatic adipose deposit and various clinical, histological and biochemical characteristics of cohort.

| | | Periprostatic adipose tissue surface area | | Spearman | |
|---|---|---|---|---|---|
| | | Small surface area (<10 cm$^2$) | Large surface area (>10 cm$^2$) | coefficient of correlation | p-value |
| Age (years), Median (range) | | 61 (61-71) | 62 (48-69) | -0.017 | 0.449 |
| Gleason score, n (in column) | Gleason < 7 | 3 (50) | 0 (0) | 0.5843 | 0.022 |
| | Gleason (3 + 4) | 3 (50) | 6 (60) | | |
| | Gleason (4 + 3) | 0 (0) | 2 (20) | | |
| | Gleason > 7 | 0 (0) | 2 (20) | | |
| Non-differentiated contingent, Median: (range) | | 5 (0-25) | 25 (20-95) | 0.461 | 0.083 |
| Tumor-stage, n (in columns) | 1 = pT2b | 0 (0) | 1 (10) | 0.38 | 0.163 |
| | 2 = pT2c | 2 (40) | 2 (20) | | |
| | 3 = pT3a | 3 (60) | 4 (40) | | |
| | 4 = pT3b | 0 (0) | 3 (30) | | |
| Prostate weight, Median (range) | | 52 (44-69) | 7.15 (6.38-8.96) | -0.24 | 0.39 |
| PSA (ng/mL), Median (range) | | 6.7 (7-7.5) | 7.15 (6.38-8.96) | -0.163 | 0.89 |
| Biological reascension, n (in column) | | 1 (20) | 2 (20) | 0.116 | 0.681 |
| BMI (kg/m2), Median (range) | | 28 (22-34) | 27 (20-31) | -0.243 | 0.3 |
| Overweight and obesity (BMI ≥ 25 kg/m2), n (in column) | | 3 (60) | 7 (70) | -0.224 | 0.38 |
| Expression of CCR3 | 1 = low, n (percentage in column) | 2 (40) | 0 (0) | 0.67 | 0.006 |
| | 2 = moderate, n (percentage in column) | 3 (60) | 7 (70) | | |
| | 3 = high, n (percentage in column) | 0 (0) | 3 (30) | | |

Figure 7A:
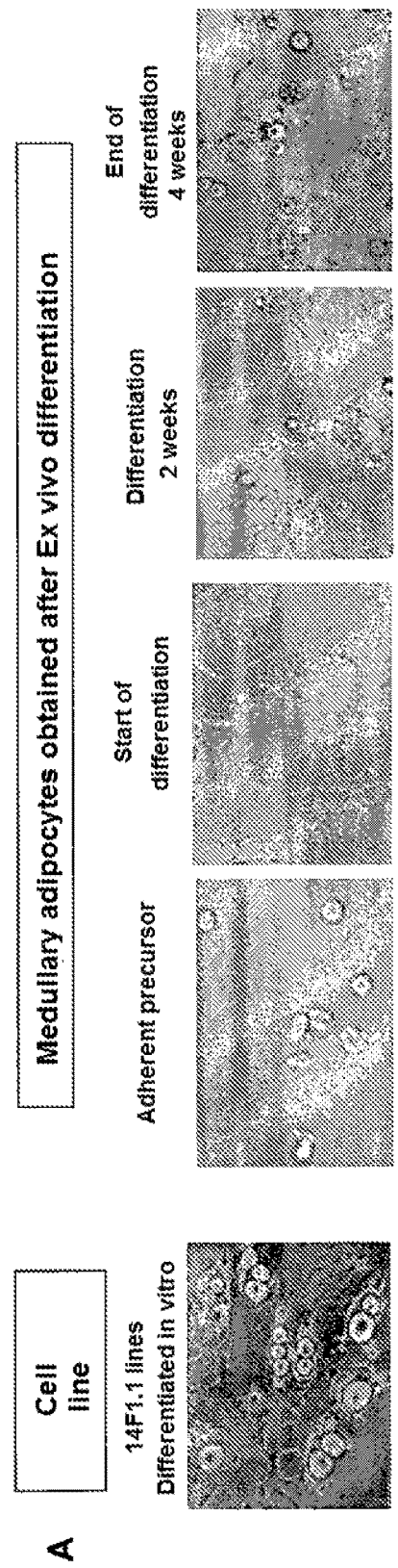

The Expression of the Receptor CCR3 Plays a Role in the Migration of Prostate Cancer Cells Induced by Medullary Adipocytes Two types of models were used: the line 14F1.1 which is a line of medullary pre-adipocytes wherein the differentiation (obtained after 21 days of confluence) in vitro makes it possible to obtain adipocytes containing lipids (Zipori, Friedman et al. 1984) (left-hand panel in FIG. 7A). Experiments were also conducted with medullary adipocytes obtained from the in vitro differentiation of progenitors derived from C57BL/6 mouse bone marrow. These progenitors were cultured for 4 weeks in a differentiation medium containing DMEM (10% serum) supplemented with 1 μM dexamethasone, 0.45 mM IBMX, 60 μM indomethacin and 10 μg/ml insulin, making it possible to obtain mature adipocytes containing lipid droplets (center panel in FIG. 7A).

Figure 7B:
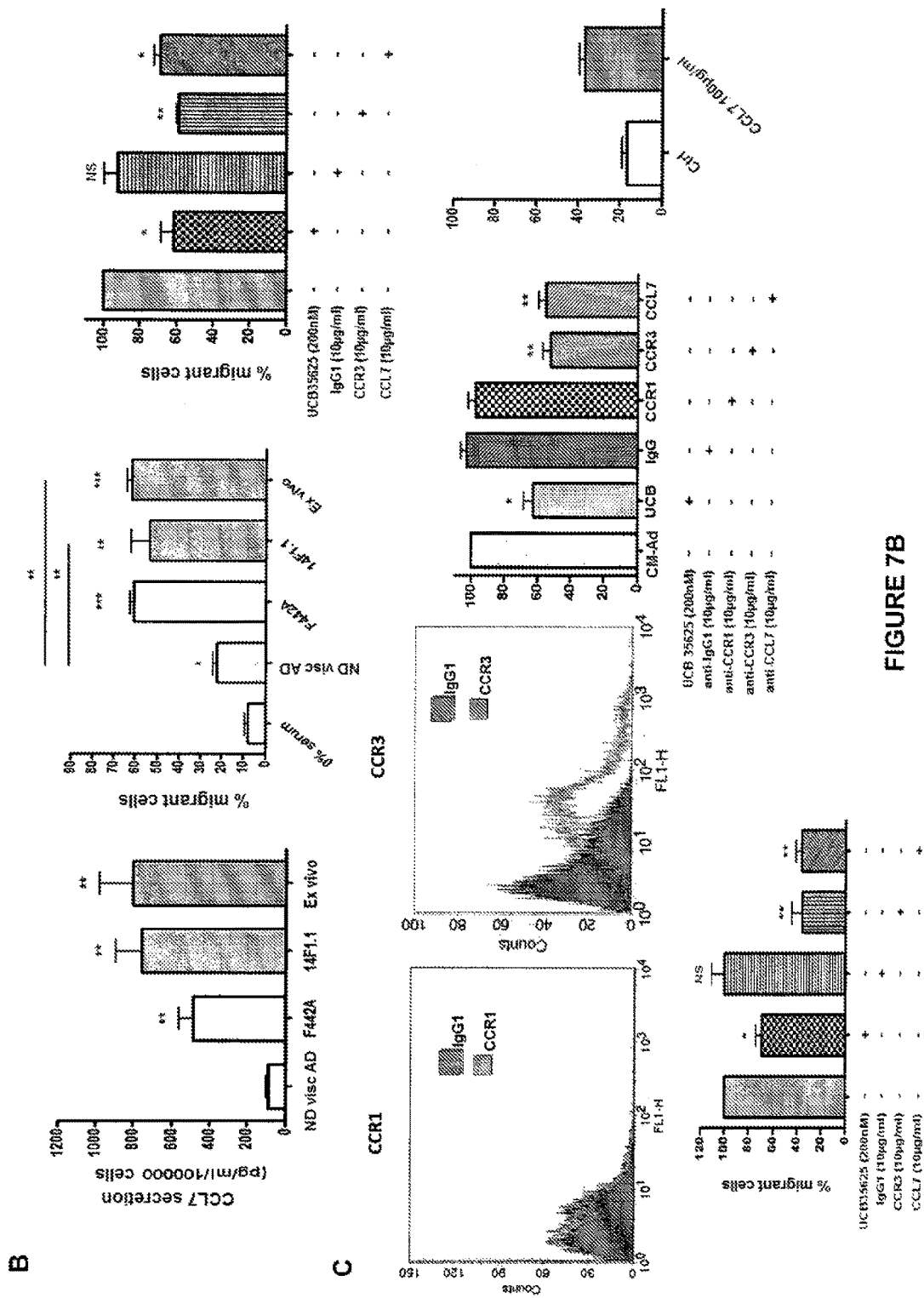

The CCL7 assay using the ELISA method demonstrates that the conditioned media of these cells contain CCL7 at a comparable level to that of 3T3F442A differentiated in vitro (3 independent samples). These experiments also made it possible to demonstrate that these medullary adipocytes secrete quantities of CCL7 greater than those generated by ND visceral adipocytes (p<0.001). In a Boyden chamber migration tests, medullary adipocytes are capable of inducing the migration of PC-3 tumor cells at a comparable level to that of F442A mature adipocytes (center panel). This migration is inhibited by UCB35625 (200 nM) and by the use of antibodies blocking CCR3 and CCL7 (10 μg/ml) (p<0.01). The results are shown in FIG. 7B.

The RM1-BM line is a prostate cancer line capable of forming bones metastases in 90% of cases in C57BL/6 mice after intracardiac injection (Ohori, Egawa et al. 1994). These cells, similar to all the prostate tumor lines studied, express the receptor CCR3 but not the receptor CCR1 as demonstrated by flow cytometry (left-hand panel in FIG. 7C). The recombinant chemokine CCL7 induces significant migration of RM1-BM cells at a dose of 100 ng/mL with respect to the control (serum-free medium, p<0.01) (center panel). The migration of RM1-BM cells against conditioned medium of medullary adipocytes is significantly inhibited by UCB35625 at the dose of 200 nM (p<0.05), and by the blocking antibodies targeted against CCR3 and CCL7 at the dose of 10 μg/ml (p<0.01) (right-hand panel). The results are given in FIG. 7C.

Human Medullary Adipocytes have the Ability to Chemoattract Human Prostate Tumor Cells, this Effect is Dependent on the CCR3/CCL7 Pathway and is Regulated by Obesity The results are given in FIG. 9.

FIG. 9A: From yellow marrow samples from patients obtained in conjunction with the Traumatology department at Hôpital Pierre Paul Riquet (Toulouse university hospital, France), the medullary adipocytes are isolated and incubated for 24 hours in serum-free medium containing 1% BSA. After 24 hours, the conditioned medium is extracted. Migration tests were conducted using PC3 tumor cells as a model and as a chemoattractant medium: either culture medium containing 0% FCS (negative control), or culture medium containing 10% FCS (positive control), or conditioned medium of human medullary adipocytes (CM-MAd). The level of migrant cells in the presence of CM-MAd is similar to that obtained in the presence of medium containing 10% FCS, confirming the existence of targeted migration induced by CM-MAd and thus the presence of chemokines in these medullary adipocyte secretions.

FIG. 9B: Using an ELISA test, the presence of the chemokine CCL7 was demonstrated in CM-MAd in a quantity four times greater than that present in the conditioned medium of human subcutaneous adipose AT and two times greater than that of human periprostatic adipose tissue.

FIGS. 9C and 9D: The chemokine (CCL7) and the receptor (CCR3) thereof play a role in the targeted migration of PC3 tumor cells against CM-MAd, since this migration is inhibited by almost 50% using a CCR1/CCR3 inhibitor (UCB35625) and by almost one third using blocking antibodies targeted against CCR3 and CCL7, whereas antibodies targeted against CCR3 are ineffective.

FIGS. 9E and 9F: In the case of obesity, there is a strengthening of the CCL7-CCR3 pathway. Firstly, the secretion of CCL7 by medullary adipocytes, assayed by ELISA, is almost doubled in obese patients (BMI>30 mg/m$^2$) compared to non-obese patients (BMI<25 mg/m$^2$). The level of secretion of CCL7 in medullary adipocytes is much greater in medullary adipocytes than subcutaneous adipocytes (including in obese subjects). Moreover, the secretions from medullary adipocytes of obese patients are more chemoattractant than those from non-obese patients and induce approximately 50% additional migration. Interestingly, using the inhibitor of CCR1 and CCR3 (UCB35625), the increase in migration associated with obesity is almost completely reversed.

REFERENCES

Agrawal, L., C. R. Maxwell. et al. (2009). J Gen Virol 90(Pt 3): 710-722.
Allott, E. H., E. M. Masko, et al. (2013). Eur Urol 63(5): 800-809.
Balkwill. F. (2004). Nat Rev Cancer 4(7): 540-550.
Begley, L. A., S. Kasina, et al. (2008). Cytokine 43(2): 194-199.
Cherney, R. J., R. Mo, et al. (2008). J Med Chem 51(4): 721-724.
Contreras, A. F., A. Ferrero Guadagnoli, et al. (2010). Rev Fac Cien Med Univ Nac Cordoba 67(3): 104-107.
Egawa, S., M. Ohori, et a). (1994). Nihon Hinyokika Gakkai Zasshi 85(10): 1543-1551.
Elsner, J., S. E. Escher, et al. (2004). Allergy 59(12): 1243-1258.
Elsner. L., H. Petering, et al. (1997). Eur J Immunol 27(11): 2892-2898.
Houimel, M. and L. Mazzucchelli (2013). Immunol Lett 149(1-2): 19-29.
Iacono, A. T., T. N. Masciangelo, et al. (1994). Chest 106(1): 311-313.
Inoue. K., 3. W. Slaton, et al. (2000). Clin Cancer Res 6(5): 2104-2119.
Johrer, K., C. Zelle-Rieser, et al. (2005). Clin Cancer Res 11(7): 2459-2465.
Joubert, P., S. Lajoie-Kadoch, et al. (2008). J Immunol 180(2): 1268-1275.
Jung, D. W., Z. M. Che, et al. (2010). Int J Cancer 127(2): 332-344.
Kanno, A., H. Amakasu, et al. (1994). Tohoku J Exp Med 172(I): 83-90.
Kiss, D. L., J. Longden, et al. (2009). Cell Mol Biol Lett 14(4): 537-547.
Kuri-Harcuch, W. and H. Green (1978). Proc Natl Acad Sci USA 75(12): 6107-6109.
Lee Y. J., D. H. Kim, et al. (2010). Ann Dermatol 22(4): 412-417.
Loberg, R. D., L. L. Day, et al. (2006). Neoplasia 8(7): 578-586.
Loetscher. P., A. Pellegrino, et al. (2001). J Biol Chem 276(5): 2986-2991.
Lu, Y., Z. Cai, et al. (2007). J Cell Biochem 101(3): 676-685.
Magi-Galluzzi, C., A. J. Evans, et al. (2011). Mod Pathol 24(1): 26-38.
Malavaud, B., D). Pehejetski, et al., (2010). Eur J Cancer. 46(18):3417-24.
Menzies, N. A. and J. A. Salomon (2011). Health Econ 20(12): 1523-1531.
Ohori, M., S. Egawa, et al. (1994). Br J Urol 74(1): 72-79.
Ohori, M. and P. T. Scardino (1994). Semin Oncol 21(5): 522-526.
Ohori, M., T. M. Wheeler, et al. (1994). J Urol 152(5 Pt 2): 1714-1720.
Ohori, N. P., A. T. Iacono, et al. (1994). Am J Surg Pathol 18(12): 1192-1204.
Ouchi, N., J. L. Parker, et al. (2011). Nat Rev Immunol 11(2): 85-97.
Rosenkilde, M. M., L. O. Gerlach, et al. (2004). J Biol Chem 279(4): 3033-3041.
Sabroe, I., M. J. Peck, et al. (2000). J Biol Chem 275(34): 25985-25992.
Saitoh. Y., M. Miura, et al. (1994). "Changes of scrum hepatitis C virus levels in patients with chronic hepatitis C treated with two courses of interferon administration." Tohoku J Exp Med 173(4): 361-369.
Salomon, L., D. Azria, et al. (2010). Prog Urol 20 Suppl 4: 5217-251.
Santini, M. S., O. D. Salomon, et al. (2010). Rev Inst Med Trop Sao Paulo 52(4); 187-191.
Sysel. A. M, V. E. Valli, et al. (2013). Anticancer Res. 33: 4203-12.
Szymezak, W. A. and G. S. Deepe, Jr. (2009). J Immunol 183(3): 1964-1974.
Taichnman, R. S., C. Cooper, et al. (2002). Cancer Res 62(6): 1832-1837.
Toumiaire, F., B. Romier-Crouzet, et al. (2013). PLoS One 8(6): e66515.
Vindrieux, D., P. Escobar. et al. (2009). Endocr Relat Cancer 16(3): 663-673.
White, J. R., J. M. Lee, et al. (1998). J Biol Chem 273(17): 10095-10098.
Winzell, M. S. and B. Ahren (2004). Diabetes 53 Suppl 3: S215-219.

Yamamura, J., G. Salomon. et al. (2011). Radiol Res Pract 2011: 616852.

Zhang. J., L. Patel, et al. (2010). Cytokine Growth Factor Rev 21(1): 41-48.

Zhu, F., P. Liu, et al. (2014). Oncol Rep 31(5): 2049-2054.

Zhu, X. H., B. Liao, et al. (2013). Zhonghua Er Bi Yan Hou Tou Jing Wai Ke Za Zhi 48(4): 316-321.

Zipori, D., A. Friedman, et al. (1984). J Cell Physiol 118(2): 143-152.

The invention claimed is:

1. A method of treating or inhibiting adipocyte-mediated migration of prostate cancer outside the prostatic capsule in a subject in need thereof comprising administering to the subject an inhibitor of a CCL7/CCR3 interaction consisting of an organic molecule selected from the group of the compounds in Table 7.

2. The method of claim 1, wherein the inhibitor of the CCL7/CCR3 interaction comprises a CCR3 antagonist.

3. The method of claim 1, wherein the organic molecule is the compound having formula DLI.

4. The method of claim 1, wherein the subject is an adult male who is obese and/or has abundant periprostatic adipose tissue (PPAT).

5. The method of claim 2, wherein the subject is an adult male who is obese and/or has abundant periprostatic adipose tissue (PPAT).

6. The method of claim 3, wherein the subject is an adult male who is obese and/or has abundant periprostatic adipose tissue (PPAT).

* * * * *